US011519016B2

(12) United States Patent
Thomann et al.

(10) Patent No.: US 11,519,016 B2
(45) Date of Patent: Dec. 6, 2022

(54) NMR METHODS AND SYSTEMS FOR THE RAPID DETECTION OF BACTERIA

(71) Applicant: T2 Biosystems, Inc., Lexington, MA (US)

(72) Inventors: Ulrich Hans Thomann, Stow, MA (US); Lori Anne Neely, Reading, MA (US); Heidi Susanne Giese, Newburyport, MA (US); Jessica Ann Townsend, Boston, MA (US); Rahul Krishan Dhanda, Dorchester, MA (US); Thomas Jay Lowery, Jr., Belmont, MA (US); Urvi Ved, Natick, MA (US); Brendan Manning, Arlington, MA (US); Nu Ai Phung, Newtonville, MA (US); Joanne Lawton Garver, Maynard, MA (US); Benjamin B. Stone, Holliston, MA (US)

(73) Assignee: T2 Biosystems, Inc., Lexington, MA (US)

(*) Notice: Subject to any disclaimer, the term of this patent is extended or adjusted under 35 U.S.C. 154(b) by 0 days.

(21) Appl. No.: 16/070,994

(22) PCT Filed: Jan. 20, 2017

(86) PCT No.: PCT/US2017/014410
§ 371 (c)(1),
(2) Date: Jul. 18, 2018

(87) PCT Pub. No.: WO2017/127731
PCT Pub. Date: Jul. 27, 2017

(65) Prior Publication Data
US 2019/0071707 A1    Mar. 7, 2019

Related U.S. Application Data

(60) Provisional application No. 62/281,608, filed on Jan. 21, 2016.

(51) Int. Cl.
C12Q 1/04 (2006.01)
C12Q 1/689 (2018.01)
C12Q 1/6825 (2018.01)
C07K 14/22 (2006.01)
G01N 33/569 (2006.01)
G01N 33/68 (2006.01)

(52) U.S. Cl.
CPC .............. *C12Q 1/04* (2013.01); *C07K 14/22* (2013.01); *C12Q 1/689* (2013.01); *C12Q 1/6825* (2013.01); *G01N 33/56911* (2013.01); *G01N 33/6893* (2013.01); *C12Q 2600/158* (2013.01); *C12Q 2600/16* (2013.01)

(58) Field of Classification Search
CPC .................................................... C12Q 1/689
See application file for complete search history.

(56) References Cited

U.S. PATENT DOCUMENTS

| 4,072,578 | A | 2/1978 | Cady et al. |
| 4,101,435 | A | 7/1978 | Hasegawa et al. |
| 4,295,613 | A | 10/1981 | Moore et al. |
| 4,374,360 | A | 2/1983 | Sepponen |
| 4,452,773 | A | 6/1984 | Molday |
| 4,471,306 | A | 9/1984 | Edelstein et al. |
| 4,485,177 | A | 11/1984 | Siedel et al. |
| 4,578,361 | A | 3/1986 | Siedel et al. |
| 4,672,040 | A | 6/1987 | Josephson |
| 4,683,195 | A | 7/1987 | Mullis et al. |
| 4,683,202 | A | 7/1987 | Mullis |
| 4,745,077 | A | 5/1988 | Holian et al. |
| 4,875,486 | A | 10/1989 | Rapoport et al. |
| 4,889,818 | A | 12/1989 | Gelfand et al. |
| 4,920,061 | A | 4/1990 | Poynton et al. |
| 4,965,188 | A | 10/1990 | Mullis et al. |
| 5,038,852 | A | 8/1991 | Johnson et al. |
| 5,049,819 | A | 9/1991 | Dechene et al. |
| 5,066,584 | A | 11/1991 | Gyllensten et al. |
| 5,079,352 | A | 1/1992 | Gelfand et al. |
| 5,135,875 | A | 8/1992 | Meucci et al. |
| 5,136,095 | A | 8/1992 | Tarnowski et al. |
| 5,164,297 | A | 11/1992 | Josephson et al. |
| 5,164,495 | A | 11/1992 | Lunetta |
| 5,204,457 | A | 4/1993 | Maruno et al. |
| 5,229,297 | A | 7/1993 | Schnipelsky et al. |
| 5,247,076 | A | 9/1993 | Goulet et al. |

(Continued)

FOREIGN PATENT DOCUMENTS

BY    6388 C1    9/2004
EP    0574267 A2    12/1993

(Continued)

OTHER PUBLICATIONS

Naimi, A. et al., Determination of the Nucleotide Sequence of the 23S Ribosomal RNA and Flanking Spacers of an Enterococcus faecium Strain, Reveals Insertion-deletion Events in the Ribosomal Spacer 1 of Enterococci, System. Appl. Microbiol., vol. 22, pp. 9-21 (Year: 1999).*
Naimi, A. et al., Primary and secondary structures of rRNA spacer regions in enterococci, Microbiol., vol. 143, pp. 823-833 (Year: 1997).*
GenBank Accession No. X79341, E. faecium 23S rRNA gene (Year: 2001).*
GenBank Accession No. X87181, E. faecium 23S-5S rRNA spacer DNA, strain ATCC-19434 (Year: 1997).*

(Continued)

*Primary Examiner* — Teresa E Strzelecka
(74) *Attorney, Agent, or Firm* — Clark & Elbing LLP

(57) ABSTRACT

The invention features methods panels, cartridges, and systems for detecting pathogens and for diagnosing and treating diseases, including bacteremia and sepsis.

11 Claims, 25 Drawing Sheets

Specification includes a Sequence Listing.

(56) References Cited

U.S. PATENT DOCUMENTS

| | | |
|---|---|---|
| 5,252,732 A | 10/1993 | Sinclair et al. |
| 5,254,460 A | 10/1993 | Josephson et al. |
| 5,262,176 A | 11/1993 | Palmacci et al. |
| 5,333,675 A | 8/1994 | Mullis et al. |
| 5,338,684 A | 8/1994 | Grenier et al. |
| 5,352,600 A | 10/1994 | Gelfand et al. |
| 5,363,842 A | 11/1994 | Mishelevich et al. |
| 5,411,173 A | 5/1995 | Weinstein |
| 5,424,419 A | 6/1995 | Hasegawa et al. |
| 5,426,026 A | 6/1995 | Jordan |
| 5,426,027 A | 6/1995 | Lott et al. |
| 5,436,149 A | 7/1995 | Barnes |
| 5,445,970 A | 8/1995 | Rohr |
| 5,445,971 A | 8/1995 | Rohr |
| 5,475,610 A | 12/1995 | Atwood et al. |
| 5,482,030 A | 1/1996 | Klein |
| 5,492,814 A | 2/1996 | Weissleder |
| 5,505,192 A | 4/1996 | Samiotes et al. |
| 5,508,164 A | 4/1996 | Kausch et al. |
| 5,512,439 A | 4/1996 | Hornes et al. |
| 5,532,137 A | 7/1996 | Niwa et al. |
| 5,543,305 A | 8/1996 | Cummins et al. |
| 5,544,647 A | 8/1996 | Jewett et al. |
| 5,578,325 A | 11/1996 | Domb et al. |
| 5,599,498 A | 2/1997 | Oh |
| 5,618,926 A | 4/1997 | Salamone et al. |
| 5,622,163 A | 4/1997 | Jewett et al. |
| 5,631,132 A | 5/1997 | Lott et al. |
| 5,635,353 A | 6/1997 | Lott et al. |
| 5,635,406 A | 6/1997 | Grenier et al. |
| 5,637,469 A | 6/1997 | Wilding et al. |
| 5,650,288 A | 7/1997 | MacFarlane et al. |
| 5,656,493 A | 8/1997 | Mullis et al. |
| 5,676,129 A | 10/1997 | Rocci, Jr. et al. |
| 5,677,133 A | 10/1997 | Oberhardt |
| 5,679,323 A | 10/1997 | Menz et al. |
| 5,688,644 A | 11/1997 | Lott et al. |
| 5,698,448 A | 12/1997 | Soldin |
| 5,705,628 A | 1/1998 | Hawkins |
| 5,708,159 A | 1/1998 | Ohno et al. |
| 5,711,871 A | 1/1998 | Miltenyi |
| 5,773,307 A | 6/1998 | Colin et al. |
| 5,776,696 A | 7/1998 | Salowe |
| 5,801,003 A | 9/1998 | Shimamura et al. |
| 5,804,375 A | 9/1998 | Gelfand et al. |
| 5,809,997 A | 9/1998 | Wolf |
| 5,837,501 A | 11/1998 | Beumer et al. |
| 5,858,534 A | 1/1999 | Sucholeiki |
| 5,898,071 A | 4/1999 | Hawkins |
| 5,910,409 A | 6/1999 | Bhattacharjee et al. |
| 5,925,573 A | 7/1999 | Colin et al. |
| 5,935,825 A | 8/1999 | Nishimura et al. |
| 5,973,138 A | 10/1999 | Collis |
| 5,994,056 A | 11/1999 | Higuchi |
| 6,007,845 A | 12/1999 | Domb et al. |
| 6,013,188 A | 1/2000 | Terstappen et al. |
| 6,020,211 A | 2/2000 | Tuunanen |
| 6,029,659 A | 2/2000 | O'Connor |
| 6,030,845 A | 2/2000 | Yamao et al. |
| 6,033,574 A | 3/2000 | Siddiqi |
| 6,040,166 A | 3/2000 | Erlich et al. |
| 6,097,188 A | 8/2000 | Sweedler et al. |
| 6,123,902 A | 9/2000 | Koch et al. |
| 6,127,155 A | 10/2000 | Gelfand et al. |
| 6,130,045 A | 10/2000 | Wurst et al. |
| 6,136,549 A | 10/2000 | Feistel |
| 6,138,669 A | 10/2000 | Rocci, Jr. et al. |
| 6,143,578 A | 11/2000 | Bendele et al. |
| 6,148,815 A | 11/2000 | Wolf |
| 6,159,378 A | 12/2000 | Holman et al. |
| 6,165,378 A | 12/2000 | Maruno et al. |
| 6,187,547 B1 | 2/2001 | Legay et al. |
| 6,194,900 B1 | 2/2001 | Freeman et al. |
| 6,197,563 B1 | 3/2001 | Erlich et al. |
| 6,228,268 B1 | 5/2001 | Siddiqi |
| 6,235,890 B1 | 5/2001 | Morrison et al. |
| 6,242,178 B1 | 6/2001 | Lott et al. |
| 6,283,365 B1 | 9/2001 | Bason |
| 6,294,342 B1 | 9/2001 | Rohr et al. |
| 6,297,062 B1 | 10/2001 | Gombinski |
| 6,307,372 B1 | 10/2001 | Sugarman et al. |
| 6,338,946 B1 | 1/2002 | Kobayashi et al. |
| 6,342,396 B1 | 1/2002 | Perrin et al. |
| 6,346,813 B1 | 2/2002 | Kleinberg |
| 6,361,944 B1 | 3/2002 | Mirkin et al. |
| 6,405,727 B1 | 6/2002 | MacMichael et al. |
| 6,423,490 B1 | 7/2002 | Takama |
| 6,431,168 B1 | 8/2002 | Rand et al. |
| 6,446,627 B1 | 9/2002 | Bowman et al. |
| 6,456,072 B1 | 9/2002 | Webb et al. |
| 6,489,767 B1 | 12/2002 | Prado et al. |
| 6,500,343 B2 | 12/2002 | Siddiqi |
| 6,514,736 B1 | 2/2003 | Erlich et al. |
| 6,548,311 B1 | 4/2003 | Knoll |
| 6,562,958 B1 | 5/2003 | Breton et al. |
| 6,566,086 B1 | 5/2003 | Al Athel et al. |
| 6,599,498 B1 | 7/2003 | Groman et al. |
| 6,605,439 B2 | 8/2003 | Einsele |
| 6,630,355 B1 | 10/2003 | Pivarnik et al. |
| 6,654,636 B1 | 11/2003 | Dev et al. |
| 6,659,307 B1 | 12/2003 | Stradella |
| 6,686,195 B1 | 2/2004 | Colin et al. |
| 6,686,454 B1 | 2/2004 | Yatscoff et al. |
| 6,761,161 B2 | 7/2004 | Scarrott et al. |
| 6,767,635 B1 | 7/2004 | Bahr et al. |
| 6,768,305 B1 | 7/2004 | Keifer |
| 6,774,635 B1 | 8/2004 | Gerald, II et al. |
| 6,788,061 B1 | 9/2004 | Sweedler et al. |
| 6,822,452 B2 | 11/2004 | Ham et al. |
| 6,822,454 B2 | 11/2004 | Peck et al. |
| 6,866,838 B1 | 3/2005 | Mondain-Monval et al. |
| 6,872,523 B1 | 3/2005 | Iwen et al. |
| 6,884,357 B2 | 4/2005 | Siddiqi |
| 6,890,765 B2 | 5/2005 | Lawrence et al. |
| 6,940,378 B2 | 9/2005 | Miller et al. |
| 6,958,609 B2 | 10/2005 | Raftery et al. |
| 7,001,589 B2 | 2/2006 | Mondain-Monval et al. |
| 7,018,849 B2 | 3/2006 | Piasio et al. |
| 7,036,667 B2 | 5/2006 | Greenstein et al. |
| 7,037,688 B2 | 5/2006 | Salituro et al. |
| 7,049,558 B2 | 5/2006 | Baer et al. |
| 7,078,495 B1 | 7/2006 | Kasper et al. |
| 7,093,482 B2 | 8/2006 | Berndt |
| 7,164,077 B2 | 1/2007 | Venkatasubramanian |
| 7,169,556 B2 | 1/2007 | Park et al. |
| 7,186,518 B2 | 3/2007 | Wang et al. |
| 7,200,430 B2 | 4/2007 | Thomas et al. |
| 7,217,457 B2 | 5/2007 | Elaissari et al. |
| 7,217,542 B2 | 5/2007 | Tyvoll et al. |
| 7,274,191 B2 | 9/2007 | Park et al. |
| 7,331,340 B2 | 2/2008 | Barney |
| 7,332,353 B2 | 2/2008 | Baudry et al. |
| 7,345,479 B2 | 3/2008 | Park et al. |
| 7,397,241 B2 | 7/2008 | Gauthausen et al. |
| 7,459,145 B2 | 12/2008 | Bao et al. |
| 7,462,475 B2 | 12/2008 | Kermekchiev et al. |
| 7,494,771 B2 | 2/2009 | Picard et al. |
| 7,517,457 B2 | 4/2009 | Siddiqi |
| 7,553,542 B2 | 6/2009 | Ou et al. |
| 7,560,923 B2 | 7/2009 | Viswanathan |
| 7,564,245 B2 | 7/2009 | Lee |
| 7,575,875 B2 | 8/2009 | Konrath et al. |
| 7,587,988 B2 | 9/2009 | Bowman et al. |
| 7,615,381 B2 | 11/2009 | Masters et al. |
| 7,637,227 B2 | 12/2009 | Stradella et al. |
| 7,651,837 B2 | 1/2010 | Ohno et al. |
| 7,670,780 B2 | 3/2010 | Hogan et al. |
| 7,704,735 B2 | 4/2010 | Facer et al. |
| 7,723,095 B2 | 5/2010 | Cleuziat et al. |
| 7,781,228 B2 | 8/2010 | Menon et al. |
| 7,829,350 B2 | 11/2010 | Josephson et al. |
| 7,867,766 B2 | 1/2011 | Wang |
| 7,906,286 B2 | 3/2011 | Fukui et al. |
| 8,044,001 B2 | 10/2011 | Putzig |

(56) References Cited

U.S. PATENT DOCUMENTS

| | | |
|---|---|---|
| 8,049,001 B2 | 11/2011 | Tomatsu et al. |
| 8,102,176 B2 | 1/2012 | Lee |
| 8,143,896 B2 | 3/2012 | McDowell et al. |
| 8,310,231 B2 | 11/2012 | Lee |
| 8,310,232 B2 | 11/2012 | Lee |
| 8,334,693 B2 | 12/2012 | Lee |
| 8,344,731 B2 | 1/2013 | Lee |
| 8,409,807 B2 | 4/2013 | Neely et al. |
| 8,563,298 B2 | 10/2013 | Lowery, Jr. et al. |
| 8,624,592 B2 | 1/2014 | Lee |
| 8,704,517 B2 | 4/2014 | Lee |
| 8,883,423 B2 | 11/2014 | Neely |
| 9,046,493 B2 | 6/2015 | Neely et al. |
| 9,360,457 B2 | 6/2016 | Neely et al. |
| 9,488,648 B2 | 11/2016 | Neely et al. |
| 9,702,852 B2 | 7/2017 | Lowery, Jr. et al. |
| 9,714,940 B2 | 7/2017 | Lowery, Jr. et al. |
| 9,932,574 B2 | 4/2018 | Burghardt et al. |
| 2002/0051974 A1 | 5/2002 | Dodge et al. |
| 2002/0120116 A1 | 8/2002 | Kunsch et al. |
| 2003/0054370 A1 | 3/2003 | Zeng et al. |
| 2003/0054436 A1 | 3/2003 | Kunsch et al. |
| 2003/0069180 A1 | 4/2003 | Jiang et al. |
| 2003/0092029 A1 | 5/2003 | Josephson et al. |
| 2003/0133282 A1 | 7/2003 | Beihoff et al. |
| 2003/0137971 A1 | 7/2003 | Gibson et al. |
| 2003/0174384 A1 | 9/2003 | Halas et al. |
| 2003/0175709 A1 | 9/2003 | Murphy et al. |
| 2003/0207296 A1 | 11/2003 | Park et al. |
| 2003/0216638 A1 | 11/2003 | Dharmakumar et al. |
| 2003/0222648 A1 | 12/2003 | Fan |
| 2004/0018611 A1 | 1/2004 | Ward et al. |
| 2004/0029129 A1 | 2/2004 | Wang et al. |
| 2004/0076990 A1 | 4/2004 | Picard et al. |
| 2004/0141887 A1 | 7/2004 | Mainquist et al. |
| 2004/0166492 A1 | 8/2004 | Engel et al. |
| 2004/0255936 A1 | 12/2004 | Urbanus |
| 2005/0142033 A1 | 6/2005 | Glezer et al. |
| 2005/0176080 A1 | 8/2005 | Bodepudi et al. |
| 2005/0239216 A1 | 10/2005 | Feistel |
| 2006/0051770 A1 | 3/2006 | Makeev |
| 2006/0053870 A1 | 3/2006 | Berndt |
| 2006/0160121 A1 | 7/2006 | Mounts et al. |
| 2006/0234219 A1 | 10/2006 | Ohno et al. |
| 2006/0254581 A1 | 11/2006 | Genova et al. |
| 2006/0269965 A1 | 11/2006 | Josephson et al. |
| 2007/0020624 A1 | 1/2007 | Rubenfield et al. |
| 2007/0027309 A1 | 2/2007 | Weinstock et al. |
| 2007/0031850 A1 | 2/2007 | Mounts et al. |
| 2007/0065817 A1 | 3/2007 | Lee et al. |
| 2007/0083945 A1 | 4/2007 | Byrum et al. |
| 2007/0111330 A1 | 5/2007 | Hong et al. |
| 2007/0116600 A1 | 5/2007 | Kochar et al. |
| 2007/0116602 A1 | 5/2007 | Lee |
| 2007/0166730 A1 | 7/2007 | Menon et al. |
| 2007/0172899 A1 | 7/2007 | Graham et al. |
| 2007/0190543 A1 | 8/2007 | Livak |
| 2007/0292891 A1 | 12/2007 | Wei et al. |
| 2007/0295329 A1 | 12/2007 | Lieberman et al. |
| 2008/0008996 A1 | 1/2008 | Byrum |
| 2008/0017193 A1 | 1/2008 | Jones et al. |
| 2008/0020401 A1 | 1/2008 | Grenier et al. |
| 2008/0056948 A1 | 3/2008 | Dale et al. |
| 2008/0066742 A1 | 3/2008 | Hodson et al. |
| 2008/0081379 A1 | 4/2008 | Sigler et al. |
| 2008/0102449 A1 | 5/2008 | Trama et al. |
| 2008/0108060 A1 | 5/2008 | Ubalijoro et al. |
| 2008/0124722 A1 | 5/2008 | Dromaretsky et al. |
| 2008/0160499 A1 | 7/2008 | Grenier et al. |
| 2008/0176756 A1 | 7/2008 | Siegel et al. |
| 2008/0204022 A1 | 8/2008 | Sillerud et al. |
| 2008/0248970 A1 | 10/2008 | Morrison et al. |
| 2008/0255498 A1 | 10/2008 | Houle |
| 2008/0305048 A1 | 12/2008 | Josephson et al. |
| 2008/0311676 A1 | 12/2008 | Brate et al. |
| 2009/0029392 A1 | 1/2009 | Josephson et al. |
| 2009/0042223 A1 | 2/2009 | Wei et al. |
| 2009/0054741 A1 | 2/2009 | McAleer |
| 2009/0077685 A1 | 3/2009 | Buehler et al. |
| 2009/0087865 A1 | 4/2009 | Kasper et al. |
| 2009/0099342 A1 | 4/2009 | Braconnot et al. |
| 2009/0119022 A1 | 5/2009 | Timberlake et al. |
| 2009/0134869 A1 | 5/2009 | Lee |
| 2009/0139516 A1 | 6/2009 | Augustyn et al. |
| 2009/0146658 A1 | 6/2009 | McDowell et al. |
| 2009/0155929 A1 | 6/2009 | Wei et al. |
| 2009/0170060 A1 | 7/2009 | Kermekchiev et al. |
| 2009/0229607 A1 | 9/2009 | Brunnberg et al. |
| 2009/0239308 A1 | 9/2009 | Dube et al. |
| 2009/0253210 A1 | 10/2009 | Kobold et al. |
| 2009/0298090 A1 | 12/2009 | Drengler et al. |
| 2009/0298129 A1 | 12/2009 | Spence et al. |
| 2009/0325193 A1 | 12/2009 | Grenier et al. |
| 2009/0325197 A1 | 12/2009 | Drengler et al. |
| 2009/0325198 A1 | 12/2009 | Holets-McCormack |
| 2010/0062090 A1 | 3/2010 | Kim et al. |
| 2010/0072994 A1 | 3/2010 | Lee et al. |
| 2010/0092979 A1 | 4/2010 | Kelso et al. |
| 2010/0099746 A1 | 4/2010 | Yamada et al. |
| 2010/0120174 A1 | 5/2010 | Josephson et al. |
| 2010/0124766 A1 | 5/2010 | Ng et al. |
| 2010/0129821 A1 | 5/2010 | Fredricks et al. |
| 2010/0180980 A1 | 7/2010 | Lee et al. |
| 2010/0219824 A1 | 9/2010 | Sillerud et al. |
| 2010/0233035 A1 | 9/2010 | Denawa et al. |
| 2010/0239504 A1 | 9/2010 | Liu et al. |
| 2010/0259259 A1 | 10/2010 | Zahn et al. |
| 2011/0018538 A1 | 1/2011 | Lee |
| 2011/0020787 A1 | 1/2011 | Lee |
| 2011/0020953 A1 | 1/2011 | Lee |
| 2011/0031038 A1 | 2/2011 | Page |
| 2011/0117202 A1 | 5/2011 | Bourke, Jr. et al. |
| 2011/0165568 A1 | 7/2011 | Vatta et al. |
| 2011/0245094 A1 | 10/2011 | Washburn et al. |
| 2011/0275985 A1 | 11/2011 | Lowery, Jr. et al. |
| 2012/0040447 A1 | 2/2012 | Barbreau et al. |
| 2012/0100546 A1 | 4/2012 | Lowery, Jr. et al. |
| 2012/0107839 A1 | 5/2012 | Lee |
| 2012/0112744 A1 | 5/2012 | McDowell et al. |
| 2012/0164644 A1 | 6/2012 | Neely et al. |
| 2012/0301888 A1 | 11/2012 | Neely et al. |
| 2012/0313639 A1 | 12/2012 | Lee |
| 2013/0029345 A1 | 1/2013 | Neely et al. |
| 2013/0095494 A1 | 4/2013 | Neely |
| 2013/0130280 A1 | 5/2013 | Fauconnier et al. |
| 2013/0229179 A1 | 9/2013 | Lee |
| 2013/0244238 A1 | 9/2013 | Neely et al. |
| 2013/0260367 A1 | 10/2013 | Lowery, Jr. et al. |
| 2013/0265054 A1 | 10/2013 | Lowery, Jr. et al. |
| 2013/0266944 A1 | 10/2013 | Neely et al. |
| 2013/0273522 A1 | 10/2013 | Lowery, Jr. et al. |
| 2013/0273523 A1 | 10/2013 | Neely et al. |
| 2014/0106442 A1 | 4/2014 | Lowery, Jr. et al. |
| 2014/0120523 A1 | 5/2014 | Lowery, Jr. et al. |
| 2014/0191109 A1 | 7/2014 | Chamberlin et al. |
| 2014/0356389 A1 | 12/2014 | Masignani et al. |
| 2017/0233798 A1 | 8/2017 | Neely et al. |
| 2019/0085381 A1 | 3/2019 | Neely et al. |

FOREIGN PATENT DOCUMENTS

| | | |
|---|---|---|
| EP | 0864863 A2 | 9/1998 |
| EP | 1870449 A1 | 12/2007 |
| EP | 2410052 A1 | 1/2012 |
| JP | 2009-506345 A | 2/2009 |
| JP | 2009-529883 A | 8/2009 |
| JP | 2009-537167 A | 10/2009 |
| RU | 2176393 C2 | 11/2001 |
| WO | WO-90/06045 A2 | 6/1990 |
| WO | WO-91/17428 A1 | 11/1991 |
| WO | WO-97/40181 A1 | 10/1997 |
| WO | WO-97/40377 A1 | 10/1997 |
| WO | WO-98/04740 A1 | 2/1998 |
| WO | WO-98/21587 A1 | 5/1998 |

(56) References Cited

FOREIGN PATENT DOCUMENTS

| | | |
|---|---|---|
| WO | WO-01/00876 A1 | 1/2001 |
| WO | WO-01/11360 A2 | 2/2001 |
| WO | WO-01/19405 A2 | 3/2001 |
| WO | WO-01/55719 A2 | 8/2001 |
| WO | WO-02/098364 A2 | 12/2002 |
| WO | WO-2004/029216 A2 | 4/2004 |
| WO | WO-2005/061724 A1 | 7/2005 |
| WO | WO-2005/099419 A2 | 10/2005 |
| WO | WO-2005/111596 A1 | 11/2005 |
| WO | WO-2006/013844 A1 | 2/2006 |
| WO | WO-2006/122083 A2 | 11/2006 |
| WO | WO-2006/138444 A2 | 12/2006 |
| WO | WO-2007/023461 A2 | 3/2007 |
| WO | WO-2007/027843 A2 | 3/2007 |
| WO | WO-2007/106579 A2 | 9/2007 |
| WO | WO-2007/106765 A2 | 9/2007 |
| WO | WO-2007/134294 A2 | 11/2007 |
| WO | WO-2007/135332 A1 | 11/2007 |
| WO | WO-2008/003114 A2 | 1/2008 |
| WO | WO-2008/003451 A1 | 1/2008 |
| WO | WO-2008/007270 A2 | 1/2008 |
| WO | WO-2008/010111 A2 | 1/2008 |
| WO | WO-2008/054517 A2 | 5/2008 |
| WO | WO-2008/072156 A2 | 6/2008 |
| WO | WO-2008/078579 A1 | 7/2008 |
| WO | WO-2008/119054 A1 | 10/2008 |
| WO | WO-2008/137721 A2 | 11/2008 |
| WO | WO-2009/004551 A1 | 1/2009 |
| WO | WO-2009/005178 A1 | 1/2009 |
| WO | WO-2009/015484 A1 | 2/2009 |
| WO | WO-2009/017697 A2 | 2/2009 |
| WO | WO-2009/025475 A2 | 2/2009 |
| WO | WO-2009/026164 A1 | 2/2009 |
| WO | WO-2009/026251 A1 | 2/2009 |
| WO | WO-2009/045354 A1 | 4/2009 |
| WO | WO-2009/045551 A1 | 4/2009 |
| WO | WO-2009/055587 A1 | 4/2009 |
| WO | WO-2009/061481 A1 | 5/2009 |
| WO | WO-2009/078875 A1 | 6/2009 |
| WO | WO-2009/085214 A1 | 7/2009 |
| WO | WO-2010/002479 A1 | 1/2010 |
| WO | WO-2010/034846 A1 | 4/2010 |
| WO | WO-2010/051362 A1 | 5/2010 |
| WO | WO-2010/062909 A1 | 6/2010 |
| WO | WO-2011/030091 A1 | 3/2011 |
| WO | WO-2011/053241 A1 | 5/2011 |
| WO | WO-2011/121288 A2 | 10/2011 |
| WO | WO-2012/054638 A2 | 4/2012 |

OTHER PUBLICATIONS

Gen Bank Accession No. NR_103401, Enterococcus faecium Aus0004 strain Aus004 5S ribosomal RNA, complete sequence (Year: 2015).*
Gen Bank Accession No. CP003583, Enterococcus facium DO, complete genome (Year: 2015).*
Wurpel, D.J. et al., Chaperone-Usher Fimbriae of *Escherichia coli*, PLOS ONE, vol. 8, e52835, pp. 1-11 (Year: 2013).*
Cheng et al., "Molecular identification of clinical "difficult-to-identify" microbes from sequencing 16S ribosomal DNA and internal transcribed spacer 2," Ann Clin Microbiol Antimicrob.13:1 (2014) (7 pages).
Extended European Search Report for European Application No. 17742048.6, dated Jul. 19, 2019 (13 pages).
Qun et al., "Surface Enhanced Raman Spectroscopy Sensor Based on Magnetic Beads-induced Nanoparticles Aggregation for Detection of Bacterial Deoxyribonucleic Acid," Chin J Anal Chem. 43(11):1676-1681 (2015).
Shao et al., "Magnetic Nanoparticles and microNMR for Diagnostic Applications," Theranostics. 2(1):55-65 (2012).
U.S. Appl. No. 13/852,556, filed Sep. 5, 2013, Lee.
Ahmad et al., "Seminested PCR for diagnosis of candidemia: comparison with culture, antigen detection, and biochemical methods for species identification," J Clin Microbiol. 40(7):2483-9 (2002).
Alhassan et al., "Comparison of polymerase chain reaction methods for the detection of *Theileria equi* infection using whole blood compared with pre-extracted DNA samples as PCR templates," Trop Anim Health Prod. 39(5):369-74 (2007).
Allice et al., "Evaluation of a novel real-time PCR system for cytomegalovirus DNA quantitation on whole blood and correlation with pp65-antigen test in guiding pre-emptive antiviral treatment," J Virol Methods. 148(1-2):9-16 (2008).
Altschul et al., "Basic local alignment search tool," J Mol Biol. 215(3):403-10 (1990).
Amaral et al., "Coagulation in sepsis," Intensive Care Med. 30(6):1032-40 (2004).
Aoki et al., "Detection of Legionella DNA by PCR of whole-blood samples in a mouse model," J Med Microbiol. 52(Pt 4):325-329 (2003).
Atanasijevic et al., "Calcium-sensitive MRI contrast agents based on superparamagnetic iron oxide nanoparticles and calmodulin," Proc Natl Acad Sci USA. 103(40):14707-12 (2006).
Attal et al., "A simple method of DNA extraction from whole tissues and blood using glass powder for detection of transgenic animals by PCR," Transgenic Res. 4(2):149-150 (1995).
Awduche et al., "RSVP-TE: Extensions to RSVP for LSP Tunnels," IETF Standard, Internet Engineering Task Force (Dec. 2001) (62 pages).
Barany, "Genetic disease detection and DNA amplification using cloned thermostable ligase," Proc Natl Acad Sci USA. 88(1):189-193 (1991).
Baudry et al., "Acceleration of the recognition rate between grafted ligands and receptors with magnetic forces," Proc Natl Acad Sci USA. 103(44):16076-16078 (2006).
Baugher et al., "Evaluation of the Tacrolimus Assay on the Abbott ARCHITECT® Analyzer," American Association for Clinical Chemistry Annual Meeting, Chicago, Illinois Jul. 23-27 (4 pages) (2006).
Benkert et al., "Development of a creatinine ELISA and an amperometric antibody-based creatinine sensor with a detection limit in the nanomolar range," Anal Chem. 72(5):916-921 (2000).
Bergman et al., "Rapid identification of pathogenic yeast isolates by real-time PCR and two-dimensional melting point analysis," Eur J Clin Microbiol Infect Dis. 26(11):813-818 (2007).
Boero et al., "An NMR magnetometer with planar microcoils and integrated electronics for signal detection and amplification," Sens and Actuators A. 67(1-3):18-23 (1998).
Bougnoux et al., "Serum is more suitable than whole blood for diagnosis of systemic Candidiasis by nested PCR," J Clin Microbiol. 37(4):925-930 (1999).
Brown et al., "Scaling of transverse nuclear magnetic relaxation due to magnetic nanoparticle aggregation" J Magn Magn Mater. 322(20):3122-3126 (2010).
Bu et al., "Direct polymerase chain reaction (PCR) from human whole blood and filter-paper-dried blood by using a PCR buffer with a higher pH," Anal Biochem. 375(2):370-372 (2008).
Buck et al., "Design strategies and performance of custom DNA sequencing primers," BioTechniques. 27(3):528-536 (1999).
Burckhardt, "Amplification of DNA from Whole Blood," PCR Methods Appl. 3(4):239-243 (1994).
Castley et al., "Clinical Applications of Whole-Blood PCR with Real-Time Instrumentation," Clin Chem. 51(11):2025-2030 (2005).
Cedervall et al., "Understanding the Nanoparticle-Protein Corona Using Methods to Quantify Exchange Rates and Affinities of Proteins for Nanoparticles," Proc Natl Acad Sci USA. 104(7):2050-2055 (2007).
Cerikcioglu et al., "Seminested PCR for Detection and Identification of Candida Species Directly from Blood Culture Bottles," New Microbiol. 33(1):57-62 (2010).
Chaffin et al., "Cell wall and secreted proteins of *Candida albicans*: identification, function, and expression," Microbiol Mol Biol Rev. 62(1):130-180 (1998).
Chisti et al., Chapter 13: Fermentation Technology, Bioprocessing, Scale-Up and Manufacture. *Biotechnology/The Science and the Business*. 177-222 (1999).
Chomczynski et al., "Alkaline polyethylene glycol-based method for direct PCR from bacteria, eukaryotic tissue samples, and whole blood," BioTechniques. 40(4):454,456,458 (2006).

(56) References Cited

OTHER PUBLICATIONS

Christians et al., Chapter 23: Tacrolimus. *Applied Pharmacokinetics and Pharmacodynamics: Principles of Therapeutic Drug Monitoring*, Fourth Edition. Burton, Schentag, Shaw, and Evans (eds.), 527-62 (2006).
Cleary et al., "Amphotericin B enzyme-linked immunosorbent assay," Antimicrob Agents Chemother. 40(3):637-41 (1996).
Cohen-Tannoudji et al., "Measuring the Kinetics of Biomolecular Recognition with Magnetic Colloids," Phys Rev Lett. 100(10):108301 (2008) (4 pages).
Colombo et al., "Femtomolar detection of autoantibodies by magnetic relaxation nanosensors." Anal Biochem. 392(1):96-102 (2009).
Communication pursuant to Article 94(3) EPC for European Application No. 17205422.3, dated Feb. 21, 2019 (5 pages).
Costanzo et al., "Protein-ligand mediated aggregation of nanoparticles: a study of synthesis and assembly mechanism," Chem Mater. 16(9):1775-85 (2004).
Curran et al., "The killing of bacterial spores in fluids by agitation with small inert particles," J Bacteriol. 43(2):125-139 (1942) (16 pages).
D'Ambrosio et al., "Improved Procedures for Enzyme Immunoassay of Tacrolimus (FK506) in Whole Blood," Clin Chem. 40(1):159-160 (1994).
Daniel et al., "Multi-reservoir device for detecting a soluble cancer biomarker," Lab Chip. 7(10):1288-1293 (2007).
De Paula et al., "Optimizing dengue diagnosis by RT-PCR in IgM-positive samples: comparison of whole blood, buffy-coat and serum as clinical samples," J Virol Methods. 102(1-2):113-117 (2002).
De Vries et al., "PCR on cell lysates obtained from whole blood circumvents DNA isolation," Clin Chem. 47(9):1701-1702 (2001).
Deak et al., "Utility of a Luminex-based assay for multiplexed, rapid species identification of *Candida* isolates from an ongoing candidemia surveillance," Can J Microbiol. 56(4):348-351 (2010).
Deback et al., "Monitoring of human cytomegalovirus infection in immunosuppressed patients using real-time PCR on whole blood," J Clin Virol. 40(3):173-9 (2007).
Delgado et al., "Surface properties of polystyrene nanoparticles coated with dextrans and dextran-PEO copolymers. Effect of polymer architecture on protein adsorption," Langmuir. 17(14):4386-4391 (2001).
Demas et al., "Electronic characterization of lithographically patterned microcoils for high sensitivity NMR detection," J Magn Reson. 200(1):56-63 (2009).
Demas et al., "Magnetic resonance for in vitro medical diagnostics: superparamagnetic nanoparticle-based magnetic relaxation switches," New J Phys. 13:025005 (2011) (25 pages).
Herberg et al., "Portable, low-cost NMR with laser-lathe lithography produced microcoils." J Magn Reson. 189(1):121-9 (2007).
Dreyfus et al., "Microscopic artificial swimmers," Nature. 437(7060):862-5 (2005).
Elie et al., "Rapid identification of *Candida* species with species-specific DNA probes," J Clin Microbiol. 36(11):3260-5 (1998).
Emery, "Investigation of CMV disease in immunocompromised patients," J Clin Pathol. 54(2):84-8 (2001).
Espy et al., "Real-time PCR in clinical microbiology: applications for routine laboratory testing," Clin Microbiol Rev. 19(1):165-256 (2006).
Examination Report for Australian Application No. 2011317073, dated Jun. 16, 2014 (4 pages).
Examination Report for Australian Application No. 2016204680, dated Mar. 15, 2017 (3 pages).
Extended European Search Report for European Application No. 11835088.3, dated Mar. 19, 2014 (11 pages).
Extended European Search Report for European Application No. 15002772.0, dated Feb. 22, 2016 (12 pages).
Extended European Search Report for European Application No. 17205422.3, dated Jan. 22, 2018 (10 pages).
Extended European Search Report for European Patent Application No. 13779063.0, dated Jun. 7, 2016 (17 pages).
Ferrer et al., "Detection and identification of fungal pathogens by PCR and by ITS2 and 5.8S ribosomal DNA typing in ocular infections," J Clin Microbiol. 39(8):2873-2879 (2001).
Fossati et al., "Enzymic creatinine assay: a new colorimetric method based on hydrogen peroxide measurement," Clin Chem. 29(8):1494-6 (1983).
Fredricks et al., "Comparison of six DNA extraction methods for recovery of fungal DNA as assessed by quantitative PCR," J Clin Microbiol. 43(10):5122-5128 (2005).
Fry et al., "A new approach to template purification for sequencing applications using paramagnetic particles," Biotechniques. 13(1):124-26, 128-31 (1992) (8 pages).
Fujita et al., "Microtitration plate enzyme immunoassay to detect PCR-amplified DNA from *Candida* species in blood," J Clin Microbiol. 33(4):962-967 (1995).
Garey et al., "Time to Initiation of Fluconazole Therapy Impacts Mortality in Patients with Candidemia: A Multi-Institutional Study," Clin Infect Dis. 43(1):25-31 (2006).
Garrigue et al., "Whole Blood Real-Time Quantitative PCR for Cytomegalovirus Infection Follow-Up in Transplant Recipients," J Clin Virol. 36(1):72-75 (2006).
GenBank Accession No. KC422427.1, Candida albicans strain Hb40 internal transcribed spacer 1, partial sequence; 5.8S ribosomal RNA gene, complete sequence; and internal transcribed spacer 2, partial sequence, retrieved from <https://www.ncbi.nlm.nih.gov/nuccore/kc422427.1> on Nov. 13, 2018 (2 pages).
George et al., "Effect of Inoculum Size on Detection of Candida Growth by the BACTEC 9240 Automated Blood Culture System Using Aerobic and Anaerobic Media," J Clin Microbiol. 43(1):433-435 (2005).
Gijs, "Magnetic bead handling on-chip: new opportunities for analytical applications," Microfluid Nanofluid. 1:22-40 (2004).
Goel et al., "Molecular beacon: a multitask probe," J Appl Microbiol. 99(3):435-42 (2005).
Gonschior et al., "Tacrolimus (FK506) Metabolite Patterns in Blood from Liver and Kidney Transplant Patients," Clin Chem 42(9):1426-1432 (1996).
Griffiths et al., "Comparison of DNA Extraction Methods for Aspergillus fumigatus Using Real-Time PCR," J Med Microbiol. 55(Pt 9):1187-1191 (2006).
Grimm et al., "Novel Nanosensors for Rapid Analysis of Telomerase Activity," Cancer Res. 64(2):639-643 (2004).
Harris et al., "Proteolytic Actuation of Nanoparticle Self-assembly," Angew Chem Int Ed Engl. 45(19):3161-3165 (2006).
Hatch et al., "Magnetic design considerations for devices and particles used for biological high-gradient magnetic separation (HGMAS) systems," J Magn Magn Mater. 225(1-2):262-76 (2001).
Hirose et al., "Simultaneous Cultivation and Disruption of *Escherichia coli* Using Glass Beads to Release Recombinant alpha-Amylase and Other Enzymes," Biotechnol Techniques 13(9):571-575 (1999).
Hong et al., "Magnetic Microparticle Aggregation for Viscosity Determination by MR," Magn Reson Med. 59(3):515-520 (2008).
Hoorfar et al., "Practical Considerations in Design of Internal Amplification Controls for Diagnostic PCR Assays," J. Clin. Microbiol. 42(5):1863-1868 (2004).
Horn et al., "Epidemiology and Outcomes of Candidemia in 2019 Patients: Data From the Prospective Antifungal Therapy Alliance Registry," Clin Infect Dis. 48(12):1695-1703 (2009).
Horvath et al., "Detection of Simulated Candidemia by the BACTEC 9240 System with Plus Aerobic/F and Anaerobic/F Blood Culture Bottles," J. Clin. Microbiol. 41(10):4714-4717 (2003).
Inglis et al., "Microfluidic high gradient magnetic cell separation," J Appl Physics 99:08K101 (2006) (3 pages).
International Preliminary Report on Patentability and Written Opinion for International Patent Application No. PCT/US2013/031774, dated Oct. 21, 2014 (6 pages).
International Preliminary Report on Patentability for International Patent Application No. PCT/US2011/056933, dated Apr. 23, 2013 (16 pages).
International Preliminary Report on Patentability for International Patent Application No. PCT/US2011/056936, dated Jun. 18, 2013 (11 pages).

(56) References Cited

OTHER PUBLICATIONS

International Search Report and Written Opinion of the International Searching Authority for International Application No. PCT/US11/56933, dated May 10, 2012 (22 pages).
International Search Report and Written Opinion of the International Searching Authority for International Application No. PCT/US11/56936, dated May 17, 2012 (15 pages).
International Search Report and Written Opinion of the International Searching Authority for International Patent Application No. PCT/US13/31774, dated Jul. 25, 2013 (9 pages).
International Search Report for International Application No. PCT/IB2008/052597, dated Nov. 11, 2008 (1 page).
International Search Report for International Application No. PCT/US2008/073346, dated Nov. 7, 2008 (1 page).
Ito et al., "Treatment of Candida infections with amphotericin B lipid complex," Clin Infect Dis. 40 Suppl 6:S384-91 (2005).
Josephson et al., "High-efficiency intracellular magnetic labeling with novel superparamagnetic-Tat peptide conjugates," Bioconjug Chem. 10(2):186-91 (1999).
Josephson et al., "Magnetic nanosensors for the detection of oligonucleotide sequences," Angew Chem Int Ed. 40(17):3204-3206 (2001).
Kaittanis et al., "One-step, nanoparticle-mediated bacterial detection with magnetic relaxation," Nano Lett. 7(2):380-3 (2007).
Keeney et al., "A Whole Blood, Multiplex PCR Detection Method for Factor V Leiden and the Prothrombin G20210A Variant," Thromb Haemost. 81(3):464-465 (1999).
Keevil et al., "Simultaneous and Rapid Analysis of Cyclosporin A and Creatinine in Finger Prick Blood Samples Using Liquid Chromatography Tandem Mass Spectrometry and its Application in C2 Monitoring," Ther Drug Monit. 24(6):757-767 (2002).
Kermekchiev et al., "Cold-sensitive Mutants of Taq DNA Polymerase Provide a Hot Start for PCR," Nucleic Acids Res. 31(21):6139-6147 (2003).
Kermekchiev et al., "Mutants of Taq DNA Polymerase Resistant to PCR Inhibitors Allow DNA Amplification from Whole Blood and Crude Soil Samples," Nucleic Acids Res. 37(5):e40 (2009) (14 pages).
Khlif et al., "Detection and identification of *Candida* sp. by PCR in candidemia diagnosis," J Mycol Med. 17(4): 256-260 (2007).
Khot et al., "Sequencing and Analysis of Fungal rRNA Operons for Development of Broad-range Fungal PCR Assays," Appl Environ Microbiol. 75(6):1559-1565 (2009).
Kim et al., "Magnetic Relaxation Switch Detection of Human Chorionic Gonadotrophin," Bioconjug. Chem. 18(6):2024-2028 (2007).
Klungthong et al., "Dengue Virus Detection Using Whole Blood for Reverse Transcriptase PCR and Virus Isolation," J. Clin. Microbiol. 45(8):2480-2485 (2007).
Koh et al., "Magnetic nanoparticle sensors." Sensors. 9(10):8130-45 (2009).
Koh et al., "Nanoparticle-target interactions parallel antibody-protein interactions." Anal Chem. 81(9):3618-22 (2009).
Koh et al., "Sensitive NMR Sensors Detect Antibodies to Influenza," available in PMC Apr. 13, 2009, published in final edited form as: Angew Chem Int Ed Engl. 47(22):4119-21 (2008) (8 pages).
Kost et al., "Multicenter Study of Whole-Blood Creatinine, Total Carbon Dioxide Content, and Chemistry Profiling for Laboratory and Point-of-Care Testing in Critical Care in the United States," Grit Care Med. 28(7):2379-2389 (2000).
Kriz et al., "Advancements toward magneto immunoassays." Biosens Bioelectron. 13(7-8):817-23 (1998).
Kriz et al., "Magnetic permeability measurements in bioanalysis and biosensors." Anal Chem. 68(11):1966-70 (1996).
Kroll et al., "Mechanism of Interference with the Jaffe Reaction for Creatinine," Clin. Chem. 33(7):1129-1132 (1987).
Kula et al., "Purification of Proteins and the Disruption of Microbial Cells," Biotechnol. Progress 3(1):31-42(1987).

Kulkarni et al., "Detection of Carbohydrate Binding Proteins Using Magnetic Relaxation Switches," Anal Chem. 82(17)7430-7435 (2010) (6 pages).
Kumar et al., "Initiation of Inappropriate Antimicrobial Therapy Results in a Fivefold Reduction of Survival in Human Septic Shock," Chest. 136(5):1237-1248 (2009).
Kumari et al., "Surface Oxidation of Nickel Thin Films," J Mater Sci Lett. 11(11)761-762 (1992).
Kötitz et al., "Determination of the binding reaction between avidin and biotin by relaxation measurements of magnetic nanoparticles," J Magn Magn Mater. 194(1-3):62-8 (1999).
Lacharme et al., "Full On-Chip Nanoliter Immunoassay by Geometrical Magnetic Trapping of Nanoparticle Chains," Anal Chem. 80(8):2905-2910 (2008).
Lamanna et al., "Use of Glass Beads for the Mechanical Rupture of Microorganisms in Concentrated Suspensions," J Bacteriol. 67(4):503-504 (1954).
Leal-Klevezas et al., "Single-step PCR for detection of *Brucella* spp. from blood and milk of infected animals," J Clin Microbiol. 33(12):3087-90 (1995).
Lee et al., "Exclude Routes-Extension to RSVP-TE," CCAMP Working Group (2003) (13 pages).
Lee et al., "Ligand-Receptor Interactions in Chains of Colloids: When Reactions are Limited by Rotational Diffusion," Langmuir. 24(4):1296-1307 (2008).
Lee et al., "Microelectromagnets for the control of magnetic nanoparticles." Appl Phys Letters. 79(20):3308-10(2001).
Lee et al., "Rapid Detection and Profiling of Cancer Cells in Fine-needle Aspirates" Proc Natl Acad Sci U.S.A. 106(30):12459-12464 (2009) (8 pages).
Lee et al., "Sequence-specific electrochemical detection of asymmetric PCR amplicons of traditional Chinese medicinal plant DNA," Anal Chem. 74(19):5057-5062 (2002).
Lee et al., "Ultrasensitive detection of bacteria using core-shell nanoparticles and a NMR-filter system," available in PMC Aug. 11, 2009, published in final edited form as: Angew Chem Int Ed Engl. 48(31):5657-60 (2009) (10 pages).
Lehmann et al., "A Multiplex Real-Time PCR Assay for Rapid Detection and Differentiation of 25 Bacterial and Fungal Pathogens from Whole Blood Samples," Med Microbiol Immunol. 197(3):313-324 (2008).
Levey et al., "Using Standardized Serum Creatinine Values in the Modification of Diet in Renal Disease Study Equation for Estimating Glomerular Filtration Rate," Ann Intern Med. 145(4):247-254 (2006).
Lewin et al., "A simple method for DNA extraction from leukocytes for use in PCR," Biotechniques. 13(4):522-3(1992) (4 pages).
Lewin et al., "Tat peptide-derivatized magnetic nanoparticles allow in vivo tracking and recovery of progenitor cells," Nat Biotechnol. 18(4):410-4 (2000).
Li et al., "Rapid Identification of Yeasts Commonly Found in Positive Blood Cultures by Amplification of the Internal Transcribed Spacer Regions 1 and 2," Eur J Clin Microbiol Infect Dis. 22(11):693-696 (2003).
Liao et al., "High-Throughput Miniaturized Immunoassay for Human lnterleukin-6 Using Electrochemical Sandwich-Type Enzyme Immunosensors," Curr Pharm Analysis 5(2):164-170 (2009).
Ling et al., "Magnetic relaxation-based platform for multiplexed assays," Analyst. 135(9):2360-4 (2010).
Liu et al., "Rapid Distribution of a Liquid col. Into a Matrix of Nanoliter Wells for Parallel Real-Time Quantitative PCR," Sens Actuators B Chem. 135(2):671-677 (2009).
Liu et al., "Self-contained, fully integrated biochip for sample preparation, polymerase chain reaction amplification, and DNA microarray detection," Anal Chem. 76(7):1824-1831 (2004).
Liu, Yong, Thesis: "CMOS Magnetic Cell Manipulator and CMOS NMR Biomolecular Sensor," Doctor of Philosophy, School of Engineering and Applied Sciences, Harvard University, 2007 (166 pages).
Lott et al., "Sequence analysis of the internal transcribed spacer 2 (ITS2) from yeast species within the genus *Candida*" Curr Microbiol. 36(2):63-9 (1998).

(56) References Cited

OTHER PUBLICATIONS

Lowery et al., Chapter 6: Application of Magnetics in Point-of-Care Testing. *Point-of-Care Testing: Needs, Opportunity and Innovation*, 3rd Edition. AACC Press (2010) (11 pages).
Lowery, Nanomaterials-Based Magnetic Relaxation Switch Biosensors. *Nanomaterials for the Life Sciences* vol. 4: Magnetic Nanomaterials. Challa S. S. R. Kumar (ed.), 3-53 (2009) (52 pages).
Lundqvist et al., "Nanoparticle Size and Surface Properties Determine the Protein Corona with Possible Implications for Biological Impacts," Proc Natl Acad Sci U S A. 105(38):14265-14270 (2008).
Lustgarten et al., "Simple, rapid, kinetic method for serum creatinine measurement," Clin Chem. 18(11):1419-22 (1972).
Lück et al., "Analysis of Plasma Protein Adsorption on Polymeric Nanoparticles with Different Surface Characteristics," J Biomed Mater Res. 39(3):478-485 (1998).
Ma et al., "Rapid and Sensitive Detection of Microcystin by Immunosensor Based on Nuclear Magnetic Resonance," Biosens Bioelectron. 25(1):240-243 (2009).
Maaroufi et al., "Early detection and identification of commonly encountered Candida species from simulated blood cultures by using a real-time PCR-based assay," J Mol Diagn. 6(2):108-14 (2004).
Magin et al., "Miniature magnetic resonance machines," IEEE Spectrum. 34(10):51-61 (1997).
Malba et al., "Laser-lathe lithography—a novel method for manufacturing nuclear magnetic resonance microcoils," Biomed Microdevices. 5(1):21-7 (2003).
Martin et al., "Development of a PCR-based line probe assay for identification of fungal pathogens," J Clin Microbiol. 38(10):3735-3742 (2000).
Martin et al., "Strong intrinsic mixing in vortex magnetic fields," Phys Rev E Stat Nonlin Soft Matter Phys. 80(1 Pt2):016312 (2009) (6 pages).
Martin et al., "The epidemiology of sepsis in the United States from 1979 through 2000," N Engl J Med. 348(16):1546-54 (2003).
Martin, "Theory of strong intrinsic mixing of particle suspensions in vortex magnetic fields," Phys Rev E Stat Nonlin Soft Matter Phys. 79(1 Pt 1):011503 (2009) (12 pages).
Massin et al., "High-Q factor RF planar microcoils for micro-scale NMR spectroscopy," Sens Actuators A Phys. 97-98:280-8 (2002).
Massin et al., "Planar microcoil-based magnetic resonance imaging of cells" 12th International Conference on Solid-State Sensors, Actuators and Microsystems, June 8-12, Boston, MA. Transducers '03. 967-70 (2003).
Massin et al., "Planar microcoil-based microfluidic NMR probes," J Magn Reson. 164(2):242-55 (2003).
Masson et al., "Combined enzymic-Jaffé method for determination of creatinine in serum," Clin Chem. 27(1):18-21 (1981).
Mccusker et al., "Improved method for direct PCR amplification from whole blood," Nucleic Acids Res. 20(24):6747 (1992) (1 page).
Mcdowell et al., "Operating Nanoliter Scale NMR Microcoils in a 1 Tesla Field," J Magn Reson. 188(1):74-82 (2007).
Mercier et al., "Direct PCR from whole blood, without DNA extraction," Nucleic Acids Res. 18(19):5908 (1990).
Metwally et al., "Improving molecular detection of *Candida* DNA in whole blood: comparison of seven fungal DNA extraction protocols using real-time PCR," J Med Microbiol. 57(Pt 3):296-303 (2008).
Morgenthaler et al., "Sensitive immunoluminometric assay for the detection of procalcitonin," Clin Chem. 48(5):788-90 (2002).
Morrell et al., "Delaying the empiric treatment of *Candida* bloodstream infection until positive blood culture results are obtained: a potential risk factor for hospital mortality," Antimicrob Agents Chemother. 49(9):3640-5 (2005).
Moser et al., "On-Chip Immuno-Agglutination Assay with Analyte Capture by Dynamic Manipulation of Superparamagnetic Beads," Lab Chip. 9(22):3261-3267 (2009).

Makiranta et al., "Modeling and Simulation of Magnetic Nanoparticle Sensor" Proceedings of the 2005 IEEE, Engineering in Medicine and Biology 27th Annual Conference, September 1-4, Shanghai, China. 1256-1259 (2005).
Makiranta et al., "Modeling and Simulation of Magnetic Nanoparticle Sensor," Master of Science in Automation, Institute of Measurement and Information Technology, Tampere University of Technology, 2004 (111 pages) (English language abstract).
Naber,"*Staphylococcus aureus* bacteremia: epidemiology, pathophysiology, and management strategies," Clin Infect Dis. 48 (Suppl 4):S231-7 (2009).
NCBI Blast for Accession No. AY198398.1. Retrieved on Apr. 14, 2012 (3 pages).
NCBI Blast for Accession No. X53497.1. Retrieved on Apr. 14, 2012 (4 pages).
Niemeyer et al., "Self-assembly of DNA-streptavidin nanostructures and their use as reagents in immuno-PCR," Nucleic Acids Res. 27(23):4553-61 (1999).
Notice of Reasons for Rejection for Japanese Patent Application No. 2013-535053, dated Sep. 2, 2015 (6 pages).
Notice of Reasons for Rejection for Japanese Patent Application No. 2016-113224, dated Apr. 26, 2017 (12 pages).
Notice of Reasons for Rejection for Japanese Patent Application No. 2016-113224, dated Dec. 11, 2017 (8 pages).
Office Action for Canadian Patent Application No. 142812, dated Aug. 27, 2012 (3 pages).
Office Action for Chinese Application No. 201180061890.1, dated Nov. 4, 2014 (20 pages).
Office Action for Russian Patent Application No. 2013112118, dated Mar. 1, 2016 (13 pages).
Office Action for Russian Patent Application No. 2013112118, dated Nov. 30, 2016 (8 pages).
Office Action for U.S. Appl. No. 13/363,916, dated Aug. 2, 2012 (64 pages).
Office Action for U.S. Appl. No. 13/402,566, dated Jan. 22, 2013 (27 pages).
Office Action for U.S. Appl. No. 13/402,566, dated May 30, 2013 (33 pages).
Office Action for U.S. Appl. No. 13/402,566, dated Oct. 29, 2012 (60 pages).
Office Action for U.S. Appl. No. 13/646,402, dated Mar. 14, 2013 (53 pages).
Office Action for U.S. Appl. No. 13/649,839, dated Mar. 14, 2013 (48 pages).
Office Action for U.S. Appl. No. 29/390,300, dated Jun. 27, 2012 (32 pages).
Panaccio et al., "FoLT PCR: a simple PCR protocol for amplifying DNA directly from whole blood," Biotechniques. 14(2):238-240, 242, 243 (1993).
Pappas et al., "Cellular separations: a review of new challenges in analytical chemistry," Anal Chim Acta. 601(1):26-35 (2007).
Park et al., "Determination of nanoparticle vehicle unpackaging by MR imaging of a T(2) magnetic relaxation switch," Biomaterials. 29(6):724-32 (2008).
Partial European Search Report for European Application No. 15002772.0, dated Nov. 4, 2015 (7 pages).
Partial Supplementary European Search Report for European Application No. 13779063.0, dated Feb. 17, 2016 (8 pages).
Peake et al., "Measurement of Serum Creatinine—Current Status and Future Goals," Clin Biochem Rev. 27(4):173-184 (2006).
Peck et al., "RF microcoils patterned using microlithographic techniques for use as microsensors in NMR," Engineering in Medicine and Biology Society, Proceedings of the 15th Annual International Conference of the IEEE, Oct. 28-31. 174-175 (1993).
Perez et al., "DNA-based magnetic nanoparticle assembly acts as a magnetic relaxation nanoswitch allowing screening of DNA-cleaving agents." J Am Chem Soc. 124(12):2856-7 (2002).
Perez et al., "Integrated Nanosensors to Determine Levels and Functional Activity of Human Telomerase," Neoplasia 10(10):1066-1072 (2008).
Perez et al., "Magnetic relaxation switches capable of sensing molecular interactions," Nat Biotechnol. 20(8):816-20 (2002).

(56) References Cited

OTHER PUBLICATIONS

Perez et al., "Peroxidase Substrate Nanosensors for MR Imaging", Nano Lett. 4(1):119-122 (2004).
Perez et al., "Use of magnetic nanoparticles as nanosensors to probe for molecular interactions," Chembiochem. 5(3):261-4 (2004).
Perez et al., "Viral-induced self-assembly of magnetic nanoparticles allows the detection of viral particles in biological media," J Am Chem Soc. 125(34):10192-3 (2003).
Pryce et al., "Real-Time Automated Polymerase Chain Reaction (PCR) to Detect Candida Albicans and Aspergillus Fumigatus DNA in Whole Blood from High-Risk Patients," Diagn Microbiol Infect Dis. 47(3):487-496 (2003).
Ramadan et al., "On-chip micro-electromagnets for magnetic-based bio-molecules separation," J Magn Magn Mater. 281 (2-3):150-72 (2004).
Renaud et al., "Implantable planar rf microcoils for NMR microspectroscopy," Sens Actuators A Phys. 99(3):244-8 (2002).
Rida et al., "Long-range transport of magnetic microbeads using simple planar coils placed in a uniform magnetostatic field," Appl Phys Lett. 83(12):2396-8 (2003).
Rosenstraus et al., "An Internal Control for Routine Diagnostic PCR: Design, Properties, and Effect on Clinical Performance," J. Clin. Microbiol. 36(1):191-197 (1998).
Routley et al., "The HALO system—a light weight portable imaging system," Magn Reson Imaging. 22(8):1145-51 (2004).
Ruttimann et al., "DNA Polymerases from the Extremely Thermophilic Bacterium Thermus Thermophilus HB-8," Eur J Biochem. 149(1):41-46 (1985).
Seeber et al., "Triaxial Magnetic Field Gradient System for Microcoil Magnetic Resonance Imaging," Rev. Sci. Instrum. 71(11):4263-4272 (2000).
Shapiro et al., "Dynamic imaging with MRI contrast agents: quantitative considerations," Magn Reson Imaging. 24(4):449-62 (2006).
Siegel et al., "Affinity Maturation of Tacrolimus Antibody for Improved Immunoassay Performance," Clin Chem. 54(6):1008-1017 (2008).
Sillerud et al., "1H NMR Detection of superparamagnetic nanoparticles at 1T using a microcoil and novel tuning circuit," J Magn Reson. 181(2):181-90 (2006).
Skurup et al., "New Creatinine Sensor for Point-of-Care Testing of Creatinine Meets the National Kidney Disease Education Program Guidelines," Clin Chem Lab Med. 46(1):3-8 (2008).
Stocklein et al., "Enzyme Kinetic Assays with Surface Plasmon Resonance (BIAcore) Based on Competition Between Enzyme and Creatinine Antibody," Biosens Bioelectron. 15(7-8):377-382 (2000).
Sullivan et al., "A Highly Specific Test for Creatinine," J Biol Chem. 233(2):530-534 (1958).
Sun et al., "Experimental Study on T2 Relaxation Time of Protons in Water Suspensions of Iron-oxide Nanoparticles: Waiting Time Dependence," J Magn Magn Mater. 321(18):2971-2975 (2009).
Syms et al., "MEMS helmholtz coils for magnetic resonance imaging," J Micromech Microeng. 15(7):S1-S9 (2005) (10 pages).
Taktak et al., "Electrode Chemistry Yields a Nanoparticle-based NMR Sensor for Calcium," Langmuir 24(14): 7596-7598 (2008).
Taktak et al., "Multiparameter Magnetic Relaxation Switch Assays," Anal Chem. 79(23):8863-8869 (2007).
Tanaka et al., "Properties of Superparamagnetic Iron Oxide Nanoparticles Assembled on Nucleic Acids," Nucleic Acids Symp Ser (Oxf). (52):693-694 (2008).
Taur et al., "Effect of Antifungal Therapy Timing on Mortality in Cancer Patients with Candidemia," Antimicrob Agents Chemother. 54(1):184-190 (2010).
Thorne et al., "Analytic Validation of a Quantitative Real-Time PCR Assay to Measure CMV Viral Load in Whole Blood," Diagn Mol Pathol. 16(2):73-80 (2007).
Tong et al., "Coating optimization of superparamagnetic iron oxide nanoparticles for high T2 relaxivity." Nano Lett. 10(11):4607-13 (2010) (7 pages).

Tsourkas et al., "Magnetic relaxation switch immunosensors detect enantiomeric impurities," Angew Chem Int Ed Engl. 43(18):2395-9 (2004).
Tsukamoto et al., "Development of a SQUID system using field reversal for rapidly detecting bacteria," IEEE Transactions on Applied Superconductivity. 19(3):853-856 (2009).
Ulvik et al., "Single Nucleotide Polymorphism (SNP) Genotyping in Unprocessed Whole Blood and Serum by Real-Time PCR: Application to SNPs Affecting Homocysteine and Folate Metabolism," Clin Chem. 47(11):2050-2053 (2001).
Van Bentum et al., "Towards Nuclear Magnetic Resonance microspectroscopy and micro-imaging," Analyst. 129(9):793-803 (2004).
Vasseur et al., "Inter-area and Inter-AS MPLS Traffic Engineering," IETF Internet draft (2004) (32 pages).
Vollenhofer-Schrumpf et al., "A simple nucleic acid hybridization/latex agglutination assay for the rapid detection of polymerase chain reaction amplicons," J Microbiol Methods. 68(3):568-576 (2007).
Von Lilienfeld-Toal et al., "Utility of a Commercially Available Multiplex Real-Time PCR Assay to Detect Bacterial and Fungal Pathogens in Febrile Neutropenia," J Clin Microbiol. 47(8):2405-2410 (2009).
Wallemacq et al., "Improvement and Assessment of Enzyme-Linked Immunosorbent Assay to Detect Low FK506 Concentrations in Plasma or Whole Blood Within 6 Hours," Clin Chem. 39(6):1045-1049 (1993).
Wang et al., "A Novel Strategy to Engineer DNA Polymerases for Enhanced Processivity and Improved Performance in vitro," Nucleic Acids Res. 32(3):1197-1207 (2004).
Weetall et al., "Antibodies Immobilized on Inorganic Supports," Appl Biochem Biotechnol. 22(3):311-330 (1989).
Weetall, "Preparation of Immobilized Proteins Covalently Coupled Through Silane Coupling Agents to Inorganic Supports," Appl Biochem Biotechnol. 41(3):157-188 (1993).
Weissleder et al., "Cell-specific targeting of nanoparticles by multivalent attachment of small molecules." Nat Biotechnol. 23(11):1418-23 (2005).
Wensink et al., "High Signal to Noise Ratio in Low Field NMR on chip, Simulations and Experimental Results" Micro Electro Mechanical Systems 17th IEEE International Conference, Netherlands, pp. 407-410 (2004).
Wildgruber et al., "Monocyte Subset Dynamics in Human Atherosclerosis can be Profiled with Magnetic Nano-Sensors" PLoS One. 4(5):e5663 (2009) (9 pages).
Wilson et al., "Creatine and Creatinine in Whole Blood and Plasma," J Biol Chem. 29:413-423 (1917).
Wu et al., "1H-NMR spectroscopy on the nanoliter scale for static and on-line measurements," Anal Chem. 66(22):3849-57 (1994).
Xing et al., "Immobilization of Biomolecules on the Surface of Inorganic Nanoparticles for Biomedical Applications," Sci. Technol. Adv. Mater. 11(1): 014101 (2010) (17 pages).
Yigit et al., "Smart "Turn-On" Magnetic Resonance Contrast Agents Based on Aptamer-Functionalized Superparamagnetic Iron Oxide Nanoparticles," Chembiochem. 8(14):1675-1678 (2007).
Zhang et al., "A probe design for the acquisition of homonuclear, heteronuclear, and inverse detected NMR spectra from multiple samples," J Magn Reson. 153(2):254-8 (2001).
Zhao et al., "Magnetic sensors for protease assays," Angew Chem Int Ed Engl. 42(12):1375-8 (2003).
Bender et al., "Complete Genome Sequence of the Gut Commensal and Laboratory Strain Enterococcus faecium 64/3," Genome Announc. 3(6):e01275-15 (2015) (2 pages).
Fiedler et al., "Tigecycline resistance in clinical isolates of Enterococcus faecium is mediated by an upregulation of plasmid-encoded tetracycline determinants tet(L) and tet(M)," J Antimicrob Chemother. 71(4):871-81 (Advanced Publication—2015).
International Search Report and Written Opinion for International Application No. PCT/US2017/014410, dated May 24, 2017 (43 pages).
International Preliminary Report on Patentability for International Application No. PCT/US2017/014410, dated Aug. 2, 2018 (35 pages).

(56) References Cited

OTHER PUBLICATIONS

Vallenet et al., "Comparative analysis of Acinetobacters: three genomes for three lifestyles," PLoS One. 3(3):e1805 (2008) (11 pages).

Wan et al., "Validation of mixed-genome microarrays as a method for genetic discrimination," Appl Environ Microbiol. 73(5):1425-32 (2007).

Yin et al., "Draft Genome Sequence of a Stable Mucoid Strain of Pseudomonas aeruginosa PAO581 with a mucA25 Mutation," Genome Announc. 1(5): e00834-13 (2013) (2 pages).

Communication pursuant to Article 94(3) EPC for European Patent Application No. 17742048.6, dated Feb. 22, 2021 (7 pages).

* cited by examiner

Figure 1A

| Species | Resistance Markers | Pan-microbe |
|---|---|---|
| Acinetobacter baumannii | vanA | Gram negative bacteria |
| Acinetobacter pittii | vanB | Gram positive bacteria |
| Acinetobacter nosocomialis | mecA | Candida spp. |
| Aspergillus fumigatus | IMP | Aspergillus spp. |
| Bacteroides fragilis | CTX-M | |
| Burkholderia cepacia | KPC | |
| Campylobacter jejuni/coli | NDM | |
| Candida guilliermondii | OXA | |
| Candida albicans | VIM | |
| Candida dubliniensis | FKS | |
| Candida glabrata | | |
| Candida krusei | | |
| Candida lusitaniae | | |
| Candida parapsilosis | | |
| Candida tropicalis | | |
| Citrobacter freundii complex | | |
| Citrobacter koseri | | |
| Clostridium perfringens | | |
| Coagulase-negative Staphylococcus | | |
| Enterobacter aerogenes | | |
| Enterobacter cloacae | | |
| Enterobacteriaceae | | |
| Enterococcus faecalis | | |
| Enterococcus faecium | | |
| Escherichia coli | | |
| Haemophilus influenzae | | |
| Kingella kingae | | |
| Klebsiella oxytoca | | |
| Klebsiella pneumoniae | | |
| Listeria spp. | | |
| Listeria monocytogenes | | |
| Morganella morgana | | |
| Neisseria meningitidis | | |
| Neisseria spp. Non-meningitidis | | |
| Prevotella buccae | | |
| Prevotella intermedia | | |
| Prevotella melaninogenica | | |
| Propionibacterium acnes | | |
| Proteus spp. | | |
| Proteus mirabilis | | |
| Proteus vulgaris | | |
| Pseudomonas spp. | | |
| Pseudomonas aeruginosa | | |
| Salmonella enterica | | |
| Serratia marcescens | | |
| Staphylococcus spp. | | |
| Staphylococcus aureus | | |
| Staphylococcus haemolyticus | | |
| Staphylococcus lugdunensis | | |
| Staphylococcus maltophilia | | |
| Staphylococcus saprophyticus | | |
| Stenotrophomonas maltophilia | | |
| Streptococcus spp. | | |
| Streptococcus agalactiae | | |
| Streptococcus anginosa | | |
| Streptococcus bovis | | |
| Streptococcus dysgalactiae | | |
| Streptococcus mitis | | |
| Streptococcus mutans | | |
| Streptococcus pneumoniae | | |
| Streptococcus pyogenes | | |
| Streptococcus sanguinis | | |

Figure 1B

| Target Bacteria Species |
|---|
| Acinetobacter baumannii |
| Enterococcus faecium |
| Enterococcus faecalis |
| Klebsiella pneumoniae |
| Pseudomonas aeruginosa |
| Staphylococcus aureus |

| Target Bacteria Species |
|---|
| Staphylococcus aureus |
| Enterococcus faecium |
| Escherichia coli |
| Klebsiella pneumonia |
| Acinetobacter baumannii |
| Pseudomonas aeruginosa |
| Enterobacter spp. |
| Enterococcus faecalis |
| Streptococcus pneumonia |

| Organism |
|---|
| Candida species (spp.) |
| Acinetobacter baumannii |
| Citrobacter koseri |
| Citrobacter freundii complex |
| Coagulase-negative Staphylococcus spp. |
| Enterobacter aerogenes |
| Enterobacter cloacae |
| Enterococcus faecalis |
| Enterococcus faecium |
| Enterococcus faecium – resistance marker vanA/B |
| Escherichia coli |
| Haemophilus influenzae |
| Klebsiella oxytoca |
| Klebsiella pneumoniae |
| Klebsiella pneumoniae – resistance marker KPC |
| Listeria monocytogenes |
| Neisseria meningitidis |
| Proteus spp. |
| Pseudomonas aeruginosa |
| Serratia marcescens |
| Staphylococcus aureus |
| Staphylococcus aureus – resistance marker mecA |
| Staphylococcus spp. |
| Streptococcus spp. |

| Target Bacteria Species | Staphylococcus aureus | Enterococcus faecium | Escherichia coli | Klebsiella pneumonia | Acinetobacter baumannii | Pseudomonas aeruginosa |
|---|---|---|---|---|---|---|

| | Ab-3 | Ab-5 | Sa-3 | Sa-5 | Efm-3 | Efm-5 | Pa-3 | Pa5 | Efs-3 | Efs-5 | Kp-3 | Kp-5 |
|---|---|---|---|---|---|---|---|---|---|---|---|---|
| target CFU/ul stock | 0.3 | 0.5 | 0.3 | 0.5 | 0.3 | 0.5 | 0.3 | 0.5 | 0.3 | 0.5 | 0.3 | 0.5 |
| # col. Plate 1 | 28 | 47 | 59 | 79 | 51 | 91 | 38 | 77 | 60 | 71 | 40 | 60 |
| # col. Plate 2 | 27 | 48 | 62 | 76 | 59 | 114 | 49 | 76 | 44 | 69 | 36 | 62 |
| # col. Plate 3 | 40 | 54 | 61 | 78 | 55 | 100 | 48 | 71 | 39 | 71 | 27 | 55 |
| avg | 31.67 | 49.67 | 60.67 | 77.67 | 55 | 101.7 | 45 | 74.67 | 48 | 70 | 34 | 59 |
| observed CFU/ul stock | 0.158 | 0.25 | 0.30 | 0.39 | 0.275 | 0.508 | 0.225 | 0.373 | 0.238 | 0.352 | 0.172 | 0.295 |
| CFU/ml Blood* | 1.58 | 2.48 | 3.03 | 3.88 | 2.75 | 5.08 | 2.25 | 3.73 | 2.38 | 3.52 | 1.72 | 2.95 |

| | Ab | Efm | Efs | Kp | Pa | Sa |
|---|---|---|---|---|---|---|
| Negatives | | | 0 CFU/mL | | | |
| Mean T2 (ms) | 33.6 | 31.1 | 32.4 | 30.4 | 32.6 | 33.4 |
| %CV | 31.5 | 3.5 | 3.2 | 2.7 | 2.4 | 2.7 |
| Positives*) | 1.6 CFU/ml | 2.8 CFU/ml | 2.4 CFU/ml | 1.7 CFU/ml | 2.3 CFU/ml | 3.0 CFU/ml |
| Mean T2 (ms) | 317.9 | 350.1 | 323.3 | 650.5 | 498.4 | 381.8 |
| %CV | 14.9 | 23.5 | 16.8 | 24.0 | 13.3 | 19.4 |
| Percent Detected | 95% | 100% | 95% | 95% | 85% | 100% |
| LOD estimate (CFU/mL) | | | <3-5 CFU/mL | | | |

Figure 10

| Patient ID | SC/Species ID | Ab | Efm | Efs | Kp | Pa | Sa |
|---|---|---|---|---|---|---|---|
| 08-020 | Ab | X | | | | | |
| 11-030 | Ab | X | | | | | |
| 15-039 | Ab, CoNS | | | | | | |
| 20-027 | Acinetobacter sp. | X | | | | | |
| 08-029 | Efm | | X | | | | |
| 08-036 | Efm | | X | | | | |
| 08-044 | Efm | | X | | | | |
| 08-114 | Efm | | | | | | |
| 11-023 | Efm | | | | | | |
| 15-025 | Efm, E.coli, Kp | | X | | X | | |
| 08-030 | Efs | | | X | X | | |
| 08-052 | Efs | | | | | | |
| 08-155 | Efs | | | X | X | | |
| 14-067 | Efs | | | | X | | |
| 20-310 | Efs | | | X | | | |
| 14-057 | E. coli, Efs | | | X | | | |
| 14-070 | Efs, CoNS | | | | | | |
| 20-362 | Efs, P. mirabilis, C. perfringens | | | X | | | X |
| 08-038 | Kp | | X | | X | | |
| 08-110 | Kp | | | | X | | |
| 08-126 | Kp | | | | | | |
| 08-150 | Kp | | | | X | X | |
| 15-019 | Kp | | | X | X | | X |
| 20-077 | Kp | | | | X | | |
| 20-177 | Kp | | | | X | | |
| 20-203 | Kp | | | | X | | |
| 20-287 | Kp, CoNS | | | | X | | |
| 14-030 | Kp, E. cloacae | | | | X | | |
| 08-151 | Kp, Pa | | | | X | X | |
| 08-049 | Kp, Efs, Sa | | | | | | |
| 20-254 | Pa, Enterococcus sp. | | | | X | X | |
| 08-107 | Pa | | | | | X | |
| 08-125 | Pa | | | | | X | |
| 08-139 | Pa | | | | | | |
| 14-060 | Pa | | | | X | X | |
| 20-131 | Pa | | | | | X | |
| 20-148 | Pa | | | | | | |
| 20-214 | Pa | | | | | X | X |
| 20-230 | Pa | | | | | X | |
| 08-080 | Pa, S. anginosus | | | | | X | |
| 15-003 | Pa, S. viridans | | | | | | X |

| Patient ID | SC/Species ID | Ab | Efm | Efs | Kp | Pa | Sa |
|---|---|---|---|---|---|---|---|
| 08-003 | Sa | | | | | | X |
| 08-013 | Sa | | | | | | X |
| 08-041 | Sa | | | | | | X |
| 08-109 | Sa | | | | | | X |
| 08-116 | Sa | | | | | | X |
| 08-138 | Sa | | | | | | X |
| 14-076 | Sa | | | | | | |
| 15-009 | Sa | | | | | | X |
| 15-017 | Sa | | | | | | |
| 15-029 | Sa | | | | | | |
| 14-092 | Sa (MRSA) | | | | | | |
| 14-097 | Sa, CoNS | | | | | | X |

NMR METHODS AND SYSTEMS FOR THE RAPID DETECTION OF BACTERIA

FIELD OF THE INVENTION

The invention features methods, panels, cartridges, and systems for detecting pathogens and for diagnosing and treating diseases, including bacteremia and sepsis.

BACKGROUND OF THE INVENTION

Bloodstream infections (BSIs) are major causes of morbidity and mortality. On the basis of data from death certificates, these infections are the 10th leading cause of death in the United States, and the age-adjusted death rate due to BSIs has risen by 78% over the last 2 decades. The true incidence of nosocomial BSIs is unknown, but it is estimated that approximately 250,000 cases occur annually in the U.S. Bacteremia is a BSI that occurs when various species of bacteria enter the bloodstream. In people at risk, bacteremia may result when a person's own colonizing flora, present within their digestive tract flora, enter the bloodstream. It can also occur when medical equipment (e.g., indwelling central venous catheters) or devices become contaminated with bacteria from the environment or the hands of healthcare workers. Bacteremia can be associated with an inflammatory response in the body (e.g., sepsis and septic shock). In particular, sepsis and septic shock have a relatively high mortality rate. Bacteria in the bloodstream can sometimes spread to other parts of the body.

The symptoms of bacteremia are typically not specific, and patients will most frequently present with a fever of unknown origin. Differential diagnosis of bacteremia and sepsis can be complicated by the fact that other conditions (e.g., systemic inflammatory response syndrome (SIRS)) can present with similar symptoms. Bacteremia is usually diagnosed by a combination of blood culture and post-culture testing, which also identifies the specific species. These procedures require multiple days and, in some cases, species identification can require longer than six days. However, early initiation of appropriate therapy is important for effective treatment. For example, inadequate initial antimicrobial therapy (e.g., therapy that begins too late and/or that involves administration of an inappropriate drug) is an independent predictor of mortality, and delayed therapy is also associated with an extended length of hospital stay.

Thus, there remains a need for rapid and sensitive methods, preferably requiring minimal or no sample preparation, for detecting the presence of pathogen-associated analytes for diagnosis and monitoring of diseases, including bacteremia, sepsis, and SIRS. In particular, there is a need for methods and panels that are able to simultaneously detect the presence of multiple pathogens in a sample and identify those that are present.

SUMMARY OF THE INVENTION

The invention features methods, systems, cartridges, and panels for detection of pathogens (including bacterial pathogens), for example, for detection of pathogens in biological samples. The invention also features methods of diagnosing and/or treating diseases.

In one aspect, the invention features a method for detecting the presence of an *Acinetobacter baumannii* (*A. baumannii*) cell in a liquid sample, the method including: (a) lysing the cells in a liquid sample to form a lysate; (b) amplifying an *A. baumannii* target nucleic acid in the lysate in the presence of a forward primer including the oligonucleotide sequence: 5'-CGT TTT CCA AAT CTG TAA CAG ACT GGG-3' (SEQ ID NO: 1) or 5'-GGA AGG GAT CAG GTG GTT CAC TCT T-3' (SEQ ID NO: 110) and a reverse primer including the oligonucleotide sequence: 5'-AGG ACG TTG ATA GG TTG GAT GTG GA-3' (SEQ ID NO: 2) to form an amplified lysate including an *A. baumannii* amplicon; (c) following step (b), adding magnetic particles to the amplified lysate to form a mixture, wherein the magnetic particles include binding moieties on their surface, the binding moieties operative to alter aggregation of the magnetic particles in the presence of the *A. baumannii* amplicon; (d) providing the mixture in a detection tube within a device, the device including a support defining a well for holding the detection tube including the mixture, and having an RF coil configured to detect a signal produced by exposing the mixture to a bias magnetic field created using one or more magnets and an RF pulse sequence; (e) exposing the mixture to a bias magnetic field and an RF pulse sequence; (f) following step (e), measuring the signal from the detection tube; and (g) on the basis of the result of step (f), determining whether an *A. baumannii* cell was present in the liquid sample. In some embodiments, the magnetic particles include a first population of magnetic particles conjugated to a first probe, and a second population of magnetic particles conjugated to a second probe, the first probe operative to bind to a first segment of the *A. baumannii* amplicon and the second probe operative to bind to a second segment of the *A. baumannii* amplicon, wherein the magnetic particles form aggregates in the presence of the *A. baumannii* amplicon. In some embodiments, the forward primer includes the oligonucleotide sequence: 5'-CGT TTT CCA AAT CTG TAA CAG ACT GGG-3' (SEQ ID NO: 1). In other embodiments, the forward primer includes the oligonucleotide sequence: 5'-GGA AGG GAT CAG GTG GTT CAC TCT T-3' (SEQ ID NO: 110). In some embodiments, the first probe includes the oligonucleotide sequence: 5'-TGA GGC TTG ACT ATA CAA CAC C-3' (SEQ ID NO: 15), and the second probe includes the oligonucleotide sequence: 5'-CTA AAA TGA ACA GAT AAA GTA AGA TTC AA-3' (SEQ ID NO: 16). In some embodiments, amplifying is performed by asymmetric polymerase chain reaction (PCR).

In another aspect, the invention features a method for detecting the presence of an *Enterococcus* species in a liquid sample, the method including: (a) lysing the cells in a liquid sample to form a lysate; (b) amplifying an *Enterococcus* target nucleic acid in the lysate in the presence of a forward primer including the oligonucleotide sequence: 5'-GGT AGC TAT GTA GGG AAG GGA TAA ACG CTG A-3' (SEQ ID NO: 3) and a reverse primer including the oligonucleotide sequence: 5'-GCG CTA AGG AGC TTA ACT TCT GTG TTC G-3' (SEQ ID NO: 4) to form an amplified lysate including an *Enterococcus* amplicon; (c) following step (b), adding magnetic particles to the amplified lysate to form a mixture, wherein the magnetic particles include binding moieties on their surface, the binding moieties operative to alter aggregation of the magnetic particles in the presence of the *Enterococcus* amplicon; (d) providing the mixture in a detection tube within a device, the device including a support defining a well for holding the detection tube including the mixture, and having an RF coil configured to detect a signal produced by exposing the mixture to a bias magnetic field created using one or more magnets and an RF pulse sequence; (e) exposing the mixture to a bias magnetic field and an RF pulse sequence; (f) following step (e), measuring the signal from the detection tube; and (g) on the basis of the result of step (f), determining whether an *Enterococcus* species was present in the liquid sample. In some embodiments, the magnetic particles include a first population of magnetic particles conjugated to a first probe, and a second population of magnetic particles conjugated to a second probe, the first probe operative to bind to a first segment of the *Enterococcus* amplicon and the second probe operative to bind to a second segment of the *Enterococcus* amplicon, wherein the magnetic particles form aggregates in the presence of the *Enterococcus* amplicon. In some embodiments, the species is *Enterococcus faecium*, and wherein the first probe includes the oligonucleotide sequence: 5'-AAA ACT TAT ATG ACT TCA AAT CCA GTT TT-3' (SEQ ID NO: 19) or 5'-AAA ACT TAT GTG ACT TCA AAT CCA GTT TT-3' (SEQ ID NO: 111), and the second probe includes the oligonucleotide sequence: 5'-TTT ACT CAA TAA AAG ATA ACA CCA CAG-3' (SEQ ID NO: 20) or 5'-TTT ACT CAA TAA AAG ATA ACA CCA CAG T-3' (SEQ ID NO: 112). In some embodiments, the species is *Enterococcus faecium*, and wherein the first probe includes the oligonucleotide sequence: 5'-AAA ACT TAT ATG ACT TCA AAT CCA GTT TT-3' (SEQ ID NO: 19), and the second probe includes the oligonucleotide sequence: 5'-TTT ACT CAA TAA AAG ATA ACA CCA CAG-3' (SEQ ID NO: 20). In other embodiments, the species is *Enterococcus faecium*, and wherein the first probe includes the oligonucleotide sequence: 5'-AAA ACT TAT GTG ACT TCA AAT CCA GTT TT-3' (SEQ ID NO: 111), and the second probe includes the oligonucleotide sequence: 5'-TTT ACT CAA TAA AAG ATA ACA CCA CAG T-3' (SEQ ID NO: 112). In some embodiments, the species is *Enterococcus faecalis*, and wherein the first probe includes the oligonucleotide sequence: 5'-TGG ATA AGT AAA AGC AAC TTG GTT-3' (SEQ ID NO: 23), and the second probe includes the oligonucleotide sequence: 5'-AAT GAA GAT TCA ACT CAA TAA GAA ACA ACA-3' (SEQ ID NO: 24). In some embodiments, amplifying is performed by asymmetric polymerase chain reaction (PCR).

In another aspect, the invention features a method for detecting the presence of a *Klebsiella pneumoniae* (*K. pneumoniae*) cell in a liquid sample, the method including: (a) lysing the cells in a liquid sample to form a lysate; (b) amplifying a *K. pneumoniae* target nucleic acid in the lysate in the presence of a forward primer including the oligonucleotide sequence: 5'-GAC GGT TGT CCC GGT TTA AGC A-3' (SEQ ID NO: 5) and a reverse primer including the oligonucleotide sequence: 5'-GCT GGT ATC TTC GAC TGG TCT-3' (SEQ ID NO: 6) to form an amplified lysate including a *K. pneumoniae* amplicon; (c) following step (b), adding magnetic particles to the amplified lysate to form a mixture, wherein the magnetic particles include binding moieties on their surface, the binding moieties operative to alter aggregation of the magnetic particles in the presence of the *K. pneumoniae* amplicon; (d) providing the mixture in a detection tube within a device, the device including a support defining a well for holding the detection tube including the mixture, and having an RF coil configured to detect a signal produced by exposing the mixture to a bias magnetic field created using one or more magnets and an RF pulse sequence; (e) exposing the mixture to a bias magnetic field and an RF pulse sequence; (f) following step (e), measuring the signal from the detection tube; and (g) on the basis of the result of step (f), determining whether a *K. pneumoniae* cell was present in the liquid sample. In some embodiments, the magnetic particles include a first population of magnetic particles conjugated to a first probe, and a second population of magnetic particles conjugated to a second probe, the first probe operative to bind to a first segment of the *K. pneumoniae* amplicon and the second probe operative to bind to a second segment of the *K. pneumoniae* amplicon, wherein the magnetic particles form aggregates in the presence of the *K. pneumoniae* amplicon. In some embodiments, the first probe includes the oligonucleotide sequence: 5'-TAC CAA GGC GCT TGA GAG AAC TC-3' (SEQ ID NO: 27), and the second probe includes the oligonucleotide sequence: 5'-CTG GTG TGT AGG TGA AGT C-3' (SEQ ID NO: 28). In some embodiments, amplifying is performed by asymmetric polymerase chain reaction (PCR).

In another aspect, the invention features a method for detecting the presence of a *Pseudomonas aeruginosa* (*P. aeruginosa*) cell in a liquid sample, the method including: (a) lysing the cells in a liquid sample to form a lysate; (b) amplifying a *P. aeruginosa* target nucleic acid in the lysate in the presence of a forward primer including the oligonucleotide sequence 5'-AGG CTG GGT GTG TAA GCG TTG T-3' (SEQ ID NO: 7) and a reverse primer including the oligonucleotide sequence 5'-CAA GCA ATT CGG TTG GAT ATC CGT T-3' (SEQ ID NO: 8) to form an amplified lysate including a *P. aeruginosa* amplicon; (c) following step (b), adding magnetic particles to the amplified lysate to form a mixture, wherein the magnetic particles include binding moieties on their surface, the binding moieties operative to alter aggregation of the magnetic particles in the presence of the *P. aeruginosa* amplicon; (d) providing the mixture in a detection tube within a device, the device including a support defining a well for holding the detection tube including the mixture, and having an RF coil configured to detect a signal produced by exposing the mixture to a bias magnetic field created using one or more magnets and an RF pulse sequence; (e) exposing the mixture to a bias magnetic field and an RF pulse sequence; (f) following step (e), measuring the signal from the detection tube; and (g) on the basis of the result of step (f), determining whether a *P. aeruginosa* cell was present in the liquid sample. In some embodiments, the magnetic particles include a first population of magnetic particles conjugated to a first probe, and a second population of magnetic particles conjugated to a second probe, the first probe operative to bind to a first segment of the *P. aeruginosa* amplicon and the second probe operative to bind to a second segment of the *P. aeruginosa* amplicon, wherein the magnetic particles form aggregates in the presence of the *P. aeruginosa* amplicon. In some embodiments, the first probe includes the oligonucleotide sequence: 5'-GTG TGT TGT AGG GTG AAG TCG AC-3' (SEQ ID NO: 31) or 5'-TCT GAC GAT TGT GTG TTG TAA GG-3' (SEQ ID NO: 114), and the second probe includes the oligonucleotide sequence: 5'-CAC CTT GAA ATC ACA TAC CTG A-3' (SEQ ID NO: 32) or 5'-GGA TAG ACG TAA GCC CAA GC-3' (SEQ ID NO: 115). In some embodiments, the first probe includes the oligonucleotide sequence: 5'-GTG TGT TGT AGG GTG AAG TCG AC-3' (SEQ ID NO: 31), and the second probe includes the oligonucleotide sequence: 5'-CAC CTT GAA ATC ACA TAC CTG A-3' (SEQ ID NO: 32). In other embodiments, the first probe includes the oligonucleotide sequence: 5'-TCT GAC GAT TGT GTG TTG TAA GG-3' (SEQ ID NO: 114), and the second probe includes the oligonucleotide sequence: 5'-GGA TAG ACG TAA GCC CAA GC-3' (SEQ ID NO: 115). In some embodiments, amplifying is performed by asymmetric polymerase chain reaction (PCR).

In another aspect, the invention features a method for detecting the presence of an *Escherichia coli* (*E. coli*) cell in a liquid sample, the method including: (a) lysing the cells in a liquid sample to form a lysate; (b) amplifying an *E. coli* target nucleic acid in the lysate in the presence of a forward primer including the oligonucleotide sequence: 5'-GCA TTA ATC GAC GGT ATG GTT GAC C-3' (SEQ ID NO: 59) and a reverse primer including the oligonucleotide sequence: 5'-CCT GCT GAA ACA GGT TTT CCC ACA TA-3' (SEQ ID NO: 61) to form an amplified lysate including an *E. coli* amplicon; (c) following step (b), adding magnetic particles to the amplified lysate to form a mixture, wherein the magnetic particles include binding moieties on their surface, the binding moieties operative to alter aggregation of the magnetic particles in the presence of the *E. coli* amplicon; (d) providing the mixture in a detection tube within a device, the device including a support defining a well for holding the detection tube including the mixture, and having an RF coil configured to detect a signal produced by exposing the mixture to a bias magnetic field created using one or more magnets and an RF pulse sequence; (e) exposing the mixture to a bias magnetic field and an RF pulse sequence; (f) following step (e), measuring the signal from the detection tube; and (g) on the basis of the result of step (f), determining whether an *E. coli* cell was present in the liquid sample. In some embodiments, the magnetic particles include a first population of magnetic particles conjugated to a first probe, and a second population of magnetic particles conjugated to a second probe, the first probe operative to bind to a first segment of the *E. coli* amplicon and the second probe operative to bind to a second segment of the *E. coli* amplicon, wherein the magnetic particles form aggregates in the presence of the *E. coli* amplicon. In some embodiments, the first probe includes the oligonucleotide sequence: 5'-AGT GAT GAT GAG TTG TTT GCC AGT G-3' (SEQ ID NO: 63), and the second probe includes the oligonucleotide sequence: 5'-TGA ATT GTC GCC GCG TGA CCA G-3' (SEQ ID NO: 64). In some embodiments, amplifying is performed by asymmetric polymerase chain reaction (PCR).

In another aspect, the invention features a method for detecting the presence of a *Staphylococcus aureus* (*S. aureus*) cell in a liquid sample, the method including: (a) lysing the cells in the liquid sample to form a lysate; (b) amplifying an *S. aureus* target nucleic acid in the lysate in the presence of a first primer pair or a second primer pair to form an amplified lysate including an *S. aureus* amplicon, wherein the first primer pair includes a forward primer including the oligonucleotide sequence: 5'-GGT AAT GAA TTA CCT/i6diPrITC TCT GCT GGTTTC TTC TT-3' (SEQ ID NO: 9) and a reverse primer including the oligonucleotide sequence: 5'-ACC AGC ATC TTC/i6diPr/GC ATC TTC TGT AAA-3' (SEQ ID NO: 10), and the second primer pair includes a forward primer including the oligonucleotide sequence: 5'-GAA GTT ATG TTT/i6diPr/CT ATT CGA ATC GTG GTC CAGT-3' (SEQ ID NO: 11) and a reverse primer including the oligonucleotide sequence: 5'-GTT GTA AAG CCA TGA TGC TCG TAA CCA-3' (SEQ ID NO: 12); (c) following step (b), adding magnetic particles to the amplified lysate to form a mixture, wherein the magnetic particles include binding moieties on their surface, the binding moieties operative to alter aggregation of the magnetic particles in the presence of the *S. aureus* amplicon; (d) providing the mixture in a detection tube within a device, the device including a support defining a well for holding the detection tube including the mixture, and having an RF coil configured to detect a signal produced by exposing the mixture to a bias magnetic field created using one or more magnets and an RF pulse sequence; (e) exposing the mixture to a bias magnetic field and an RF pulse sequence; (f) following step (e), measuring the signal from the detection tube; and (g) on the basis of the result of step (f), determining whether a *S. aureus* cell was present in the liquid sample. In some embodiments, the magnetic particles include a first population of magnetic particles conjugated to a first probe, and a second population of magnetic particles conjugated to a second probe, the first probe operative to bind to a first segment of the *S. aureus* amplicon and the second probe operative to bind to a second segment of the *S. aureus* amplicon, wherein the magnetic particles form aggregates in the presence of the *S. aureus* amplicon. In some embodiments, step (b) includes amplifying an *S. aureus* target nucleic acid in the presence of the first primer pair, and the first probe includes the oligonucleotide sequence: 5'-CCA TTT GAA GTT GTT TAT TAT GC-3' (SEQ ID NO: 35), and the second probe includes the oligonucleotide sequence: 5'-GGG AAA TGA TTA ATT ATG CAT TAA ATC-3' (SEQ ID NO: 36). In some embodiments, step (b) includes amplifying an *S. aureus* target nucleic acid in the presence of the second primer pair, and the first probe includes the oligonucleotide sequence: 5'-TT TTT CAG ATT TAG GAT TAG TTG ATT-3' (SEQ ID NO: 39), and the second probe includes the oligonucleotide sequence: 5'-GAT CCG TAT TGG TTA TAT CAT C-3' (SEQ ID NO: 40). In some embodiments, step (b) includes amplifying the first *S. aureus* target nucleic acid in the presence of the first primer pair to form a first *S. aureus* amplicon and amplifying the second *S. aureus* target nucleic acid in the presence of the second primer pair to form a second *aureus* amplicon, and step (g) includes detecting the first *S. aureus* amplicon and the second *S. aureus* amplicon. In some embodiments, the magnetic particles include a first population of magnetic particles conjugated to a first probe and a second probe, and a second population of magnetic particles conjugated to a third probe and a fourth probe, wherein the first probe and third probe are operative to bind a first segment and a second segment, respectively, of the first *S. aureus* amplicon; and the second probe and fourth probe are operative to bind a first segment and a second segment, respectively, of the second *S. aureus* amplicon, wherein the magnetic particles form aggregates in the presence of the first *S. aureus* amplicon and form aggregates in the presence of the second *S. aureus* amplicon. In some embodiments, the first probe includes an oligonucleotide sequence of SEQ ID NO: 35, the second probe includes an oligonucleotide sequence of SEQ ID NO: 39, the third probe includes an oligonucleotide sequence of SEQ ID NO: 36, and the fourth probe includes an oligonucleotide sequence of SEQ ID NO: 40. In some embodiments, step (b) results in the production of at least a third amplicon. In some embodiments, the third amplicon includes a first region that operably binds to the oligonucleotide sequence of SEQ ID NO: 35, a second region that operably binds to the oligonucleotide sequence of SEQ ID NO: 39, a third region that operably binds to the oligonucleotide sequence of SEQ ID NO: 36, and a fourth region that operably binds to the oligonucleotide sequence of SEQ ID NO: 40. In some embodiments, the third amplicon includes the nucleotide sequence of the first amplicon and the nucleotide sequence of the second amplicon. In some embodiments, the third amplicon is produced by partial run-through of strand synthesis. In some embodiments, amplifying is performed by asymmetric polymerase chain reaction (PCR).

In some embodiments of any of the preceding aspects, steps (a) through (g) of the method are completed within 5 hours. In some embodiments, steps (a) through (g) of the method are completed within 3 hours.

In some embodiments of any of the preceding aspects, the method is capable of detecting a concentration of 10 colony-forming units (CFU)/mL of *A. baumannii*, an *Enterococcus* species, *K. pneumoniae, P. aeruginosa*, or *S. aureus* in the liquid sample. In some embodiments, the method is capable of detecting a concentration of 3 CFU/mL. In some embodiments, the method is capable of detecting a concentration of 2 CFU/mL. In some embodiments, the method is capable of detecting a concentration of 1 CFU/mL. In some embodiments, the method is capable of detecting from 1-10 CFU/mL (e.g., 1, 2, 3, 4, 5, 6, 7, 8, 9, or 10 CFU/mL) of *A. baumannii*, an *Enterococcus* species, *K. pneumoniae, P. aeruginosa*, or *S. aureus* in the liquid sample.

In some embodiments of any of the preceding aspects, the liquid sample is selected from whole blood, urine, liquid biopsy, synovial fluid, skin biopsy, cerebrospinal fluid, sputum, gastric lavage, bronchoaveolar lavage, or homogenized tissue. In some embodiments, the liquid sample is whole blood. In some embodiments, step (a) includes lysing the red blood cells in a whole blood sample from a subject, centrifuging the sample to form a supernatant and a pellet, discarding some or all of the supernatant, optionally washing the pellet, and lysing the cells in the pellet to form a lysate.

In some embodiments of any of the preceding aspects, step (b) includes adding to the liquid sample from $1 \times 10^6$ to $1 \times 10^{13}$ magnetic particles per milliliter of the liquid sample. In some embodiments, the magnetic particles have a mean diameter of from 700 nm to 950 nm. In some embodiments, the magnetic particles have a $T_2$ relaxivity per particle of from $1 \times 10^9$ to $1 \times 10^{12}$ mM$^{-1}$s$^{-1}$. In some embodiments, the magnetic particles are substantially monodisperse.

In another aspect, the invention features a method for detecting the presence of a species in a liquid sample, the method including: (a) amplifying in the liquid sample a first target nucleic acid and a second target nucleic acid to form a solution including a first amplicon and a second amplicon, wherein each target nucleic acid is characteristic of the species to be detected; (b) adding magnetic particles to the liquid sample to form a mixture, wherein the magnetic particles include binding moieties on their surface, the binding moieties operative to alter aggregation of the magnetic particles in the presence of the first amplicon or the second amplicon; (c) providing the mixture in a detection tube within a device, the device including a support defining a well for holding the detection tube including the mixture, and having an RF coil configured to detect a signal produced by exposing the mixture to a bias magnetic field created using one or more magnets and an RF pulse sequence; (d) exposing the mixture to a bias magnetic field and an RF pulse sequence; (e) following step (d), measuring the signal; and (f) on the basis of the result of step (e), determining whether the species was present in the liquid sample. In some embodiments, the species is a plant species, a mammalian species, or a microbial species. In some embodiments, the species is a microbial species. In some embodiments, the first target nucleic acid is amplified in the presence of a first primer pair including a forward primer and a reverse primer, and the second target nucleic acid is amplified in the presence of a second primer pair including a forward primer and a reverse primer. In some embodiments, the magnetic particles include a first population of magnetic particles conjugated to a first probe and a second probe, and a second population of magnetic particles conjugated to a third probe and a fourth probe, wherein the first probe and third probe are operative to bind a first segment and a second segment, respectively, of the first amplicon; and the second probe and fourth probe are operative to bind a first segment and a second segment, respectively, of the second amplicon, wherein the magnetic particles form aggregates in the presence of the first amplicon and form aggregates in the presence of the second amplicon. In some embodiments, step (a) further includes amplifying a third amplicon, wherein the third amplicon includes a nucleic acid sequence that includes the nucleic acid sequence of the first target nucleic acid and the nucleic acid sequence of the second target nucleic acid. In some embodiments, the first target nucleic acid and the second target nucleic acid are located on a chromosome or a plasmid. In some embodiments, the first target nucleic acid and the second target nucleic acid are separated by between about 10 and about 1000 base pairs (e.g., about 10, 20, 30, 40, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 base pairs). In some embodiments, the third amplicon is produced by partial run-through of strand synthesis. In some embodiments, the method is capable of detecting a concentration of 10 colony-forming units (CFU)/mL of the microbial species in the liquid sample. In some embodiments, the method is capable of detecting a concentration of 3 CFU/mL of the microbial species in the liquid sample. In some embodiments, the method is capable of detecting a concentration of 1 CFU/mL of the microbial species in the liquid sample. In some embodiments, the steps (a) through (f) of the method are completed within 5 hours. In some embodiments, the steps (a) through (f) of the method are completed within 3 hours. In some embodiments, the microbial species is selected from *A. baumannii, E. faecalis, E. faecium, K. pneumoniae, P. aeruginosa, E. coli*, and *S. aureus*. In some embodiments, the liquid sample is selected from whole blood, urine, liquid biopsy, synovial fluid, skin biopsy, cerebrospinal fluid, sputum, gastric lavage, bronchoaveolar lavage, or homogenized tissue. In some embodiments, the liquid sample is whole blood. In some embodiments, the method further includes, prior to step (a), providing a whole blood sample from a subject, lysing the red blood cells in the whole blood sample, centrifuging the sample to form a supernatant and a pellet, discarding some or all of the supernatant, optionally washing the pellet, and lysing the cells in the pellet to form a lysate. In some embodiments, step (b) includes adding to the liquid sample from $1 \times 10^5$ to $1 \times 10^{13}$ magnetic particles per milliliter of the liquid sample. In some embodiments, the magnetic particles have a mean diameter of from 700 nm to 950 nm. In some embodiments, the magnetic particles have a $T_2$ relaxivity per particle of from $1 \times 10^9$ to $1 \times 10^{12}$ mM$^{-1}$s$^{-1}$. In some embodiments, the magnetic particles are substantially monodisperse. In some embodiments, amplifying is performed by asymmetric polymerase chain reaction (PCR).

In another aspect, the invention features a composition including: (a) a liquid sample, wherein the liquid sample (i) is suspected of containing an *A. baumannii* target nucleic acid, or (ii) contains an *A. baumannii* amplicon generated by amplifying the *A. baumannii* target nucleic acid; and (b) within the liquid sample, from $1 \times 10^6$ to $1 \times 10^{13}$ magnetic particles per milliliter of the liquid sample, the magnetic particles having a mean diameter of from 700 nm to 950 nm, a $T_2$ relaxivity per particle of from $1 \times 10^4$ to $1 \times 10^{12}$ mM$^{-1}$s$^{-1}$, wherein the magnetic particles include a first population of magnetic particles conjugated to a first nucleic acid probe including the oligonucleotide sequence: 5'-TGA GGC TTG ACT ATA CAA CAC C-3' (SEQ ID NO: 15), and a second population of magnetic particles conjugated to a second nucleic acid probe including the oligonucleotide sequence: 5'-CTA AAA TGA ACA GAT AAA GTA AGA TTC AA-3' (SEQ ID NO: 16). In some embodiments, the magnetic particles have a $T_2$ relaxivity per particle of from $1\times10^9$ to $1\times10^{12}$ mM$^{-1}$s$^{-1}$.

In another aspect, the invention features a composition including: (a) a liquid sample, wherein the liquid sample (i) is suspected of containing an *Enterococcus* target nucleic acid, or (ii) contains an *Enterococcus* amplicon generated by amplifying the *Enterococcus* target nucleic acid; and (b) within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, wherein the magnetic particles include a first population of magnetic particles conjugated to a first nucleic acid probe including the oligonucleotide sequence: 5'-AAA ACT TAT ATG ACT TCA AAT CCA GTT TT-3' (SEQ ID NO: 19) or 5'-AAA ACT TAT GTG ACT TCA AAT CCA GTT TT-3' (SEQ ID NO: 111), and a second population of magnetic particles conjugated to a second nucleic acid probe including the oligonucleotide sequence: 5'-TTT ACT CAA TAA AAG ATA ACA CCA CAG-3' (SEQ ID NO: 20) or 5'-TTT ACT CAA TAA AAG ATA ACA CCA CAG T-3' (SEQ ID NO: 112). In some embodiments, the first nucleic acid probe includes the oligonucleotide sequence: 5'-AAA ACT TAT ATG ACT TCA AAT CCA GTT TT-3' (SEQ ID NO: 19) and the second nucleic acid probe includes the oligonucleotide sequence: 5'-TTT ACT CAA TAA AAG ATA ACA CCA CAG-3' (SEQ ID NO: 20). In other embodiments, the first nucleic acid probe includes the oligonucleotide sequence: 5'-AAA ACT TAT GTG ACT TCA AAT CCA GTT TT-3' (SEQ ID NO: 111) and the second nucleic acid probe includes the oligonucleotide sequence: 5'-TTT ACT CAA TAA AAG ATA ACA CCA CAG T-3' (SEQ ID NO: 112). In some embodiments, the *Enterococcus* target nucleic acid is an *Enterococcus faecium* target nucleic acid. In some embodiments, the magnetic particles have a $T_2$ relaxivity per particle of from $1\times10^9$ to $1\times10^{12}$ mM$^{-1}$s$^{-1}$.

In another aspect, the invention features a composition including: (a) a liquid sample, wherein the liquid sample (i) is suspected of containing an *Enterococcus* target nucleic acid, or (ii) contains an *Enterococcus* amplicon generated by amplifying the *Enterococcus* target nucleic acid; and (b) within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, wherein the magnetic particles include a first population of magnetic particles conjugated to a first nucleic acid probe including the oligonucleotide sequence: 5'-TGG ATA AGT AAA AGC AAC TTG GTT-3' (SEQ ID NO: 23), and a second population of magnetic particles conjugated to a second nucleic acid probe including the oligonucleotide sequence: 5'-AAT GAA GAT TCA ACT CAA TAA GAA ACA ACA-3' (SEQ ID NO: 24). In some embodiments, the *Enterococcus* target nucleic acid is an *Enterococcus faecalis* target nucleic acid. In some embodiments, the magnetic particles have a $T_2$ relaxivity per particle of from $1\times10^9$ to $1\times10^{12}$ mM$^{-1}$s$^{-1}$.

In another aspect, the invention features a composition including: (a) a liquid sample, wherein the liquid sample (i) is suspected of containing a *K. pneumoniae* target nucleic acid, or (ii) contains a *K. pneumoniae* amplicon generated by amplifying the *K. pneumoniae* target nucleic acid; and (b) within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, wherein the magnetic particles include a first population of magnetic particles conjugated to a first nucleic acid probe including the oligonucleotide sequence: 5'-TAC CAA GGC GCT TGA GAG AAC TC-3' (SEQ ID NO: 27), and a second population of magnetic particles conjugated to a second nucleic acid probe including the oligonucleotide sequence: 5'-CTG GTG TGT AGG TGA AGT C-3' (SEQ ID NO: 28). In some embodiments, the magnetic particles have a $T_2$ relaxivity per particle of from $1\times10^9$ to $1\times10^{12}$ mM$^{-1}$s$^{-1}$.

In another aspect, the invention features a composition including: (a) a liquid sample, wherein the liquid sample (i) is suspected of containing a *P. aeruginosa* target nucleic acid, or (ii) contains a *P. aeruginosa* amplicon generated by amplifying the *P. aeruginosa* target nucleic acid; and (b) within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, wherein the magnetic particles include a first population of magnetic particles conjugated to a first nucleic acid probe including the oligonucleotide sequence: 5'-GTG TGT TGT AGG GTG AAG TCG AC-3' (SEQ ID NO: 31) or 5'-TCT GAC GAT TGT GTG TTG TAA GG-3' (SEQ ID NO: 114), and a second population of magnetic particles conjugated to a second nucleic acid probe including the oligonucleotide sequence: 5'-CAC CTT GAA ATC ACA TAC CTG A-3' (SEQ ID NO: 32) or 5'-GGA TAG ACG TAA GCC CAA GC-3' (SEQ ID NO: 115). In some embodiments, the magnetic particles have a $T_2$ relaxivity per particle of from $1\times10^9$ to $1\times10^{12}$ mM$^{-1}$s$^{-1}$. In some instances, the first nucleic acid probe includes the oligonucleotide sequence: 5'-GTG TGT TGT AGG GTG AAG TCG AC-3' (SEQ ID NO: 31) and the second nucleic acid probe includes the oligonucleotide sequence 5'-CAC CTT GAA ATC ACA TAC CTG A-3' (SEQ ID NO: 32). In other instances, the first nucleic acid probe includes the oligonucleotide sequence: 5'-TCT GAC GAT TGT GTG TTG TAA GG-3' (SEQ ID NO: 114) and the second nucleic acid probe includes the oligonucleotide sequence 5'-GGA TAG ACG TAA GCC CAA GC-3' (SEQ ID NO: 115).

In another aspect, the invention features a composition including: (a) a liquid sample, wherein the liquid sample (i) is suspected of containing an *E. coli* target nucleic acid, or (ii) contains an *E. coli* amplicon generated by amplifying the *E. coli* target nucleic acid; and (b) within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, wherein the magnetic particles include a first population of magnetic particles conjugated to a first nucleic acid probe including the oligonucleotide sequence: 5'-AGT GAT GAT GAG TTG TTT GCC AGT G-3' (SEQ ID NO: 63), and a second population of magnetic particles conjugated to a second nucleic acid probe including the oligonucleotide sequence: 5'-TGA ATT GTC GCC GCG TGA CCA G-3' (SEQ ID NO: 64). In some embodiments, the magnetic particles have a $T_2$ relaxivity per particle of from $1\times10^9$ to $1\times10^{12}$ mM$^{-1}$s$^{-1}$.

In another aspect, the invention features a composition including: (a) a liquid sample, wherein the liquid sample (i) is suspected of containing an *S. aureus* target nucleic acid, or (ii) contains an *S. aureus* amplicon generated by amplifying the *S. aureus* target nucleic acid; and (b) within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, wherein the magnetic particles include a first population of magnetic particles conjugated to a first nucleic acid probe including the oligonucleotide sequence: 5'-CCA TTT GAA GTT GTT TAT TAT GC-3' (SEQ ID NO: 35), and a second population of magnetic particles conjugated to a second nucleic acid probe including the oligonucleotide sequence: 5'-GGG AAA TGA TTA ATT ATG CAT TAA ATC-3' (SEQ ID NO: 36). In some embodiments, the magnetic particles have a $T_2$ relaxivity per particle of from $1 \times 10^9$ to $1 \times 10^{12}$ mM$^{-1}$s$^{-1}$.

In another aspect, the invention features a composition including: (a) a liquid sample, wherein the liquid sample (i) is suspected of containing an *S. aureus* target nucleic acid, or (ii) contains an *S. aureus* target nucleic acid amplicon generated from an amplification reaction; and (b) within the liquid sample, from $1 \times 10^6$ to $1 \times 10^{13}$ magnetic particles per milliliter of the liquid sample, the magnetic particles having a mean diameter of from 700 nm to 950 nm, a $T_2$ relaxivity per particle of from $1 \times 10^4$ to $1 \times 10^{12}$ mM$^{-1}$s$^{-1}$, wherein the magnetic particles include a first population of magnetic particles conjugated to a first nucleic acid probe including the oligonucleotide sequence: 5'-TT TTT CAG ATT TAG GAT TAG TTG ATT-3' (SEQ ID NO: 39), and a second population of magnetic particles conjugated to a second nucleic acid probe including the oligonucleotide sequence: 5'-GAT CCG TAT TGG TTA TAT CAT C-3' (SEQ ID NO: 40). In some embodiments, the magnetic particles have a $T_2$ relaxivity per particle of from $1 \times 10^9$ to $1 \times 10^{12}$ mM$^{-1}$s$^{-1}$.

In another aspect, the invention features a composition including: (a) a liquid sample, wherein the liquid sample (i) is suspected of containing an *S. aureus* target nucleic acid, or (ii) contains an *S. aureus* target nucleic acid amplicon generated from an amplification reaction; and (b) within the liquid sample, from $1 \times 10^6$ to $1 \times 10^{13}$ magnetic particles per milliliter of the liquid sample, the magnetic particles having a mean diameter of from 700 nm to 950 nm, a $T_2$ relaxivity per particle of from $1 \times 10^4$ to $1 \times 10^{12}$ mM$^{-1}$s$^{-1}$, the magnetic particles including a first population and a second population, the first population having a first nucleic acid probe and a second nucleic acid probe conjugated to their surface and the second population having a third nucleic acid probe and a fourth nucleic acid probe conjugated to their surface, wherein the first nucleic acid probe includes an oligonucleotide sequence of SEQ ID NO: 35, the second nucleic acid probe includes an oligonucleotide sequence of SEQ ID NO: 39, the third nucleic acid probe includes an oligonucleotide sequence of SEQ ID NO: 36, and the fourth nucleic acid probe includes an oligonucleotide sequence of SEQ ID NO: 40. In some embodiments, the magnetic particles have a $T_2$ relaxivity per particle of from $1 \times 10^9$ to $1 \times 10^{12}$ mM-1s$^{-1}$.

In another aspect, the invention features a composition including: (a) a liquid sample, wherein the liquid sample (i) is suspected of containing a first target nucleic acid and a second target nucleic acid, wherein each target nucleic acid is characteristic of a microbial species, or (ii) contains a first amplicon and a second amplicon generated by amplifying the first target nucleic acid and the second target nucleic acid; and (b) within the liquid sample, from $1 \times 10^6$ to $1 \times 10^{13}$ magnetic particles per milliliter of the liquid sample, the magnetic particles having a mean diameter of from 700 nm to 950 nm, a $T_2$ relaxivity per particle of from $1 \times 10^4$ to $1 \times 10^{12}$ mM$^{-1}$s$^{-1}$, and having binding moieties conjugated to their surface, wherein the magnetic particles are capable of operably binding the first amplicon to form aggregates and are capable of binding the second amplicon to form aggregates. In some embodiments, the magnetic particles include a first population of magnetic particles conjugated to a first probe and a second probe, and a second population of magnetic particles conjugated to a third probe and a fourth probe, wherein the first probe and third probe are operative to bind a first segment and a second segment, respectively, of the first target nucleic acid; and the second probe and fourth probe are operative to bind a first segment and a second segment, respectively, of the second target nucleic acid. In some embodiments, the magnetic particles have a $T_2$ relaxivity per particle of from $1 \times 10^9$ to $1 \times 10^{12}$ mM$^{-1}$s$^{-1}$.

In another aspect, the invention features an amplified lysate solution produced by a method for amplifying a target nucleic acid in a whole blood sample, the method including: (a) providing a first sample produced by lysing the red blood cells in a whole blood sample suspected of containing one or more bacterial cells from a subject, centrifuging the first sample to form a supernatant and a pellet, discarding some or all of the supernatant, and resuspending the pellet; (b) lysing remaining cells in the pellet to form a lysate including both subject cell nucleic acid and bacterial nucleic acid; and (c) providing the lysate of step (b) in a detection tube and amplifying a target bacterial nucleic acid therein to form an amplified lysate solution using one or more primer pairs selected from the following: (i) a primer pair for amplification of an *A. baumannii* target nucleic acid including a forward primer including the oligonucleotide sequence: 5'-CGT TTT CCA AAT CTG TAA CAG ACT GGG-3' (SEQ ID NO: 1) or 5'-GGA AGG GAT CAG GTG GTT CAC TCT T-3' (SEQ ID NO: 110) and a reverse primer including the oligonucleotide sequence: 5'-AGG ACG TTG ATA GG TTG GAT GTG GA-3' (SEQ ID NO: 2); (ii) a primer pair for amplification of an *Enterococcus* target nucleic acid including a forward primer including the oligonucleotide sequence: 5'-GGT AGC TAT GTA GGG AAG GGATAA ACG CTG A-3' (SEQ ID NO: 3) and a reverse primer including the oligonucleotide sequence: 5'-GCG CTA AGG AGC TTA ACT TCT GTG TTC G-3' (SEQ ID NO: 4); (iii) a primer pair for amplification of a *K. pneumoniae* target nucleic including a forward primer including the oligonucleotide sequence: 5'-GAC GGT TGT CCC GGT TTA AGC A-3' (SEQ ID NO: 5) and a reverse primer including the oligonucleotide sequence: 5'-GCT GGT ATC TTC GAC TGG TCT-3' (SEQ ID NO: 6); (iv) a primer pair for amplification of a *P. aeruginosa* target nucleic acid including a forward primer including the oligonucleotide sequence 5'-AGG CTG GGT GTG TAA GCG TTG T-3' (SEQ ID NO: 7) and a reverse primer including the oligonucleotide sequence 5'-CAA GCA ATT CGG TTG GAT ATC CGT T-3' (SEQ ID NO: 8); (v) a primer pair for amplification of an E. colitarget nucleic acid including a forward primer including the oligonucleotide sequence: 5'-GCA TTA ATC GAC GGT ATG TT GAC C-3' (SEQ ID NO: 59) and a reverse primer including the oligonucleotide sequence: 5'-CCT GCT GAA ACA GGT TTT CCC ACA TA-3' (SEQ ID NO: 61); and/or (vi) a first primer pair and/or a second primer pair for amplification of an *S. aureus* target nucleic acid, wherein the first primer pair includes a forward primer including the oligonucleotide sequence: 5'-GGT AAT GAA TTA CCT/i6diPr/TC TCT GCT GGTTTC TTC TT-3' (SEQ ID NO: 9) and a reverse primer including the oligonucleotide sequence: 5'-ACC AGC ATC TTC/i6diPr/GC ATC TTC TGT AAA-3' (SEQ ID NO: 10), and the second primer pair includes a forward primer including the oligonucleotide sequence: 5'-GAA GTT ATG TTT/i6diPr/CT ATT CGA ATC GTG GTC CAGT-3' (SEQ ID NO: 11) and a reverse primer including the oligonucleotide sequence: 5'-GTT GTA AAG CCA TGA TGC TCG TAA CCA-3' (SEQ ID NO: 12). In some embodiments, the amplifying of step (c) includes amplifying the *S. aureus* target nucleic acid in the lysate in the presence of the first primer pair. In some embodiments, the amplifying of step (c) includes amplifying the *S. aureus* target nucleic acid in the lysate in the presence of the second primer pair. In some embodiments, the amplifying of step (c) includes amplifying two *S. aureus* target nucleic acids in the presence of the first primer pair and the second primer pair to generate a first amplicon and a second amplicon. In some embodiments, the amplifying of step (c) results in the production of a third amplicon, wherein the nucleic acid sequence of the third amplicon includes the nucleic acid sequence of the first amplicon and the nucleic acid sequence of the second amplicon. In some embodiments, 10 CFU/mL or less (e.g., 10, 9, 8, 7, 6, 5, 4, 3, 2, or 1 CFU/mL) of bacteria in said whole blood sample is sufficient to permit amplification of the target bacterial nucleic acid. In some embodiments, 5 CFU/mL or less of bacteria in said whole blood sample is sufficient to permit amplification of the target bacterial nucleic acid. In some embodiments, 3 CFU/mL or less of bacteria in said whole blood sample is sufficient to permit amplification of the target bacterial nucleic acid. In some embodiments, 1 CFU/mL of bacteria in said whole blood sample is sufficient to permit amplification of the target bacterial nucleic acid.

In another aspect, the invention features an amplified lysate solution produced by a method for amplifying a target nucleic acid in a whole blood sample, the method including: (a) providing a first sample produced by lysing the red blood cells in a whole blood sample suspected of containing one or more bacterial cells from a subject, centrifuging the first sample to form a supernatant and a pellet, discarding some or all of the supernatant, and resuspending the pellet; (b) lysing remaining cells in the pellet to form a lysate including both subject cell nucleic acid and bacterial nucleic acid; and (c) providing the lysate of step (b) in a detection tube and amplifying two or more target bacterial nucleic acids therein to form an amplified lysate solution including two or more bacterial amplicons, wherein 10 CFUmL or less (e.g., 1, 2, 3, 4, 5, 6, 7, 8, 9, or 10 CFU/mL) of bacteria in said whole blood sample is sufficient to permit amplification of said two or more target bacterial nucleic acids. In some embodiments, step (a) includes resuspending the pellet without a prior wash step. In some embodiments, step (a) includes a wash step prior to resuspending the pellet. In some embodiments, the two or more target bacterial nucleic acids are characteristic of a single bacterial pathogen. In some embodiments, the amplifying of step (c) results in the production of a third amplicon. In some embodiments, the third amplicon is produced by partial run-through of strand synthesis. In some embodiments, about 10 CFU/mL or less of bacteria in said whole blood sample is sufficient to permit amplification of said two or more target bacterial nucleic acids. In some embodiments, about 5 CFU/mL or less of bacteria in said whole blood sample is sufficient to permit amplification of said two or more target bacterial nucleic acids. In some embodiments, about 3 CFU/mL or less of bacteria in said whole blood sample is sufficient to permit amplification of said two or more target bacterial nucleic acids. In some embodiments, about 1 CFU/mL of bacteria in said whole blood sample is sufficient to permit amplification of said two or more target bacterial nucleic acids.

In another aspect, the invention features a composition, including: (a) a portion of an extract from a whole blood sample suspected of containing a bacterial pathogen prepared by (i) lysing the red blood cells, (ii) centrifuging the sample to form a supernatant and a pellet, (iii) discarding some or all of the supernatant, and (iv) without washing, lysing any residual cells to form the extract; (b) a forward primer including an oligonucleotide sequence that is at least 80% identical to any one of SEQ ID NOs: 1, 3, 5, 7, 9, 11, 59, or 110; (c) a reverse including an oligonucleotide sequence that is at least 80% identical to any one of SEQ ID NOs: 2, 4, 6, 8, 10, 12, or 61; (d) a thermal stable polymerase; and (e) deoxynucleotide triphosphates, buffer, and magnesium. In some embodiments, the forward primer includes an oligonucleotide sequence that is at least 90% identical to any one of SEQ ID NOs: 1, 3, 5, 7, 9, 11, 59, or 110. In some embodiments, the forward primer includes an oligonucleotide sequence that is at least 95% identical to any one of SEQ ID NOs: 1, 3, 5, 7, 9, 11, 59, or 110. In some embodiments, the forward primer includes an oligonucleotide sequence selected from any one of SEQ ID NOs: 1, 3, 5, 7, 9, 11, 59, or 110. In some embodiments, the reverse primer includes an oligonucleotide sequence that is at least 90% identical to any one of SEQ ID NOs: 2, 4, 6, 8, 10, 12, or 61. In some embodiments, the reverse primer includes an oligonucleotide sequence that is at least 95% identical to any one of SEQ ID NOs: 2, 4, 6, 8, 10, 12, or 61. In some embodiments, the reverse primer includes an oligonucleotide sequence selected from any one of SEQ ID NOs: 2, 4, 6, 8, 10, 12, or 61.

In another aspect, the invention features a removable cartridge including a plurality of wells, wherein the removable cartridge includes any of the preceding compositions. In some embodiments, the removable cartridge includes a plurality of wells, wherein the removable cartridge includes one or more of the following: (a) a first well including a composition including: (a') a liquid sample, wherein the liquid sample (i) is suspected of containing an *A. baumannii* target nucleic acid, or (ii) contains an *A. baumannii* amplicon generated by amplifying the *A. baumannii* target nucleic acid; and (b') within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, wherein the magnetic particles include a first population of magnetic particles conjugated to a first nucleic acid probe including the oligonucleotide sequence: 5'-TGA GGC TTG ACT ATA CAA CAC C-3' (SEQ ID NO: 15), and a second population of magnetic particles conjugated to a second nucleic acid probe including the oligonucleotide sequence: 5'-CTA AAA TGA ACA GAT AAA GTA AGA TTC AA-3' (SEQ ID NO: 16); (b) a second well including a composition including: (a") a liquid sample, wherein the liquid sample (i) is suspected of containing an *Enterococcus* target nucleic acid, or (ii) contains an *Enterococcus* amplicon generated by amplifying the *Enterococcus* target nucleic acid; and (b') within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, wherein the magnetic particles include a first population of magnetic particles conjugated to a first nucleic acid probe including the oligonucleotide sequence: 5'-AAA ACT TAT ATG ACT TCA AAT CCA GTT TT-3' (SEQ ID NO: 19) or 5'-AAA ACT TAT GTG ACT TCA AAT CCA GTT TT-3' (SEQ ID NO: 111), and a second population of magnetic particles conjugated to a second nucleic acid probe including the oligonucleotide sequence: 5'-TTT ACT CAA TAA AAG ATA ACA CCA CAG-3' (SEQ ID NO: 20) or 5'-TTT ACT CAA TAA AAG ATA ACA CCA CAG T-3' (SEQ ID NO: 112); (c) a third well including a composition including: (a''') a liquid sample, wherein the liquid sample (i) is suspected of containing an *Enterococcus* target nucleic acid, or (ii) contains an *Enterococcus* amplicon generated by amplifying the *Enterococcus* target nucleic acid; and (b''') within the liquid sample, from 1×10⁵ to 1×10¹³ magnetic particles per milliliter of the liquid sample, the magnetic particles having a mean diameter of from 700 nm to 950 nm, a $T_2$ relaxivity per particle of from 1×10⁴ to 1×10¹² mM⁻¹s⁻¹, wherein the magnetic particles include a first population of magnetic particles conjugated to a first nucleic acid probe including the oligonucleotide sequence: 5'-TGG ATA AGT AAA AGC AAC TTG GTT-3' (SEQ ID NO: 23), and a second population of magnetic particles conjugated to a second nucleic acid probe including the oligonucleotide sequence: 5'-AAT GAA GAT TCA ACT CAA TAA GAA ACA ACA-3' (SEQ ID NO: 24); (d) a fourth well including a composition including: (a'''') a liquid sample, wherein the liquid sample (i) is suspected of containing a *K. pneumoniae* target nucleic acid, or (ii) contains a *K. pneumoniae* amplicon generated by amplifying the *K. pneumoniae* target nucleic acid; and (b'''') within the liquid sample, from 1×10⁶ to 1×10¹³ magnetic particles per milliliter of the liquid sample, the magnetic particles having a mean diameter of from 700 nm to 950 nm, a $T_2$ relaxivity per particle of from 1×10⁴ to 1×10¹² mM⁻¹s⁻¹, wherein the magnetic particles include a first population of magnetic particles conjugated to a first nucleic acid probe including the oligonucleotide sequence: 5'-TAC CAA GGC GCT TGA GAG AAC TC-3' (SEQ ID NO: 27), and a second population of magnetic particles conjugated to a second nucleic acid probe including the oligonucleotide sequence: 5'-CTG GTG TGT AGG TGA AGT C-3' (SEQ ID NO: 28); (e) a fifth well including a composition including: (a''''') a liquid sample, wherein the liquid sample (i) is suspected of containing a *P. aeruginosa* target nucleic acid, or (ii) contains a *P. aeruginosa* amplicon generated by amplifying the *P. aeruginosa* target nucleic acid; and (b''''') within the liquid sample, from 1×10⁶ to 1×10¹³ magnetic particles per milliliter of the liquid sample, the magnetic particles having a mean diameter of from 700 nm to 950 nm, a $T_2$ relaxivity per particle of from 1×10⁴ to 1×10¹² mM⁻¹s⁻¹, wherein the magnetic particles include a first population of magnetic particles conjugated to a first nucleic acid probe including the oligonucleotide sequence: 5'-GTG TGT TGT AGG GTG AAG TCG AC-3' (SEQ ID NO: 31) or 5'-TCT GAC GAT TGT GTG TTG TAA GG-3' (SEQ ID NO: 114), and a second population of magnetic particles conjugated to a second nucleic acid probe including the oligonucleotide sequence: 5'-CAC CTT GAA ATC ACA TAC CTG A-3' (SEQ ID NO: 32) or 5'-GGA TAG ACG TAA GCC CAA GC-3' (SEQ ID NO: 115); (f) a sixth well including a composition including: (a'''''') a liquid sample, wherein the liquid sample (i) is suspected of containing an *S. aureus* target nucleic acid, or (ii) contains an *S. aureus* target nucleic acid amplicon generated from an amplification reaction; and (b'''''') within the liquid sample, from 1×10⁶ to 1×10¹³ magnetic particles per milliliter of the liquid sample, the magnetic particles having a mean diameter of from 700 nm to 950 nm, a $T_2$ relaxivity per particle of from 1×10⁴ to 1×10¹² mM⁻¹s⁻¹, the magnetic particles including a first population and a second population, the first population having a first nucleic acid probe and a second nucleic acid probe conjugated to their surface and the second population having a third nucleic acid probe and a fourth nucleic acid probe conjugated to their surface, wherein the first nucleic acid probe includes an oligonucleotide sequence of SEQ ID NO: 35, the second nucleic acid probe includes an oligonucleotide sequence of SEQ ID NO: 39, the third nucleic acid probe includes an oligonucleotide sequence of SEQ ID NO: 36, and the fourth nucleic acid probe includes an oligonucleotide sequence of SEQ ID NO: 40. In some embodiments, the magnetic particles have a $T_2$ relaxivity per particle of from 1×10⁹ to 1×10¹² mM-1s⁻¹. In some embodiments, the removable cartridge includes two or more of (a) through (f). In some embodiments, the removable cartridge includes three or more of (a) through (f). In some embodiments, the removable cartridge includes four or more of (a) through (f). In some embodiments, the removable cartridge includes five or more of (a) through (f). In some embodiments, the removable cartridge includes (a) through (f).

In another aspect, the invention features a removable cartridge including a plurality of wells, wherein the removable cartridge includes any of the preceding compositions. In some embodiments, the removable cartridge includes a plurality of wells, wherein the removable cartridge includes one or more of the following: (a) a first well including a composition including: (a') a liquid sample, wherein the liquid sample (i) is suspected of containing an *A. baumannii* target nucleic acid, or (ii) contains an *A. baumannii* amplicon generated by amplifying the *A. baumannii* target nucleic acid; and (b') within the liquid sample, from 1×10⁶ to 1×10¹³ magnetic particles per milliliter of the liquid sample, the magnetic particles having a mean diameter of from 700 nm to 950 nm, a $T_2$ relaxivity per particle of from 1×10⁴ to 1×10¹² mM⁻¹s⁻¹, wherein the magnetic particles include a first population of magnetic particles conjugated to a first nucleic acid probe including the oligonucleotide sequence: 5'-TGA GGC TTG ACT ATA CAA CAC C-3' (SEQ ID NO: 15), and a second population of magnetic particles conjugated to a second nucleic acid probe including the oligonucleotide sequence: 5'-CTA AAA TGA ACA GAT AAA GTA AGA TTC AA-3' (SEQ ID NO: 16); (b) a second well including a composition including: (a'') a liquid sample, wherein the liquid sample (i) is suspected of containing an *Enterococcus* target nucleic acid, or (ii) contains an *Enterococcus* amplicon generated by amplifying the *Enterococcus* target nucleic acid; and (b'') within the liquid sample, from 1×10⁶ to 1×10¹³ magnetic particles per milliliter of the liquid sample, the magnetic particles having a mean diameter of from 700 nm to 950 nm, a $T_2$ relaxivity per particle of from 1×10⁴ to 1×10¹² mM⁻¹s⁻¹, wherein the magnetic particles include a first population of magnetic particles conjugated to a first nucleic acid probe including the oligonucleotide sequence: 5'-AAA ACT TAT ATG ACT TCA AAT CCA GTT TT-3' (SEQ ID NO: 19) or 5'-AAA ACT TAT GTG ACT TCA AAT CCA GTT TT-3' (SEQ ID NO: 111), and a second population of magnetic particles conjugated to a second nucleic acid probe including the oligonucleotide sequence: 5'-TTT ACT CAA TAA AAG ATA ACA CCA CAG-3' (SEQ ID NO: 20) or 5'-TTT ACT CAA TAA AAG ATA ACA CCA CAG T-3' (SEQ ID NO: 112); (c) a third well including a composition including: (a''') a liquid sample, wherein the liquid sample (i) is suspected of containing an E. colitarget nucleic acid, or (ii) contains an *E. coli* amplicon generated by amplifying the *E. coli* target nucleic acid; and (b''') within the liquid sample, from 1×10⁶ to 1×10³ magnetic particles per milliliter of the liquid sample, the magnetic particles having a mean diameter of from 700 nm to 950 nm, a $T_2$ relaxivity per particle of from 1×10⁴ to 1×10¹² mM⁻¹s⁻¹, wherein the magnetic particles include a first population of magnetic particles conjugated to a first nucleic acid probe including the oligonucleotide sequence: 5'-AGT GAT GAT GAG TTG TTT GCC AGT G-3' (SEQ ID NO: 63), and a second population of magnetic particles conjugated to a second nucleic acid probe including the oligonucleotide sequence: 5'-TGA ATT GTC GCC GCG TGA CCA G-3' (SEQ ID NO: 64); (d) a fourth well including a composition including: (a'''') a liquid sample, wherein the liquid sample (i) is suspected of containing a *K. pneumoniae* target nucleic acid, or (ii) contains a *K. pneumoniae* amplicon generated by amplifying the *K. pneumoniae* target nucleic acid; and (b'''') within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, wherein the magnetic particles include a first population of magnetic particles conjugated to a first nucleic acid probe including the oligonucleotide sequence: 5'-TAC CAA GGC GCT TGA GAG AAC TC-3' (SEQ ID NO: 27), and a second population of magnetic particles conjugated to a second nucleic acid probe including the oligonucleotide sequence: 5'-CTG GTG TGT AGG TGA AGT C-3' (SEQ ID NO: 28); (e) a fifth well including a composition including: (a'''') a liquid sample, wherein the liquid sample (i) is suspected of containing a *P. aeruginosa* target nucleic acid, or (ii) contains a *P. aeruginosa* amplicon generated by amplifying the *P. aeruginosa* target nucleic acid; and (b'''') within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, wherein the magnetic particles include a first population of magnetic particles conjugated to a first nucleic acid probe including the oligonucleotide sequence: 5'-GTG TGT TGT AGG GTG AAG TCG AC-3' (SEQ ID NO: 31) or 5'-TCT GAC GAT TGT GTG TTG TAA GG-3' (SEQ ID NO: 114), and a second population of magnetic particles conjugated to a second nucleic acid probe including the oligonucleotide sequence: 5'-CAC CTT GAA ATC ACA TAC CTG A-3' (SEQ ID NO: 32) or 5'-GGA TAG ACG TAA GCC CAA GC-3' (SEQ ID NO: 115); (f) a sixth well including a composition including: (a'''') a liquid sample, wherein the liquid sample (i) is suspected of containing an *S. aureus* target nucleic acid, or (ii) contains an *S. aureus* target nucleic acid amplicon generated from an amplification reaction; and (b'''') within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, the magnetic particles including a first population and a second population, the first population having a first nucleic acid probe and a second nucleic acid probe conjugated to their surface and the second population having a third nucleic acid probe and a fourth nucleic acid probe conjugated to their surface, wherein the first nucleic acid probe includes an oligonucleotide sequence of SEQ ID NO: 35, the second nucleic acid probe includes an oligonucleotide sequence of SEQ ID NO: 39, the third nucleic acid probe includes an oligonucleotide sequence of SEQ ID NO: 36, and the fourth nucleic acid probe includes an oligonucleotide sequence of SEQ ID NO: 40. In some embodiments, the magnetic particles have a $T_2$ relaxivity per particle of from $1\times10^9$ to $1\times10^{12}$ mM$^{-1}$s$^{-1}$. In some embodiments, the removable cartridge includes two or more of (a) through (f). In some embodiments, the removable cartridge includes three or more of (a) through (f). In some embodiments, the removable cartridge includes four or more of (a) through (f). In some embodiments, the removable cartridge includes five or more of (a) through (f). In some embodiments, the removable cartridge includes (a) through (f).

In some embodiments of any of the preceding aspects, the removable cartridge further includes one or more chambers for holding a plurality of reagent modules for holding one or more assay reagents. In some embodiments, the removable cartridge further includes a chamber including beads for lysing cells. In some embodiments, the removable cartridge further includes a chamber including a polymerase. In some embodiments, the removable cartridge further includes a chamber including one or more primers. In some embodiments, the one or more primers include oligonucleotide sequences selected from SEQ ID NOs: 1-14, 59, 61, and 110.

In another aspect, the invention features a method of diagnosing a bloodstream infection or sepsis in a subject, the method including: detecting, in a liquid sample obtained from the patient, the presence of an *A. baumannii* cell, an *Enterococcus* species, a *K. pneumoniae* cell, a *P. aeruginosa* cell, an *E. coli* cell, or a *S. aureus* cell according to the method of any one of the preceding methods; wherein the presence of an *A. baumannii* cell, an *Enterococcus* species, a *K. pneumoniae* cell, a *P. aeruginosa* cell, an *E. coli* cell, or a *S. aureus* cell in the liquid sample identifies the subject as one who may have a bloodstream infection or sepsis. In some embodiments, the method includes detecting the presence of at least two of an *A. baumannii* cell, an *Enterococcus* species, a *K. pneumoniae* cell, a *P. aeruginosa* cell, an *E. coli* cell, and a *S. aureus* cell. In some embodiments, the method includes detecting the presence of at least three of an *A. baumannii* cell, an *Enterococcus* species, a *K. pneumoniae* cell, a *P. aeruginosa* cell, an *E. coli* cell, and a *S. aureus* cell. In some embodiments, the method includes detecting the presence of at least four of an *A. baumannii* cell, an *Enterococcus* species, a *K. pneumoniae* cell, a *P. aeruginosa* cell, an *E. coli* cell, and a *S. aureus* cell. In some embodiments, the method includes detecting the presence of at least five of an *A. baumannii* cell, an *Enterococcus* species, a *K. pneumoniae* cell, a *P. aeruginosa* cell, an *E. coli* cell, and a *S. aureus* cell. In some embodiments, the method includes detecting the presence of an *A. baumannii* cell, an *Enterococcus* species, a *K. pneumoniae* cell, a *P. aeruginosa* cell, an *E. coli* cell, and a *S. aureus* cell. In some embodiments, the *Enterococcus* species is *Enterococcus faecium* or *Enterococcus faecalis*. In some embodiments, the *Enterococcus* species is *Enterococcus faecium*.

In another aspect, the invention features a method of diagnosing a bloodstream infection or sepsis in a subject, the method including: detecting, in a liquid sample obtained from the patient, detecting the presence of a microbial species according to any one of the preceding methods; wherein the presence of a microbial species in the liquid sample identifies the subject as one who may have a bloodstream infection or sepsis.

In another aspect, the invention features a method of treating a bloodstream infection or sepsis in a subject, the method including: detecting, in a liquid sample obtained from the patient, the presence of an *A. baumannii* cell, an *Enterococcus* species, a *K. pneumoniae* cell, a *P. aeruginosa* cell, an *E. coli* cell, or a *S. aureus* cell according to any one of the preceding methods, wherein the presence of an *A. baumannii* cell, an *Enterococcus* species, a *K. pneumoniae* cell, a *P. aeruginosa* cell, an *E. coli* cell, or a *S. aureus* cell in the liquid sample identifies the subject as one who may have a bloodstream infection or sepsis; and (c) administering a bloodstream infection or sepsis therapy to the subject identified as one who may have a bloodstream infection or sepsis. In some embodiments, the method includes detecting the presence of at least two of an *A. baumannii* cell, an *Enterococcus* species, a *K. pneumoniae* cell, a *P. aeruginosa* cell, an *E. coli* cell, and a *S. aureus* cell. In some embodiments, the method includes detecting the presence of at least three of an *A. baumannii* cell, an *Enterococcus* species, a *K.* pneumoniae cell, a *P. aeruginosa* cell, an *E. coli* cell, and a *S. aureus* cell. In some embodiments, the method includes detecting the presence of at least four of an *A. baumannii* cell, an *Enterococcus* species, a *K. pneumoniae* cell, a *P. aeruginosa* cell, an *E. coli* cell, and a *S. aureus* cell. In some embodiments, the method includes detecting the presence of at least five of an *A. baumannii* cell, an *Enterococcus* species, a *K. pneumoniae* cell, a *P. aeruginosa* cell, an *E. coli* cell, and a *S. aureus* cell. In some embodiments, the method includes detecting the presence of an *A. baumannii* cell, an *Enterococcus* species, a *K. pneumoniae* cell, a *P. aeruginosa* cell, an *E. coli* cell, and a *S. aureus* cell. In some embodiments, the *Enterococcus* species is *Enterococcus faecium* or *Enterococcus faecalis*. In some embodiments, the *Enterococcus* species is *Enterococcus faecium*.

In another aspect, the invention features a method of treating a bloodstream infection or sepsis in a subject, the method including: detecting, in a liquid sample obtained from the patient, the presence of a microbial species according to any one of the preceding methods, wherein the presence of a microbial species in the liquid sample identifies the subject as one who may have a bloodstream infection or sepsis; and (c) administering a bloodstream infection or sepsis therapy to the subject identified as one who may have a bloodstream infection or sepsis.

In some embodiments of any of the preceding aspects, the bloodstream infection is bacteremia.

In some embodiments of any of the preceding aspects, the subject is a human.

Other features and advantages of the invention will be apparent from the following detailed description, drawings, and the claims.

BRIEF DESCRIPTION OF THE DRAWINGS

FIG. 1A is a table showing exemplary targets of the invention.

FIGS. 1B-1E are tables showing exemplary panels of the invention.

FIG. 5A shows results from 5 *A. baumannii* (Ab) strains, FIG. 5B shows results from 5 *E. faecium* (Efm) strains, FIG. 5C shows results from 5 *E. faecalis* (Efs) strains, FIG. 5D shows results from 5 *K. pneumoniae* (Kp) strains, and FIG. 5E shows results from 5 *P. aeruginosa* (Pa) strains. Internal control (IC) served as a positive control. N=4.

FIG. 6A shows results from *Acinetobacter* spp. that are very close near neighbors to *Acinetobacter baumannii*; FIG. 6B shows results from *S. warneri* species, near neighbor to *S. aureus*; and FIG. 6C shows results from *E. coli* and *A. hydrophila* strains that are close neighbors to *K. pneumoniae*. All assays were performed with isolated DNA at $10^4$ and 10 cp/reaction spiked into negative whole blood lysate. IC served as a positive control. N=4 for each experiment.

FIG. 7 is a table showing spike levels determined by parallel plating of 200 µl of cell bullet dilutions that were also used for spiking into healthy blood (0.4 ml into 40 ml) (see Example 5). Ab-3 and Ab-5 indicate 3 CFU/mL and 5 CFU/mL targets, respectively, for *A. baumannii*. Sa-3 and Sa-5 indicate 3 CFU/mL and 5 CFU/mL targets, respectively, for *S. aureus*.

FIG. 8 is a table showing average (Avg), standard deviation (stdev) and coefficient of variation (% CV) of all $T_2$ signals obtained during an LoD study of healthy blood double-spiked with the indicated bacterial species (see Example 5). Gray-shaded fields/bold numbers show the signals for spiked species in that assay series. The fields in the % FN (% false-negative) rows depict the percent drop-outs observed for that assay series. False-negative values ≤15% equate to ≥85% detection with a confidence of 95%. The dark gray-shaded field depicts a detection level <85%. % FP indicates % false-positive. % FP indicates false positive samples.

FIG. 9 is a table summarizing the results of the assay sensitivities of the manual bacterial panel assay described in Example 3 in contrived healthy blood specimens.

FIG. 10 is a table summarizing the results of clinical discard specimens analyzed by the bacterial panel assay described in Example 3. Blood culture (BC) species identification and bacterial panel assay identification are shown in adjacent columns. Gray-shaded fields depict concordant results. Light gray-shaded fields (#20-027 and 20-254) are deemed concordant since the BC report lacks the exact species identification and only lists a family identification. Fields labeled with circles are possibly false positives or species that were not identified by BC due to lack of growth.

DETAILED DESCRIPTION OF EMBODIMENTS OF THE INVENTION

Figure 2A:
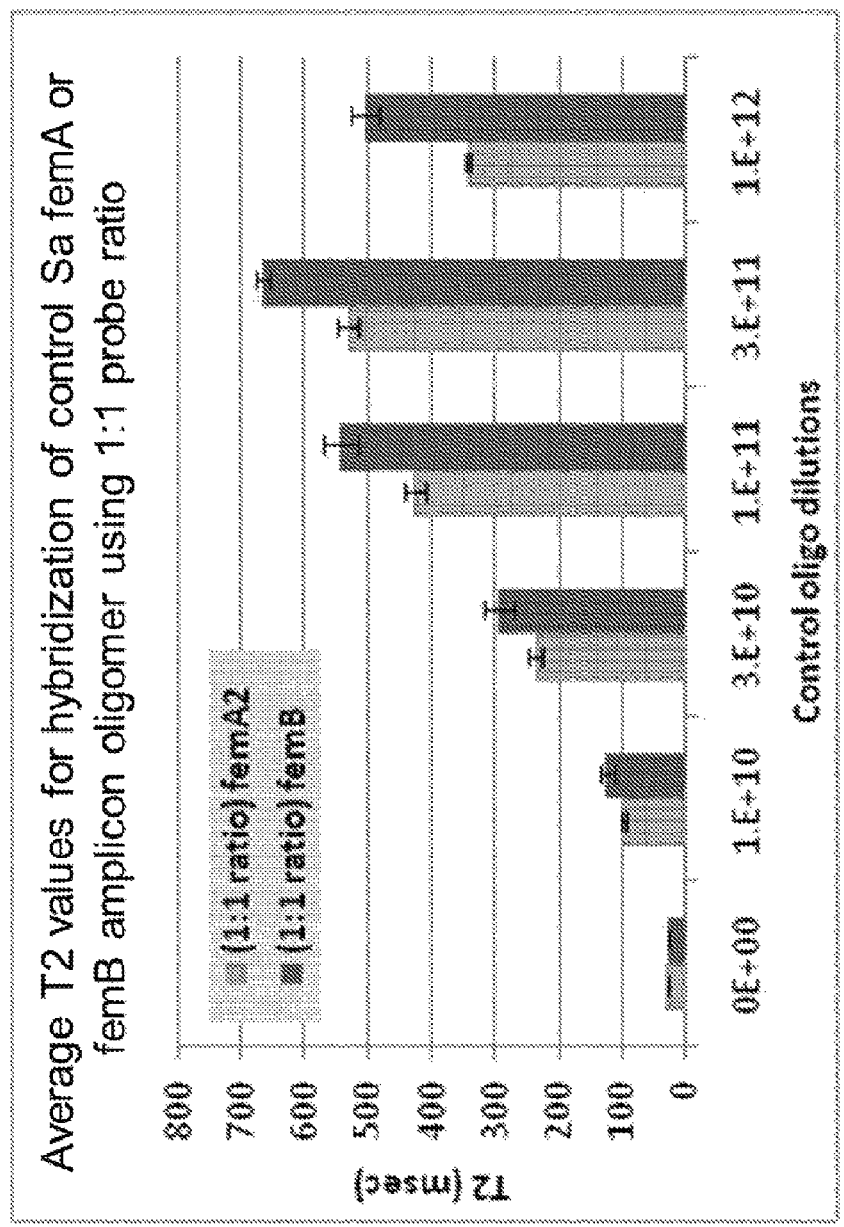
FIGS. 2A-2C are graphs showing titration profiles obtained following hybridization of the indicated control femA or femB oligomer with scrambled magnetic particle pairs (see Example 2). Control oligomer concentration ranged from 0 to $1\times10^{12}$ molecules/hybridization reaction. The femA probe:femB probe ratio on each particle was 1:1 (FIG. 2A), 1:2 (FIG. 2B), or 2:1 (FIG. 2C). *S. aureus*, Sa.

The invention provides methods, systems, cartridges, and panels for detection of pathogens (including bacterial pathogens), for example, for detection of pathogens in biological samples. In several embodiments, the analyte is derived from a microbial pathogen. In some embodiments, the analyte is derived from a Gram-negative bacterium, a Gram-positive bacterium, or a fungal pathogen (e.g., yeast (e.g., *Candida* spp.) or *Aspergillus* spp.). In some embodiments, the analyte is derived from a bacterial pathogen, including *Acinetobacter* spp. (e.g., *Acinetobacter baumannii*, *Acinetobacter pittii*, and *Acinetobacter nosocomialis*), Enterobacteriaceae spp., *Enterococcus* spp. (e.g., *Enterococcus faecium* (including *E. faecium* with resistance marker vanA/B) and *Enterococcus faecalis*), *Klebsiella* spp. (e.g., *Klebsiella pneumoniae* (including, e.g., *K. pneumoniae* with resistance marker KPC) and *Klebsiella oxytoca*), *Pseudomonas* spp. (e.g., *Pseudomonas aeruginosa*), *Staphylococcus* spp. (including, e.g., *Staphylococcus aureus* (e.g., *S. aureus* with resistance marker mecA), *Staphylococcus haemolyticus*, *Staphylococcus lugdunensis*, *Staphylococcus maltophilia*, *Staphylococcus saprophyticus*, coagulase-positive *Staphylococcus* species, and coagulase-negative (CONS) *Staphylococcus* species), *Streptococcus* spp. (e.g., *Streptococcus mitis, Streptococcus pneumoniae, Streptococcus agalactiae, Streptococcus anginosa, Streptococcus bovis, Streptococcus dysgalactiae, Streptococcus mutans, Streptococcus sanguinis*, and *Streptococcus pyogenes*), *Escherichia* spp. (e.g., *Escherichia coli*), *Stenotrophomonas* spp. (e.g., *Stenotrophomonas maltophilia*), *Proteus* spp. (e.g., *Proteus mirabilis* and *Proteus vulgaris*), *Serratia* spp. (e.g., *Serratia marcescens*), *Citrobacter* spp. (e.g., *Citrobacter freundii* and *Citrobacter kosen*), *Haemophilus* spp. (e.g., *Haemophilus influenzae*), *Listeria* spp. (e.g., *Listeria monocytogenes*), *Neisseria* spp. (e.g., *Neisseria meningitidis*), *Bacteroides* spp. (e.g., *Bacteroides fragilis*), *Burkholderia* spp. (e.g., *Burkholderia cepacia*), *Campylobacter* (e.g., *Campylobacter jejuni* and *Campylobacter coli*), *Clostridium* spp. (e.g., *Clostridium perfringens*), *Kingella* spp. (e.g., *Kingella kingae*), *Morganella* spp. (e.g., *Morganella* morgana), *Prevotella* spp. (e.g., *Prevotella buccae, Prevotella intermedia*, and *Prevotella melaninogenica*), *Propionibacterium* spp. (e.g., *Propionibacterium acnes*), *Salmonella* spp. (e.g., *Salmonella enterica*), *Shigella* spp. (e.g., *Shigella dysenteriae* and *Shigella flexneri*), and *Enterobacter* spp. (e.g., *Enterobacter aerogenes* and *Enterobacter cloacae*). In some embodiments, the methods, systems, cartridges, and panels of the invention may further detect antimicrobial resistance markers, including but not limited to vanA, vanB, mecA, IMP, CTX-M, KPC, NDM, OXA, VIM, and FKS. In some embodiments, the methods, systems, cartridges, and panels of the invention may further detect additional pathogens, for example, fungal pathogens including *Candida* spp. (e.g., *Candida albicans, Candida guilliermondii, Candida glabrata, Candida krusei, Candida lusitaniae, Candida parapsilosis, Candida dublinensis*, and *Candida tropicalis*) and *Aspergillus* spp. (e.g., *Aspergillus fumigatus*). The invention also provides methods, systems, cartridges, and panels for detection of multiple amplicons derived from a single pathogen (e.g., microbial) species. In some embodiments, the methods, systems, cartridges, and panels of the invention may be used in the diagnosis and/or treatment of disease, for example, invasive bacterial infection, BSIs including bacteremia, sepsis, septic shock, and diseases that may manifest with similar symptoms to diseases caused by or associated with microbial pathogens, e.g., systemic inflammatory response syndrome (SIRS).

In some embodiments, the methods and systems of the invention employ magnetic particles. In some embodiments, the methods and systems employ an NMR unit, optionally one or more magnetic assisted agglomeration (MAA) units, optionally one or more incubation stations at different temperatures, optionally one or more vortexers, optionally one or more centrifuges, optionally a fluidic manipulation station, optionally a robotic system, and optionally one or more modular cartridges, as described in International Patent Application Publication No. WO 2012/054639, which is incorporated herein by reference in its entirety. In some embodiments, the methods of the invention are performed using a fully-automated system. The methods, systems, devices, panels, and cartridges of the invention can be used to assay a biological sample (e.g., whole blood, serum, plasma, cerebrospinal fluid (CSF), urine, synovial fluid, breast milk, sweat, tears, saliva, semen, feces, vaginal fluid or tissue, sputum, nasopharyngeal aspirate or swab, lacrimal fluid, mucous, or epithelial swab (buccal swab), and tissues (e.g., tissue homogenates), organs, bones, teeth, among others).

Definitions

The terms "aggregation," "agglomeration," and "clustering" are used interchangeably in the context of the magnetic particles described herein and mean the binding of two or more magnetic particles to one another, for example, via a multivalent analyte, multimeric form of analyte, antibody, nucleic acid molecule, or other binding molecule or entity. In some instances, magnetic particle agglomeration is reversible. Such aggregation may lead to the formation of "aggregates," which may include amplicons and magnetic particles bearing binding moieties.

The terms "amplification" or "amplify" or derivatives thereof as used herein mean one or more methods known in the art for copying a target or template nucleic acid, thereby increasing the number of copies of a selected nucleic acid sequence. Amplification may be exponential or linear. A target or template nucleic acid may be either DNA or RNA. The sequences amplified in this manner form an "amplified region" or "amplicon." Primer probes can be readily designed by those skilled in the art to target a specific template nucleic acid sequence.

By "analyte" is meant a substance or a constituent of a sample to be analyzed. Exemplary analytes include one or more species of one or more of the following: a protein, a peptide, a polypeptide, an amino acid, a nucleic acid, an oligonucleotide, RNA, DNA, an antibody, a carbohydrate, a polysaccharide, glucose, a lipid, a gas (e.g., oxygen or carbon dioxide), an electrolyte (e.g., sodium, potassium, chloride, bicarbonate, blood urea nitrogen (BUN), magnesium, phosphate, calcium, ammonia, lactate), a lipoprotein, cholesterol, a fatty acid, a glycoprotein, a proteoglycan, a lipopolysaccharide, a cell surface marker (e.g., a cell surface protein of a pathogen), a cytoplasmic marker (e.g., CD4/CD8 or CD4/viral load), a therapeutic agent, a metabolite of a therapeutic agent, a marker for the detection of a weapon (e.g., a chemical or biological weapon), an organism, a pathogen, a pathogen byproduct, a parasite (e.g., a protozoan or a helminth), a protist, a fungus (e.g., yeast or mold), a bacterium, an actinomycete, a cell (e.g., a whole cell, a tumor cell, a stem cell, a white blood cell, a T cell (e.g., displaying CD3, CD4, CD8, IL2R, CD35, or other surface markers), or another cell identified with one or more specific markers), a virus, a prion, a plant component, a plant by-product, algae, an algae by-product, plant growth hormone, an insecticide, a man-made toxin, an environmental toxin, an oil component, and components derived therefrom.

A "biological sample" is a sample obtained from a subject including but not limited to whole blood, serum, plasma, cerebrospinal fluid (CSF), urine, synovial fluid, breast milk, sweat, tears, saliva, semen, feces, vaginal fluid or tissue, sputum, nasopharyngeal aspirate or swab, lacrimal fluid, mucous, or epithelial swab (buccal swab), tissues (e.g., tissue homogenates), organs, bones, teeth, among others).

As used herein, the term "small molecule" refers to a drug, medication, medicament, or other chemically synthesized compound that is contemplated for human therapeutic use.

A "biomarker" is a biological substance that can be used as an indicator of a particular disease state or particular physiological state of an organism, generally a biomarker is a protein or other native compound measured in bodily fluid whose concentration reflects the presence or severity or staging of a disease state or dysfunction, can be used to monitor therapeutic progress of treatment of a disease or disorder or dysfunction, or can be used as a surrogate measure of clinical outcome or progression.

By an "isolated" nucleic acid molecule is meant a nucleic acid molecule that is removed from the environment in which it naturally occurs. For example, a naturally-occurring nucleic acid molecule present in the genome of cell or as part of a gene bank is not isolated, but the same molecule, separated from the remaining part of the genome, as a result of, e.g., a cloning event, amplification, or enrichment, is "isolated." Typically, an isolated nucleic acid molecule is free from nucleic acid regions (e.g., coding regions) with which it is immediately contiguous, at the 5' or 3' ends, in the naturally occurring genome. Such isolated nucleic acid molecules can be part of a vector or a composition and still be isolated, as such a vector or composition is not part of its natural environment.

As used herein, "linked" means attached or bound by covalent bonds, non-covalent bonds, and/or linked via Van der Waals forces, hydrogen bonds, and/or other intermolecular forces.

The term "magnetic particle" refers to particles including materials of high positive magnetic susceptibility such as paramagnetic compounds, superparamagnetic compounds, and magnetite, gamma ferric oxide, or metallic iron.

As used herein, "nonspecific reversibility" refers to the colloidal stability and robustness of magnetic particles against non-specific aggregation in a liquid sample and can be determined by subjecting the particles to the intended assay conditions in the absence of a specific clustering moiety (i.e., an analyte or an agglomerator). For example, nonspecific reversibility can be determined by measuring the $T_2$ values of a solution of magnetic particles before and after incubation in a uniform magnetic field (defined as <5000 ppm) at 0.45 T for 3 minutes at 37° C. Magnetic particles are deemed to have nonspecific reversibility if the difference in $T_2$ values before and after subjecting the magnetic particles to the intended assay conditions vary by less than 10% (e.g., vary by less than 9%, 8%, 6%, 4%, 3%, 2%, or 1%). If the difference is greater than 10%, then the particles exhibit irreversibility in the buffer, diluents, and matrix tested, and manipulation of particle and matrix properties (e.g., coating and buffer formulation) may be required to produce a system in which the particles have nonspecific reversibility. In another example, the test can be applied by measuring the $T_2$ values of a solution of magnetic particles before and after incubation in a gradient magnetic field 1 Gauss/mm-10000 Gauss/mm.

As used herein, the term "NMR relaxation rate" refers to a measuring any of the following in a sample $T_1$, $T_2$, $T_1/T_2$ hybrid, $T_{1rho}$, $T_{2rho}$, and $T_2^*$. The systems and methods of the invention are designed to produce an NMR relaxation rate characteristic of whether an analyte is present in the liquid sample. In some instances the NMR relaxation rate is characteristic of the quantity of analyte present in the liquid sample.

As used herein, the term "$T_1/T_2$ hybrid" refers to any detection method that combines a $T_1$ and a $T_2$ measurement. For example, the value of a $T_1/T_2$ hybrid can be a composite signal obtained through the combination of, ratio, or difference between two or more different $T_1$ and $T_2$ measurements. The $T_1/T_2$ hybrid can be obtained, for example, by using a pulse sequence in which $T_1$ and $T_2$ are alternatively measured or acquired in an interleaved fashion. Additionally, the $T_1/T_2$ hybrid signal can be acquired with a pulse sequence that measures a relaxation rate that is comprised of both $T_1$ and $T_2$ relaxation rates or mechanisms.

A "pathogen" means an agent causing disease or illness to its host, such as an organism or infectious particle, capable of producing a disease in another organism, and includes but is not limited to bacteria, viruses, protozoa, prions, yeast and fungi or pathogen by-products. "Pathogen by-products" are those biological substances arising from the pathogen that can be deleterious to the host or stimulate an excessive host immune response, for example pathogen antigen/s, metabolic substances, enzymes, biological substances, or toxins.

By "pathogen-associated analyte" is meant an analyte characteristic of the presence of a pathogen (e.g., a bacterium, fungus, or virus) in a sample. The pathogen-associated analyte can be a particular substance derived from a pathogen (e.g., a protein, nucleic acid, lipid, polysaccharide, or any other material produced by a pathogen) or a mixture derived from a pathogen (e.g., whole cells, or whole viruses). In certain instances, the pathogen-associated analyte is selected to be characteristic of the genus, species, or specific strain of pathogen being detected. Alternatively, the pathogen-associated analyte is selected to ascertain a property of the pathogen, such as resistance to a particular therapy. In some embodiments, a pathogen-associated analyte may be a target nucleic acid that has been amplified. In other embodiments, a pathogen-associated analyte may be a host antibody or other immune system protein that is expressed in response to an infection by a pathogen (e.g., an IgM antibody, an IgA antibody, an IgG antibody, or a major histocompatibility complex (MHC) protein).

By "pulse sequence" or "RF pulse sequence" is meant one or more radio frequency pulses to be applied to a sample and designed to measure, e.g., certain NMR relaxation rates, such as spin echo sequences. A pulse sequence may also include the acquisition of a signal following one or more pulses to minimize noise and improve accuracy in the resulting signal value.

As used herein, the term "signal" refers to an NMR relaxation rate, frequency shift, susceptibility measurement, diffusion measurement, or correlation measurements.

As used herein, reference to the "size" of a magnetic particle refers to the average diameter for a mixture of the magnetic particles as determined by microscopy, light scattering, or other methods.

A "subject" is an animal, preferably a mammal (including, for example, rodents (e.g., mice or rats), farm animals (e.g., cows, sheep, horses, and donkeys), pets (e.g., cats and dogs), or primates (e.g., non-human primates and humans)). In particular embodiments, the subject is a human. A subject may be a patient (e.g., a patient having or suspected of having a disease associated with or caused by a pathogen).

As used herein, the term "substantially monodisperse" refers to a mixture of magnetic particles having a polydispersity in size distribution as determined by the shape of the distribution curve of particle size in light scattering measurements. The FWHM (full width half max) of the particle distribution curve less than 25% of the peak position is considered substantially monodisperse. In addition, only one peak should be observed in the light scattering experiments and the peak position should be within one standard deviation of a population of known monodisperse particles.

By "$T_2$ relaxivity per particle" is meant the average $T_2$ relaxivity per particle in a population of magnetic particles.

As used herein, "unfractionated" refers to an assay in which none of the components of the sample being tested are removed following the addition of magnetic particles to the sample and prior to the NMR relaxation measurement.

It is contemplated that units, methods, systems, and processes of the claimed invention encompass variations and adaptations developed using information from the embodiments described herein. Throughout the description, where units and systems are described as having, including, or including specific components, or where processes and methods are described as having, including, or including specific steps, it is contemplated that, additionally, there are units and systems of the present invention that consist essentially of, or consist of, the recited components, and that there are processes and methods according to the present invention that consist essentially of, or consist of, the recited processing steps. It should be understood that the order of steps or order for performing certain actions is immaterial, unless otherwise specified, so long as the invention remains operable. Moreover, in many instances two or more steps or actions may be conducted simultaneously.

Magnetic Particles and NMR-Based Detection

The methods and systems of the invention may involve use of magnetic particles and NMR. The magnetic particles can be coated with a binding moiety (e.g., oligonucleotide, antibody, etc.) such that in the presence of analyte, or multivalent binding agent, aggregates are formed. Aggregation depletes portions of the sample from the microscopic magnetic non-uniformities that disrupt the solvent's $T_2$ signal, leading to an increase in $T_2$ relaxation (see, e.g., FIG. 3 of International Patent Application Publication No. WO 2012/054639, which is incorporated herein by reference in its entirety).

The $T_2$ measurement is a single measure of all spins in the ensemble, measurements lasting typically 1-10 seconds, which allows the solvent to travel hundreds of microns, a long distance relative to the microscopic non-uniformities in the liquid sample. Each solvent molecule samples a volume in the liquid sample and the $T_2$ signal is an average (net total signal) of all (nuclear spins) on solvent molecules in the sample; in other words, the $T_2$ measurement is a net measurement of the entire environment experienced by a solvent molecule, and is an average measurement of all microscopic non-uniformities in the sample.

The observed $T_2$ relaxation rate for the solvent molecules in the liquid sample is dominated by the magnetic particles, which in the presence of a magnetic field form high magnetic dipole moments. In the absence of magnetic particles, the observed $T_2$ relaxation rates for a liquid sample are typically long (i.e., $T_2$ (water)=approximately 2000 ms, $T_2$ (blood)=approximately 1500 ms). As particle concentration increases, the microscopic non-uniformities in the sample increase and the diffusion of solvent through these microscopic non-uniformities leads to an increase in spin decoherence and a decrease in the $T_2$ value. The observed $T_2$ value depends upon the particle concentration in a non-linear fashion, and on the relaxivity per particle parameter.

In the aggregation assays of the invention, the number of magnetic particles, and if present the number of agglomerant particles, remain constant during the assay. The spatial distribution of the particles changes when the particles cluster. Aggregation changes the average "experience" of a solvent molecule because particle localization into clusters is promoted rather than more even particle distributions. At a high degree of aggregation, many solvent molecules do not experience microscopic non-uniformities created by magnetic particles and the $T_2$ approaches that of solvent. As the fraction of aggregated magnetic particles increases in a liquid sample, the observed $T_2$ is the average of the non-uniform suspension of aggregated and single (unaggregated) magnetic particles. The assays of the invention are designed to maximize the change in $T_2$ with aggregation to increase the sensitivity of the assay to the presence of analytes, and to differences in analyte concentration.

In some embodiments, the methods of the invention involve contacting a solution (e.g., a biological sample) with between from $1\times10^6$ to $1\times10^{13}$ magnetic particles per milliliter of the liquid sample (e.g., from $1\times10^6$ to $1\times10^8$, $1\times10^7$ to $1\times10^8$, $1\times10^7$ to $1\times10^9$, $1\times10^6$ to $1\times10^{10}$, $1\times10^9$ to $1\times10^{11}$, or $1\times10^{10}$ to $1\times10^{13}$ magnetic particles per milliliter).

In some embodiments, the magnetic particles used in the methods and systems of the invention have a mean diameter of from 150 nm to 1200 nm (e.g., from 150 to 250, 200 to 350, 250 to 450, 300 to 500, 450 to 650, 500 to 700 nm, 700 to 850, 800 to 950, 900 to 1050, or from 1000 to 1200 nm). For example, in some embodiments, the magnetic particles used in the methods of the invention may have a mean diameter of from 150 nm to 699 nm (e.g., from 150 to 250, 200 to 350, 250 to 450, 300 to 500, 450 to 650, or from 500 to 699 nm). In other embodiments, the magnetic particles used in the methods of the invention may have a mean diameter of from 700 nm to 1200 nm (e.g., from 700 to 850, 800 to 950, 900 to 1050, or from 1000 to 1200 nm). In particular embodiments, the magnetic particles may have a mean diameter of from 700 nm to 950 nm (e.g., from 700 to 750, 700 to 800, 700 to 850, or from 700 to 900 nm).

In some embodiments, the magnetic particles used in the methods of the invention may have a $T_2$ relaxivity per particle of from $1\times10^8$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ mM$^{-1}$s$^{-1}$). In some embodiments, the magnetic particles have a $T_2$ relaxivity per particle of from $1\times10^9$ to $1\times10^{12}$ mM$^{-1}$s$^{-1}$ (e.g., from $1\times10^9$ to $1\times10^{10}$, $1\times10^9$ to $1\times10^{11}$, or from $1\times10^{10}$ to $1\times10^{12}$ mM$^{-1}$s$^{-1}$).

In some embodiments, the magnetic particles may be substantially monodisperse. In some embodiments, the magnetic particles in a liquid sample (e.g., a biological sample such as whole blood) may exhibit nonspecific reversibility in the absence of the one or more analytes and/or multivalent binding agent. In some embodiments, the magnetic particles may further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran.

Analytes

Embodiments of the invention include methods and systems for detecting and/or measuring the concentration of one or more analytes. In several embodiments, the analyte may be a nucleic acid derived from an organism. In some embodiments, the nucleic acid is a target nucleic acid derived from the organism that has been amplified to form an amplicon. In some embodiments, the organism is a plant, a mammal, or a microbial species.

In some embodiments, the analyte may be derived from a microbial pathogen. In some embodiments, the analyte is derived from a Gram-negative bacterium, a Gram-positive bacterium, or a fungal pathogen (e.g., a yeast (e.g., *Candida* spp.) or *Aspergillus* spp.). In some embodiments, the analyte is derived from a bacterial pathogen, including *Acinetobacter* spp. (e.g., *Acinetobacter baumannii*, *Acinetobacter pittii*, and *Acinetobacter nosocomialis*), Enterobacteriaceae spp., *Enterococcus* spp. (e.g., *Enterococcus faecium* (including *E. faecium* with resistance marker vanAfB) and *Enterococcus faecalis*), *Klebsiella* spp. (e.g., *Klebsiella pneumoniae* (e.g., *K. pneumoniae* with resistance marker KPC) and *Klebsiella oxytoca*), *Pseudomonas* spp. (e.g., *Pseudomonas aeruginosa*), *Staphylococcus* spp. (e.g., *Staphylococcus aureus* (e.g., *S. aureus* with resistance marker mecA), *Staphylococcus haemolyticus, Staphylococcus lugdunensis, Staphylococcus maltophilia, Staphylococcus saprophyticus*, coagulase-positive *Staphylococcus* species, and coagulase-negative (CONS) *Staphylococcus* species), *Streptococcus* spp. (e.g., *Streptococcus mitis, Streptococcus pneumoniae, Streptococcus agalactiae, Streptococcus anginosa, Streptococcus bovis, Streptococcus dysgalactiae, Streptococcus mutans, Streptococcus sanguinis*, and *Streptococcus pyogenes*), *Escherichia* spp. (e.g., *Escherichia coli*), *Stenotrophomonas* spp. (e.g., *Stenotrophomonas maltophilia*), *Proteus* spp. (e.g., *Proteus mirabilis* and *Proteus vulgaris*), *Serratia* spp. (e.g., *Serratia marcescens*), *Citrobacter* spp. (e.g., *Citrobacter freundii* and *Citrobacter kosern*), *Haemophilus* spp. (e.g., *Haemophilus influenzae*), *Listeria* spp. (e.g., *Listeria monocytogenes*), *Neisseria* spp. (e.g., *Neisseria meningitidis*), *Bacteroides* spp. (e.g., *Bacteroides fragilis*), *Burkholderia* spp. (e.g., *Burkholderia cepacia*), *Campylobacter* (e.g., *Campylobacter jejuni* and *Campylobacter coli*), *Clostridium* spp. (e.g., *Clostridium perfringens*), *Kingella* spp. (e.g., *Kingella kingae*), *Morganella* spp. (e.g., *Morganella morgana*), *Prevotella* spp. (e.g., *Prevotella buccae, Prevotella intermedia*, and *Prevotella melaninogenica*), *Propionibacterium* spp. (e.g., *Propionibacterium acnes*), *Salmonella* spp. (e.g., *Salmonella enterica*), *Shigella* spp. (e.g., *Shigella dysenteriae* and *Shigella flexneri*), and *Enterobacter* spp. (e.g., *Enterobacter aerogenes* and *Enterobacter cloacae*). In some embodiments, the analyte is an antimicrobial resistance marker. Exemplary non-limiting antimicrobial resistance markers include vanA, vanB, mecA, IMP, CTX-M, KPC, NDM, OXA, VIM, and FKS. In some embodiments, the analyte is derived from a fungal pathogen, for example, *Candida* spp. (e.g., *Candida albicans, Candida guilliermondii, Candida glabrata, Candida krusei, Candida lusitaniae, Candida parapsilosis, Candida dublinensis*, and *Candida tropicalis*) and *Aspergillus* spp. (e.g., *Aspergillus fumigatus*).

In particular embodiments, a pathogen-associated analyte may be derived from a bacterial pathogen selected from *Acinetobacter baumannii, Enterococcus faecium, Enterococcus faecalis, Klebsiella pneumonia, Pseudomonas aeruginosa, Escherichia coli*, and *Staphylococcus aureus*. In some embodiments, an analyte be derived from a fungal pathogen, for example, *Candida* spp. (e.g., *Candida albicans, Candida guilliermondii, Candida glabrata, Candida krusei, Candida lusitaniae, Candida parapsilosis*, and *Candida tropicalis*).

In some embodiments, a pathogen-associated analyte may be a nucleic acid derived from any of the organisms described above, for example, DNA or RNA (e.g., mRNA). In some embodiments, the nucleic acid is a target nucleic acid derived from the organism that has been amplified to form an amplicon. In some embodiments, the target nucleic acid may be a multi-copy locus. Use of a target nucleic acid derived from a multi-copy locus, in particular in methods involving amplification, may lead to an increase in sensitivity in the assay. Exemplary multi-copy loci may include, for example, ribosomal DNA (rDNA) operons and multi-copy plasmids. In other embodiments, the target nucleic acid may be a single-copy locus. In particular embodiments, the target nucleic acid may be derived from an essential locus, for example, an essential house-keeping gene. In particular embodiments, the target nucleic acid may be derived from a locus that is involved in virulence (e.g., a virulence gene). In any of the above embodiments, a locus may include a gene and/or an intragenic region, for example, an internally transcribed sequence (ITS) between rRNA genes (e.g., ITS1, between the 16S and 23S rRNA genes, or ITS2, between the 5S and 23S rRNA genes).

In some embodiments, a target nucleic acid may be (a) species-specific, (b) species-inclusive (in other words, present in all strains or subspecies of a given species), (c) compatible with an amplification/detection protocol, and/or (d) present in multiple copies. In particular embodiments, a target nucleic acid is chromosomally-encoded, which can help avoid loss by, for example, plasmid exchange and plasmid curing/transduction events.

*Acinetobacter* Target Nucleic Acids

In some embodiments, a target nucleic acid may include sequence elements that are specific for an *Acinetobacter* spp., for example, *Acinetobacter baumannii*. For example, in some embodiments, an *Acinetobacter baumannii* target nucleic acid may be amplified in the presence of a forward primer and a reverse primer which are specific to *Acinetobacter baumannii*, as described below. Detection of such a target nucleic acid in a sample would typically indicate that an *Acinetobacter baumannii* bacterium was present in the sample. In other embodiments, a target nucleic acid of the invention may include sequence elements that are common to all *Acinetobacter* spp. For example, in some embodiments, an *Acinetobacter* spp. target nucleic acid may be amplified in the presence of a forward primer and a reverse primer, each of which is universal to all *Acinetobacter* spp. Detection of such a target nucleic acid in a sample typically would indicate that an *Acinetobacter* spp. bacterium was present in the sample. In yet other embodiments, these approaches may be combined.

In some embodiments, an *Acinetobacter* spp. target nucleic acid may be derived from a linear chromosome or a linear or circular plasmid (e.g., a single-, low-, or multi-copy plasmid). In some embodiments, an *Acinetobacter* spp. target nucleic acid may be derived from an essential locus (e.g., an essential housekeeping gene) or a locus involved in virulence (e.g., a gene essential for virulence). In some embodiments, an *Acinetobacter* spp. target nucleic acid may be derived from a multi-copy locus. In other embodiments, an *Acinetobacter* spp. target nucleic acid may be derived from a multi-copy plasmid.

In some embodiments, an *Acinetobacter baumannii* target nucleic acid is derived from a region that spans part or all of the internally transcribed sequence (ITS) between the 5S and 23S rRNA genes (i.e., the ITS2 region). For example, in particular embodiments, an *Acinetobacter baumannii* target nucleic acid may be amplified in the presence of a forward primer that includes the oligonucleotide sequence 5'-CGT TTT CCA AAT CTG TAA CAG ACT GGG-3' (SEQ ID NO: 1) or 5'-GGA AGG GAT CAG GTG GTT CAC TCT T-3' (SEQ ID NO: 110) and a reverse primer that includes the oligonucleotide sequence 5'-AGG ACG TTG ATA GG TTG GAT GTG GA-3' (SEQ ID NO: 2). For example, in particular embodiments, an *Acinetobacter baumannii* target nucleic acid may be amplified in the presence of a forward primer that includes the oligonucleotide sequence 5'-GGA AGG GAT CAG GTG GTT CAC TCT T-3' (SEQ ID NO: 110) and a reverse primer that includes the oligonucleotide sequence 5'-AGG ACG TTG ATA GG TTG GAT GTG GA-3' (SEQ ID NO: 2). In some embodiments, an amplicon produced using these primers is detected by hybridization using a 5' capture probe that includes the oligonucleotide sequence 5'-TGA GGC TTG ACT ATA CAA CAC C-3' (SEQ ID NO: 15) and/or a 3' capture probe that includes the oligonucleotide sequence 5'-CTA AAA TGA ACA GAT AAA GTA AGA TTC AA-3' (SEQ ID NO: 16) to detect the presence of *Acinetobacter baumannii* in a biological sample. Alternative forward primers that can be used to amplify an *Acinetobacter baumannii* target nucleic acid include: 5'-CTG AGT TCG GGA AGG GAT CAG G-3' (SEQ ID NO: 66), 5'-CCA AAT CTG TAA CAG ACT GGG CTG A-3' (SEQ ID NO: 67), 5'-AAA CCA AAT CTG TAA CAG ACT GGG CTG A-3' (SEQ ID NO: 68), 5'-ATG GGT AAT CCC ACA CTA CCA TCA G-3' (SEQ ID NO: 69), 5'-GGA AGG GAT CAG GTG GTT CAC TCT T-3' (SEQ ID NO: 69), and 5'-ACT CTT GCT ATG GTC GCC AGC ACA ACT-3' (SEQ ID NO: 70). Alternative reverse primers that can be used to amplify an *Acinetobacter baumannii* target nucleic acid include: 5'-CGT GAG GCT TGA CTA TAC AAC ACC C-3' (SEQ ID NO: 72), 5'-CTT GAC TAT ACA ACA CCC AAG CAG TT-3' (SEQ ID NO: 73), and 5'-GGC TTG ACT ATA CAA CAC CCA AGC AGT T-3' (SEQ ID NO: 74).

In some embodiments, a control target nucleic acid for *A. baumannii* may comprise the nucleic acid sequence of SEQ ID NO: 45.

*Enterococcus* Target Nucleic Acids

In some embodiments, a target nucleic acid may include sequence elements that are specific for an *Enterococcus* spp., for example, *Enterococcus faecium* or *Enterococcus faecalis*. For example, in some embodiments, an *Enterococcus faecium* target nucleic acid may be amplified in the presence of a forward primer and a reverse primer which are specific to *Enterococcus faecium*. Detection of such a target nucleic acid in a sample would typically indicate that an *Enterococcus faecium* bacterium was present in the sample. In other embodiments, a target nucleic acid may include sequence elements that are specific for multiple (e.g., 2, 3, 4, or 5) *Enterococcus* spp. For example, in some embodiments, a target nucleic acid may include sequence elements that are specific for *Enterococcus faecium* and *Enterococcus faecalis*, as described below. In other embodiments, a target nucleic acid of the invention may include sequence elements that are common to all *Enterococcus* spp. For example, in some embodiments, an *Enterococcus* spp. target nucleic acid may be amplified in the presence of a forward primer and a reverse primer, each of which is universal to all *Enterococcus* spp. Detection of such a target nucleic acid in a sample typically would indicate that an *Enterococcus* spp. bacterium was present in the sample. In yet other embodiments, these approaches may be combined.

In some embodiments, an *Enterococcus* spp. target nucleic acid may be derived from a linear chromosome or a linear or circular plasmid (e.g., a single-, low-, or multi-copy plasmid). In some embodiments, an *Enterococcus* spp. target nucleic acid may be derived from an essential locus (e.g., an essential housekeeping gene) or a locus involved in virulence (e.g., a gene essential for virulence). In some embodiments, an *Enterococcus* spp. target nucleic acid may be derived from a multi-copy locus. In particular embodiments, an *Enterococcus* spp. target nucleic acid may be derived from a multi-copy plasmid.

In some embodiments, an *Enterococcus* spp. target nucleic acid is derived from a region that spans part or all of the ITS between the 23S and 5S rRNA genes. For example, in particular embodiments, a target nucleic acid that is specific for *Enterococcus faecium* and *Enterococcus faecalis* may be amplified in the presence of a forward primer that includes the oligonucleotide sequence 5'-GGT AGC TAT GTA GGG AAG GGA TAA ACG CTG A-3' (SEQ ID NO: 3) and a reverse primer that includes the oligonucleotide sequence 5'-GCG CTA AGG AGC TTA ACT TCT GTG TTC G-3' (SEQ ID NO: 4). In some embodiments, an amplicon produced using these primers is detected by hybridization using a 5' capture probe that includes the oligonucleotide sequence 5'-AAA ACT TAT ATG ACT TCA AAT CCA GTT TT-3' (SEQ ID NO: 19) or 5'-AAA ACT TAT GTG ACT TCA AAT CCA GTT TT-3' (SEQ ID NO: 111) and/or a 3' capture probe that includes the oligonucleotide sequence 5'-TTT ACT CAA TAA AAG ATA ACA CCA CAG-3' (SEQ ID NO: 20) or 5'-TTT ACT CAA TAA AAG ATA ACA CCA CAG T-3' (SEQ ID NO: 112) to detect the presence of *Enterococcus faecium* in a biological sample. In particular embodiments, an amplicon produced using these primers is detected by hybridization using a 5' capture probe that includes the oligonucleotide sequence 5'-AAA ACT TAT GTG ACT TCA AAT CCA GTT TT-3' (SEQ ID NO: 111) and/or a 3' capture probe that includes the oligonucleotide sequence 5'-TTT ACT CAA TAA AAG ATA ACA CCA CAG T-3' (SEQ ID NO: 112) to detect the presence of *Enterococcus faecium* in a biological sample. In some embodiments, an amplicon produced using these primers is detected by hybridization using a 5' capture probe that includes the oligonucleotide sequence 5'-TGG ATA AGT AAA AGC AAC TTG GTT-3' (SEQ ID NO: 23) and/or a 3' capture probe that includes the oligonucleotide sequence 5'-AAT GAA GAT TCA ACT CAA TAA GAA ACA ACA-3' (SEQ ID NO: 24) to detect the presence of *Enterococcus faecalis* in a biological sample. Alternative forward primers that can be used to amplify a target nucleic acid that is specific for *Enterococcus faecium* and *Enterococcus faecalis* include: 5'-GTG AAG CCC ACC TCA AGA TGA GAT-3' (SEQ ID NO: 75), 5'-TGT TCT GCC AAG GGC ATT GCT G-3' (SEQ ID NO: 76), and 5'-CTA TGT AGG GAA GGG ATA AAC GCT GA-3' (SEQ ID NO: 77). Alternative reverse primers that can be used to amplify a target nucleic acid that is specific for *Enterococcus faecium* and *Enterococcus faecalis* include: 5'-ACA ATC GGC GCT AGA AGC TTA ACT-3' (SEQ ID NO: 78), 5'-ACA GGT GTA TCC TTC TCG CTA TCG C-3' (SEQ ID NO: 79), 5'-GCG CTA AGG AGC TTA ACT TCT GTG TTC G-3' (SEQ ID NO: 80), and 5'-TCG GCG CTA AGG AGC TTA ACT TCT GTG TTC G-3' (SEQ ID NO: 81).

In some embodiments, a control target nucleic acid for *Enterococcus faecium* may comprise the nucleic acid sequence of SEQ ID NO: 46. In other embodiments, a control target nucleic acid for *Enterococcus faecium* may comprise the nucleic acid sequence of SEQ ID NO: 118. In some embodiments, a control target nucleic acid for *Enterococcus faecalis* may comprise the nucleic acid sequence of SEQ ID NO: 47.

*Klebsiella* Target Nucleic Acids

In some embodiments, a target nucleic acid may include sequence elements that are specific for a *Klebsiella* spp., for example, *Klebsiella pneumoniae*. For example, in some embodiments, a *Klebsiella pneumoniae* target nucleic acid may be amplified in the presence of a forward primer and a reverse primer which are specific to *Klebsiella pneumoniae*, as described below. Detection of such a target nucleic acid in a sample would typically indicate that a *Klebsiella pneumoniae* bacterium was present in the sample. In other embodiments, a target nucleic acid of the invention may include sequence elements that are common to all *Klebsiella* spp. For example, in some embodiments, a *Klebsiella* spp. target nucleic acid may be amplified in the presence of a forward primer and a reverse primer, each of which is universal to all *Klebsiella* spp. Detection of such a target nucleic acid in a sample typically would indicate that a *Klebsiella* spp. bacterium was present in the sample. In yet other embodiments, these approaches may be combined.

In some embodiments, a *Klebsiella* spp. target nucleic acid may be derived from a linear chromosome or a linear or circular plasmid (e.g., a single-, low-, or multi-copy plasmid). In some embodiments, a *Klebsiella* spp. target nucleic acid may be derived from an essential locus (e.g., an essential housekeeping gene) or a locus involved in virulence (e.g., a gene essential for virulence). In some embodiments, a *Klebsiella* spp. target nucleic acid may be derived from a multi-copy locus. In particular embodiments, a *Klebsiella* spp. target nucleic acid may be derived from a multi-copy plasmid.

In some embodiments, a *Klebsiella pneumoniae* target nucleic acid is derived from a 23S rRNA gene. For example, in particular embodiments, a *Klebsiella pneumoniae* target nucleic acid may be amplified in the presence of a forward primer that includes the oligonucleotide sequence 5'-GAC GGT TGT CCC GGT TTA AGC A-3' (SEQ ID NO: 5) or 5'-GAG GCA CTA CGG TGC TGA AGT A-3' (SEQ ID NO: 82) and a reverse primer that includes the oligonucleotide sequence 5'-GCT GGT ATC TTC GAC TGG TCT-3' (SEQ ID NO: 6). In some embodiments, an amplicon produced using these primers is detected by hybridization using a 5' capture probe that includes the oligonucleotide sequence 5'-TAC CAA GGC GCT TGA GAG AAC TC-3' (SEQ ID NO: 27) and/or a 3' capture probe that includes the oligonucleotide sequence 5'-CTG GTG TGT AGG TGA AGT C-3' (SEQ ID NO: 28) to detect the presence of *Klebsiella pneumoniae* in a biological sample.

In some embodiments, a control target nucleic acid for *Klebsiella pneumoniae* may comprise the nucleic acid sequence of SEQ ID NO: 48.

*Pseudomonas* Target Nucleic Acids

In some embodiments, a target nucleic acid may include sequence elements that are specific for a *Pseudomonas* spp., for example, *Pseudomonas aeruginosa*. For example, in some embodiments, a *Pseudomonas aeruginosa* target nucleic acid may be amplified in the presence of a forward primer and a reverse primer which are specific to *Pseudomonas aeruginosa*, as described below. Detection of such a target nucleic acid in a sample would typically indicate that a *Pseudomonas aeruginosa* bacterium was present in the sample. In other embodiments, a target nucleic acid of the invention may include sequence elements that are common to all *Pseudomonas* spp. For example, in some embodiments, a *Pseudomonas* spp. target nucleic acid may be amplified in the presence of a forward primer and a reverse primer, each of which is universal to all *Pseudomonas* spp. Detection of such a target nucleic acid in a sample typically would indicate that a *Pseudomonas* spp. bacterium was present in the sample. In yet other embodiments, these approaches may be combined.

In some embodiments, a *Pseudomonas* spp. target nucleic acid may be derived from a linear chromosome or a linear or circular plasmid (e.g., a single-, low-, or multi-copy plasmid). In some embodiments, a *Pseudomonas* spp. target nucleic acid may be derived from an essential locus (e.g., an essential housekeeping gene) or a locus involved in virulence (e.g., a gene essential for virulence). In some embodiments, a *Pseudomonas* spp. target nucleic acid may be derived from a multi-copy locus. In particular embodiments, a *Pseudomonas* spp. target nucleic acid may be derived from a multi-copy plasmid.

In some embodiments, a *Pseudomonas aeruginosa* target nucleic acid is derived from a region that spans part or all of the ITS between the 23S and 5S rRNA genes. For example, in particular embodiments, a *Pseudomonas aeruginosa* target nucleic acid may be amplified in the presence of a forward primer that includes the oligonucleotide sequence 5'-AGG CTG GGT GTG TAA GCG TTG T-3' (SEQ ID NO: 7) and a reverse primer that includes the oligonucleotide sequence 5'-CAA GCA ATT CGG TTG GAT ATC CGT T-3' (SEQ ID NO: 8). In some embodiments, an amplicon produced using these primers is detected by hybridization using a 5' capture probe that includes the oligonucleotide sequence 5'-GTG TGT TGT AGG GTG AAG TCG AC-3' (SEQ ID NO: 31) or 5'-TCT GAC GAT TGT GTG TTG TAA GG-3' (SEQ ID NO: 114) and/or a 3' capture probe that includes the oligonucleotide sequence 5'-CAC CTT GAA ATC ACA TAC CTG A-3' (SEQ ID NO: 32) or 5'-GGA TAG ACG TAA GCC CAA GC-3' (SEQ ID NO: 115) to detect the presence of *Pseudomonas aeruginosa* in a biological sample. In particular embodiments, an amplicon produced using these primers is detected by hybridization using a 5' capture probe that includes the oligonucleotide sequence 5'-TCT GAC GAT TGT GTG TTG TAA GG-3' (SEQ ID NO: 114) and/or a 3' capture probe that includes the oligonucleotide 5'-GGA TAG ACG TAA GCC CAA GC-3' (SEQ ID NO: 115) to detect the presence of *Pseudomonas aeruginosa* in a biological sample. Alternative forward and reverse primers that can be used to amplify a target nucleic acid that is specific for *Pseudomonas aeruginosa* are 5'-CTC ACT GGG AAC TTG ATT CCC CTG-3' (SEQ ID NO: 83) and 5'-GGT GGT TCC AAC GCT CTA TGA TCG T-3' (SEQ ID NO: 84), respectively.

In some embodiments, a control target nucleic acid for *Pseudomonas aeruginosa* may comprise the nucleic acid sequence of SEQ ID NO: 49.

*Staphylococcus* Target Nucleic Acids

In some embodiments, a target nucleic acid may include sequence elements that are specific for a *Staphylococcus* spp., for example, *Staphylococcus aureus*. For example, in some embodiments, a *Staphylococcus aureus* target nucleic acid may be amplified in the presence of a forward primer and a reverse primer which are specific to *Staphylococcus aureus*, as described below. Detection of such a target nucleic acid in a sample would typically indicate that a *Staphylococcus aureus* bacterium was present in the sample. In other embodiments, a target nucleic acid of the invention may include sequence elements that are common to all *Staphylococcus* spp. For example, in some embodiments, a *Staphylococcus* spp. target nucleic acid may be amplified in the presence of a forward primer and a reverse primer, each of which is universal to all *Staphylococcus* spp. Detection of such a target nucleic acid in a sample typically would indicate that a *Staphylococcus* spp. bacterium was present in the sample. In yet other embodiments, these approaches may be combined.

In some embodiments, a *Staphylococcus* spp. target nucleic acid may be derived from a linear chromosome or a linear or circular plasmid (e.g., a single-, low-, or multi-copy plasmid). In some embodiments, a *Staphylococcus* spp. target nucleic acid may be derived from an essential locus (e.g., an essential housekeeping gene), a locus involved in virulence (e.g., a gene essential for virulence), or a gene involved in antibiotic resistance (e.g., femA and femB). In some embodiments, a *Staphylococcus* spp. target nucleic acid may be derived from a multi-copy locus. In particular embodiments, a *Staphylococcus* spp. target nucleic acid may be derived from a multi-copy plasmid.

In some embodiments, a *Staphylococcus aureus* target nucleic acid is derived from the femAB operon. The femAB operon codes for two nearly identical approximately 50 kDa proteins involved in the formation of the Staphylococcal pentaglycine interpeptide bridge in peptidoglycan. These chromosomally-encoded proteins are considered as factors that influence the level of methicillin resistance and as essential housekeeping genes. femB is one gene in the femA/B operon, also referred to as graR, the two component response regulator of methicillin resistance. femB encodes a aminoacyltransferase, whereas femA encodes a regulatory factor that is essential for expression of femB and therefore methicillin resistance expression.

In some embodiments, a *Staphylococcus aureus* target nucleic acid is derived from the femA gene. For example, in particular embodiments, a *Staphylococcus aureus* target nucleic acid may be amplified in the presence of a forward primer that includes the oligonucleotide sequence 5'-GGT AAT GAATTA CCT/i6diPr/TC TCT GCT GGTTTC TTC TT-3' (SEQ ID NO: 9) and a reverse primer that includes the oligonucleotide sequence 5'-ACC AGC ATC TTC/i6diPr/ GC ATC TTC TGT AAA-3' (SEQ ID NO: 10). Note that "/i6diPr/" indicates 2,6-Diaminopurine, a modified base that can form three hydrogen bonds when base-paired with dT. In some embodiments, an amplicon produced using these primers is detected by hybridization using a 5' capture probe that includes the oligonucleotide sequence 5'-CCA TTT GAA GTT GTT TAT TAT GC-3' (SEQ ID NO: 35) and/or a 3' capture probe that includes the oligonucleotide sequence 5'-GGG AAA TGA TTA ATT ATG CAT TAA ATC-3' (SEQ ID NO: 36) to detect the presence of *Staphylococcus aureus* in a biological sample. Alternative forward primers useful for amplifying the femA gene include: 5'-ACT GCT GTA CCT GTT ATG AAA GTG T-3' (SEQ ID NO: 85), 5'-GCT TGC TTA CTT ACT GCT GTA CCT G-3' (SEQ ID NO: 86), 5'-GCC ATA CAG TCA TTT CAC GCA AAC-3' (SEQ ID NO: 87), 5'-CCT GTG TTA CAA ATT CGT TAT CAC T-3' (SEQ ID NO: 88), and 5'-ACC T/i6diPr/T CTC TGC TGG TTT CTT CTT-3' (SEQ ID NO: 89). Alternative reverse primers useful for amplifying parts of the femA gene include 5'-GCA TTA CCT GTA ATC TCG CCA TCA T-3' (SEQ ID NO: 90), 5'-AGC TTT TGA TTC TGA CGT ATC TTC C-3' (SEQ ID NO: 91), 5'-GAT CAG CGA AAG CTT TTG ATT CTG ACG T-3' (SEQ ID NO: 92), and 5'-CAG CAT CTT C/i6diPr/G CAT CTT CTG TAA A-3' (SEQ ID NO: 93), In some embodiments, a *Staphylococcus aureus* target nucleic acid is derived from the femB gene. For example, in other particular embodiments, a *Staphylococcus aureus* target nucleic acid may be amplified in the presence of a forward primer that includes the oligonucleotide sequence 5'-GAA GTT ATG TTT/i6diPr/CT ATT CGA ATC GTG GTC CAGT-3' (SEQ ID NO: 11) and a reverse primer that includes the oligonucleotide sequence 5'-GTT GTA AAG CCA TGA TGC TCG TAA CCA-3' (SEQ ID NO: 12). In some embodiments, an amplicon produced using these primers is detected by hybridization using a 5' capture probe that includes the oligonucleotide sequence 5'-TT TTT CAG ATT TAG GAT TAG TTG ATT-3' (SEQ ID NO: 39) and/or a 3' capture probe that includes the oligonucleotide sequence 5'-GAT CCG TAT TGG TTA TAT CAT C-3' (SEQ ID NO: 40) to detect the presence of *Staphylococcus aureus* in a biological sample. In some embodiments, a *Staphylococcus aureus* target nucleic acid includes all or a portion of both the femA gene and the femB gene.

In some embodiments, a control target nucleic acid for *Staphylococcus aureus* femA may comprise the nucleic acid sequence of SEQ ID NO: 50. In some embodiments, a control target nucleic acid for *Staphylococcus aureus* femB may comprise the nucleic acid sequence of SEQ ID NO: 51.

*Escherichia* Target Nucleic Acids

In some embodiments, a target nucleic acid may include sequence elements that are specific for an *Escherichia* spp., for example, *Escherichia coli*. For example, in some embodiments, an *Escherichia* coil target nucleic acid may be amplified in the presence of a forward primer and a reverse primer which are specific to *Escherichia coli*, as described below. Detection of such a target nucleic acid in a sample would typically indicate that an *Escherichia coli* bacterium was present in the sample. In other embodiments, a target nucleic acid of the invention may include sequence elements that are common to all *Escherichia* spp. For example, in some embodiments, an *Escherichia* spp. target nucleic acid may be amplified in the presence of a forward primer and a reverse primer, each of which is universal to all *Escherichia* spp. Detection of such a target nucleic acid in a sample typically would indicate that a *Escherichia* spp. bacterium was present in the sample. In yet other embodiments, these approaches may be combined.

In some embodiments, an *Escherichia* spp. target nucleic acid may be derived from a linear chromosome or a linear or circular plasmid (e.g., a single-, low-, or multi-copy plasmid). In some embodiments, an *Escherichia* spp. target nucleic acid may be derived from an essential locus (e.g., an essential housekeeping gene), a locus involved in virulence (e.g., a gene essential for virulence), or a gene involved in antibiotic resistance. In some embodiments, an *Escherichia* spp. target nucleic acid may be derived from a multi-copy locus. In particular embodiments, an *Escherichia* spp. target nucleic acid may be derived from a multi-copy plasmid. In particular embodiments, an *Escherichia coli* target nucleic acid is the yfcL gene. The yfcL gene is within an *E. coli*-specific Chaperone-Usher Fimbriae gene cluster (see, e.g., Wurpel et al. PLoS One Vol 8, e52835, 2013). The Yfc type operon is present in all examined strains. yfcL is highly conserved within *E. coli* and present in all strains with available sequence information.

For example, in some embodiments, *Escherichia coli* yfcL may be amplified in the presence of a forward primer that includes the oligonucleotide sequence 5'-GCA TTA ATC GAC GGT ATG GTT GAC C-3' (SEQ ID NO: 59) or 5'-CGA CGG TAT GGT TGA CCA TGC-3' (SEQ ID NO: 60) and a reverse primer that includes the oligonucleotide sequence 5'-CCT GCT GAA ACA GGT TTT CCC ACA TA-3' (SEQ ID NO: 61) or 5'-GAC GCC TGC TGA AAC AGG TTT TCC-3' (SEQ ID NO: 62). In particular embodiments, *Escherichia coli* yfcL may be amplified in the presence of a forward primer that includes the oligonucleotide sequence 5'-GCA TTA ATC GAC GGT ATG GTT GAC C-3' (SEQ ID NO: 59) and a reverse primer that includes the oligonucleotide sequence 5'-CCT GCT GAA ACA GGT TTT CCC ACA TA-3' (SEQ ID NO: 61). In some embodiments, an amplicon produced using these primers is detected by hybridization using a 5' capture probe that includes the oligonucleotide sequence 5'-AGT GAT GAT GAG TTG TTT GCC AGT G-3' (SEQ ID NO: 63), 5'-GAT GAT GAG TTG TTT GCC AGT G-3' (SEQ ID NO: 107). 5'-TGC CAG TGA TGA TGA GTT GT-3' (SEQ ID NO: 108), or 5'-GCC ACC TGA CAT TAG CCA TC-3' (SEQ ID NO: 109) and/or a 3' capture probe that includes the oligonucleotide sequence 5'-TGA ATT GTC GCC GCG TGA CCA G-3' (SEQ ID NO: 64) or 5'-GGT GCA TAC GAC CGT TAG CCA GAG TC-3' (SEQ ID NO: 65) to detect the presence of *Escherichia coli* in a biological sample. In some embodiments, an amplicon produced using these primers is detected by hybridization using a 5' capture probe that includes the oligonucleotide sequence 5'-AGT GAT GAT GAG TTG TTT GCC AGT G-3' (SEQ ID NO: 63) and/or a 3' capture probe that includes the oligonucleotide sequence 5'-TGA ATT GTC GCC GCG TGA CCA G-3' (SEQ ID NO: 64) to detect the presence of *Escherichia coli* in a biological sample. In some embodiments, an amplicon produced using these primers is detected by hybridization using a 5' capture probe that includes the oligonucleotide sequence 5'-GAT GAT GAG TTG TTT GCC AGT G-3' (SEQ ID NO: 107) and/or a 3' capture probe that includes the oligonucleotide sequence 5'-TGA ATT GTC GCC GCG TGA CCA G-3' (SEQ ID NO: 64) to detect the presence of *Escherichia coli* in a biological sample. In some embodiments, an amplicon produced using these primers is detected by hybridization using a 5' capture probe that includes the oligonucleotide sequence 5'-TGC CAG TGA TGA TGA GTT GT-3' (SEQ ID NO: 108) and/or a 3' capture probe that includes the oligonucleotide sequence 5'-TGA ATT GTC GCC GCG TGA CCA G-3' (SEQ ID NO: 64) to detect the presence of *Escherichia coli* in a biological sample. In some embodiments, an amplicon produced using these primers is detected by hybridization using a 5' capture probe that includes the oligonucleotide sequence 5'-GCC ACC TGA CAT TAG CCA TC-3' (SEQ ID NO: 109) and/or a 3' capture probe that includes the oligonucleotide sequence 5'-TGA ATT GTC GCC GCG TGA CCA G-3' (SEQ ID NO: 64) to detect the presence of *Escherichia coli* in a biological sample. In some embodiments, the 5' capture probe and/or the 3' capture probe is conjugated to a magnetic nanoparticle.

*Candida* Target Nucleic Acids

In some embodiments, a target nucleic acid may include sequence elements that are specific for a *Candida* spp. (e.g., *Candida albicans, Candida guilliermondii, Candida glabrata, Candida krusei, Candida lusitaniae, Candida parapsilosis,* and *Candida tropicalis*). For example, in some embodiments, a *Candida albicans* target nucleic acid may be amplified in the presence of a forward primer and a reverse primer which are specific to *Candida albicans*. Detection of such a target nucleic acid in a sample would typically indicate that a *Candida albicans* cell was present in the sample. In other embodiments, a target nucleic acid of the invention may include sequence elements that are common to all *Candida* spp. For example, in some embodiments, a *Candida* spp. target nucleic acid may be amplified in the presence of a forward primer and a reverse primer, each of which is universal to all *Candida* spp., as described below. Detection of such a target nucleic acid in a sample typically would indicate that a *Candida* spp. cell was present in the sample. In yet other embodiments, these approaches may be combined.

In some embodiments, a *Candida* spp. target nucleic acid may be derived from a linear chromosome or a linear or circular plasmid (e.g., a single-, low-, or multi-copy plasmid). In some embodiments, a *Candida* spp. target nucleic acid may be derived from an essential locus (e.g., an essential housekeeping gene) or a locus involved in virulence (e.g., a gene essential for virulence). In some embodiments, a *Candida* spp. target nucleic acid may be derived from a multi-copy locus. For example, in some embodiments, a *Candida* spp. target nucleic acid may be derived from a ribosomal DNA operon.

In particular embodiments, a *Candida* spp. target nucleic acid may be amplified in the presence of a forward primer that includes the oligonucleotide sequence 5'-GGC ATG CCT GTT TGA GCG TC-3' (SEQ ID NO: 13) and a reverse primer that includes the oligonucleotide sequence 5'-GCT TAT TGA TAT GCT TAA GTT CAG CGG GT-3' (SEQ ID NO: 14).

Variant Primers and Probes

In some embodiments, the invention provides a primer that has at least 80% identity (e.g., at least 80%, 81%, 82%, 83%, 84%, 85%, 86%, 87%, 88%, 89%, 90%, 91%, 92%, 93%, 94%, 95%, 96%, 97%, 98%, 99%, or 100%) identity with any of the primers described above. For example, in some embodiments, the invention provides a forward primer comprising an oligonucleotide sequence that is at least 80% identical (e.g., at least 80%, 81%, 82%, 83%, 84%, 85%, 86%, 87%, 88%, 89%, 90%, 91%, 92%, 93%, 94%, 95%, 96%, 97%, 98%, 99%, or 100% identical) to any one of SEQ ID NOs: 1, 3, 5, 7, 9, 11, 59, or 110. In some embodiments, the invention provides a reverse primer comprising an oligonucleotide sequence that is at least 80% identical (e.g., at least 80%, 81%, 82%, 83%, 84%, 85%, 86%, 87%, 88%, 89%, 90%, 91%, 92%, 93%, 94%, 95%, 96%, 97%, 98%, 99%, or 100% identical) to any one of SEQ ID NOs: 2, 4, 6, 8, 10, 12, or 61. Such primers can be used in any of the methods of the invention described herein.

In some embodiments, the invention provides a probe that has at least 80% identity (e.g., at least 80%, 81%, 82%, 83%, 84%, 85%, 86%, 87%, 88%, 89%, 90%, 91%, 92%, 93%, 94%, 95%, 96%, 97%, 98%, 99%, or 100%) identity with any of the probes described above or herein. For example, in some embodiments, the invention provides a 5' capture probe comprising an oligonucleotide sequence that is at least 80% identical (e.g., at least 80%, 81%, 82%, 83%, 84%, 85%, 86%, 87%, 88%, 89%, 90%, 91%, 92%, 93%, 94%, 95%, 96%, 97%, 98%, 99%, or 100% identical) to any one of SEQ ID NOs: 15, 19, 23, 27, 31, 35, 39, 63, 107, 108, 109, 111, or 114. In some embodiments, the invention provides a 3' capture probe comprising an oligonucleotide sequence that is at least 80% identical (e.g., at least 80%, 81%, 82%, 83%, 84%, 85%, 86%, 87%, 88%, 89%, 90%, 91%, 92%, 93%, 94%, 95%, 96%, 97%, 98%, 99%, or 100% identical) to any one of SEQ ID NOs: or 16, 20, 24, 28, 32, 36, 40, 64, 112, or 115.

Such probes can be used in any of the methods of the invention described herein.

In some embodiments, any of the preceding primers or probes may include one or more modified bases, for example, 2,6-Diaminopurine (abbreviated herein as "/i6diPr/"), or other modified bases known in the art.

Medical Conditions

The methods of the invention can also be used to monitor and diagnose diseases and other medical conditions. In some embodiments, the methods of the invention may be used to monitor and diagnose disease in a multiplexed, automated, no sample preparation system.

The methods and systems of the invention can be used to identify and monitor the pathogenesis of disease in a subject, to select therapeutic interventions, and to monitor the effectiveness of the selected treatment. For example, for a patient having or at risk of bacteremia and/or sepsis, the methods and systems of the invention can be used to identify the infectious pathogen, pathogen load, and to monitor white blood cell count and/or biomarkers indicative of the status of the infection. The identity of the pathogen can be used to select an appropriate therapy. In some embodiments, the methods may further include administering a therapeutic agent following monitoring or diagnosing an infectious disease. The therapeutic intervention (e.g., a particular antibiotic agent) can be monitored as well to correlate the treatment regimen to the circulating concentration of antibiotic agent and pathogen load to ensure that the patient is responding to treatment.

Exemplary diseases that can be diagnosed and/or monitored by the methods and systems of the invention include diseases caused by or associated with microbial pathogens (e.g., bacterial infection or fungal infection), Lyme disease, bloodstream infection (e.g., bacteremia or fungemia), pneumonia, peritonitis, osteomyeletis, meningitis, empyema, urinary tract infection, sepsis, septic shock, and septic arthritis) and diseases that may manifest with similar symptoms to diseases caused by or associated with microbial pathogens (e.g., SIRS).

For example, the methods and systems of the invention may be used to diagnose and/or monitor a disease caused by the following non-limiting examples of pathogens: bacterial pathogens, including *Acinetobacter* spp. (e.g., *Acinetobacter baumannii*, *Acinetobacter pittii*, and *Acinetobacter nosocomialis*), Enterobacteriaceae spp., *Enterococcus* spp. (e.g., *Enterococcus faecium* (including *E. faecium* with resistance marker vanA/B) and *Enterococcus faecalis*), *Klebsiella* spp. (e.g., *Klebsiella pneumoniae* (e.g., *K. pneumoniae* with resistance marker KPC) and *Klebsiella oxytoca*), *Pseudomonas* spp. (e.g., *Pseudomonas aeruginosa*), *Staphylococcus* spp. (e.g., *Staphylococcus aureus* (e.g., *S. aureus* with resistance marker mecA), *Staphylococcus haemolyticus*, *Staphylococcus lugdunensis*, *Staphylococcus maltophilia*, *Staphylococcus saprophyticus*, coagulase-positive *Staphylococcus* species, and coagulase-negative (CoNS) *Staphylococcus* species), *Streptococcus* spp. (e.g., *Streptococcus mitis*, *Streptococcus pneumoniae*, *Streptococcus agalactiae*, *Streptococcus anginosa*, *Streptococcus bovis*, *Streptococcus dysgalactiae*, *Streptococcus mutans*, *Streptococcus sanguinis*, and *Streptococcus pyogenes*), *Escherichia* spp. (e.g., *Escherichia coli*), *Stenotrophomonas* spp. (e.g., *Stenotrophomonas maltophilia*), *Proteus* spp. (e.g., *Proteus mirabilis* and *Proteus vulgaris*), *Serratia* spp. (e.g., *Serratia marcescens*), *Citrobacter* spp. (e.g., *Citrobacter freundii* and *Citrobacter koseri*), *Haemophilus* spp. (e.g., *Haemophilus influenzae*), *Listeria* spp. (e.g., *Listeria monocytogenes*), *Neisseria* spp. (e.g., *Neisseria meningitidis*), *Bacteroides* spp. (e.g., *Bacteroides fragilis*), *Burkholderia* spp. (e.g., *Burkholderia cepacia*), *Campylobacter* (e.g., *Campylobacter jejuni* and *Campylobacter coli*), *Clostridium* spp. (e.g., *Clostridium perfringens*), *Kingella* spp. (e.g., *Kingella kingae*), *Morganella* spp. (e.g., *Morganella* morgana), *Prevotella* spp. (e.g., *Prevotella buccae*, *Prevotella intermedia*, and *Prevotella melaninogenica*), *Propionibacterium* spp. (e.g., *Propionibacterium acnes*), *Salmonella* spp. (e.g., *Salmonella enterica*), *Shigella* spp. (e.g., *Shigella dysenteriae* and *Shigella flexneri*), and *Enterobacter* spp. (e.g., *Enterobacter aerogenes* and *Enterobacter cloacae*); and fungal pathogens including but not limited to *Candida* spp. (e.g., *Candida albicans*, *Candida guilliermondii*, *Candida glabrata*, *Candida krusei*, *Candida lusitaniae*, *Candida parapsilosis*, *Candida dublinensis*, and *Candida tropicalis*) and *Aspergillus* spp. (e.g., *Aspergillus fumigatus*).

Acinetobacter baumannii

*Acinetobacter baumannii* is phylogenetically classified within the class Gammaproteobacteria, the order Pseudomonadales, the family Moraxellaceae, and the genus *Acinetobacter*. Within the genus are at least 18 known species including *A. lwoffii*, *A. junii* and a closely-related group including *A. baumannii*, *A. calcoaceticus*, *A. pitti*, and *A. nosocomiali*. The members of the genus *Acinetobacter*, as currently defined, are characterized as gram-negative, strictly aerobic, nonfermenting, nonfastidious, nonmotile, catalase-positive, oxidase-negative bacteria with a DNA G/C content of 39% to 47%.

*A. baumannii* is extremely adaptive to antibiotic use by acquiring resistance. Strains resistant to all known antibiotics have been reported. *A. baumannii* causes pneumonia in hospital settings but also infections involving the central nervous system, skin and soft tissue, and bone. *A. baumannii* is typically an intensive care unit (ICU)-associated agent that causes about 1.3% of all bacteremia cases. However, mortality rates of *A. baumannii* sepsis cases are only exceeded by *Pseudomonas* and *Candida* infections (see, e.g., Peleg et al. *Clin. Microbiol. Rev.* 21(3): 538-582, 2008).

Enterococcus spp.

*Enterococcus* spp. are part of the normal intestinal flora of humans and animals but are also important pathogens responsible for serious infections. They are phylogenetically classified within the genus *Enterococcus*, the family Enterococcaceae, the order Lactobaciliales, class Bacilli and phylum Firmicutes (which includes most gram-positive species). The genus *Enterococcus* includes more than 20 species, but only a few cause clinical infections in humans. With increasing antibiotic resistance, Enterococci are recognized as nosocomial pathogens that can be challenging to treat.

*Enterococcus* species are gram-positive, hardy, facultative anaerobic organisms that can survive and grow in many environments. *Enterococcus faecalis* and *Enterococcus faecium* are the most prevalent species of that genus cultured from humans, accounting for more than 90% of clinical isolates. Other enterococcal species known to cause human infection include *E. avium*, *E. gallinarum*, *E. casseliflavus*, *E. durans*, *E. raffinosus* and *E. mundtii*. *E. faecium* represents the most prevalent vancomycin-resistant (VRE) *Enterococcus* spp.

Klebsiella pneumoniae

*Klebsiella pneumoniae* belongs to the family of lactose-fermenting Enterobacteriacea, and is a rod-shaped, Gram-negative gamma-proteobacterium that can live in water, soil, and plants and that is pathogenic to humans and animals. This species is divided into subspecies *pneumonia*, *ozaenae* and *rhinoscleromatis* that can be differentiated phenotypically by the Methyl-Red test and the Voges-Proskauer reaction (MR-VP). Subspecies *rhinoscleromatis* causes upper airway infections and is mostly confined to tropical climates.

Pseudomonas aeruginosa

Species of the genus *Pseudomonas*, of the family Pseudomonadaceae, are motile gram-negative aerobic bacteria, typically approximately 2-4 µm long plump-shaped rods, with polar flagella. *P. aeruginosa* can produce a large variety of extracellular toxins, including exotoxin A and enterotoxins. Other substances such as hydrocyanic acid, proteolytic enzymes, toxic surface slime, and haemolytic substances may also contribute to the pathogenicity of this species. Toxins combined with harmful substances are determinant factors in the high virulence of *P. aeruginosa* in a variety of different hosts. *P. aeruginosa* can also readily colonize on open burn wounds, causing infections, abscesses, and sepsis, with edema and/or discoloration of unburned skin at wound margins and green pigment in subcutaneous fat. *P. aeruginosa* is also associated with swimmer's ear (otitis externa). Other *Pseudomonas* species are also opportunistic; however, cases of infection are rare.

*Escherichia coli*

*Escherichia coli* are gram-negative rod-shaped bacteria belonging to the family of Enterobacteriaceae. The bacteria is a facultative inhabitant of human and animal gut microbiota and a such ubiquitously and abundant in the environment. *Escherichia coli* accounts for approximately 17% of clinical infections requiring hospitalization, second only to *Staphylococcus aureus*. *Escherichia coli* causes infections such a *pneumonia*, cholecystitis, bacteremia, cholangitis, *pneumonia*, and urinary tract infections. *Escherichia coli* is also increasingly associated with neonatal meningitis, which has a mortality rate of approximately 8%. *E. coli* is phylogenetically diverse, as is reflected in the large number of antigens (>700 antigenic types) or serotypes of *E. coli* isolates. Such antigens are based on the 0, H, and K antigen classification. E. co/i and *Shigella* are very close near neighbors and share a number of characteristics such as virulence, enteroinvasiveness, and toxicity. *E. coli* has become a major focus of antibiotic resistance, especially since the emergence of a strain of *E. coli* known as sequence type ST131, which is resistant to most common antibiotics but also fluoroquinolones. This strain type is most commonly found in nursing homes, hospitals, and long-term care facilities, and plays a major role in the severity of bloodstream infections.

*Staphylococcus aureus*

*Staphylococcus aureus* are Gram-positive, catalase-positive cocci belonging to the Staphylococcaceae family. They are approximately 0.5-1.5 µm in diameter, nonmotile, non-spore-forming, facultative anaerobes that usually form in clusters. Many strains produce staphylococcal enterotoxins, including, for example, the superantigen toxic shock syndrome toxin (TSST-1), and exfoliative toxins. *Staphylococcus aureus* bacteria are part of human flora, and are primarily found in the nose and skin. Around 20% of individuals are persistent carriers of *Staphylococcus aureus*, about 60% are intermittent carriers, and approximately 20% rarely carry it. *Staphylococcus aureus* is an opportunistic pathogen that can cause a variety of self-limiting to life-threatening diseases in humans and is one of the most common causes of skin, soft-tissue, and nosocomial infection. Rates of infection in community settings are increasing. Residents of nursing homes are also at an increased risk of acquiring MRSA (methicillin resistant *Staphylococcus aureus*).

Treatment

In some embodiments, the methods further include administering a therapeutic agent to a subject following a diagnosis. Typically, the identification of a particular pathogen will guide the selection of the appropriate therapeutic agent.

For example, for a bacterial infection (e.g., bacteremia), a therapy may include an antibiotic. In some instances, an antibiotic may be administered orally. In other instances, the antibiotic may be administered intravenously. Exemplary non-limiting antibiotics that may be used in the methods of the invention include but are not limited to, acrosoxacin, amifloxacin, amikacin, amoxycillin, ampicillin, aspoxicillin, azidocillin, azithromycin, aztreonam, balofloxacin, benzylpenicillin, biapenem, brodimoprim, cefaclor, cefadroxil, cefatrizine, cefcapene, cefdinir, cefetamet, ceftmetazole, cefoxitin, cefprozil, cefroxadine, ceftarolin, ceftazidime, ceftibuten, ceftobiprole, cefuroxime, cephalexin, cephalonium, cephaloridine, cephamandole, cephazolin, cephradine, chlorquinaldol, chlortetracycline, ciclacillin, cinoxacin, ciprofloxacin, clarithromycin, clavulanic acid, clindamycin, clofazimine, cloxacillin, colistin, danofloxacin, dapsone, daptomycin, demeclocycline, dicloxacillin, difloxacin, doripenem, doxycycline, enoxacin, enrofloxacin, erythromycin, fleroxacin, flomoxef, flucloxacillin, flumequine, fosfomycin, gentamycin, isoniazid, imipenem, kanamycin, levofloxacin, linezolid, mandelic acid, mecillinam, meropenem, metronidazole, minocycline, moxalactam, mupirocin, nadifloxacin, nafcillin, nalidixic acid, netilmycin, netromycin, nifuirtoinol, nitrofurantoin, nitroxoline, norfloxacin, ofloxacin, oxacillin, oxytetracycline, panipenem, pefloxacin, phenoxymethylpenicillin, pipemidic acid, piromidic acid, pivampicillin, pivmecillinam, polymixin-b, prulifloxacin, rufloxacin, sparfloxacin, sulbactam, sulfabenzamide, sulfacytine, sulfametopyrazine, sulphacetamide, sulphadiazine, sulphadimidine, sulphamethizole, sulphamethoxazole, sulphanilamide, sulphasomidine, sulphathiazole, teicoplanin, temafioxacin, tetracycline, tetroxoprim, tigecycline, tinidazole, tobramycin, tosufloxacin, trimethoprim, vancomycin, and pharmaceutically acceptable salts or esters thereof.

In another example, for a fungal infection, a treatment may include an antifungal agent. Exemplary antifungal agents include, but are not limited to, polyenes (e.g., amphotericin B, candicidin, filipin, hamycin, natamycin, nystatin, and rimocidin), azoles (e.g., imidazoles such as bifonazole, butoconazole, clotrimazole, eberconazole, econazole, fenticonazole, flutrimazole, isoconazole, ketoconazole, luliconazole, miconazole, omoconazole, oxiconazole, serlaconazole, sulconazole, and tioconazole; triazoles such as albaconazole, efinaconazole, epoxiconazole, fluconazole, isavuconazole, itraconazole, posaconazole, propiconazole, ravuconazole, terconazole, and voriconazole; and thiazoles such as abafungin), allylamines (e.g., amorolfin, butenafine, naftifine, and terbinafine), echinocandins (e.g., anidulafungin, caspofungin, and micafungin), and other antifungal agents including but not limited to benzoic acid, ciclopirox olamine, 5-flucytosin, griseofulvin, haloprogin, tolnaftate, aminocandin, chlordantoin, chlorphenesin, nifuroxime, undecylenic acid, crystal violet, and pharmaceutically acceptable salts or esters thereof.

In some embodiments, a method of treatment may include administering a treatment to an asymptomatic patient, for example, based on the detection and/or identification of a pathogen present in a biological sample derived from the patient by the methods of the invention. In other embodiments, a method of treatment may include administering a treatment to a symptomatic patient based on the detection of identification of a pathogen present in a biological sample derived from the patient by the methods of the invention.

In some embodiments, the treatment selected for a patient is based on the detection and/or identification of a pathogen by the methods of the invention. Appropriate treatments for different pathogen species are known in the art. In one example, if a Gram positive bacterium is detected in a biological derived from a patient, a method of treatment may involve administration of vancomycin. In another example, if a Gram negative bacterium is detected in a biological derived from a patient, a method of treatment may involve administration of pipercillin-tazobactam. In another example, in some embodiments, if an *Acinetobacter* spp. (e.g., *Acinetobacter baumannii*) is detected in a biological sample derived from a patient, a method of treatment may involve administration of colistin, meropenem, and/or gentamicin. In another example, in some embodiments, if a *Klebsiella* spp. (e.g., *Klebsiella pneumoniae*) is detected in a biological sample derived from a patient, a method of treatment may involve administration of meropenem. In yet another example, in some embodiments, if a *Pseudomonas* spp. (e.g., *Pseudomonas aeruginosa*) is detected in a biological sample derived from a patient, a method of treatment may involve administration of pipercillin-tazobactam. In a further example, in some embodiments, if an *Escherichia* spp. (e.g., *Escherichia coli*) is detected in a biological sample derived from a patient, a method of treatment may involve administration of meropenem. In another example, in some embodiments, if an *Enterococcus* spp. (e.g., *Enterococcus faecium*) is detected in a biological sample derived from a patient, a method of treatment may involve administration of daptomycin.

Assay Reagents

The methods described herein may include any suitable reagents, for example, surfactants, buffer components, additives, chelating agents, and the like. The surfactant may be selected from a wide variety of soluble non-ionic surface active agents including surfactants that are generally commercially available under the IGEPAL® trade name from GAF Company. The IGEPAL® liquid non-ionic surfactants are polyethylene glycol p-isooctylphenyl ether compounds and are available in various molecular weight designations, for example, IGEPAL® CA720, IGEPAL® CA630, and IGEPAL® CA890. Other suitable non-ionic surfactants include those available under the trade name TETRONIC® 909 from BASF Corporation. This material is a tetrafunctional block copolymer surfactant terminating in primary hydroxyl groups. Suitable non-ionic surfactants are also available under the ALPHONIC® trade name from Vista Chemical Company and such materials are ethoxylates that are non-ionic biodegradables derived from linear primary alcohol blends of various molecular weights. The surfactant may also be selected from poloxamers, such as polyoxyethylene-polyoxypropylene block copolymers, such as those available under the trade names SYNPERONIC® PE series (ICI), PLURONIC® series (BASF), Supronic, MONOLAN®, PLURACARE®, and PLURODAC®, polysorbate surfactants, such as TWEEN® 20 (PEG-20 sorbitan monolaurate), and glycols such as ethylene glycol and propylene glycol.

Such non-ionic surfactants may be selected to provide an appropriate amount of detergency for an assay without having a deleterious effect on assay reactions. In particular, surfactants may be included in a reaction mixture for the purpose of suppressing non-specific interactions among various ingredients of the aggregation assays of the invention. The non-ionic surfactants are typically added to the liquid sample prior in an amount from 0.01% (w/w) to 5% (w/w).

The non-ionic surfactants may be used in combination with one or more proteins (e.g., albumin, fish skin gelatin, lysozyme, or transferrin) also added to the liquid sample prior in an amount from 0.01% (w/w) to 5% (w/w).

Furthermore, the assays, methods, and cartridge units of the invention can include additional suitable buffer components (e.g., Tris base, selected to provide a pH of about 7.8 to 8.2 in the reaction milieu); and chelating agents to scavenge cations (e.g., ethylene diamine tetraacetic acid (EDTA), EDTA disodium, citric acid, tartaric acid, glucuronic acid, saccharic acid or suitable salts thereof).

Sample Preparation and Cell Lysis

The methods and systems of the invention may involve sample preparation and/or cell lysis. For example, a pathogen present in a biological sample may be lysed prior to amplification of a target nucleic acid. Suitable lysis methods for lysing pathogen cells in a biological sample (e.g., whole blood, urine, cerebrospinal fluid, synovial fluid, liquid biopsy, skin biopsy, sputum, gastric lavage, bronchoaveolar lavage, and tissue homogenates) include, for example, mechanical lysis (e.g., beadbeating and sonication), heat lysis, and alkaline lysis. In some embodiments, beadbeating may be performed by adding glass beads (e.g., 0.5 mm glass beads) to a biological sample to form a mixture and agitating the mixture. As an example, the sample preparation and cell lysis (e.g., beadbeating) may be performed using any of the approaches and methods described in WO 2012/054639.

In some embodiments, the methods of the invention involve detection of one or more pathogen-associated analytes in a whole blood sample. In some embodiments, the methods may involve disruption of red blood cells (erythrocytes). In some embodiments, the disruption of the red blood cells can be carried out using an erythrocyte lysis agent (i.e., a lysis buffer, an isotonic lysis agent, or a nonionic detergent). Erythrocyte lysis buffers which can be used in the methods of the invention include, without limitation, isotonic solutions of ammonium chloride (optionally including carbonate buffer and/or EDTA), and hypotonic solutions. The basic mechanism of hemolysis using isotonic ammonium chloride is by diffusion of ammonia across red blood cell membranes. This influx of ammonium increases the intracellular concentration of hydroxyl ions, which in turn reacts with $CO_2$ to form hydrogen carbonate. Erythrocytes exchange excess hydrogen carbonate with chloride which is present in blood plasma via anion channels and subsequently increase in intracellular ammonium chloride concentrations. The resulting swelling of the cells eventually causes loss of membrane integrity.

Alternatively, the erythrocyte lysis agent can be an aqueous solution of nonionic detergents (e.g., nonyl phenoxypolyethoxylethanol (NP-40), 4-octylphenol polyethoxylate (TRITON™ X-100), BRIJ® 58, or related nonionic surfactants, and mixtures thereof). The erythrocyte lysis agent disrupts at least some of the red blood cells, allowing a large fraction of certain components of whole blood (e.g., certain whole blood proteins) to be separated (e.g., as supernatant following centrifugation) from the white blood cells or other cells (e.g., pathogen cells (e.g., bacterial cells and/or fungal cells)) present in the whole blood sample. Following erythrocyte lysis and centrifugation, the resulting pellet may be lysed, for example, as described above.

In some embodiments, the methods of the invention may include (a) providing a whole blood sample from a subject; (b) mixing the whole blood sample with an erythrocyte lysis agent solution to produce disrupted red blood cells; (c) following step (b), centrifuging the sample to form a supernatant and a pellet, discarding some or all of the supernatant, and resuspending the pellet to form an extract, (d) lysing cells of the extract (which may include white blood cells and/or pathogen cells) to form a lysate. In some embodiments, the method further comprises amplifying one or more target nucleic acids in the lysate. In some embodiments, the sample of whole blood is from about 0.5 to about 10 mL of whole blood, for example, 0.5 mL, 1 mL, 2 mL, 3 mL, 4 mL, 5 mL, 6 mL, 7 mL, 8 mL, 9 mL, or 10 mL of whole blood. In some embodiments, the method may include washing the pellet (e.g., with a buffer such as TE buffer) prior to resuspending the pellet and optionally repeating step (c). In some embodiments, the method may include 1, 2, 3, 4, 5, or more wash steps. In other embodiments, the method is performed without performing any wash step. In some embodiments, the amplifying is in the presence of whole blood proteins, non-target nucleic acids, or both. In some embodiments, the amplifying may be in the presence of from 0.5 µg to 60 µg (e.g., 0.5 µg, 1 µg, 5 µg, 10 µg, 15 µg, 20 µg, 25 µg, 30 µg, 35 µg, 40 µg, 45 µg, 50 µg, 55 µg, or 60 µg) of subject DNA. In some embodiments, the subject DNA is from white blood cells of the subject.

Amplification and Detection of Nucleic Acids from Complex Samples

In several embodiments, the methods and systems of the invention involve amplification of one or more nucleic acids. Amplification may be exponential or linear. A target or template nucleic acid may be either DNA or RNA. The sequences amplified in this manner form an "amplified region" or "amplicon." Primer probes can be readily designed by those skilled in the art to target a specific template nucleic acid sequence. In certain preferred embodiments, resulting amplicons are short to allow for rapid cycling and generation of copies. The size of the amplicon can vary as needed, for example, to provide the ability to discriminate target nucleic acids from non-target nucleic acids. For example, amplicons can be less than about 1,000 nucleotides in length. Desirably the amplicons are from 100 to 500 nucleotides in length (e.g., 100 to 200, 150 to 250, 300 to 400, 350 to 450, or 400 to 500 nucleotides in length). In some embodiments, more than one (e.g., 1, 2, 3, 4, 5, 6, 7, 8, 9, 10, or more than 10) target nucleic acids may be amplified in one reaction. In other embodiments, a single target nucleic acid may be amplified in one reaction. In some embodiments, the invention provides amplification-based nucleic acid detection assays conducted in complex samples (e.g., whole blood).

Sample preparation typically involves removing or providing resistance for common PCR inhibitors found in complex samples (e.g., body fluids and tissue homogenates). Common inhibitors are listed in Table 1 (see also Wilson, Appl. Environ. Microbiol., 63:3741 (1997)). The "facilitators" in Table 1 indicate methodologies or compositions that may be used to reduce or overcome inhibition. Inhibitors typically act by either prevention of cell lysis, degradation or sequestering a target nucleic acid, and/or inhibition of a polymerase activity. The most commonly employed polymerase, Taq, is inhibited by the presence of 0.1% blood in a reaction. Mutant Taq polymerases have been engineered that are resistant to common inhibitors (e.g., hemoglobin and/or humic acid) found in blood (Kermekchiev et al., Nucl. Acid. Res., 37(5): e40, (2009)). Manufacturer recommendations indicate these mutations enable direct amplification from up to 20% blood. Despite resistance afforded by the mutations, accurate real time PCR detection is complicated due to fluorescence quenching observed in the presence of blood sample (Kermekchiev et al., Nucl. Acid. Res., 37:e40 (2009)).

TABLE 1

PCR inhibitors and facilitators for overcoming inhibition.

| Sample or Specimen Type | Target | Inhibitor | Facilitator |
|---|---|---|---|
| feces | Escherichia coli | >10³ bacterial cells | ion-exchange column |
| CSF | Treponema pallidum | Cellular debris causing nonspecific amplification | nested primers |
| whole blood | mammalian tissue | >4 µl of blood/100-ml reaction mix (hemoglobin) | 1-2% blood per reaction |
| feces | Rotavirus | unknown dilution | cellulose fiber |
| clinical specimens | Cytomegalovirus | unidentified components | glass bead extraction |
| human blood and tissue | human genes | DNA binding proteins | thermophilic protease from Thermus strain rt44A |
| mammalian tissue | Mammalian tissue genetics | thermal cycler variations | formamide |
| mammalian tissue | Mammalian tissue genetics | thermal cycler variations | DMSO, glycerol, PEG, organic solvents |
| clinical specimens | Treponema pallidum | unknown factors | Various substrate-specific physicochemical methods |
| forensic semen samples | Sperm | Genotyping errors; selective/total PCR inhibition by vaginal microorganisms | |
| feces | Salmonella enterica | various body fluids | immunomagnetic separation |
| feces | Various enteric viruses | unknown | size exclusion chromatography, physicochemical extraction |
| clinical specimens | Herpes simplex virus | endogenous inhibitors, random effects | repurification, coamplified positive control |
| feces | Escherichia coli | nonspecific inhibitors, urea, hemoglobin, heparin, phenol, SDS | additional primers and reaction cyclers, booster PCR |
| tissue culture | Cytomegalovirus HIV | glove powder | |
| suspensions, skin biopsies | Mycobacterium leprae | mercury-based fixatives, neutral buffered formaline | reduced fixation times, ethanol fixation |
| clinical specimens | Mycobacterium tuberculosis | unknown inhibitors in pus, tissue biopsies, sputum, pleural fluid | physicochemical extraction |
| mammalian tissue | mammalian tissue genetics | unknown contaminant of reverse transcriptase | additional DNA |
| formalin-fixed paraffin tissue | Hepatitis C virus | ribonucleotide vanadyl complexes | phenol/chloroform extraction |
| nasopharyngeal aspirates and swabs | Bordetella pertussis | unknown inhibitors | phenol/chloroform extraction |

TABLE 1-continued

PCR inhibitors and facilitators for overcoming inhibition.

| Sample or Specimen Type | Target | Inhibitor | Facilitator |
|---|---|---|---|
| human mononuclear blood cells | HIV type I | detergents | mineral oil |
| bloodstain | human mitochondrial DNA | unidentified heme compound, hemin | BSA |
| blood | various | heparin | alternative polymerases and buffers, chelex, spermine, [Mg2+], glycerol, BSA, heparinase |
| sputa | *Mycoplasma pneumoniae* | N-acetyl-L-cysteine, dithiothreitol, mucolytic agents | |
| human tissue | HLA-DRB1 genotyping | pollen, glove powder, impure DNA, heparin, hemoglobin | |
| clinical specimens | *Mycobacterium tuberculosis* | unknown | competitive internal control |
| dental plaque | many | unknown | diatomaceous earth, guanidium isothiocyante, ethanol, acetone |
| ancient mammalian tissues | Cytochrome b gene | unknown | ammonium acetate, ethidium bromide |

Polymerase chain reaction amplification of DNA or cDNA is a tried and trusted methodology; however, as discussed above, polymerases are inhibited by agents contained in crude samples, including but not limited to commonly used anticoagulants and hemoglobin. Recently mutant Taq polymerases have been engineered to harbor resistance to common inhibitors found in blood and soil. Currently available polymerases, e.g., HemoKlenTaq™ (New England BioLabs, Inc., Ipswich, Mass.) as well as OmniTaq™ and OmniKlenTaq™ (DNA Polymerase Technology, Inc., St. Louis, Mo.) are mutant (e.g., N-terminal truncation and/or point mutations) Taq polymerase that render them capable of amplifying DNA in the presence of up to 10%, 20% or 25% whole blood, depending on the product and reaction conditions (See, e.g., Kermekchiev et al. Nucl. Acids Res. 31:6139 (2003); and Kermekchiev et al., Nucl. Acid. Res., 37:e40 (2009); and see U.S. Pat. No. 7,462,475). Additionally, PHUSION® Blood Direct PCR Kits (Finnzymes Oy, Espoo, Finland), include a unique fusion DNA polymerase enzyme engineered to incorporate a double-stranded DNA binding domain, which allows amplification under conditions which are typically inhibitory to conventional polymerases such as Taq or Pfu, and allow for amplification of DNA in the presence of up to about 40% whole blood under certain reaction conditions. See Wang et al., Nucl. Acids Res. 32:1197 (2004); and see U.S. Pat. Nos. 5,352,778 and 5,500,363. Furthermore, Kapa Blood PCR Mixes (Kapa Biosystems, Woburn, Mass.), provide a genetically engineered DNA polymerase enzyme which allows for direct amplification of whole blood at up to about 20% of the reaction volume under certain reaction conditions. Despite these breakthroughs, direct optical detection of generated amplicons is not possible with existing methods since fluorescence, absorbance, and other light based methods yield signals that are quenched by the presence of blood. See Kermekchiev et al., Nucl. Acid. Res., 37:e40 (2009).

A variety of impurities and components of whole blood can be inhibitory to the polymerase and primer annealing. These inhibitors can lead to generation of false positives and low sensitivities. To reduce the generation of false positives and low sensitivities when amplifying and detecting nucleic acids in complex samples, it is desirable to utilize a thermal stable polymerase not inhibited by whole blood samples, for example as described above, and include one or more internal PCR assay controls (see Rosenstraus et al. J. Clin Microbiol. 36:191 (1998) and Hoofar et al., J. Clin. Microbiol. 42:1863 (2004)).

For example, the assay can include an internal control nucleic acid that contains primer binding regions identical to those of the target sequence to assure that clinical specimens are successfully amplified and detected. In some embodiments, the target nucleic acid and internal control can be selected such that each has a unique probe binding region that differentiates the internal control from the target nucleic acid. The internal control is, optionally, employed in combination with a processing positive control, a processing negative control, and a reagent control for the safe and accurate determination and identification of an infecting organism in, e.g., a whole blood clinical sample. The internal control can be an inhibition control that is designed to co-amplify with the nucleic acid target being detected. Failure of the internal inhibition control to be amplified is evidence of a reagent failure or process error. Universal primers can be designed such that the target sequence and the internal control sequence are amplified in the same reaction tube. Thus, using this format, if the target DNA is amplified but the internal control is not it is then assumed that the target DNA is present in a proportionally greater amount than the internal control and the positive result is valid as the internal control amplification is unnecessary. If, on the other hand, neither the internal control nor the target is amplified it is then assumed that inhibition of the PCR reaction has occurred and the test for that particular sample is not valid. Exemplary non-limiting internal control nucleic acids that may be used in the methods of the invention include internal control sequences derived from *Citrus sinensis* or scrambled *S. aureus* femA nucleic acid sequences.

For example, the *Citrus sinensis* internal control nucleic acid, which includes the nucleic acid sequence of SEQ ID NO: 94 cloned into plasmid pBR322, may be amplified in the presence of a forward primer comprising the nucleic acid sequence 5'-GGA AAT CTA ACG AGA GAG CAT GCT-3' (SEQ ID NO: 95) or 5'-GGA AAT CTA ACG AGA GAG CAT GC-3' (SEQ ID NO: 96) and a reverse primer comprising the nucleic acid sequence 5'-CGA TGC GTG ACA CCC AGG C-3' (SEQ ID NO: 97) or 5'-GAT GCG TGA CAC CCA GGC-3' (SEQ ID NO: 98). In some embodiments, an amplicon produced using these primers is detected by hybridization using a 5' capture probe that includes the oligonucleotide sequence 5'-GAG ACG TTT TGG ATA CAT GTG AAA GAA GGC-3' (SEQ ID NO: 99) and/or a 3' capture probe that includes the oligonucleotide sequence 5'-CGA TGG TTC ACG GGA TTC TGC AAT TC-3' (SEQ ID NO: 100) to detect the presence of the *Citrus sinensis* internal control nucleic acid in a biological sample. In some embodiments, the 5' capture probe and/or the 3' capture probe is conjugated to a magnetic nanoparticle.

In another example, the randomized *S. aureus* internal control nucleic acid, which includes the nucleic acid sequence of SEQ ID NO: 101 cloned into plasmid pBR322, may be amplified in the presence of a forward primer comprising the nucleic acid sequence 5'-GCA GCA ACA ACA GAT TCC-3' (SEQ ID NO: 102) and a reverse primer comprising the nucleic acid sequence 5'-GTA GCC GTT ATG TCC TGG TG-3' (SEQ ID NO: 103). In some embodiments, an amplicon produced using these primers is detected by hybridization using a 5' capture probe that includes the oligonucleotide sequence 5'-TCG AAC AAT GAA GAA CTG TAC ACA ACT TTC G-3' (SEQ ID NO: 104) and/or a 3' capture probe that includes the oligonucleotide sequence 5'-GGT TTG TCA TGT TAT TGT ATG AGA AGC AAG-3' (SEQ ID NO: 105) to detect the presence of the randomized *S. aureus* internal control nucleic acid in a biological sample. In some embodiments, the 5' capture probe and/or the 3' capture probe is conjugated to a magnetic nanoparticle.

The assays of the invention can include one or more positive processing controls in which one or more target nucleic acids is included in the assay (e.g., each included with one or more cartridges) at 3× to 5× the limit of detection. The measured $T_2$ for each of the positive processing controls must be above the pre-determined threshold indicating the presence of the target nucleic acid. The positive processing controls can detect all reagent failures in each step of the process (e.g., lysis, PCR, and $T_2$ detection), and can be used for quality control of the system. The assays of the invention can include one or more negative processing controls consisting of a solution free of target nucleic acid (e.g., buffer alone). The $T_2$ measurements for the negative processing control should be below the threshold indicating a negative result while the $T_2$ measured for the internal control is above the decision threshold indicating an internal control positive result. The purpose of the negative control is to detect carry-over contamination and/or reagent contamination. The assays of the invention can include one or more reagent controls. The reagent control will detect reagent failures in the PCR stage of the reaction (i.e. incomplete transfer of master mix to the PCR tubes). The reagent controls can also detect gross failures in reagent transfer prior to $T_2$ detection.

In some embodiments, complex biological samples, which may be a liquid sample (including whole blood, cerebrospinal fluid, urine, synovial fluid, and tissue biopsy homogenates (e.g., skin biopsies) can be directly amplified using about 5%, about 10%, about 20%, about 25%, about 30%, about 25%, about 40%, and about 45% or more complex liquid sample in amplification reactions, and that the resulting amplicons can be directly detected from amplification reaction using magnetic resonance (MR) relaxation measurements upon the addition of conjugated magnetic particles bound to oligonucleotides complementary to the target nucleic acid sequence. Alternatively, the magnetic particles can be added to the sample prior to amplification. Thus, provided are methods for the use of nucleic acid amplification in a complex dirty sample, hybridization of the resulting amplicon to paramagnetic particles, followed by direct detection of hybridized magnetic particle conjugate and target amplicons using magnetic particle based detection systems. In particular embodiments, direct detection of hybridized magnetic particle conjugates and amplicons is via MR relaxation measurements (e.g., $T_2$, $T_1$, $T_1/T_2$ hybrid, $T_2$*, etc). Further provided are methods which are kinetic, in order to quantify the original nucleic acid copy number within the sample (e.g., sampling and nucleic acid detection at pre-defined cycle numbers, comparison of endogenous internal control nucleic acid, use of exogenous spiked homologous competitive control nucleic acid).

While the exemplary methods described hereinafter relate to amplification using polymerase chain reaction ("PCR"), numerous other methods are known in the art for amplification of nucleic acids (e.g., isothermal methods, rolling circle methods, etc.). Those skilled in the art will understand that these other methods may be used either in place of, or together with, PCR methods. See, e.g., Saiki, "Amplification of Genomic DNA" in PCR Protocols, Innis et al., Eds., Academic Press, San Diego, Calif., pp 13-20 (1990); Wharam et al., Nucleic Acids Res. 29:E54 (2001); Hafner et al., Biotechniques, 30:852 (2001). Further amplification methods suitable for use with the present methods include, for example, reverse transcription PCR (RT-PCR), ligase chain reaction (LCR), transcription based amplification system (TAS), transcription mediated amplification (TMA), nucleic acid sequence based amplification (NASBA) method, the strand displacement amplification (SDA) method, the loop mediated isothermal amplification (LAMP) method, the isothermal and chimeric primer-initiated amplification of nucleic acid (ICAN) method, and the smart amplification system (SMAP) method. These methods, as well as others are well known in the art and can be adapted for use in conjunction with provided methods of detection of amplified nucleic acid.

The PCR method is a technique for making many copies of a specific template DNA sequence. The PCR process is disclosed in U.S. Pat. Nos. 4,683,195; 4,683,202; and 4,965,188, each of which is incorporated herein by reference. One set of primers complementary to a template DNA are designed, and a region flanked by the primers is amplified by DNA polymerase in a reaction including multiple amplification cycles. Each amplification cycle includes an initial denaturation, and up to 50 cycles of annealing, strand elongation (or extension) and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan, et al, Journal of Clinical Microbiology, 33:556(1995). Various modified PCR methods are available and well known in the art. Various modifications such as the "RT-PCR" method, in which DNA is synthesized from RNA using a reverse transcriptase before performing PCR; and the "TaqMan® PCR" method, in which only a specific allele is amplified and detected using a fluorescently labeled TaqMan® probe, and Taq DNA polymerase, are known to those skilled in the art. RT-PCR and variations thereof have been described, for example, in U.S. Pat. Nos. 5,804,383; 5,407,800; 5,322,770; and 5,310,652, and references described therein, which are hereby incorporated by reference; and TaqMan® PCR and related reagents for use in the method have been described, for example, in U.S. Pat. Nos. 5,210,015; 5,876,930; 5,538, 848; 6,030,787; and 6,258,569, which are hereby incorporated by reference.

In some embodiments, asymmetric PCR is performed to preferentially amplify one strand of a double-stranded DNA template. Asymmetric PCR typically involves addition of an excess of the primer for the strand targeted for amplification. An exemplary asymmetric PCR condition is 300 nM of the excess primer and 75 nM of the limiting primer to favor single strand amplification. In other embodiments, 400 nM of the excess primer and 100 nM of the limiting primer may be used to favor single strand amplification.

In some embodiments, including embodiments that employ multiplexed PCR reactions, hot start PCR conditions may be used to reduce mis-priming, primer-dimer formation, improve yield, and/or and ensure high PCR specificity and sensitivity. A variety of approaches may be employed to achieve hot start PCR conditions, including hot start DNA polymerases (e.g., hot start DNA polymerases with aptamer-based inhibitors or with mutations that limit activity at lower temperatures) as well as hot start dNTPs (e.g., CLEAN-AMP™ dNTPs, TriLink Biotechnologies).

In some embodiments, a PCR reaction may include from about 20 cycles to about 55 cycles or more (e.g., about 20, 25, 30, 35, 40, 45, 50, or 55 cycles).

LCR is a method of DNA amplification similar to PCR, except that it uses four primers instead of two and uses the enzyme ligase to ligate or join two segments of DNA. Amplification can be performed in a thermal cycler (e.g., LCx of Abbott Labs, North Chicago, Ill.). LCR can be performed for example, as according to Moore et al., Journal of Clinical Microbiology 36:1028 (1998). LCR methods and variations have been described, for example, in European Patent Application Publication No. EP0320308, and U.S. Pat. No. 5,427,930, each of which is incorporated herein by reference.

The TAS method is a method for specifically amplifying a target RNA in which a transcript is obtained from a template RNA by a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., PNAS 86:1173 (1989). The TAS method has been described, for example, in International Patent Application Publication No. WO1988/010315, which is incorporated herein by reference.

Transcription mediated amplification (TMA) is a transcription-based isothermal amplification reaction that uses RNA transcription by RNA polymerase and DNA transcription by reverse transcriptase to produce an RNA amplicon from target nucleic acid. TMA methods are advantageous in that they can produce 100 to 1000 copies of amplicon per amplification cycle, as opposed to PCR or LCR methods that produce only 2 copies per cycle. TMA has been described, for example, in U.S. Pat. No. 5,399,491, which is incorporated herein by reference. NASBA is a transcription-based method which for specifically amplifying a target RNA from either an RNA or DNA template. NASBA is a method used for the continuous amplification of nucleic acids in a single mixture at one temperature. A transcript is obtained from a template RNA by a DNA-dependent RNA polymerase using a forward primer having a sequence identical to a target RNA and a reverse primer having a sequence complementary to the target RNA a on the 3' side and a promoter sequence that recognizes $T_7$ RNA polymerase on the 5' side. A transcript is further synthesized using the obtained transcript as template. This method can be performed as according to Heim, et al., Nucleic Acids Res., 26:2250 (1998). The NASBA method has been described in U.S. Pat. No. 5,130, 238, which is incorporated herein by reference.

The SDA method is an isothermal nucleic acid amplification method in which target DNA is amplified using a DNA strand substituted with a strand synthesized by a strand substitution type DNA polymerase lacking 5'→3' exonuclease activity by a single stranded nick generated by a restriction enzyme as a template of the next replication. A primer containing a restriction site is annealed to template, and then amplification primers are annealed to 5' adjacent sequences (forming a nick). Amplification is initiated at a fixed temperature. Newly synthesized DNA strands are nicked by a restriction enzyme and the polymerase amplification begins again, displacing the newly synthesized strands. SDA can be performed according to Walker, et al., PNAS, 89:392 (1992). SDA methods have been described in U.S. Pat. Nos. 5,455,166 and 5,457,027, each of which are incorporated by reference.

The LAMP method is an isothermal amplification method in which a loop is always formed at the 3' end of a synthesized DNA, primers are annealed within the loop, and specific amplification of the target DNA is performed isothermally. LAMP can be performed according to Nagamine et al., Clinical Chemistry. 47:1742 (2001). LAMP methods have been described in U.S. Pat. Nos. 6,410,278; 6,974,670; and 7,175,985, each of which are incorporated by reference.

The ICAN method is anisothermal amplification method in which specific amplification of a target DNA is performed isothermally by a strand substitution reaction, a template exchange reaction, and a nick introduction reaction, using a chimeric primer including RNA-DNA and DNA polymerase having a strand substitution activity and RNase H. ICAN can be performed according to Mukai et al., J. Biochem. 142: 273(2007). The ICAN method has been described in U.S. Pat. No. 6,951,722, which is incorporated herein by reference.

The SMAP (MITANI) method is a method in which a target nucleic acid is continuously synthesized under isothermal conditions using a primer set including two kinds of primers and DNA or RNA as a template. The first primer included in the primer set includes, in the 3' end region thereof, a sequence (Ac') hybridizable with a sequence (A) in the 3' end region of a target nucleic acid sequence as well as, on the 5' side of the above-mentioned sequence (Ac'), a sequence (B') hybridizable with a sequence (Bc) complementary to a sequence (B) existing on the 5' side of the above-mentioned sequence (A) in the above-mentioned target nucleic acid sequence. The second primer includes, in the 3' end region thereof, a sequence (Cc') hybridizable with a sequence (C) in the 3' end region of a sequence complementary to the above-mentioned target nucleic acid sequence as well as a loopback sequence (D-Dc') including two nucleic acid sequences hybridizable with each other on an identical strand on the 5' side of the above-mentioned sequence (Cc'). SMAP can be performed according to Mitani et al., Nat. Methods, 4(3): 257 (2007). SMAP methods have been described in U.S. Patent Application Publication Nos. 2006/0160084, 2007/0190531 and 2009/0042197, each of which is incorporated herein by reference.

The amplification reaction can be designed to produce a specific type of amplified product, such as nucleic acids that are double stranded; single stranded; double stranded with 3' or 5' overhangs; or double stranded with chemical ligands on the 5' and 3' ends. The amplified PCR product can be detected by: (i) hybridization of the amplified product to magnetic particle bound complementary oligonucleotides, where two different oligonucleotides are used that hybridize to the amplified product such that the nucleic acid serves as an interparticle tether promoting particle agglomeration; (ii) hybridization mediated detection where the DNA of the amplified product must first be denatured; (iii) hybridization mediated detection where the particles hybridize to 5' and 3' overhangs of the amplified product; (iv) binding of the particles to the chemical or biochemical ligands on the termini of the amplified product, such as streptavidin functionalized particles binding to biotin functionalized amplified product.

The systems and methods of the invention can be used to perform real time PCR and provide quantitative information about the amount of target nucleic acid present in a sample (see, e.g., FIG. 52 and Example 18 of WO 2012/054639). Methods for conducting quantitative real time PCR are provided in the literature (see for example: RT-PCR Protocols. Methods in Molecular Biology, Vol. 193. Joe O'Connell, ed. Totowa, N.J.: Humana Press, 2002, 378 pp. ISBN 0-89603-875-0.). Example 18 of WO 2012/054639 describes use of the methods of the invention for real time PCR analysis of a whole blood sample.

The systems and methods of the invention can be used to perform real time PCR directly in opaque samples, such as whole blood, using magnetic nanoparticles modified with capture probes and magnetic separation. Using real-time PCR allows for the quantification of a target nucleic acid without opening the reaction tube after the PCR reaction has commenced.

In one approach, biotin or avidin labeled primers can be used to perform real-time PCR. These labels would have corresponding binding moieties on the magnetic particles that could have very fast binding times. This allows for a double stranded product to be generated and allows for much faster particle binding times, decreasing the overall turnaround time. The binding chemistry would be reversible, preventing the primers from remaining particle bound. In order to reverse the binding, the sample can be heated or the pH adjusted.

In another approach, the real-time PCR can be accomplished through the generation of duplex DNA with overhangs that can hybridize to the superparamagnetic particles. Additionally, LNA and/or fluorinated capture probes may speed up the hybridization times.

In still another approach, the particles are designed to have a hairpin that buries the capture probe binding site to the amplicon. Heating the particles to a higher melt temperature would expose the binding site of the hairpin of the capture probes on the particles to allow binding to the target.

In another approach, a probe that hybridizes to an amplicon is tethering two (or more) particles. The reaction would be conducted in the presence of a polymerase with 5' exonuclease activity, resulting in the cleavage of the interparticle tether and a subsequent change in $T_2$. The polymerase is selected to have exonuclease activity and compatibility with the matrix of choice (e.g. blood). In this approach, smaller particles (e.g., 30 nm CLIO) can be used to reduce steric hindrance of the hybridization to target or subsequent enzymatic digestion during polymerization (see, e.g., Heid et al Genome Research 1996 6: 986-994).

In another approach, two particle populations can be synthesized to bear complementary capture probes. In the absence of amplicon, the capture probes hybridize promoting particle clustering. Upon generation of amplicon, the amplicon can compete, hybridize, and displace the capture probes leading to particle declustering. The method can be conducted in the presence or absence of nanoparticles. The particles free in solution will cluster and decluster due to the thermocycling (because, e.g., the Tm can be below 95° C.). The Tm of the amplicon binding to one of the particle-immobilized capture probes can be designed such that that binding interaction is more favorable than the particle-to-particle binding interaction (by, e.g., engineering point mutations within the capture probes to thermodynamically destabilize the duplexes). In this embodiment, the particle concentration can be kept at, e.g., low or high levels.

Previous work showed that in some cases the presence of particles in the PCR reaction could inhibit PCR. For these inhibitory particles, it is envisioned that the particles could be pulled to the side of the tube (or other location within the container) to keep them out of solution during the PCR reaction. Methods can be used to release the particles back into suspension to allow them to hybridize to the PCR product and then pull them back out of solution. Other previous work has shown that specific formulations of particles are not inhibitory to the PCR reaction and can remain in solution during amplification.

In certain embodiments, the invention features the use of enzymes compatible with whole blood, including but not limited to NEB HemoKlenTaq™, DNAP OmniKlenTaq™, Kapa Biosystems whole blood enzyme, and Thermo-Fisher Finnzymes PHUSION® enzyme.

The invention also features quantitative asymmetric PCR. In any of the real-time PCR methods of the invention, the method can involve the following steps:
1. aliquoting whole blood into a prepared PCR mastermix containing superparamagnetic particles;
2. prior to the first PCR cycle, closing the tube until PCR cycling is completed;
3. loading the tube onto thermal cycler;
4. running "n" cycles of standard PCR thermal cycling;
5. conducting a $T_2$ detection (the exact time duration and steps for this vary depending on the biochemical and particle design approach described below); and
6. repeating steps 4 and 5 until enough $T_2$ readings have been taken for an accurate quantification of initial target concentration.

The above methods can be used with any of the following categories of detection of aggregation or disaggregation described herein, including those described in Table 2.

TABLE 2

Categories of Detection of Aggregation or Disaggregation

| Name | Description |
|---|---|
| Clustering-based detection and magnetic separation | Particles > 100 nm or magnetic-separation compatible. Particles removed from solution during PCR $T_2$ goes up with amplicon generation Agitation during step 5 |
| Clustering-based detection with particles > 100 nm | Particles > 100 nm Particles do not inhibit PCR $T_2$ goes up with amplicon generation Agitation during step 5 |
| De-clustering-based detection and magnetic separation | Particles > 100 nm Particles on the side of the tube during PCR $T_2$ goes down with amplicon generation Agitation during step 5 |
| De-clustering-based detection with particles > 100 nm | Particles > 100 nm Particles do not inhibit PCR $T_2$ goes down with amplicon generation Agitation during step 5 |
| Clustering-based detection with particles < 100 nm | Particles < 100 nm (e.g., 30 nm particles) $T_2$ goes down with amplicon appearance (at least for initial cycles, $T_2$ may subsequently increase as cluster size increases) Has potential for much more rapid hybridization times No agitation required to keep particles suspended Particle concentration in nM range |
| De-clustering-based detection with particles < 100 nm | Particles < 100 nm (e.g., 30 nm particles) $T_2$ goes up with amplicon appearance $T_2$ could decrease as the cluster size increase above 100 nm No agitation required to keep particles suspended Has potential for most rapid detection times Particle concentration in nM range |

Amplifying Multiple Amplicons Characteristic of a Species for Improved Sensitivity and/or Specificity In some embodiments, the methods of the invention may involve amplification and detection of more than one amplicon characteristic of a species. In some embodiments, amplification of more than one target nucleic acid characteristic of a species increases the total amount of amplicons characteristic of the species in an assay (in other words, the amount of analyte is increased in the assay). This increase may allow, for example, an increase in sensitivity and/or specificity of detection of the species compared to a method that involves amplification and detection of a single amplicon characteristic of a species. In some embodiments, the methods of the invention may involve amplifying 2, 3, 4, 5, 6, 7, 8, 9, or 10 amplicons characteristic of a species.

In some embodiments, the species is a microbial species. In some embodiments, the microbial species is a bacterial pathogen, including *Acinetobacter* spp. (e.g., *Acinetobacter baumannii, Acinetobacter pittii*, and *Acinetobacter nosocomialis*), Enterobacteriaceae spp., *Enterococcus* spp. (e.g., *Enterococcus faecium* (including *E. faecium* with resistance marker vanA/B) and *Enterococcus faecalis*), *Klebsiella* spp. (e.g., *Klebsiella pneumoniae* (e.g., *K. pneumoniae* with resistance marker KPC) and *Klebsiella oxytoca*), *Pseudomonas* spp. (e.g., *Pseudomonas aeruginosa*), *Staphylococcus* spp. (e.g., *Staphylococcus aureus* (e.g., *S. aureus* with resistance marker mecA), *Staphylococcus haemolyticus, Staphylococcus lugdunensis, Staphylococcus maltophilia, Staphylococcus saprophyticus*, coagulase-positive *Staphylococcus* species, and coagulase-negative (CoNS) *Staphylococcus* species), *Streptococcus* spp. (e.g., *Streptococcus mitis, Streptococcus pneumoniae, Streptococcus agalactiae, Streptococcus anginosa, Streptococcus bovis, Streptococcus dysgalactiae, Streptococcus mutans, Streptococcus sanguinis*, and *Streptococcus pyogenes*), *Escherichia* spp. (e.g., *Escherichia coli*), *Stenotrophomonas* spp. (e.g., *Stenotrophomonas maltophilia*), *Proteus* spp. (e.g., *Proteus mirabilis* and *Proteus vulgaris*), *Serratia* spp. (e.g., *Serratia marcescens*), *Citrobacter* spp. (e.g., *Citrobacter freundii* and *Citrobacter kosen*), *Haemophilus* spp. (e.g., *Haemophilus influenzae*), *Listeria* spp. (e.g., *Listeria monocytogenes*), *Neisseria* spp. (e.g., *Neisseria meningitidis*), *Bacteroides* spp. (e.g., *Bacteroides fragilis*), *Burkholderia* spp. (e.g., *Burkholderia cepacia*), *Campylobacter* (e.g., *Campylobacter jejuni* and *Campylobacter coli*), *Clostridium* spp. (e.g., *Clostridium perfringens*), *Kingella* spp. (e.g., *Kingella kingae*), *Morganella* spp. (e.g., *Morganella morgana*), *Prevotella* spp. (e.g., *Prevotella buccae, Prevotella intermedia*, and *Prevotella melaninogenica*), *Propionibacterium* spp. (e.g., *Propionibacterium acnes*), *Salmonella* spp. (e.g., *Salmonella enterica*), *Shigella* spp. (e.g., *Shigella dysenteriae* and *Shigella flexneri*), and *Enterobacter* spp. (e.g., *Enterobacter aerogenes* and *Enterobacter cloacae*). In some embodiments, the microbial species is a fungal pathogen, for example, *Candida* spp. (e.g., *Candida albicans, Candida guilliermondii, Candida glabrata, Candida krusei, Candida lusitaniae, Candida parapsilosis, Candida dublinensis*, and *Candida tropicalis*) and *Aspergillus* spp. (e.g., *Aspergillus fumigatus*). In some embodiments, the species is *Staphylococcus aureus*. In some embodiments, multiple (e.g., 2, 3, 4, 5, 6, 7, 8, 9, or 10) single-copy loci from a species are amplified and detected. In some embodiments, 2 single-copy loci from a species are amplified and detected. In some embodiments, amplification and detection of multiple single-copy loci from a species may allow for a sensitivity of detection comparable with methods that involve detecting an amplicon that is derived from a multi-copy locus. In some embodiments, methods involving detection of multiple single-copy loci amplified from a microbial species can detect from about 1-10 CFU/mL (e.g., 1, 2, 3, 4, 5, 6, 7, 8, 9 or 10 CFU/mL) of the microbial species in a liquid sample. In some embodiments, methods involving detection of multiple single-copy loci amplified from a microbial species have at least 95% correct detection when the microbial species is present in the liquid sample at a frequency of less than or equal to 5 CFU/mL (e.g., 1, 2, 3, 4, or 5 CFU/mL) of liquid sample.

The invention also provides embodiments in which at least three amplicons are produced by amplification of two target nucleic acids, each of which is characteristic of a species. For example, in some embodiments, a first target nucleic acid and a second target nucleic acid to be amplified may be separated (for example, on a chromosome or on a plasmid) by a distance ranging from about 50 base pairs to about 1500 base pairs (bp), e.g., about 50, 100, 150, 200, 250, 300, 400, 500, 600, 700, 800, 900, 1000, 1100, 1200, 1300, 1400, or 1500 bp. In some embodiments, a first target nucleic acid and a second target nucleic acid to be amplified may be separated (for example, on a chromosome or on a plasmid) by a distance ranging from about 50 bp to about 1000 bp (e.g., about 50, 100, 150, 200, 250, 300, 400, 500, 600, 700, 800, 900, or 1000 bp). In some embodiments the first target nucleic acid and the second target nucleic acid to be amplified may be separated by a distance ranging from about 50 bp to about 1500 bp, from about 50 bp to about 1400 bp, from about 50 bp to about 1300 bp, from about 50 bp to about 1200 bp, from about 50 bp to about 1100 bp, from about 50 bp to about 1000 bp, from about 50 bp to about 950 bp, from about 50 bp to about 900 bp, from about 50 bp to about 850 bp, from about 50 bp to about 800 bp, from about 50 bp to about 800 bp, from about 50 bp to about 750 bp, from about 50 bp to about 700 bp, from about 50 bp to about 650 bp, from about 50 bp to about 600 bp, from about 50 bp to about 550 bp, from about 50 bp to about 500 bp, from about 50 bp to about 500 bp, from about 50 bp to about 450 bp, from about 50 bp to about 400 bp, from about 50 bp to about 350 bp, from about 50 bp to about 300 bp, from about 50 bp to about 250 bp, from about 50 bp to about 200 bp, from about 50 bp to about 150 bp, or from about 50 bp to about 100 bp. In some embodiments, amplification of the first and second target nucleic acids using individual primer pairs (each having a forward and a reverse primer) may lead to amplification of an amplicon that includes the first target nucleic acid, an amplicon that includes the second target nucleic acid, and an amplicon that contains both the first and the second target nucleic acid. This may result in an increase in sensitivity of detection of the species compared to samples in which the third amplicon is not present. In any of the preceding embodiments, amplification may be by asymmetric PCR.

The invention provides magnetic particles decorated with nucleic acid probes to detect two or more amplicons characteristic of a species. For example, in some embodiments, the magnetic particles include two populations, wherein each population is conjugated to probes such that the magnetic particle that can operably bind each of the two or more amplicons. For instance, in embodiments where two target nucleic acids have been amplified to form a first amplicon and a second amplicon, a pair of particles each of which have a mix of capture probes on their surface may be used. In some embodiments, the first population of magnetic particles may be conjugated to a nucleic acid probe that operably binds a first segment of the first amplicon and a nucleic acid probe that operably binds a first segment of the second amplicon, and the second population of magnetic particles may be conjugated to a nucleic acid probe that operably binds a second segment of the first amplicon and a nucleic acid probe that operably binds a second segment of the second amplicon. For instance, one particle population may be conjugated with a 5' capture probe specific to the first amplicon and a 5' capture probe specific to second amplicon, and the other particle population may be conjugated with a 3' capture probe specific to the first amplicon and a 3' capture probe specific to the second amplicon.

In such embodiments, the magnetic particles may aggregate in the presence of the first amplicon and aggregate in the presence of the second amplicon. Aggregation may occur to a greater extent when both amplicons are present.

In some embodiments, a magnetic particle may be conjugated to two, three, four, five, six, seven, eight, nine, or ten nucleic acid probes, each of which operably binds a segment of a distinct target nucleic acid. In some embodiments, a magnetic particle may be conjugated to a first nucleic acid probe and a second nucleic acid probe, wherein the first nucleic acid probe operably binds to a first target nucleic acid, and the second nucleic acid probe operably binds to a second target nucleic acid. In other embodiments, a magnetic particle may be conjugated to a first nucleic acid probe that operably binds a first target nucleic acid, a second nucleic acid probe that operably binds a second target nucleic acid, and a third nucleic acid that operably binds a third target nucleic acid. In yet other embodiments, a magnetic particle may be conjugated to a first nucleic acid probe that operably binds a first target nucleic acid, a second nucleic acid probe that operably binds a second target nucleic acid, a third nucleic acid that operably binds a third target nucleic acid, and a fourth nucleic acid probe that operably binds a fourth target nucleic acid. In still other embodiments, a magnetic particle may be conjugated to a first nucleic acid probe that operably binds a first target nucleic acid, a second nucleic acid probe that operably binds a second target nucleic acid, a third nucleic acid that operably binds a third target nucleic acid, a fourth nucleic acid probe that operably binds a fourth target nucleic acid, and a fifth nucleic acid probe that operably binds a fifth target nucleic acid.

Contamination Control

One potential problem in the use of PCR as an analytical tool is the risk of having new reactions contaminated with old, amplified products. Potential sources of contamination include a) large numbers of target organisms in clinical specimens that may result in cross-contamination, b) plasmid clones derived from organisms that have been previously analyzed and that may be present in larger numbers in the laboratory environment, and c) repeated amplification of the same target sequence leading to accumulation of amplification products in the laboratory environment. A common source of the accumulation of the PCR amplicon is aerosolization of the product. Typically, if uncontrolled aerosolization occurs, the amplicon will contaminate laboratory reagents, equipment, and ventilation systems. When this happens, all reactions will be positive, and it is not possible to distinguish between amplified products from the contamination or a true, positive sample. In addition to taking precautions to avoid or control this carry-over of old products, preferred embodiments include a blank reference reaction in every PCR experiment to check for carry-over. For example, carry-over contamination will be visible on the agarose gel as faint bands or fluorescent signal when TaqMan® probes, MolBeacons, or intercalating dyes, among others, are employed as detection mechanisms. Furthermore, it is preferred to include a positive sample. As an example, in some embodiments, contamination control is performed using any of the approaches and methods described in WO 2012/054639. In some embodiments, a bleach solution is used to neutralize potential amplicons, for example, in a reaction tube of a T2Dx® device being used to perform a method of the invention. In some embodiments, contamination control includes the use of ethylene oxide (EtO) treatment, for example, of cartridge components.

Typically, the instrumentation and processing areas for samples that undergo amplification are split into pre- and post-amplification zones. This minimizes the chances of contamination of samples with amplicon prior to amplification. For example, the T2Dx® instrument design is such that the pre- and post-amplification instrumentation and processing areas are integrated into a single instrument. This is made possible as described in the sections below.

Systems

The invention provides systems for carrying out the methods of the invention, which may include one or more NMR units, MAA units, cartridge units, and agitation units, as described in WO 2012/054639. Such systems may further include other components for carrying out an automated assay of the invention, such as a thermocycling unit for the amplification of oligonucleotides; a centrifuge, a robotic arm for delivery an liquid sample from unit to unit within the system; one or more incubation units; a fluid transfer unit (i.e., pipetting device) for combining assay reagents and a biological sample to form the liquid sample; a computer with a programmable processor for storing data, processing data, and for controlling the activation and deactivation of the various units according to a one or more preset protocols; and a cartridge insertion system for delivering pre-filled cartridges to the system, optionally with instructions to the computer identifying the reagents and protocol to be used in conjunction with the cartridge. FIG. 42 of WO 2012/054639 depicts an exemplary system of the invention.

The systems of the invention can provide an effective means for high throughput and real-time detection of analytes present in a bodily fluid from a subject. The detection methods may be used in a wide variety of circumstances including, without limitation, identification and/or quantification of analytes that are associated with specific biological processes, physiological conditions, disorders or stages of disorders. As such, the systems have a broad spectrum of utility in, for example, disease diagnosis, parental and forensic identification, disease onset and recurrence, individual response to treatment versus population bases, and monitoring of therapy. The devices and systems can provide a flexible system for personalized medicine. The system of the invention can be changed or interchanged along with a protocol or instructions to a programmable processor of the system to perform a wide variety of assays as described herein. The systems of the invention offer many advantages of a laboratory setting contained in a desk-top or smaller size automated instrument.

The systems of the invention can be used to simultaneously assay analytes that are present in the same liquid sample over a wide concentration range, and can be used to monitor the rate of change of an analyte concentration and/or or concentration of PD or PK markers over a period of time in a single subject, or used for performing trend analysis on the concentration, or markers of PD, or PK, whether they are concentrations of drugs or their metabolites. Thus, the data generated with the use of the subject fluidic devices and systems can be utilized for performing a trend analysis on the concentration of an analyte in a subject.

For example, a subject (e.g., a patient having or suspected of having a disease caused by or associated with a bacterial pathogen) may be provided with a plurality of cartridge units to be used for detecting a variety of analytes, such as analytes sampled from different tissues, and at predetermined times. A subject may, for example, use different cartridge units on different days of the week. In some embodiments the software on the system is designed to recognize an identifier on the cartridge instructing the system computer to run a particular protocol for running the assay and/or processing the data. The protocols on the system can be updated through an external interface, such as an USB drive or an Ethernet connection, or in some embodiments the entire protocol can be recorded in the barcode attached to the cartridge. The protocol can be optimized as needed by prompting the user for various inputs (i.e., for changing the dilution of the sample, the amount of reagent provided to the liquid sample, altering an incubation time or MAA time, or altering the NMR relaxation collection parameters).

A multiplexed assay can be performed using a variety of system designs. For example, a multiplexed assay can performed using any of the following configurations:

(i) a spatially-based detection array can be used to direct magnetic particles to a particular region of a tube (i.e., without aggregation) and immobilize the particles in different locations according to the particular analyte being detected. The immobilized particles are detected by monitoring their local effect on the relaxation effect at the site of immobilization. The particles can be spatially separated by gravimetric separation in flow (i.e., larger particles settling faster along with a slow flow perpendicular to gravity to provide spatial separation based on particle size with different magnetic particle size populations being labeled with different targets). Alternatively, of capture probes can be used to locate magnetic particles in a particular region of a tube (i.e., without aggregation) and immobilize the particles in different locations (i.e., on a functionalized surface, foam, or gel). Optionally, the array is flow through system with multiple coils and magnets, each coil being a separate detector that has the appropriate particles immobilized within it, and the presence of the analyte detected with signal changes arising from clustering in the presence of the analyte. Optionally, once the particles are spatially separated, each individual analyte in the multiplexed assay can be detected by sliding a coil across the sample to read out the now spatially separated particles.

(ii) A microfluidic tube where the sample is physically split amongst many branches and a separate signal is detected in each branch, each branch configured for detection of a separate analyte in the multiplexed assay.

(iii) An array of 96 wells (or less or more) where each well has its own coil and magnet, and each well is configured for detection of a separate analyte in the multiplexed assay.

(iv) A sipper or flow through device with multiple independently addressable coils inside one magnet or inside multiple mini magnets that can be used for sequential readings, each reading being a separate reaction for detection of a separate analyte in the multiplexed assay.

(v) A sipper or flow through device with multiple independently addressable wells on a plate inside one magnet or inside multiple mini magnets that can be used for sequential readings using a single sided coil that can be traversed along the plate, each reading being a separate reaction for detection of a separate analyte in the multiplexed assay.

(vi) A tube containing two compartments read simultaneously, resulting in one relaxation curve which is then fit using bi-exponential fitting to produce the separate readings for the multiplexed array.

(vii) A microfluidics system where each droplet of liquid is moved around individually, to produce readings for the multiplexed array.

(viii) Sequential measurements using magnetic separation and resuspension requires novel binding probes or the ability to turn them on and off. This method would be used for nucleic acid analytes in which turn on/off mechanism is based mostly on melting temperature (at higher temperatures hairpin loops relax, denaturation of double strand binding), and hybridization will occur at different temperatures.

(ix) Individual capillaries, each equipped with dried particles within them, allow for small volume rapid multiplexing of one small aliquot. The dried particles are spatially separated, and this spatial separation permits the MR Reader to read each capillary tube independently.

(x) Binding moieties conjugated to nanoparticles are placed in a gel or other viscous material forming a region and analyte specific viscous solution. The gel or viscous solution enhances spatial separation of more than one analyte in the starting sample because after the sample is allowed to interact with the gel, the target analyte can readily diffuse through the gel and specifically bind to a conjugated moiety on the gel or viscous solution held nanoparticle. The clustering or aggregation of the specific analyte, optionally enhanced via one of the described magnetic assisted agglomeration methods, and detection of analyte specific clusters can be performed by using a specific location NMR reader. In this way a spatial array of nanoparticles, and can be designed, for example, as a 2d array.

(xi) Magnetic particles can be spotted and dried into multiple locations in a tube and then each location measured separately. For example, one type of particle can be bound to a surface and a second particle suspended in solution, both of which hybridize to the analyte to be detected. Clusters can be formed at the surface where hybridization reactions occur, each surface being separately detectable.

(xii) A spotted array of nucleic acids can be created within a sample tube, each configured to hybridize to a first portion of an array of target nucleic acids. Magnetic particles can be designed with probes to hybridize to a second portion of the target nucleic acid. Each location can be measured separately. Alternatively, any generic beacon or detection method could be used to produce output from the nucleic acid array.

(xiii) An array of magnetic particles for detecting an array of targets can be included in a single sample, each configured (e.g., by size, or relaxation properties) to provide a distinct NMR relaxation signature with aggregate formation. For example, each of the particles can be selected to produce distinct $T_2$ relaxation times (e.g., one set of particles covers 10-200 ms, a second set from 250-500 ms, a third set from 550-1100 ms, and so on). Each can be measured as a separate band of relaxation rates.

(xiv) For detection of analytes of various size or magnetic particles, or aggregates of various size, a single sample with multiple analytes and magnetic particles can undergo separation in the presence of a magnetic or electric field (i.e., electrophoretic separation of magnetic particles coated with analytes), the separate magnetic particles and/or aggregates reaching the site of a detector at different times, accordingly.

(xv) The detection tube could be separated into two (or more) chambers that each contain a different nanoparticle for detection. The tube could be read using the reader and through fitting a multiple exponential curve such as $A*\exp(T_2\_1)+B*\exp(T_2\_2)$, the response of each analyte could be determined by looking at the relative size of the constants A and B and $T_2\_1$ and $T_2\_2$.

(xvi) Gradient magnetic fields can be shimmed to form narrow fields. Shim pulses or other RF based Shimming within a specific field can be performed to pulse and receive signals within a specific region. In this way one could envision a stratification of the RF pulse within a shim and specific resonance signals could be received from the specific shim. While this method relies on shimming the gradient magnetic field, multiplexing would include then, to rely on one of the other methods described to get different nanoparticles and the clusters to reside in these different shims. Thus there would be two dimensions, one provided by magnetic field shims and a second dimension provided by varying nanoparticle binding to more than one analyte. Nanoparticles having two distinct NMR relaxation signals upon clustering with an analyte may be employed in a multiplexed assay. In this method, the observation that small particles (30-200 nm) cause a decrease in $T_2$ with clustering whereas large particles (>800 nm) cause an increase with clustering. The reaction assay is designed as a competitive reaction, so that with the addition of the target it changes the equilibrium relaxation signal. For example, if the $T_2$ relaxation time is shorter, clusters forming of analyte with small particles are forming. If on the other hand, the $T_2$ relaxation becomes longer, clusters of analyte with larger particles are forming. It's probably useful to change the density/viscosity of the solution with additives such as trehalose or glucose or glycerol to make sure the big particles stay in solution. One nanoparticle having binding moieties to a specific analyte for whose $T_2$ signal is decreased on clustering may be combined with a second nanoparticle having a second binding moiety to a second analyte for whose $T_2$ signal is increased on clustering. In the case for which the sample is suspected to have both analytes and the clustering reaction may cancel each other out (the increased clustering cancels the decreased clustering), one could envision an ordering of the analysis, i.e. addition of competitive binding agents to detect a competitive binding and thus $T_2$ signal that would be related to the presence/absence of the analyte of interest in the sample. Alternatively, if the increased clustering cancels the decreased clustering in this multiplexing format, one could envision use of different relaxation pulse sequences or relaxation determinants to identify the presence/absence or concentration of analyte in the sample.

(xvii) Precipitation measurement of particles. In this method, multiple types of particles designed to capture different target sequences of nucleic acid are designed So that the particle size is small enough that the particles bound with analyte remain suspended in solution. Sequential addition of an "initiator" sequence that is complementary to a nucleic acid sequence conjugated to a second set of particles (a larger particle, not necessarily having magnetic properties) and contains a complementary sequence to the captured target DNA sequence. After hybridization, clusters will form if the target DNA sequence is present, e.g. the magnetic nanoparticle conjugated with probe anneals to one specific sequence on the target analyte and the other particle binds to another sequence on the target nucleic acid sequence. These clusters will be big enough to precipitate (this step may require a centrifugation step). In the same reaction, and simultaneously, one could design an additional magnetic particle, second particle set to anneal with a second nucleic acid sequence for which formation of the magnetic nanoparticle-analyte-second particle clusters do not precipitate. In this way sequential addition of particles can result in differential signaling.

(xvii) One possible different detection technique includes phase separated signals, which would stem from differing RF coil pulse sequences that are optimized for the conjugated nanoparticle-analyte interaction. Optimally, this could be achieved with multiple coils in an array that would optimize the ability of the different RF pulses and relaxation signal detection to be mapped and differentiated to ascertain the presence/absence of more than one analyte. Multiplexing may also employ the unique characteristic of the nanoparticle-analyte clustering reaction and subsequent detection of water solvent in the sample, the ability of the clusters to form various "pockets" and these coordinated clusters to have varying porosity. For example, linkers having varying length or conformational structures can be employed to conjugate the binding moiety to the magnetic nanoparticle. In this way, more than one type of cluster formed in the presence of an analyte could be designed having the ability of differing solvent water flow, and thus relaxation signal differences, through the aggregated nanoparticle-analyte-nanoparticle formation. In this way, two or more linker/binding moiety designs would then allow for detection of more than one analyte in the same sample.

(xviii) The methods of the invention can include a fluorinated oil/aqueous mixture for capturing particles in an emulsion. In this design one hydrophobic capture particle set and an aqueous capture set are used, the hydrophobic capture particle set is designed to bind and aggregate more readily in an hydrophobic environment, whereas the aqueous capture particle set is designed to bind and aggregate in an aqueous environment. Introduction of an analyte containing sample having specific analytes that will bind to either the hydrophobic or aqueous particle, and subsequent mixing in the detection tube having both hydrophobic and aqueous solvents, binding and clustering would then result in a physical separation of analytes to either the aqueous or hydrophobic phase. The relaxation signal could be detected in either solution phase. In the event that the analytes and nanoparticles designed in this manner are physically found in an emulsion created by the mixing of the hydrophobic/aqueous phases, relaxation curves would be distinguishable in the emulsion phase. The detection tube may have a capsular design to enhance the ability to move the capsules through an MR detector to read out the signal. Further, additional use of a fluorescent tag to read out probe identity may be employed, i.e. in the case of two different analytes in the same aqueous or hydrophobic phase, the addition of a fluorescent tag can assist determination of the identity of the analyte. This method is amenable in samples for which limited isolation or purification of the target analyte away from the other material in the sample because the described resonance signals are independent of sample quality. Further, the addition of the fluorescent tag can be added in much higher concentrations that usually added in typical fluorescent studies because these tags will never interfere with the relaxation measurements. In this method, oligonucleotide capture probes that are conjugated to the magnetic nanoparticles are designed so that specific restriction endonuclease sites are located within the annealed section. After hybridization with the sample forming nanoparticle-analyte clusters, a relaxation measurement then provides a base signal. Introduction of a specific restriction endonuclease to the detection tube and incubation will result in a specific reduction of the nanoparticle/analyte cluster after restriction digestion has occurred. After a subsequent relaxation measurement, the pattern of signal and restriction enzyme digestion, one can deduce the target.

(xix) In a combined method, a magnetic nanoparticle is conjugated with two separate and distinct binding moieties, i.e. an oligonucleotide and an antibody. This nanoparticle when incubated with a sample having both types of analytes in the sample will form nanoparticle-analyte complexes, and a baseline $T_2$ relaxation signal will be detectable. Subsequent addition of a known concentration of one of the analytes can be added to reduce the clustering formed by that specific analyte from the sample. After known analyte addition a subsequent $T_2$ relaxation signal is detected and the presence/absence of the sample analyte can be surmised. Further, a second analyte can be added to compete with the analyte in the sample to form clusters. Again, after a subsequent $T_2$ relaxation signal detection the presence/absence of the second sample analyte can be surmised. This can be repeated.

Broadly, a multiplexed assay employing the methods of this invention can be designed so that the use of one non-superparamagnetic nanoparticle to generate clusters with analyte from a sample, will reduce the overall $Fe^{2+}$ in assay detection vessel and will extend the dynamic range so that multiple reactions can be measured in the same detection vessel.

Multiplexing nucleic acid detection can make use of differing hybridization qualities of the conjugated magnetic nanoparticle and the target nucleic acid analyte. For example, capture probes conjugated to magnetic nanoparticles can be designed so that annealing the magnetic nanoparticle to the target nucleic acid sequence is different for more than one nucleic acid target sequence. Factors for the design of these different probe-target sequences include G-C content (time to form hybrids), varying salt concentration, hybridization temperatures, and/or combinations of these factors. This method then would entail allowing various nucleic acid conjugated magnetic nanoparticles to interact with a sample suspected of having more than one target nucleic acid analyte. Relaxation times detected after various treatments, i.e. heating, addition of salt, hybridization timing, would allow for the ability to surmise which suspected nucleic acid sequence is present or absent in the sample.

Use complimentary amplicons to block one reaction and allow serial hybridizations. In this method, universal amplification primers are used to amplify more than one specific nucleic acid sequence in the starting sample, forming an amplicon pool. Specific oligonucleotides conjugated to magnetic nanoparticles are added to the sample and a relaxation measurement is taken. The sample is then exposed to a temperature to melt the oligonucleotide-analyte interaction and addition of an oligonucleotide that is not attached to a magnetic nanoparticle is added to compete away any analyte binding to the magnetic nanoparticle. A second magnetic nanoparticle having a second oligonucleotide conjugated to it is then added to form clusters with a second specific target nucleic acid analyte. Alternatively, the method could have a step prior to the addition of the second magnetic nanoparticle that would effectively sequester the first magnetic nanoparticle from the reaction vessel, i.e. exposing the reaction vessel to a magnetic field to move the particles to an area that would not be available to the second, or subsequent reaction.

Each of the multiplexing methods above can employ a step of freezing the sample to slow diffusion and clustering time and thus alter the measurement of the relaxation time. Slowing the diffusion and clustering of the method may enhance the ability to separate and detect more than one relaxation time. Each of the multiplexing methods above can make use of sequential addition of conjugated nanoparticles followed by relaxation detection after each addition. After each sequential addition, the subsequent relaxation baseline becomes the new baseline from the last addition and can be used to assist in correlating the relaxation time with presence/absence of the analyte or analyte concentration in the sample.

In some embodiments, the method of multiplexing may involve hidden capture probes. In this method of multiplexing, oligonucleotides conjugated to the magnetic nanoparticles are designed so that secondary structure or a complementary probe on the surface of the particle hides or covers the sequence for hybridization initially in the reaction vessel. These hidden hybridization sequences are then exposed or revealed in the sample vessel spatially or temporally during the assay. For example, as mentioned above, hybridization can be affected by salt, temperature and time to hybridize. Thus, in one form of this method, secondary or complementary structures on the oligonucleotide probe conjugated to the magnetic nanoparticle can be reduced or relaxed to then expose or reveal the sequence to hybridize to the target nucleic acid sample. Further, secondary structures could be reduced or relaxed using a chemical compound, e.g., DMSO. Another method to selectively reveal or expose a sequence for hybridization of the oligonucleotide conjugated nanoparticle with the target analyte is to design stem-loop structures having a site for a restriction endonuclease; subsequent digestion with a restriction endonuclease would relax the stem-loop structure and allow for hybridization to occur. Alternatively, a chemical cut of the stem-loop structure, releasing one end could make the sequence free to then hybridize to the target nucleic acid sequence.

Where the multiplexed array is configured to detect a target nucleic acid, the assay can include a multiplexed PCR to generate different amplicons and then serially detect the different reactions.

The multiplexed assay optionally includes a logical array in which the targets are set up by binary search to reduce the number of assays required (e.g., gram positive or negative leads to different species based tests that only would be conducted for one group or the other).

The systems of the invention can run a variety of assays, regardless of the analyte being detected from a bodily fluid sample. A protocol dependent on the identity of the cartridge unit being used can be stored on the system computer. In some embodiments, the cartridge unit has an identifier (ID) that is detected or read by the system computer, or a bar code (1D or 2D) on a card that then supplies assay specific or patient or subject specific information needed to be tracked or accessed with the analysis information (e.g., calibration curves, protocols, previous analyte concentrations or levels). Where desired, the cartridge unit identifier is used to select a protocol stored on the system computer, or to identify the location of various assay reagents in the cartridge unit. The protocol to be run on the system may include instructions to the controller of the system to perform the protocol, including but not limited to a particular assay to be run and a detection method to be performed. Once the assay is performed by the system, data indicative of an analyte in the biological sample is generated and communicated to a communications assembly, where it can either be transmitted to the external device for processing, including without limitation, calculation of the analyte concentration in the sample, or processed by the system computer and the result presented on a display readout.

For example, the identifier may be a bar code identifier with a series of black and white lines, which can be read by a bar code reader (or another type of detector) upon insertion of the cartridge unit. Other identifiers could be used, such as a series of alphanumerical values, colors, raised bumps, RFID, or any other identifier which can be located on a cartridge unit and be detected or read by the system computer. The detector may also be an LED that emits light which can interact with an identifier which reflects light and is measured by the system computer to determine the identity of a particular cartridge unit. In some embodiments, the system includes a storage or memory device with the cartridge unit or the detector for transmitting information to the system computer.

Thus, the systems of the invention can include an operating program to carry out different assays, and cartridges encoded to: (i) report to the operating program which pre-programmed assay was being employed; (ii) report to the operating program the configuration of the cartridges; (iii) inform the operating system the order of steps for carrying out the assay; (iv) inform the system which pre-programmed routine to employ; (v) prompt input from the user with respect to certain assay variables; (vi) record a patient identification number (the patient identification number can also be included on the VACUTAINER® holding the blood sample); (vii) record certain cartridge information (e.g., lot number, calibration data, assays on the cartridge, analytic data range, expiration date, storage requirements, acceptable sample specifics); or (viii) report to the operating program assay upgrades or revisions (i.e., so that newer versions of the assay would occur on cartridge upgrades only and not to the larger, more costly system).

The systems of the invention can include one or more fluid transfer units configured to adhere to a robotic arm (see, e.g., FIGS. 43A-43C of WO 2012/054639). The fluid transfer unit can be a pipette, such as an air-displacement, liquid backed, or syringe pipette. For example, a fluid transfer unit can further include a motor in communication with a programmable processor of the system computer and the motor can move the plurality of heads based on a protocol from the programmable processor. Thus, the programmable processor of a system can include instructions or commands and can operate a fluid transfer unit according to the instructions to transfer liquid samples by either withdrawing (for drawing liquid in) or extending (for expelling liquid) a piston into a closed air space. Both the volume of air moved and the speed of movement can be precisely controlled, for example, by the programmable processor. Mixing of samples (or reagents) with diluents (or other reagents) can be achieved by aspirating components to be mixed into a common tube and then repeatedly aspirating a significant fraction of the combined liquid volume up and down into a tip. Dissolution of reagents dried into a tube can be done is similar fashion.

A system can include one or more incubation units for heating the liquid sample and/or for control of the assay temperature. Heat can be used in the incubation step of an assay reaction to promote the reaction and shorten the duration necessary for the incubation step. A system can include a heating block configured to receive a liquid sample for a predetermined time at a predetermined temperature. The heating block can be configured to receive a plurality of samples.

The system temperature can be carefully regulated. For example, the system includes a casing kept at a predetermined temperature (e.g., 37° C.) using stirred temperature controlled air. Waste heat from each of the units will exceed what can be passively dissipated by simple enclosure by conduction and convection to air. To eliminate waste heat, the system can include two compartments separated by an insulated floor. The upper compartment includes those portions of the components needed for the manipulation and measurement of the liquid samples, while the lower compartment includes the heat generating elements of the individual units (e.g., the motor for the centrifuge, the motors for the agitation units, the electronics for each of the separate units, and the heating blocks for the incubation units). The lower floor is then vented and forced air cooling is used to carry heat away from the system. See, e.g., FIGS. 44A and 44B of WO 2012/054639.

The MR unit may require more closely controlled temperature (e.g., ±0.1° C.), and so may optionally include a separate casing into which air heated at a predetermined temperature is blown. The casing can include an opening through which the liquid sample is inserted and removed, and out of which the heated air is allowed to escape. See, e.g., FIGS. 45A and 45B of WO 2012/054639. Other temperature control approaches may also be utilized.

Cartridge Units

The invention provides methods and systems that may involve one or more cartridge units to provide a convenient method for placing all of the assay reagents and consumables onto the system. For example, the system may be customized to perform a specific function, or adapted to perform more than one function, e.g., via changeable cartridge units containing arrays of micro wells with customized magnetic particles contained therein. The system can include a replaceable and/or interchangeable cartridge containing an array of wells pre-loaded with magnetic particles, and designed for detection and/or concentration measurement of a particular analyte. Alternatively, the system may be usable with different cartridges, each designed for detection and/or concentration measurements of different analytes, or configured with separate cartridge modules for reagent and detection for a given assay. The cartridge may be sized to facilitate insertion into and ejection from a housing for the preparation of a liquid sample which is transferred to other units in the system (e.g., a magnetic assisted agglomeration unit, or an NMR unit). The cartridge unit itself could potentially interface directly with manipulation stations as well as with the MR reader(s). The cartridge unit can be a modular cartridge having an inlet module that can be sterilized independent of the reagent module.

For handling biological samples, such as blood samples, there are numerous competing requirements for the cartridge design, including the need for sterility for the inlet module to prevent cross contamination and false positive test results, and the need to include reagents in the package which cannot be easily sterilized using standard terminal sterilization techniques like irradiation. An inlet module for sample aliquoting can be designed to interface with uncapped VACUTAINER® tubes, and to aliquot two a sample volume that can be used to perform, for example, an assay to detect a pathogen (see FIGS. 7D-7F of WO 2012/054639). The VACUTAINER® permits a partial or full fill. The inlet module has two hard plastic parts, that get ultrasonically welded together and foil sealed to form a network of channels to allow a flow path to form into the first well overflow to the second sample well. A soft VACUTAINER® seal part is used to for a seal with the VACUTAINER®, and includes a port for sample flow, and a venting port. To overcome the flow resistance once the VACUTAINER® is loaded and inverted, some hydrostatic pressure is needed. Every time sample is removed from a sample well, the well will get replenished by flow from the VACUTAINER®.

A modular cartridge can provide a simple means for cross contamination control during certain assays, including but not limited to distribution of amplification (e.g., PCR) products into multiple detection aliquots. In addition, a modular cartridge can be compatible with automated fluid dispensing, and provides a way to hold reagents at very small volumes for long periods of time (in excess of a year). Finally, pre-dispensing these reagents allows concentration and volumetric accuracy to be set by the manufacturing process and provides for a point of care use instrument that is more convenient as it can require much less precise pipetting.

The modular cartridge of the invention is a cartridge that is separated into modules that can be packaged and if necessary sterilized separately. They can also be handled and stored separately, if for example the reagent module requires refrigeration but the detection module does not. FIG. 6 of WO 2012/054639 shows a representative cartridge with an inlet module, a reagent module and a detection module that are snapped together. In this embodiment, the inlet module would be packaged separately in a sterile package and the reagent and detection modules would be pre-assembled and packaged together.

During storage, the reagent module could be stored in a refrigerator while the inlet module could be stored in dry storage. This provides the additional advantage that only a very small amount of refrigerator or freezer space is required to store many assays. At time of use, the operator would retrieve a detection module and open the package, potentially using sterile technique to prevent contamination with skin flora if required by the assay. The VACUTAINER® tube is then decapped and the inverted inlet module is placed onto the tube as shown in FIG. 7A of WO 2012/054639. This module has been designed to be easily moldable using single draw tooling as shown in FIGS. 7B and 7C of WO 2012/054639 and the top and bottom of the cartridge are sealed with foil to prevent contamination and also to close the channels. Once the tube has been re-sealed using the inlet module, the assembly is turned right side up and snapped onto the remainder of the cartridge. The inlet section includes a well with an overflow that allows sample tubes with between 2 and 6 ml of blood to be used and still provide a constant depth interface to the system automation. It accomplishes this by means of the overflow shown in FIG. 8 of WO 2012/054639, where blood that overflows the sampling well simply falls into the cartridge body, preventing contamination.

FIGS. 9A-9C of WO 2012/054639 show the means of storing precisely pipetted small volume reagents. The reagents are kept in pipette tips that are shown in FIG. 9C of WO 2012/054639. These are filled by manufacturing automation and then are placed into the cartridge to seal their tips in tight fitting wells which are shown in a cutaway view FIG. 9B of WO 2012/054639. Finally, foil seals are placed on the back of the tips to provide a complete water vapor proof seal. It is also possible to seal the whole module with a seal that will be removed by the operator, either in place of or in addition to the aforementioned foils. This module also provides storage for empty reaction vessels and pipette tips for use by the instrument while the detection module provides storage for capped 200 μl PCR vials used by the instrument to make final measurements from.

FIGS. 10-13C of WO 2012/054639 show an alternative embodiment of the detection module of the cartridge which is design to provide for contamination control during, for example, pipetting of post-amplification (e.g., PCR) products. This is required because the billion-fold amplification produced by DNA amplification (e.g., PCR) presents a great risk of cross contamination and false positives. However, it is desirable to be able to aliquot this mixture safely, because low frequency analytes will have been amplified up and can be distributed for separate detection or identification. There are three ways in which this portion of the cartridge aids in contamination control during this aliquoting operation.

Figure 11:
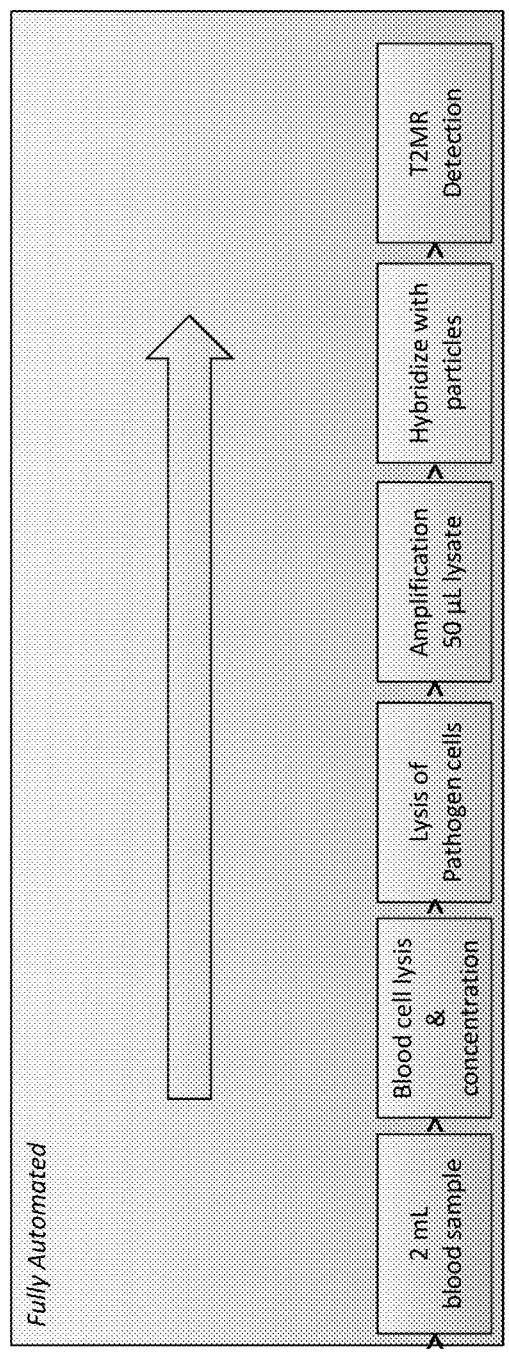
FIG. 11 shows an exemplary workflow for detecting pathogens described herein using the T2Dx® instrument (T2 Biosystems, Inc., Lexington, Mass.).

First, the cartridge contains a recessed well to perform the transfer operations in as shown in FIGS. 10A and 10B of WO 2012/054639. Second, the machine provides airflow through this well and down into the cartridge through holes in the bottom of the well, as shown in FIG. 11 of WO 2012/054639. The depth of the well is such that a pipette tip will remain in the airflow and prevent any aerosol from escaping. FIG. 12 of WO 2012/054639 depicts a bottom view of the detection module, showing the bottom of the detection tubes and the two holes used to ensure airflow. An optional filter can be inserted here to capture any liquid aerosol and prevent it from entering the machine. This filter could also be a sheet of a hydrophobic material like GORE-TEX® that will allow air but not liquids to escape. Finally, there is a special seal cap on each 200 µl tube to provide a make then break seal for each pipette tip as it enters the vessel, as shown in FIGS. 13A-13C of WO 2012/054639. It is contemplated that the pipette tip used for aliquoting be stored in this well at all, thus making it possible for the tip never to leave the controlled air flow region.

Alternatively, the modular cartridge is designed for a multiplexed assay. The challenge in multiplexing assays is combining multiple assays which have incompatible assay requirements (i.e., different incubation times and/or temperatures) on one cartridge. The cartridge format depicted in FIGS. 14A-14C of WO 2012/054639 allows for the combination of different assays with dramatically different assay requirements. The cartridge features two main components: (i) a reagent module (i.e., the reagent strip portion) that contains all of the individual reagents required for the full assay panel (for example, a panel as described below), and (ii) the detection module. In some embodiments, a cartridge may be configured to detect from 2 to 24 or more pathogens (e.g., 2, 3, 4, 5, 6, 7, 8, 9, 10, 11, 12, 13, 14, 15, 16, 17, 18, 19, 20, 21, 22, 23, 24, or more pathogens). The detection modules contain only the parts of the cartridge that carry through the incubation, and can carry single assays or several assays, as needed. The detection module depicted in FIG. 14B of WO 2012/054639 includes two detection chambers for a single assay, the first detection chamber as the control and the second detection chamber for the sample. This cartridge format is expandable in that additional assays can be added by including reagents and an additional detection module.

The operation of the module begins when the user inserts the entire or a portion of the cartridge into the instrument. The instruments performs the assay actuation, aliquoting the assays into the separate detection chambers. These individual detection chambers are then disconnected from the reagent strip and from each other, and progress through the system separately. Because the reagent module is separated and discarded, the smallest possible sample unit travels through the instrument, conserving internal instrument space. By splitting up each assay into its own unit, different incubation times and temperatures are possible as each multiplexed assay is physically removed from the others and each sample is individually manipulated.

The cartridge units of the invention can include one or more populations of magnetic particles, either as a liquid suspension or dried magnetic particles which are reconstituted prior to use. For example, the cartridge units of the invention can include a compartment including from $1 \times 10^6$ to $1 \times 10^{13}$ magnetic particles (e.g., from $1 \times 10^6$ to $1 \times 10^8$, $1 \times 10^7$ to $1 \times 10^9$, $1 \times 10^8$ to $1 \times 10^{10}$, $1 \times 10^9$ to $1 \times 10^{11}$, $1 \times 10^{10}$ to $1 \times 10^{12}$, $1 \times 10^{11}$ to $1 \times 10^{13}$, or from $1 \times 10^7$ to $5 \times 10^8$ magnetic particles) for assaying a single liquid sample.

Panels

The methods, systems, and cartridges of the invention can be configured to detect a predetermined panel of pathogens. In some embodiments, the panel may be a bacterial pathogen panel configured to individually detect between 1 and 18 (e.g., 1, 2, 3, 4, 5, 6, 7, 8, 9, 10, 11, 12, 13, 14, 15, 16, 17, or 18) pathogens selected from the following: *Acinetobacter* spp. (e.g., *Acinetobacter* baumannii, *Acinetobacter pittii*, and *Acinetobacter nosocomialis*), Enterobacteriaceae spp., *Enterococcus* spp. (e.g., *Enterococcus faecium* (including *E. faecium* with resistance marker vanAfB) and *Enterococcus faecalis*), *Klebsiella* spp. (e.g., *Klebsiella pneumoniae* (including, e.g., *K. pneumoniae* with resistance marker KPC) and *Klebsiella oxytoca*), *Pseudomonas* spp. (e.g., *Pseudomonas aeruginosa*), *Staphylococcus* spp. (including, e.g., *Staphylococcus aureus* (e.g., *S. aureus* with resistance marker mecA), *Staphylococcus haemolyticus*, *Staphylococcus lugdunensis*, *Staphylococcus maltophilia*, *Staphylococcus saprophyticus*, coagulase-positive *Staphylococcus* species, and coagulase-negative (CONS) *Staphylococcus* species), *Streptococcus* spp. (e.g., *Streptococcus mitis*, *Streptococcus pneumoniae*, *Streptococcus agalactiae*, *Streptococcus anginosa*, *Streptococcus bovis*, *Streptococcus dysgalactiae*, *Streptococcus mutans*, *Streptococcus sanguinis*, and *Streptococcus pyogenes*), *Escherichia* spp. (e.g., *Escherichia coli*), *Stenotrophomonas* spp. (e.g., *Stenotrophomonas maltophilia*), *Proteus* spp. (e.g., *Proteus mirabilis* and *Proteus vulgaris*), *Serratia* spp. (e.g., *Serratia marcescens*), *Citrobacter* spp. (e.g., *Citrobacter freundii* and *Citrobacter koseri*), *Haemophilus* spp. (e.g., *Haemophilus influenzae*), *Listeria* spp. (e.g., *Listeria monocytogenes*), *Neisseria* spp. (e.g., *Neisseria meningitidis*), *Bacteroides* spp. (e.g., *Bacteroides fragilis*), *Burkholderia* spp. (e.g., *Burkholderia cepacia*), *Campylobacter* (e.g., *Campylobacter jejuni* and *Campylobacter coli*), *Clostridium* spp. (e.g., *Clostridium perfringens*), *Kingella* spp. (e.g., *Kingella kingae*), *Morganella* spp. (e.g., *Morganella morgana*), *Prevotella* spp. (e.g., *Prevotella buccae*, *Prevotella intermedia*, and *Prevotella melaninogenica*), *Propionibacterium* spp. (e.g., *Propionibacterium acnes*), *Salmonella* spp. (e.g., *Salmonella enterica*), *Shigella* spp. (e.g., *Shigella dysenteriae* and *Shigella* flexnern), and *Enterobacter* spp. (e.g., *Enterobacter aerogenes* and *Enterobacter cloacae*). In some embodiments, the bacterial pathogen panel is further configured to detect a fungal pathogen, for example, *Candida* spp. (e.g., *Candida albicans, Candida guilliermondii, Candida glabrata, Candida krusei, Candida lusitaniae, Candida parapsilosis, Candida dublinensis*, and *Candida tropicalis*) and *Aspergillus* spp. (e.g., *Aspergillus fumigatus*). In some embodiments, the bacterial pathogen panel is further configured to detect a *Candida* spp. (including *Candida albicans, Candida guilliermondi, Candida glabrata, Candida krusei, Candida lusitaniae, Candida parapsilosis, Candida dublinensis*, and *Candida tropicalis*). In cases where multiple species of a genus are detected, the species may be detected using individual target nucleic acids or using target nucleic acids that are universal to all of the species, for example, target nucleic acids amplified using universal primers.

In some embodiments, the panel may be configured to individually detect one or more (e.g., 1, 2, 3, 4, 5, 6, or 7) of *Acinetobacter baumannii, Enterococcus faecium, Enterococcus faecalis, Klebsiella pneumoniae, Pseudomonas aeruginosa, Escherichia coli*, and *Staphylococcus aureus*.

For example, in some embodiments, the panel is configured to individually detect *Acinetobacter baumannii* and *Enterococcus faecium*. In some embodiments, the panel is configured to individually detect *Acinetobacter baumannii* and *Enterococcus faecalis*. In some embodiments, the panel is configured to individually detect *Acinetobacter baumannii* and *Klebsiella pneumoniae*. In some embodiments, the panel is configured to individually detect *Acinetobacter baumannii* and *Pseudomonas aeruginosa*. In some embodiments, the panel is configured to individually detect *Acinetobacter baumannii* and *Escherichia coli*. In some embodiments, the panel is configured to individually detect *Acinetobacter baumannii* and *Staphylococcus aureus*. In some embodiments, the panel is configured to individually detect *Enterococcus faecium* and *Enterococcus faecalis*. In some embodiments, the panel is configured to individually detect *Enterococcus faecium* and *Klebsiella pneumoniae*. In some embodiments, the panel is configured to individually detect *Enterococcus faecium* and *Pseudomonas aeruginosa*. In some embodiments, the panel is configured to individually detect *Enterococcus faecium* and *Escherichia coli*. In some embodiments, the panel is configured to individually detect *Enterococcus faecium* and *Staphylococcus aureus*. In some embodiments, the panel is configured to individually detect *Enterococcus faecalis* and *Klebsiella pneumoniae*. In some embodiments, the panel is configured to individually detect *Enterococcus faecalis* and *Pseudomonas aeruginosa*. In some embodiments, the panel is configured to individually detect *Enterococcus faecalis* and *Escherichia coli*. In some embodiments, the panel is configured to individually detect *Enterococcus faecalis* and *Staphylococcus aureus*. In some embodiments, the panel is configured to individually detect *Klebsiella pneumoniae* and *Pseudomonas aeruginosa*. In some embodiments, the panel is configured to individually detect *Klebsiella pneumoniae* and *Escherichia coli*. In some embodiments, the panel is configured to individually detect *Klebsiella pneumoniae* and *Staphylococcus aureus*. In some embodiments, the panel is configured to individually detect *Pseudomonas aeruginosa* and *Escherichia coli*. In some embodiments, the panel is configured to individually detect *Pseudomonas aeruginosa* and *Staphylococcus aureus*. In some embodiments, the panel is configured to individually detect *Escherichia coli* and *Staphylococcus aureus*.

In another example, in some embodiments, the panel is configured to individually detect *Acinetobacter baumannii*, *Enterococcus faecium*, and *Enterococcus faecalis*. In some embodiments, the panel is configured to individually detect *Acinetobacter baumannii*, *Enterococcus faecium*, and *Klebsiella pneumoniae*. In some embodiments, the panel is configured to individually detect *Acinetobacter baumannii*, *Enterococcus faecium*, and *Pseudomonas aeruginosa*. In some embodiments, the panel is configured to individually detect *Acinetobacter baumannii*, *Enterococcus faecium*, and *Escherichia coli*. In some embodiments, the panel is configured to individually detect *Acinetobacter baumannii*, *Enterococcus faecium*, and *Staphylococcus aureus*. In some embodiments, the panel is configured to individually detect *Acinetobacter baumannii*, *Enterococcus faecalis*, and *Klebsiella pneumoniae*. In some embodiments, the panel is configured to individually detect *Acinetobacter baumannii*, *Enterococcus faecalis*, and *Pseudomonas aeruginosa*. In some embodiments, the panel is configured to individually detect *Acinetobacter baumannii*, *Enterococcus faecalis*, and *Escherichia coli*. In some embodiments, the panel is configured to individually detect *Acinetobacter baumannii*, *Enterococcus faecalis*, and *Staphylococcus aureus*. In some embodiments, the panel is configured to individually detect *Acinetobacter baumannii*, *Klebsiella pneumoniae*, and *Pseudomonas aeruginosa*. In some embodiments, the panel is configured to individually detect *Acinetobacter baumannii*, *Klebsiella pneumoniae*, and *Escherichia coli*. In some embodiments, the panel is configured to individually detect *Acinetobacter baumannii*, *Klebsiella pneumoniae*, and *Staphylococcus aureus*. In some embodiments, the panel is configured to individually detect *Acinetobacter baumannii*, *Pseudomonas aeruginosa*, and *Escherichia coli*. In some embodiments, the panel is configured to individually detect *Acinetobacter baumannii*, *Pseudomonas aeruginosa*, and *Staphylococcus aureus*. In some embodiments, the panel is configured to individually detect *Acinetobacter baumannii*, *Escherichia coli*, and *Staphylococcus aureus*. In some embodiments, the panel is configured to individually detect *Enterococcus faecium*, *Enterococcus faecalis*, and *Klebsiella pneumoniae*. In some embodiments, the panel is configured to individually detect *Enterococcus faecium*, *Enterococcus faecalis*, and *Pseudomonas aeruginosa*. In some embodiments, the panel is configured to individually detect *Enterococcus faecium*, *Enterococcus faecalis*, and *Escherichia coli*. In some embodiments, the panel is configured to individually detect *Enterococcus faecium*, *Enterococcus faecalis*, and *Staphylococcus aureus*. In some embodiments, the panel is configured to individually detect *Enterococcus faecium*, *Klebsiella pneumoniae*, and *Pseudomonas aeruginosa*. In some embodiments, the panel is configured to individually detect *Enterococcus faecium*, *Klebsiella pneumoniae*, and *Escherichia coli*. In some embodiments, the panel is configured to individually detect *Enterococcus faecium*, *Klebsiella pneumoniae*, and *Staphylococcus aureus*. In some embodiments, the panel is configured to individually detect *Enterococcus faecium*, *Pseudomonas aeruginosa*, and *Escherichia coli*. In some embodiments, the panel is configured to individually detect *Enterococcus faecium*, *Pseudomonas aeruginosa*, and *Staphylococcus aureus*. In some embodiments, the panel is configured to individually detect *Enterococcus faecium*, *Escherichia coli*, and *Staphylococcus aureus*. In some embodiments, the panel is configured to individually detect *Enterococcus faecalis*, *Klebsiella pneumoniae*, and *Pseudomonas aeruginosa*. In some embodiments, the panel is configured to individually detect *Enterococcus faecalis*, *Klebsiella pneumoniae*, and *Escherichia coli*. In some embodiments, the panel is configured to individually detect *Enterococcus faecalis*, *Klebsiella pneumoniae*, and *Staphylococcus aureus*. In some embodiments, the panel is configured to individually detect *Enterococcus faecalis*, *Pseudomonas aeruginosa*, and *Escherichia coli*. In some embodiments, the panel is configured to individually detect *Enterococcus faecalis*, *Pseudomonas aeruginosa*, and *Staphylococcus aureus*. In some embodiments, the panel is configured to individually detect *Enterococcus faecalis*, *Escherichia coli*, and *Staphylococcus aureus*. In some embodiments, the panel is configured to individually detect *Klebsiella pneumoniae*, *Pseudomonas aeruginosa*, and *Escherichia coli*. In some embodiments, the panel is configured to individually detect *Klebsiella pneumoniae*, *Pseudomonas aeruginosa*, and *Staphylococcus aureus*. In some embodiments, the panel is configured to individually detect *Klebsiella pneumoniae*, *Escherichia coi*, and *Staphylococcus aureus*. In some embodiments, the panel is configured to individually detect *Pseudomonas aeruginosa*, *Escherichia coli*, and *Staphylococcus aureus*.

In another example, in some embodiments, the panel is configured to individually detect *Acinetobacter baumannii*,

*Enterococcus faecium, Enterococcus faecalis*, and *Klebsiella pneumoniae*. In some embodiments, the panel is configured to individually detect *Acinetobacter baumannii, Enterococcus faecium, Enterococcus faecalis*, and *Pseudomonas aeruginosa*. In some embodiments, the panel is configured to individually detect *Acinetobacter baumannii, Enterococcus faecium, Enterococcus faecalis*, and *Escherichia coli*. In some embodiments, the panel is configured to individually detect *Acinetobacter baumannii, Enterococcus faecium, Enterococcus faecalis*, and *Staphylococcus aureus*. In some embodiments, the panel is configured to individually detect *Acinetobacter baumannii, Enterococcus faecium, Klebsiella pneumoniae*, and *Pseudomonas aeruginosa*. In some embodiments, the panel is configured to individually detect *Acinetobacter baumannii, Enterococcus faecium, Klebsiella pneumoniae*, and *Escherichia coli*. In some embodiments, the panel is configured to individually detect *Acinetobacter baumannii, Enterococcus faecium, Klebsiella pneumoniae*, and *Staphylococcus aureus*. In some embodiments, the panel is configured to individually detect *Acinetobacter baumannii, Enterococcus faecium, Pseudomonas aeruginosa*, and *Escherichia coli*. In some embodiments, the panel is configured to individually detect *Acinetobacter baumannii, Enterococcus faecium, Pseudomonas aeruginosa*, and *Staphylococcus aureus*. In some embodiments, the panel is configured to individually detect *Acinetobacter baumannii, Enterococcus faecium, Escherichia coli*, and *Staphylococcus aureus*. In some embodiments, the panel is configured to individually detect *Acinetobacter baumannii, Enterococcus faecalis, Klebsiella pneumoniae*, and *Pseudomonas aeruginosa*. In some embodiments, the panel is configured to individually detect *Acinetobacter baumannii, Enterococcus faecalis, Klebsiella pneumoniae*, and *Escherichia coli*. In some embodiments, the panel is configured to individually detect *Acinetobacter baumannii, Enterococcus faecalis, Klebsiella pneumoniae*, and *Staphylococcus aureus*. In some embodiments, the panel is configured to individually detect *Acinetobacter baumannii, Enterococcus faecalis, Pseudomonas aeruginosa*, and *Escherichia coli*. In some embodiments, the panel is configured to individually detect *Acinetobacter baumannii, Enterococcus faecalis, Pseudomonas aeruginosa*, and *Staphylococcus aureus*. In some embodiments, the panel is configured to individually detect *Acinetobacter baumannii, Enterococcus faecalis, Escherichia coli*, and *Staphylococcus aureus*. In some embodiments, the panel is configured to individually detect *Acinetobacter baumannii, Klebsiella pneumoniae, Pseudomonas aeruginosa*, and *Escherichia coli*. In some embodiments, the panel is configured to individually detect *Acinetobacter baumannii, Klebsiella pneumoniae, Pseudomonas aeruginosa*, and *Staphylococcus aureus*. In some embodiments, the panel is configured to individually detect *Acinetobacter baumannii, Klebsiella pneumoniae, Escherichia coli*, and *Staphylococcus aureus*. In some embodiments, the panel is configured to individually detect *Acinetobacter baumannii, Pseudomonas aeruginosa, Escherichia coli*, and *Staphylococcus aureus*. In some embodiments, the panel is configured to individually detect *Enterococcus faecium, Enterococcus faecalis, Klebsiella pneumoniae*, and *Pseudomonas aeruginosa*. In some embodiments, the panel is configured to individually detect *Enterococcus faecium, Enterococcus faecalis, Klebsiella pneumoniae*, and *Escherichia coli*. In some embodiments, the panel is configured to individually detect *Enterococcus faecium, Enterococcus faecalis, Klebsiella pneumoniae*, and *Staphylococcus aureus*. In some embodiments, the panel is configured to individually detect *Enterococcus faecium, Enterococcus faecalis, Pseudomonas aeruginosa*, and *Escherichia coli*. In some embodiments, the panel is configured to individually detect *Enterococcus faecium, Enterococcus faecalis, Pseudomonas aeruginosa*, and *Staphylococcus aureus*. In some embodiments, the panel is configured to individually detect *Enterococcus faecium, Enterococcus faecalis, Escherichia coli*, and *Staphylococcus aureus*. In some embodiments, the panel is configured to individually detect *Enterococcus faecium, Klebsiella pneumoniae, Pseudomonas aeruginosa*, and *Escherichia coli*. In some embodiments, the panel is configured to individually detect *Enterococcus faecium, Klebsiella pneumoniae, Pseudomonas aeruginosa*, and *Staphylococcus aureus*. In some embodiments, the panel is configured to individually detect *Enterococcus faecium, Klebsiella pneumoniae, Escherichia coli*, and *Staphylococcus aureus*. In some embodiments, the panel is configured to individually detect *Enterococcus faecium, Pseudomonas aeruginosa, Escherichia coli*, and *Staphylococcus aureus*. In some embodiments, the panel is configured to individually detect *Enterococcus faecalis, Klebsiella pneumoniae, Pseudomonas aeruginosa*, and *Escherichia col*. In some embodiments, the panel is configured to individually detect *Enterococcus faecalis, Klebsiella pneumoniae, Pseudomonas aeruginosa*, and *Staphylococcus aureus*. In some embodiments, the panel is configured to individually detect *Enterococcus faecalis, Klebsiella pneumoniae, Escherichia coli*, and *Staphylococcus aureus*. In some embodiments, the panel is configured to individually detect *Enterococcus faecalis, Pseudomonas aeruginosa, Escherichia coli*, and *Staphylococcus aureus*. In some embodiments, the panel is configured to individually detect *Klebsiella pneumoniae, Pseudomonas aeruginosa, Escherichia coli*, and *Staphylococcus aureus*.

In a still further example, in some embodiments, the panel is configured to individually detect *Acinetobacter baumannii, Enterococcus faecium, Enterococcus faecalis, Klebsiella pneumoniae*, and *Pseudomonas aeruginosa*. In some embodiments, the panel is configured to individually detect *Acinetobacter baumannii, Enterococcus faecium, Enterococcus faecalis, Klebsiella pneumoniae*, and *Escherichia coli*. In some embodiments, the panel is configured to individually detect *Acinetobacter baumannii, Enterococcus faecium, Enterococcus faecalis, Klebsiella pneumoniae*, and *Staphylococcus aureus*. In some embodiments, the panel is configured to individually detect *Acinetobacter baumannii, Enterococcus faecium, Enterococcus faecalis, Pseudomonas aeruginosa*, and *Escherichia coli* In some embodiments, the panel is configured to individually detect *Acinetobacter baumannii, Enterococcus faecium, Enterococcus faecalis, Pseudomonas aeruginosa*, and *Staphylococcus aureus*. In some embodiments, the panel is configured to individually detect *Acinetobacter baumannii, Enterococcus faecium, Enterococcus faecalis, Escherichia coli*, and *Staphylococcus aureus*. In some embodiments, the panel is configured to individually detect *Acinetobacter baumannii, Enterococcus faecium, Klebsiella pneumoniae, Pseudomonas aeruginosa*, and *Escherichia coli*. In some embodiments, the panel is configured to individually detect *Acinetobacter baumannii, Enterococcus faecium, Klebsiella pneumoniae, Pseudomonas aeruginosa*, and *Staphylococcus aureus*. In some embodiments, the panel is configured to individually detect *Acinetobacter baumannii, Enterococcus faecium, Klebsiella pneumoniae, Escherichia coli*, and *Staphylococcus aureus*. In some embodiments, the panel is configured to individually detect *Acinetobacter baumannii, Enterococcus faecium, Pseudomonas aeruginosa, Escherichia coli*, and *Staphylo-

*coccus aureus*. In some embodiments, the panel is configured to individually detect *Acinetobacter baumannii, Enterococcus faecalis, Klebsiella pneumoniae, Pseudomonas aeruginosa,* and *Escherichia coli*. In some embodiments, the panel is configured to individually detect *Acinetobacter baumannii, Enterococcus faecalis, Klebsiella pneumoniae, Pseudomonas aeruginosa,* and *Staphylococcus aureus*. In some embodiments, the panel is configured to individually detect *Acinetobacter baumannii, Enterococcus faecalis, Klebsiella pneumoniae, Escherichia coli,* and *Staphylococcus aureus*. In some embodiments, the panel is configured to individually detect *Acinetobacter baumannii, Enterococcus faecalis, Pseudomonas aeruginosa, Escherichia coli,* and *Staphylococcus aureus*. In some embodiments, the panel is configured to individ ually detect *Acinetobacter baumannii, Klebsiella pneumoniae, Pseudomonas aeruginosa, Escherichia coli,* and *Staphylococcus aureus*. In some embodiments, the panel is configured to individually detect *Enterococcus faecium, Enterococcus faecalis, Klebsiella pneumoniae, Pseudomonas aeruginosa,* and *Escherichia coli*.

In another further example, in some embodiments, the panel is configured to individually detect *Acinetobacter baumannii, Enterococcus faecium, Enterococcus faecalis, Klebsiella pneumoniae, Pseudomonas aeruginosa,* and *Escherichia coli*. In some embodiments, the panel is configured to individ ually detect *Acinetobacter baumannii, Enterococcus faecium, Enterococcus faecalis, Klebsiella pneumoniae, Pseudomonas aeruginosa,* and *Staphylococcus aureus*. In some embodiments, the panel is configured to individually detect *Acinetobacter baumannii, Enterococcus faecium, Enterococcus faecalis, Klebsiella pneumoniae, Escherichia coli,* and *Staphylococcus aureus*. In some embodiments, the panel is configured to individually detect *Acinetobacter baumannii, Enterococcus faecium, Enterococcus faecalis, Pseudomonas aeruginosa, Escherichia coli,* and *Staphylococcus aureus*. In some embodiments, the panel is configured to individually detect *Acinetobacter baumannii, Enterococcus faecium, Klebsiella pneumoniae, Pseudomonas aeruginosa, Escherichia coli,* and *Staphylococcus aureus*. In some embodiments, the panel is configured to individually detect *Acinetobacter baumannii, Enterococcus faecalis, Klebsiella pneumoniae, Pseudomonas aeruginosa, Escherichia coli,* and *Staphylococcus aureus*. In some embodiments, the panel is configured to individually detect *Enterococcus faecium, Enterococcus faecalis, Klebsiella pneumoniae, Pseudomonas aeruginosa, Escherichia coli,* and *Staphylococcus aureus*.

In particular embodiments, the panel is configured to individually detect *Acinetobacter baumannii, Enterococcus faecium, Klebsiella pneumoniae, Pseudomonas aeruginosa, Escherichia coli,* and *Staphylococcus aureus*. In other particular embodiments, the panel is configured to individually detect *Acinetobacter baumannii, Enterococcus faecium, Enterococcus faecalis, Klebsiella pneumoniae, Pseudomonas aeruginosa, Escherichia coli,* and *Staphylococcus aureus*.

In some embodiments, the panel may be configured to individually detect one or more (e.g., 1, 2, 3, 4, 5, 6, 7, 8, or 9) of *Acinetobacter baumannii, Enterococcus faecium, Enterococcus faecalis, Klebsiella pneumoniae, Pseudomonas aeruginosa, Escherichia coli, Staphylococcus aureus, Streptococcus pneumoniae,* and an *Enterobacter* spp. For example, in some embodiments, the panel may be configured to individually detect *Acinetobacter baumannii, Enterococcus faecium, Enterococcus faecalis, Klebsiella* *pneumoniae, Pseudomonas aeruginosa, Escherichia coli, Staphylococcus aureus, Streptococcus pneumoniae,* and an *Enterobacter* spp.

In some embodiments, the panel may be configured to individually detect one or more (e.g., 1, 2, 3, 4, 5, 6, 7, or 8) of *Acinetobacter baumannii, Enterococcus faecium, Enterococcus faecalis, Klebsiella pneumoniae, Pseudomonas aeruginosa, Escherichia coli, Staphylococcus aureus,* and a *Candida* spp. (e.g., *Candida albicans, Candida guilliermondii, Candida glabrata, Candida krusei, Candida lusitaniae, Candida parapsilosis, Candida dublinensis,* and *Candida tropicalis*). For example, in some embodiments, the panel is configured to individually detect *Acinetobacter baumannii, Enterococcus faecium, Enterococcus faecalis, Klebsiella pneumoniae, Pseudomonas aeruginosa, Staphylococcus aureus,* and a *Candida* spp. In other embodiments, the panel is configured to individually detect *Acinetobacter baumannii, Enterococcus faecium, Klebsiella pneumoniae, Pseudomonas aeruginosa, Escherichia coli, Staphylococcus aureus,* and a *Candida* spp.

In any of the above embodiments, the panel may be configured to detect a pan-bacterial marker. In any of the above panels, the analyte may be a nucleic acid (e.g., an amplified target nucleic acid, as described above), or a polypeptide (e.g., a polypeptide derived from the pathogen or a pathogen-specific antibody produced by a host subject, for example, an IgM or IgG antibody). In some embodiments, multiple analytes (e.g., multiple amplicons) are used to detect a pathogen. In any of the above panels, the biological sample may be whole blood, urine, cerebrospinal fluid, respiratory secretions, or a tissue sample (e.g., a wound sample).

EXAMPLES

The following examples are put forth so as to provide those of ordinary skill in the art with a complete disclosure and description of how the devices, systems, and methods described herein are performed, made, and evaluated, and are intended to be purely exemplary of the invention and are not intended to limit the scope of what the inventors regard as their invention.

Example 1: Panels for Detection of Pathogens in Whole Blood

FIG. 1A shows a list of exemplary, non-limiting target organisms and markers of the invention. FIGS. 1B-1E show exemplary panels of pathogens useful for diagnosis and treatment of diseases caused by or associated with microbial pathogens (e.g., bacterial infection or fungal infection), Lyme disease, bloodstream infection (e.g., bacteremia or fungemia), pneumonia, peritonitis, osteomyeletis, meningitis, empyema, urinary tract infection, sepsis, septic shock, and septic arthritis) and diseases that may manifest with similar symptoms to diseases caused by or associated with microbial pathogens (e.g., SIRS).

For example, the six bacterial species selected for the panel shown in FIG. 1B account for the vast majority of antimicrobial-resistant pathogens. Previous studies have determined that greater than 70% of hospital-acquired infections are due to *S. aureus, Enterococcus* spp., *K. pneumoniae, P. aeruginosa,* and *A. baumannii*. Another survey conducted by the Centers for Disease Control and Prevention (CDC) found that the antibacterial agents most frequently employed for empiric therapy in the United States were levofloxacin, vancomycin, cefotaxime, and piperacillin/tazobactam. None of these agents are considered to be the drug of choice for the pathogens in the panel shown in FIG. 1B. Furthermore, these organisms are the most frequent cause of breakthrough infections in patients on broad-spectrum antimicrobial therapy. Thus, these significant clinical factors support the need in the healthcare market for assays that can rapidly and accurately detect the pathogens in the panel in FIG. 1B in order to reduce bacteremia morbidity rates, decrease mortality rates, and improve economic costs that impact patients and hospitals in the United States. In another example, the six bacterial species selected for the panel shown in FIG. 1E covers approximately 50% of the species most likely to receive inappropriate empiric treatment. The panel shown in FIG. 1E is also inclusive of species associated with the highest bloodstream infection mortality rates.

Detection of the targets and panels described in this example enables rapid and accurate differential diagnosis of diseases caused by or associated with microbial pathogens (e.g., bacterial infection or fungal infection), Lyme disease, bloodstream infection (e.g., bacteremia or fungemia), pneumonia, peritonitis, osteomyeletis, meningitis, empyema, urinary tract infection, sepsis, septic shock, and septic arthritis) and diseases that may manifest with similar symptoms to diseases caused by or associated with microbial pathogens (e.g., SIRS). A patient presenting with symptoms consistent with one of these conditions may be tested for one of the panels, which may be performed in a multiplexed assay, for example, using the T2Dx® instrument, as described below. Detection and identification of the bacterial agent present in the whole blood sample can then be used to determine an optimized course of therapy.

Example 2: Improving Detection Sensitivity of a Pathogen by Amplifying and Detecting Multiple Amplicons from the Pathogen During development of a panel assay, a relatively high false positive rate was observed for detection of S. aureus by amplifying a portion of the 23ITS5 rRNA locus and detecting the resulting amplicon. This was likely due to the lack of discriminating hybridization against amplified homologous 23ITS5 targets of near neighbors of S. aureus such as S. epidermidis, S. warnei, S. hominis and the like, which are common on the skin of humans.

The single-copy femB gene was initially chosen as a single-copy target to replace the multi-copy 23ITS5S target to increase the specificity of detection of S. aureus. However, frequent dropouts occurred, leading to false negative results of up to about 25%, and the sensitivity of detection was not as high as when detecting a multi-copy target. To further improve sensitivity and robustness of detection of S. aureus, another specific single-copy target was chosen for simultaneous amplification in order to increase the product synthesized from this species by a factor of 2 (theoretical stochiometric increase due to co-synthesized products). The primer pairs used in this Example are shown below ("dAP"=2,6-diaminopurine).

```
femA-Forward:
                                 (SEQ ID NO: 53)
5'-ACC T/dAP/T CTC TGC TGG TTT CTT CTT-3' femA-Reverse:
                                 (SEQ ID NO: 54)
5'-CAG CAT CTT C/dAP/A GCA TCT TCT GTA AA-3'
```

```
femB-Forward:
                                 (SEQ ID NO: 55)
5'-GTT T/dAP/C TAT TCG AAT CGT GGT CCA GT-3' femB-Reverse:
                                 (SEQ ID NO: 12)
5'-GTT GTA AAG CCA TGA TGC TCG TAA CCA-3'
```

For hybridization-based particle agglomeration and $T_2$ magnetic resonance (T2MR) detection, two populations of magnetic particles, each bearing a probe that hybridizes to the femA amplicon and a probe that binds to the femB amplicon (also referred to as "scrambled" magnetic particle pairs) were generated. One particle population was conjugated with a 5' capture probe specific to femA (5'-CCA TTT GAA GTT GTT TAT TAT GC-3'; SEQ ID NO: 35) and a 5' capture probe specific to femB (5'-TT TTT CAG ATT TAG GAT TAG TTG ATT-3'; SEQ ID NO: 39). The other particle population was conjugated with a 3' capture probe specific to femA (5'-GGG AAA TGA TTA ATT ATG CAT TAA ATC-3'; SEQ ID NO: 36) and a 3' capture probe specific to femB (5'-GAT CCG TAT TGG TTA TAT CAT C-3'; SEQ ID NO: 40).

Figure 2B:
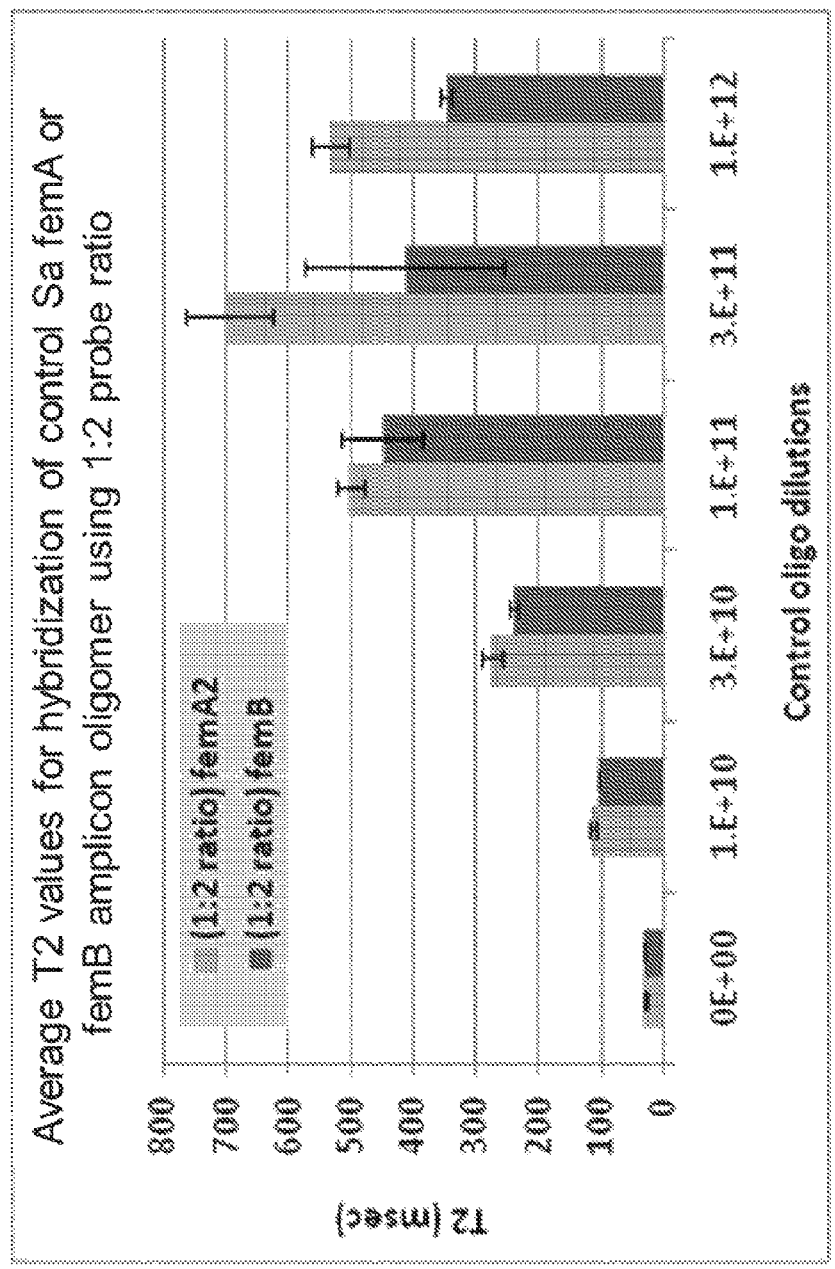
Figure 2C:
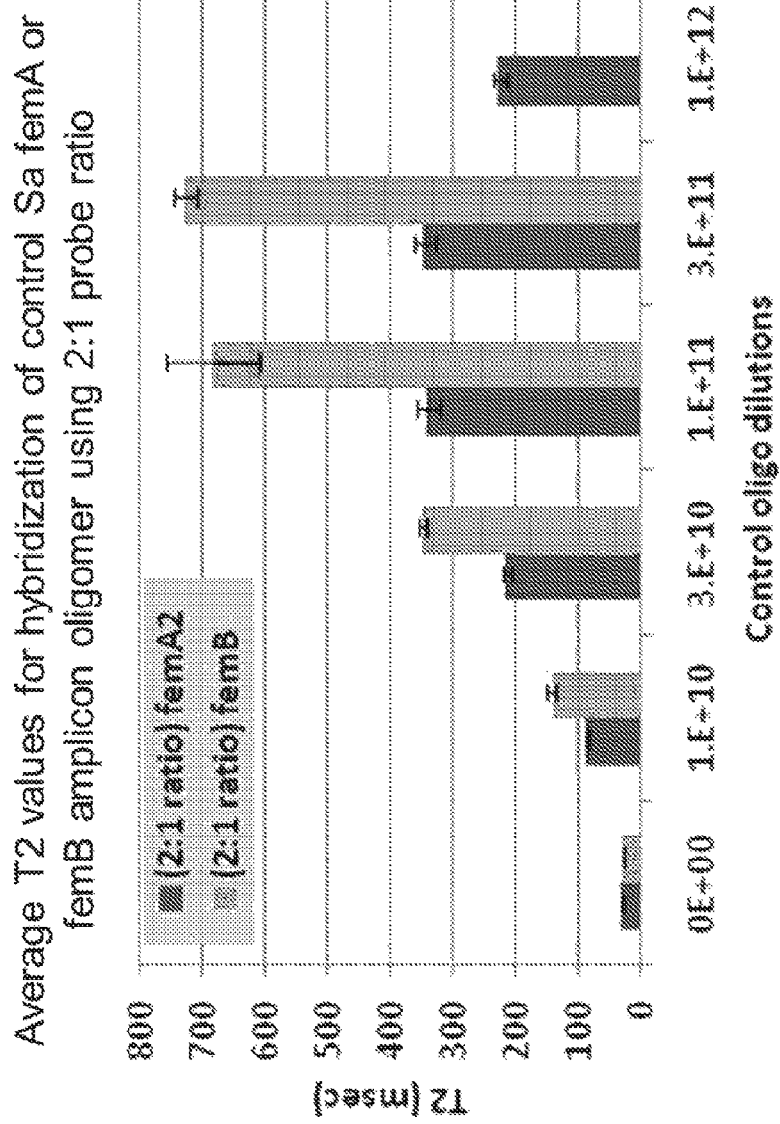

Particles were generated with different probe ratios during crosslinking (i.e., femA:B probe=1:1, 2:1 or 1:2) and hybridized to control femA or femB amplicon oligomers. These oligomers represent the amplified single-stranded target (strand amplified by extending primer in excess in asymmetric PCR) from the 5' end of the 5' capture probe to the 3' end of the 3' capture probe. FIGS. 2A-2C show an oligomer titration of particles conjugated in presence of each of the three ratios. While each probe ratio led to detectable increase in average $T_2$ values, particles having a 1:1 probe concentration ratio showed the most balanced detection profiles as compared to 2:1 ratios (FIGS. 2A-2C).

Figure 3A:
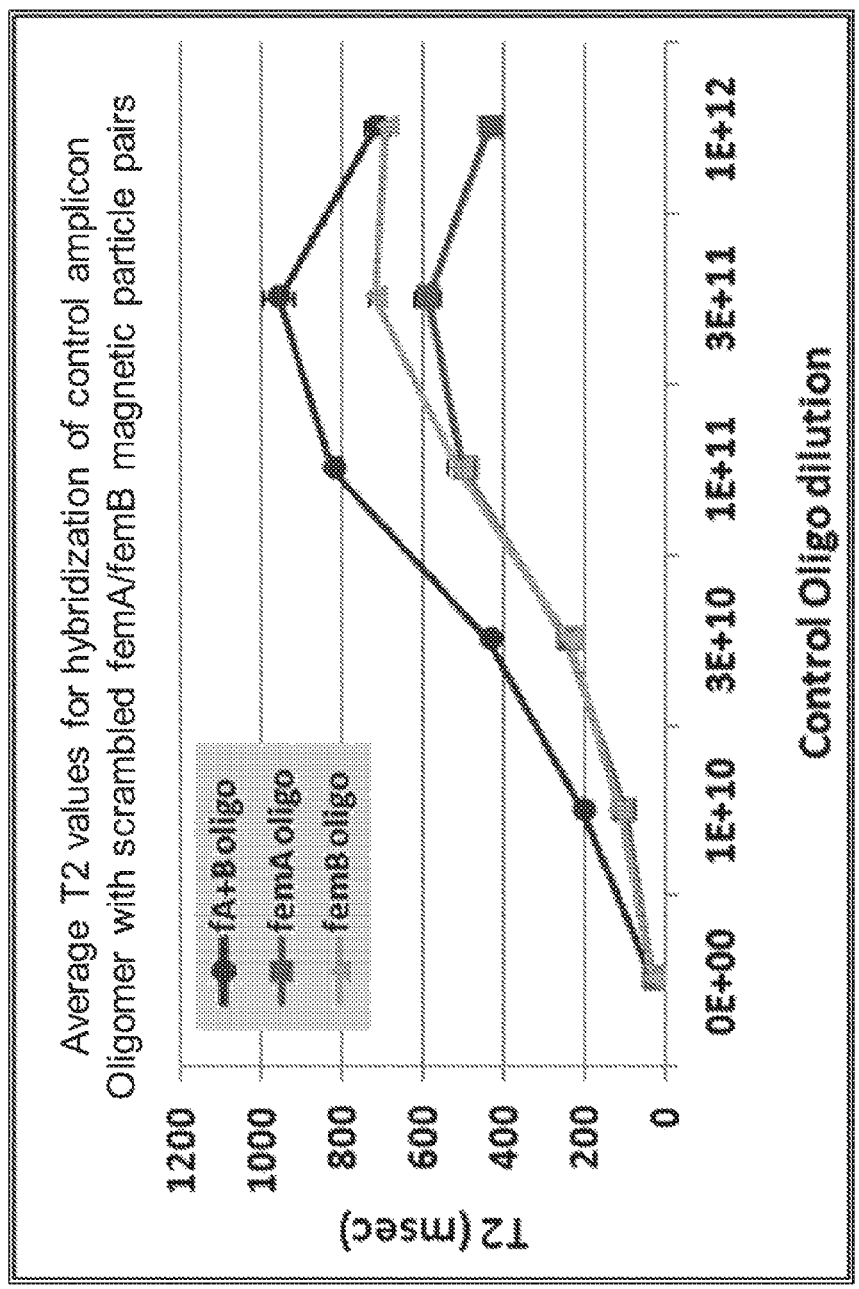
FIG. 3A is a graph showing titration of scrambled (femA/femB) magnetic particle pairs with oligomers specific for the femA and femB amplicons/PCR products. The femA+femB ("fA+fB") curve was obtained by adding equimolar amounts of either oligonucleotide to the hybridization reaction.
Figure 3B:
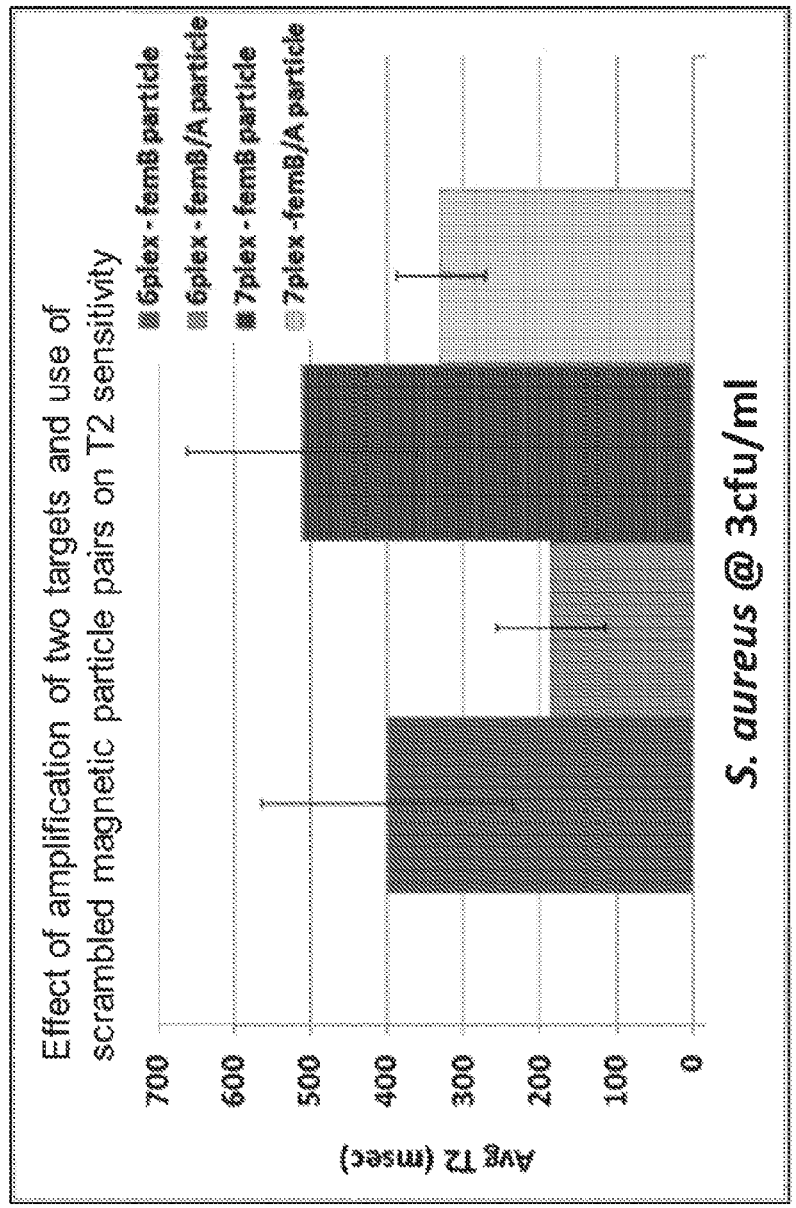
FIG. 3B is a graph showing the results of a combined PCR/T2MR assay of blood spiked with 3 CFU/mL of *S. aureus* strain TCH595 cells. femB/A particle indicates scrambled magnetic particle pairs (see Example 2). N=12.

The impact of an additional S. aureus-specific primer pair on sensitivity was evaluated. Without If simultaneous amplification using both primer pairs generated twice the amount of amplicons compared to amplification using a single primer pair, the sensitivity of the assay should increase provided that both amplicons can be detected by a scrambled magnetic particle pair that carries probes for either PCR product. To test the validity of this approach, the particles were first challenged with control oligomers for femA and femB. Addition of both oligomers (femA+femB oligo) at equal concentrations to a hybridization containing the scrambled femA/B magnetic particle pairs described above resulted in a 60-70% increase of the $T_2$ signal as compared to a hybridization with either femA or femB added singly (FIG. 3A). Hybridizations were performed using 15 μl scrambled femA/B magnetic particles+15 μl oligomer mix hybridized for 30 min at 62° C.

To test whether amplification of both the femA and femB amplicons resulted in improved detection sensitivity of S. aureus cells, combined PCR/T2MR assays were performed comparing a 6-plex PCR assay (A. baumannii, E. faecalis/E. faecium, K. pneumoniae, P. aeruginosa, S. aureus-femB, and internal control primers) with a 7-plex assay (same as 6-plex with the addition of S. aureus-femA primers) and detection by the scrambled femA/B magnetic particle pairs. Surprisingly, an increase in S. aureus detection sensitivity was not only observed when the PCR products in the 7-plex assay were detected by the scrambled femA/B magnetic particle pairs (second vs. fourth columns in FIG. 3B), but also when only femB-specific magnetic particle (two pools of magnetic particles having either the 5' capture probe or the 3' capture probe conjugated to their surface) were used for detection (first vs. third columns in FIG. 3B).

Figure 4:
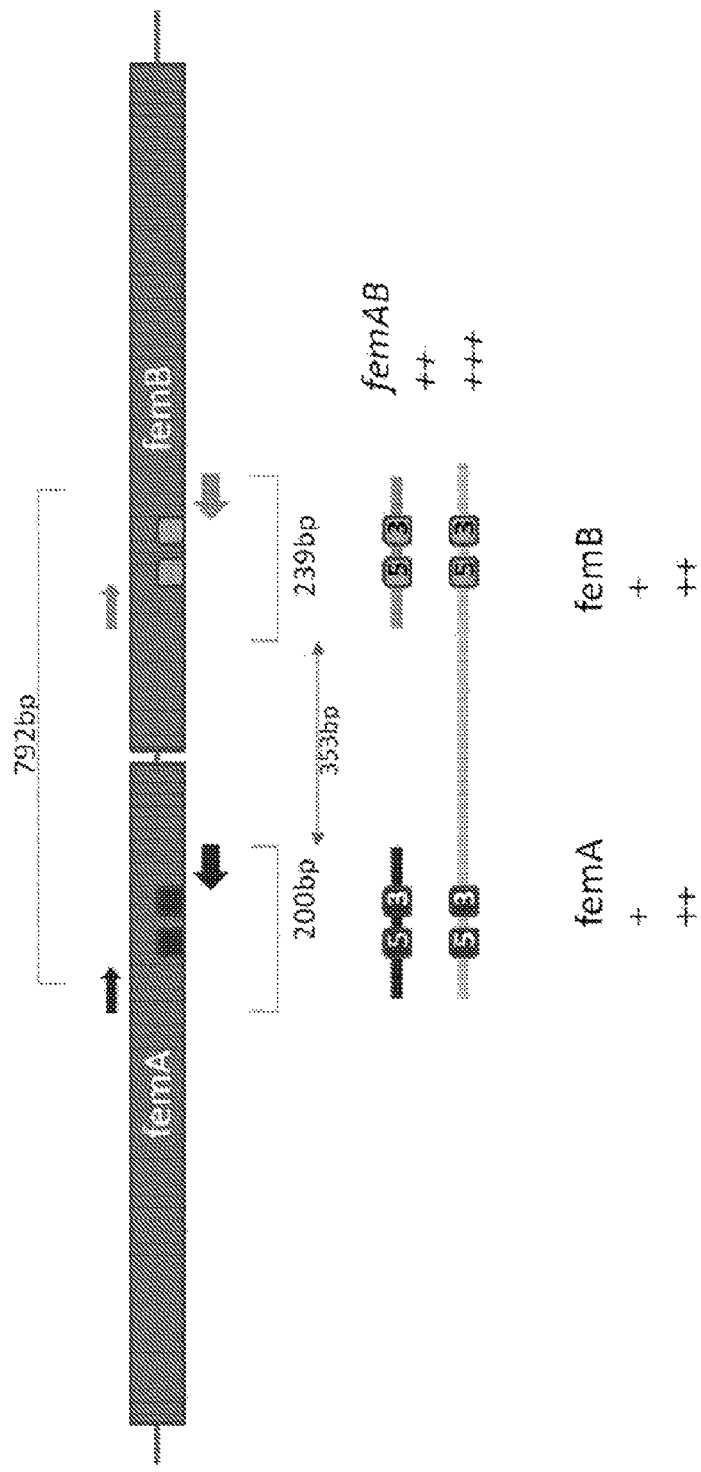
FIG. 4 is a schematic representation of PCR products that can be expected in presence of two primer pairs that amplify loci separated by 353 bp. Probe binding sites (5' capture probe ("5") and 3' capture probe ("3")) are shown as dark gray and light gray rectangles (femA and femB, respectively). Distances between amplicon and amplicon lengths can also be deduced from the femA/B operon sequence (see SEQ ID NO: 56 for the femA/femB operon sequence of *S. aureus* strain Mu3).
Figure 5A:
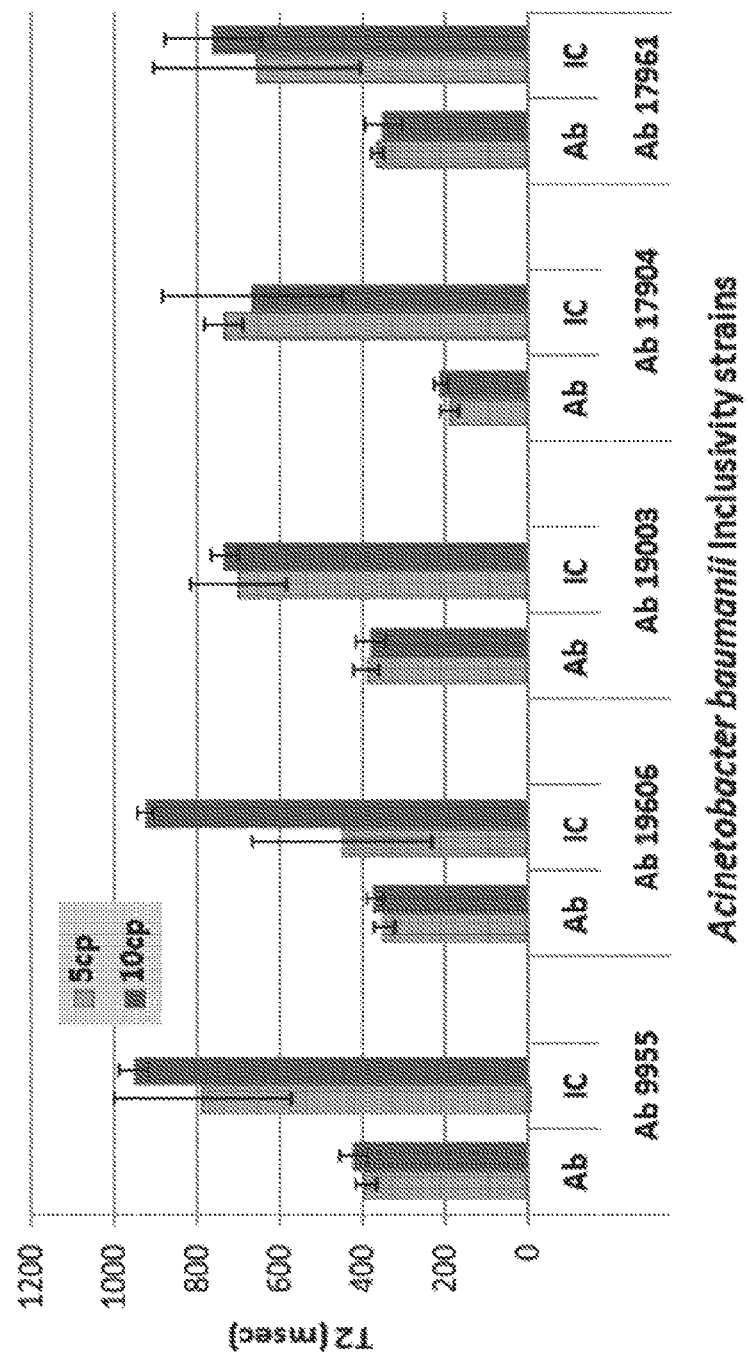
FIGS. 5A-5E are graphs showing average $T_2$ detection signals obtained in a 7-plex bacterial panel assay with spiked genomic DNA into negative whole blood lysate at 5 and 10 genome copy equivalents (cp)/reaction.
Figure 5B:
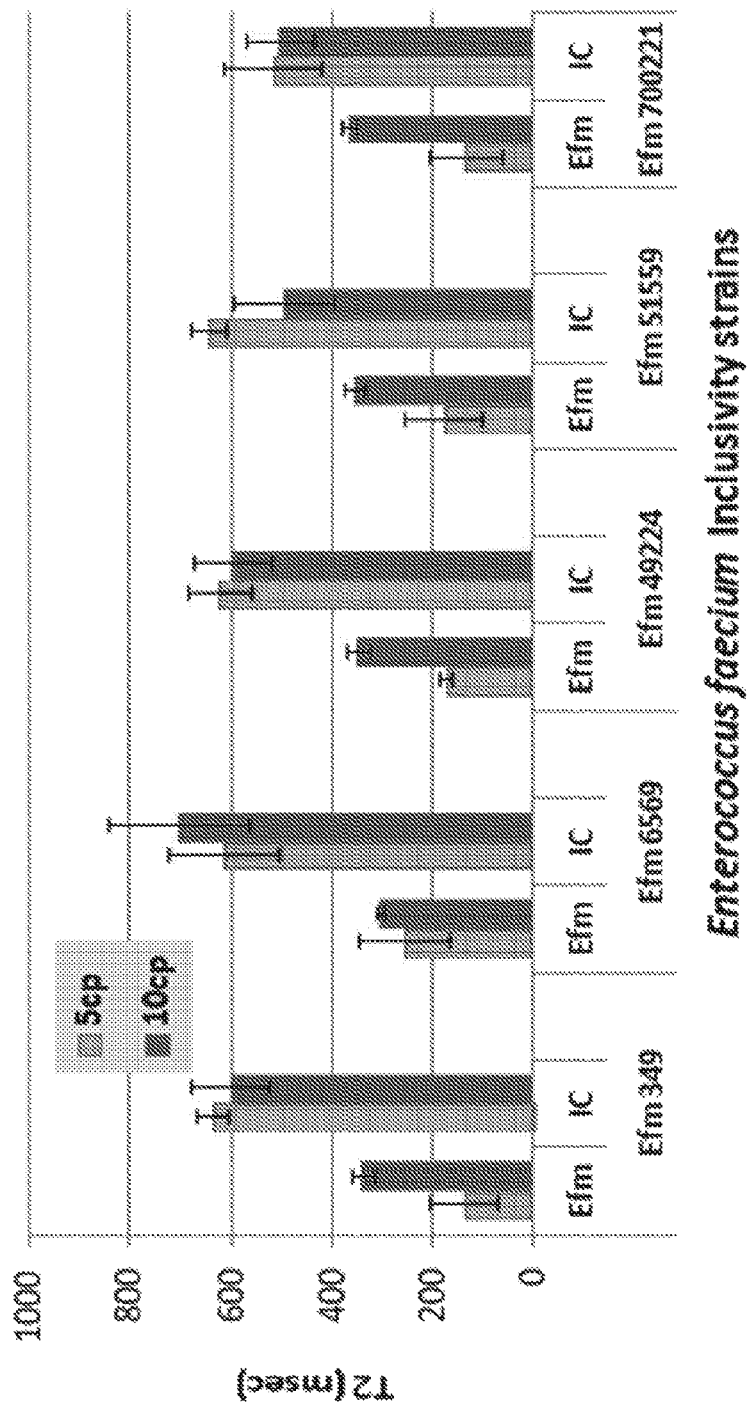
Figure 5C:
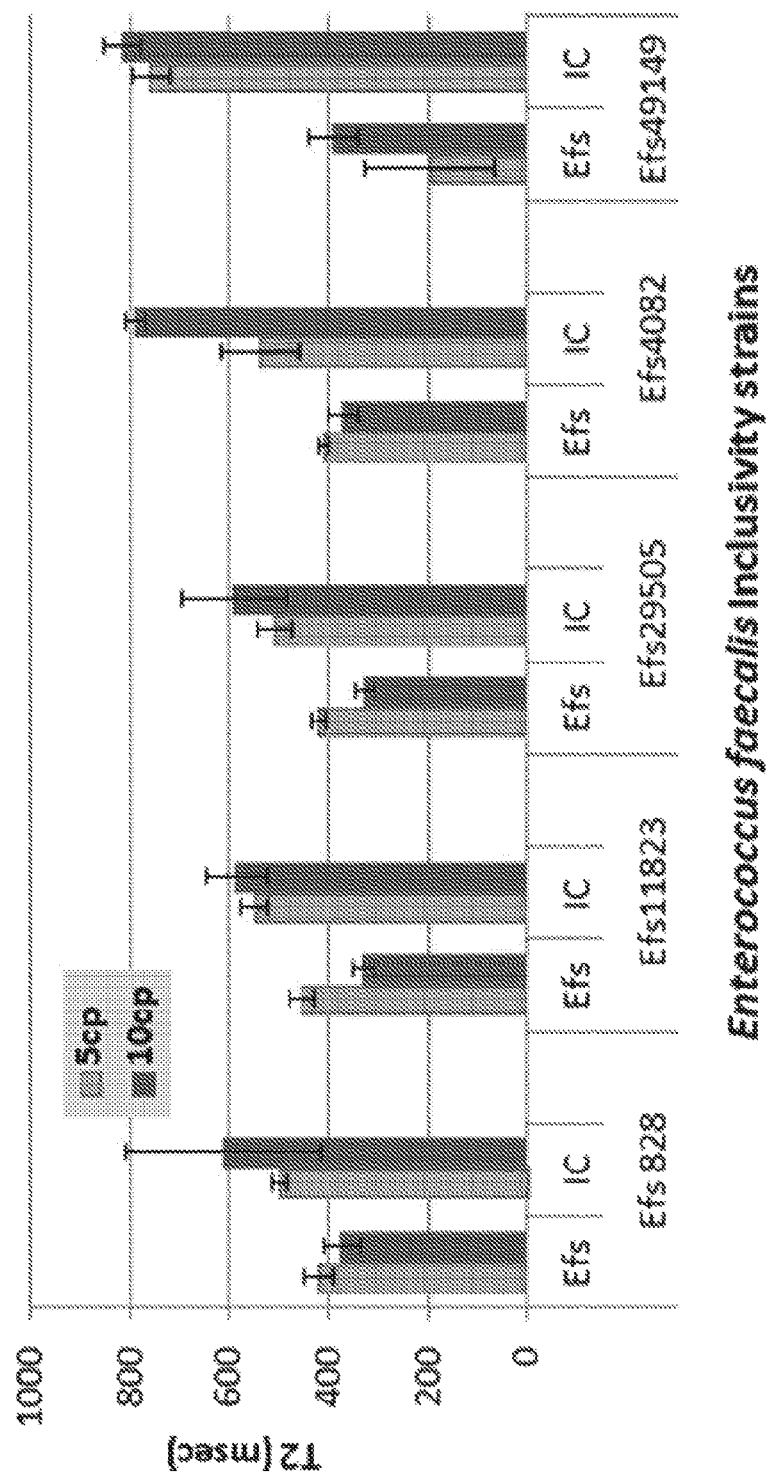
Figure 5D:
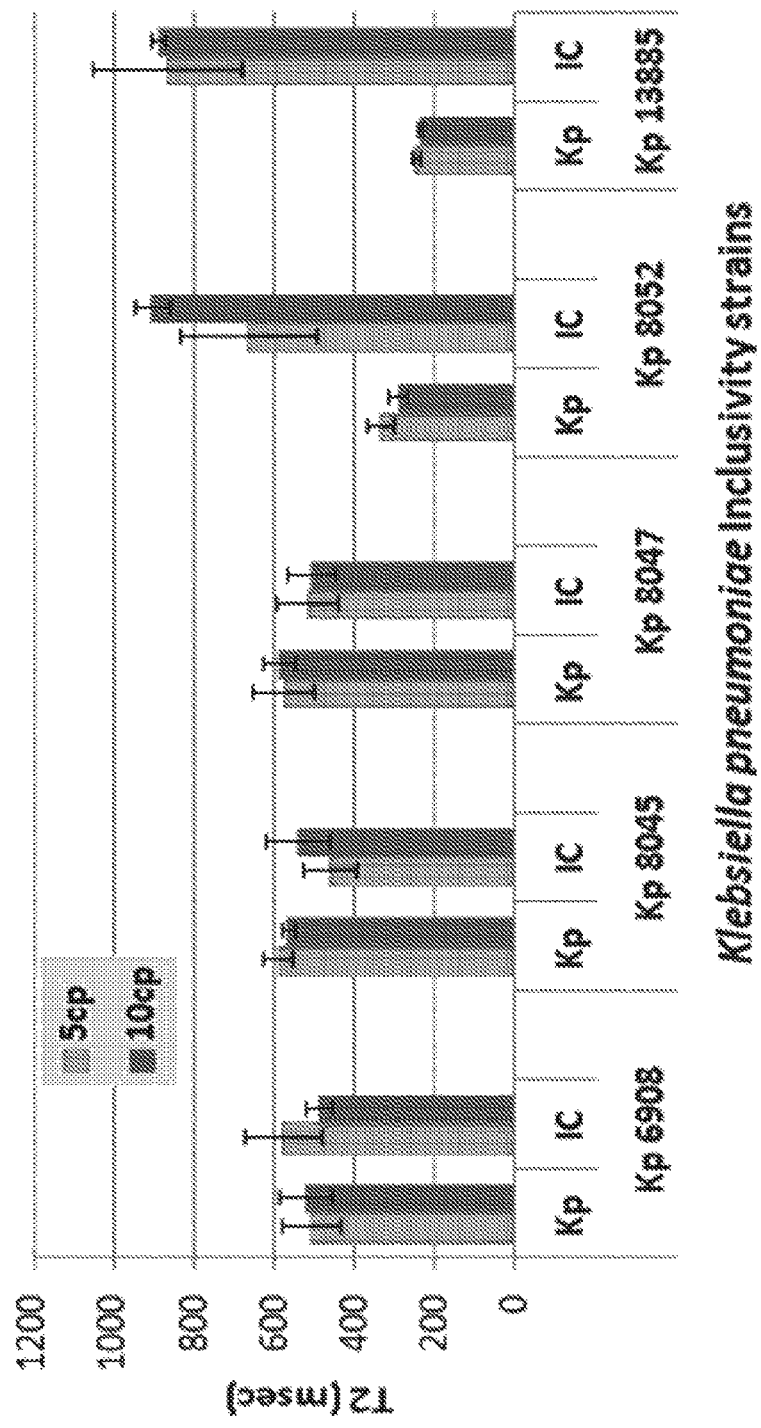
Figure 5E:
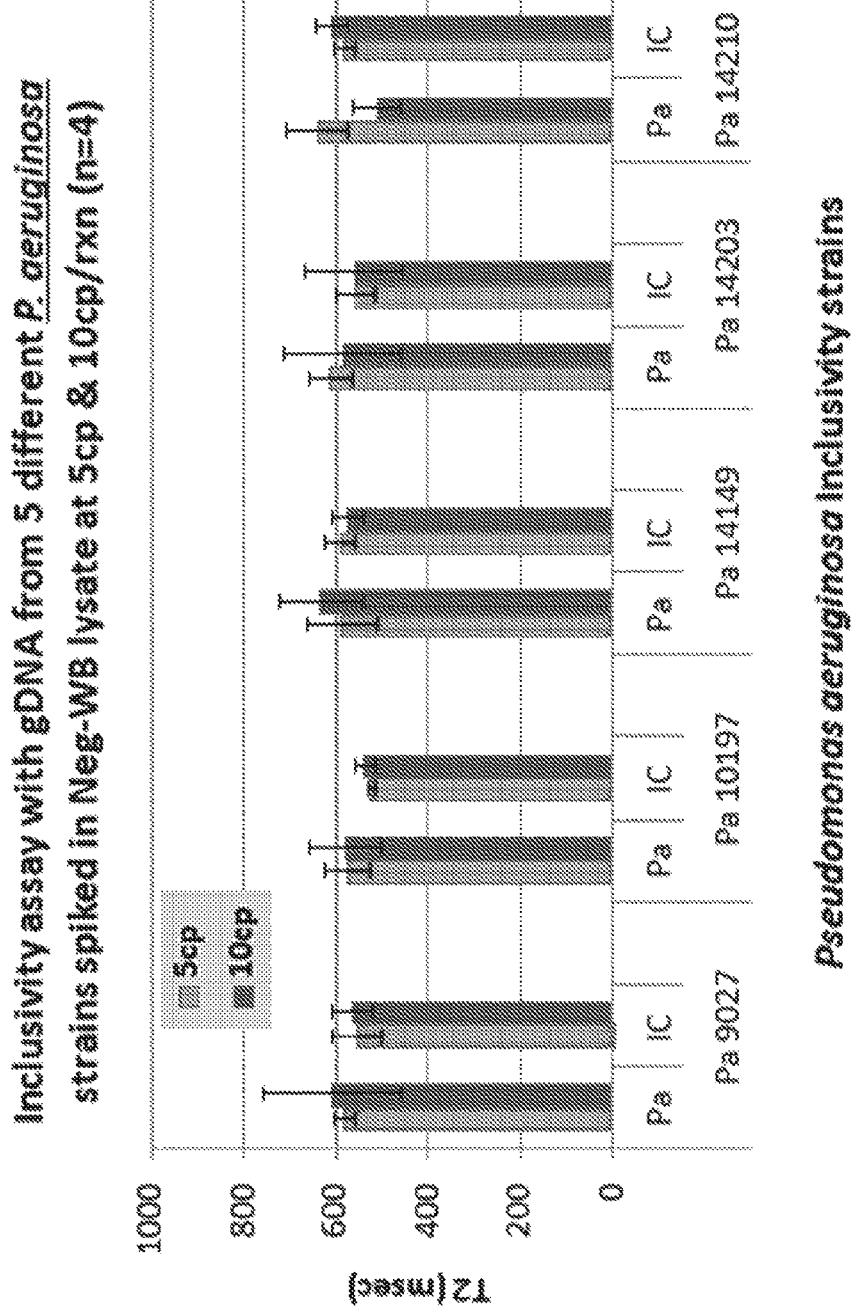
Figure 5F:
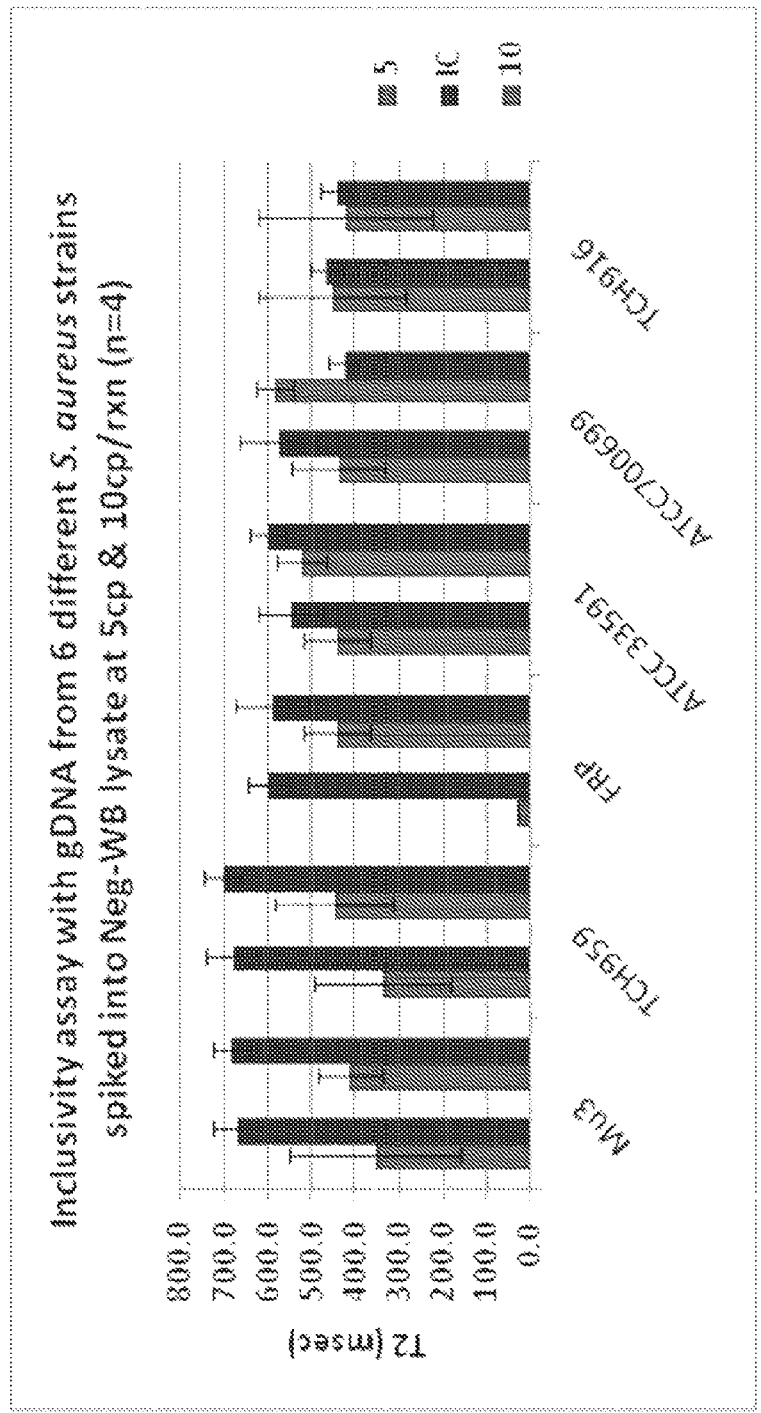
FIG. 5F is a graph showing average $T_2$ detection signals obtained in a 6-plex bacterial panel assay with spiked Sa genomic DNA from the indicated strains into negative whole blood lysate at 5 and 10 genome equivalents/reaction. N=4.

Without wishing to be bound by theory, this unexpected result can be explained by a partial run-through of strand synthesis beyond amplicon/primer sites, thereby covering the entire span of >790 nts between the femA-forward and femB-reverse primers. The femA- and femB-Forward primers were both present in 4-fold lower concentration as compared to the femA- and femB-Reverse primers to facilitate asymmetric product (single-stranded lower strand) synthesis. If both primers are extended beyond the binding site of femB-Reverse, both reverse primers can extend the resulting product and eventually create an excess of single-stranded products that contain either femA or femB lower strand products or a lower strand product that contains both femA and femB (FIG. 4).

Example 3: 7-Plex PCR/T2MR Assay for Detection of a Diagnostic Bacterial Panel

A rapid, accurate, and reproducible molecular diagnostic test was developed for the detection of the panel of microbial species shown in FIG. 1B directly within human whole blood with a limit of detection (LOD) of 2-4 CFU/mL. This diagnostic method is rapid, amenable to automation (e.g., in a fully-automated system), and offers clinicians the opportunity to detect multiple human pathogens within complex biological specimens for diagnosis and treatment of bacteremia, sepsis, and other diseases.

Some embodiments of the assay include the optional detection of an internal control (IC) to control for PCR inhibition. The IC template and the primers (Pan-*Candida*/Forward and Reverse, SEQ ID NO: 13 and 14, respectively) were added to the multiplex primer mix described below to test their performance. The sequence of the internal control that will be amplified in excess is: 5'-GGC ATG CCT GTT TGA GCG TCC TGC ATC ATA CTG AAA TAG ATC CTT CGA CAA CCT CGG TAC ACT GGG AAC AAG GCC TCA AAC ATT GAT GCT CGA CTA CAC GTA GGG CAATGC GTC TTG CTA GAA GCG AAA TCT GTG GCT TGC TAG TGC AAG CTG GTC GGC GTA TTA TTC CAA CCC GCT GAA CTT AAG CAT ATC AAT AAG CA-3' (SEQ ID NO. 106). The internal control template includes the nucleic acid sequence of SEQ ID NO: 106 cloned into the publically-available plasmid pBR322. Adding these primers had no impact on the detection sensitivities for all of the panel targets. Other IC templates and primers may be used as well.

Whole Blood Multiplexed PCR

Approximately 2.0 mL of whole blood was combined with 100 μL of TRAX erythrocyte lysis buffer (i.e., a mixture of nonyl phenoxy-polyethoxylethanol (NP-40) and 4-octylphenol polyethoxylate (Triton-X100)) and incubated for about 5 minutes. The sample was centrifuged for 5 minutes at 6000 g and the resulting supernatant was removed and discarded. To wash the pellet, the pellet was mixed with 200 μL of Tris EDTA (TE) buffer pH 8.0 and subjected to vortexing. The sample was again centrifuged for 5 minutes at 6000 g and the resulting supernatant was removed and discarded. Following the wash step the pellet was mixed with 100 μL TE buffer containing 1500 copies of the inhibition control (internal control) and subjected to bead beating using 1 mm tungsten carbide beads (alternative bead beating approaches include using 0.65 mm high density $ZrO_2+HfO_2$ and $Y_2O_3$ beads (Glen Mills, N.J.) for 5-10 min or using 0.8 mm high density $ZrO_2$ beads for 5-15 min) with vigorous agitation. The sample was again centrifuged.

50 μL of the resulting lysate was then added to 30 μL of an asymmetric PCR master mix containing the PCR primers shown in Table 3 as well as 200 mM dNTPs, 4 mM magnesium chloride, Tricine buffer, and 5% glycerol. The resulting mixture was denatured for 5 min at 95° C. and then centrifuged. 20 μL of a mixture including a hot start- and whole blood-compatible thermostable DNA polymerase and dNTPs were added (alternatively, hot start compatible dNTPs, such as CLEANAMP™ (TriLink)) may be used with a whole blood-compatible DNA polymerase). Next, thermocycling was conducted using the following cycle parameters: heat denaturation at 95° C. for 5 minutes, 50 cycles consisting of a 30 second 95° C. heat denaturation step, a 20 second annealing step at 61° C. (temperatures from 59° C. to 61° C. may also be used), and a 30 second 68° C. elongation step, and a final extension at 68° C. for 10 minutes.

TABLE 3

Primers used in this Example

| Species | Target | Primers | Primer Concentration (nM final) |
|---|---|---|---|
| *Acinetobacter baumannii* | 23S-ITS-5S rRNA gene locus | Forward: 5'-GGA AGG GAT CAG GTG GTT CAC TCT T-3' (SEQ ID NO: 57) | 400 |
| | | Reverse: 5'-AGG ACG TTG ATA GG TTG GAT GTG GA-3' (SEQ ID NO: 2) | 100 |
| *Enterococcus faecium* and *Enterococcus faecalis* | 23S-ITS-5S rRNA gene locus | Forward: 5'-CTA TGT AGG GAA GGG ATA AAC GCT GA-3' (SEQ ID NO: 58) | 100 |
| | 23S-ITS-5S rRNA gene locus | Reverse: 5'-GCG CTA AGG AGC TTA ACT TCT GTG TTC G-3' (SEQ ID NO: 4) | 400 |
| *Klebsiella pneumoniae* | 23S rRNA gene locus | Forward: 5'-GAC GGT TGT CCC GGT TTA AGC A-3' (SEQ ID NO: 5) | 100 |
| | | Reverse: 5'-GCT GGT ATC TTC GAC TGG TCT-3' (SEQ ID NO: 6) | 400 |
| *Pseudomonas aeruginosa* | 23S-ITS-5S rRNA gene locus | Forward: 5'-AGG CTG GGT GTG TAA GCG TTG T-3' (SEQ ID NO: 7) | 100 |
| | | Reverse: 5'-CAA GCA ATT CGG TTG GAT ATC CGT T-3' (SEQ ID NO: 8) | 400 |

TABLE 3-continued

Primers used in this Example

| Species | Target | Primers | Primer Concentration (nM final) |
|---|---|---|---|
| Staphylococcus aureus | femA | Forward: 5'-ACC T/i6diPr/T CTC TGC TGG TTT CTT CTT-3' (SEQ ID NO: 53) | 100 |
| | | Reverse: 5'-CAG CAT CTT C/i6diPr/A GCA TCT TCT GTA AA-3' (SEQ ID NO: 54) | 400 |
| | femB | Forward: 5'-GTT T/i6diPr/C TAT TCG AAT CGT GGT CCA GT-3' (SEQ ID NO: 55) | 100 |
| | | Reverse: 5'-GTT GTA AAG CCA TGA TGC TCG TAA CCA-3' (SEQ ID NO: 12) | 400 |
| Internal control | IC | Forward: 5'-GGC ATG CCT GTT TGA GCG TC-3' (SEQ ID NO: 13) | 400 |
| | | Reverse: 5'-GCT TAT TGA TAT GCT AAG TTC AGC GGG T-3' (SEQ ID NO: 14) | 100 |

Table 4 shows another panel of primers that can be used for amplification of pathogen-specific amplicons in a multiplexed assay, for example, for the panel shown in FIG. 1B. The *Candida* spp. Forward and Reverse primers can be used for the optional detection of the Internal Control sequence. Alternative *A. baumannii* forward primers that can be used can include the oligonucleotide sequence of 5'-GGA AGG GAT CAG GTG GTT CAC TCT T-3' (SEQ ID NO: 110).

TABLE 4

Primers

| Primers | Sequence | SEQ ID NO: |
|---|---|---|
| A. baumannii Forward Primer | 5'-CGT TTT CCA AAT CTG TAA CAG ACT GGG-3' | 1 |
| A. baumannii Reverse Primer | 5'-AGG ACG TTG ATA GG TTG GAT GTG GA-3' | 2 |
| Enterococcus spp. Forward Primer | 5'-GGT AGC TAT GTA GGG AAG GGA TAA ACG CTG A-3' | 3 |
| Enterococcus spp. Reverse Primer | 5'-GCG CTA AGG AGC TTA ACT TCT GTG TTC G-3' | 4 |
| K. pneumoniae Forward Primer | 5'-GAC GGT TGT CCC GGT TTA AGC A-3' | 5 |
| K. pneumoniae Reverse Primer | 5'-GCT GGT ATC TTC GAC TGG TCT-3' | 6 |
| P. aeruginosa Forward Primer | 5'-AGG CTG GGT GTG TAA GCG TTG T-3' | 7 |
| P. aeruginosa Reverse Primer | 5'-CAA GCA ATT CGG TTG GAT ATC CGT T-3' | 8 |
| S. aureus femA Forward Primer | 5'-GGT AAT GAATTA CCT/i6diPr/TC TCT GCT GGTTTC TTC TT-3' | 9 |
| S. aureus femA Reverse Primer | 5'-ACC AGC ATC TTC/i6diPr/GC ATC TTC TGT AAA-3' | 10 |
| S. aureus femB Forward Primer | 5'-GAA GTT ATG TIT/i6diPr/CT ATT CGA ATC GTG GTC CAGT-3' | 11 |
| S. aureus femB Reverse Primer | 5'-GTT GTA AAG CCA TGA TGC TCG TAA CCA-3' | 12 |
| Candida spp. Forward Primer | 5'-GGC ATG CCT GTT TGA GCG TC-3' | 13 |
| Candida spp. Reverse Primer | 5'-GCT TAT TGA TAT GCT AAG TTC AGC GGG T-3' | 14 |

Note:
"/i6diPr/" indicates 2,6-Diaminopurine

Hybridization Induced Agglomeration Assays

Fifteen microliters of the resulting amplification reaction was aliquoted into 0.2 mL thin walled PCR tubes and incubated within a sodium phosphate hybridization buffer (4×SSPE) with pairs of oligonucleotide derivatized nanoparticles at a final iron concentration of 0.2 mM iron per reaction. Hybridization reactions were incubated for 3 minutes at 95° C. followed by 30 minutes incubation at 60° C. within a shaking incubator set at an agitation speed of 1000 rpm (Vortemp, LabNet International). Hybridized samples are then placed in a 37° C. heating block to equilibrate the temperature to that of the MR reader for 3 minutes. Each sample is then subjected to a 5 second vortexing step (3000 rpm) and inserted into the MR reader for Tz measurement. Table 5 shows the nucleic acid sequences of the amplicon-specific portions of the probes used for detection of the indicated species. Alternative *E. faecium* 5' capture probes that can be used can include the oligonucleotide sequence 5'-AAA ACT TAT GTG ACT TCA AAT CCA GTT TT-3' (SEQ ID NO: 111). Alternative *E. faecium* 3' capture probes that can be used can include the oligonucleotide sequence: 5'-TTT ACT CAA TAA AAG ATA ACA CCA CAG T-3' (SEQ ID NO: 112). Alternative *P. aeruginosa* 5' capture probes that can be used can include the oligonucleotide sequence 5'-TCT GAC GAT TGT GTG TTG TAA GG-3' (SEQ ID NO: 114). Alternative *P. aeruginosa* 3' capture probes that can be used can include the oligonucleotide sequence: 5'-GGA TAG ACG TAA GCC CAA GC-3' (SEQ ID NO: 115). The probes also include linker sequences that allow conjugation to magnetic particles at either the 5' or 3' end. The nucleic acid sequences of the probes including linker sequences are shown in Table 6. Alternative *E. faecium* 5' capture probes that can be used can include the oligonucleotide sequence/5AmMC12/ttt ttt ttt AAA ACT TAT GTG ACT TCA AAT CCA GTT TT (SEQ ID NO: 113). Alternative *P. aeruginosa* 5' capture probes that can be used can include the oligonucleotide sequence/5AmMC12/ttt ttt ttt TCT GAC GAT TGT GTG TTG TAA GG (SEQ ID NO: 116). Alternative *P. aeruginosa* 3' capture probes that can be used can include the oligonucleotide sequence: GGA TAG ACG TAA GCC CAA GCtt ttt ttt t/3AmMO/(SEQ ID NO: 117).

TABLE 5

Probes used in this Example

| Probes | Sequence | SEQ ID NO: |
|---|---|---|
| A. baumannii 5' Capture Probe | 5'-TGA GGC TTG ACT ATA CAA CAC C-3' | 15 |
| A. baumannii 3' Capture Probe | 5'-CTA AAA TGA ACA GAT AAA GTA AGA TTC AA-3' | 16 |
| E. faecium 5' Capture Probe | 5'-AAA ACT TAT ATG ACT TCA AAT CCA GTT TT-3' | 19 |
| E. faecium 3' Capture Probe | 5'-TTT ACT CAA TAA AAG ATA ACA CCA CAG-3' | 20 |
| E. faecalis 5' Capture Probe | 5'-TGG ATA AGT AAA AGC AAC TTG GTT-3' | 23 |
| E. faecalis 3' Capture Probe | 5'-AAT GAA GAT TCA ACT CAA TAA GAA ACA ACA-3' | 24 |
| K. pneumoniae 5' Capture Probe | 5'-TAC CAA GGC GCT TGA GAG AAC TC-3' | 27 |
| K. pneumoniae 3' Capture Probe | 5'-CTG GTG TGT AGG TGA AGT C-3' | 28 |
| P. aeruginosa 5' Capture Probe | 5'-GTG TGT TGT AGG GTG AAG TCG AC-3' | 31 |
| P. aeruginosa 3' Capture Probe | 5'-CAC CTT GAA ATC ACA TAC CTG A-3' | 32 |
| S. aureus femA 5' Capture Probe | 5'-CCA TTT GAA GTT GTT TAT TAT GC-3' | 35 |
| S. aureus femA 3' Capture Probe | 5'-GGG AAA TGA TTA ATT ATG CAT TAA ATC-3' | 36 |
| S. aureus femB 5' Capture Probe | 5'-TT TTT CAG ATT TAG GAT TAG TTG ATT-3' | 39 |
| S. aureus femB 3' Capture Probe | 5'-GAT CCG TAT TGG TTA TAT CAT C-3' | 40 |
| Internal Control | 5'-TGG AAT AAT ACG CCG ACC AGC-3' | 43 |
| Internal Control | 5'-AAG GAT CTA TTT CAG TAT GAT GCA G-3' | 44 |

TABLE 6

Probes used in this Example

| Probes | Sequence | SEQ ID NO: |
|---|---|---|
| A. baumannii 5' Capture Probe | /5AmMC12/TTT TTT TTT TGA GGC TTG ACT ATA CAA CAC C | 17 |
| A. baumannii 3' Capture Probe | CTA AAA TGA ACA GAT AAA GTA AGA TTC AAT TTT TTT TT/3AmMO/ | 18 |
| E. faecium 5' Capture Probe | /5AmMC12/ttt ttt ttt AAA ACT TAT ATG ACT TCA AAT CCA GTT TT | 21 |
| E. faecium 3' Capture Probe | TTT ACT CAA TAA AAG ATA ACA CCA CAG Ttt ttt ttt t/3AmMO/ | 22 |
| E. faecalis 5' Capture Probe | /5AmMC12/ttt ttt ttt TGG ATA AGT AAA AGC AAC TTG GTT | 25 |
| E. faecalis 3' Capture Probe | AAT GAA GAT TCA ACT CAA TAA GAA ACA ACA ttt ttt ttt/3AmMO/ | 26 |
| K. pneumoniae 5' Capture Probe | /5AmMC12/TTT TTT TTT TAC CAA GGC GCT TGA GAG AAC TC | 29 |
| K. pneumoniae 3' Capture Probe | CTG GTG TGT AGG TGA AGT CTT TTT TTT T/3AmMO/ | 30 |
| P. aeruginosa 5' Capture Probe | /5AmMC12/ttt ttt ttt GTG TGT TGT AGG GTG AAG TCG AC | 33 |
| P. aeruginosa 3' Capture Probe | CAC CTT GAA ATC ACA TAC CTG Att ttt ttt t/3AmMO/ | 34 |
| S. aureus femA 5' Capture Probe | /5AmMC12/TTT TTT TTT CCA TTT GAA GTT GTT TAT TAT GC | 37 |
| S. aureus femA 3' Capture Probe | GGG AAA TGA TTA ATT ATG CAT TAA ATC TTT TTT TTT/3AmMO/ | 38 |
| S. aureus femB 5' Capture Probe | /5AmMC12/TT TTT TTT TTT CAG ATT TAG GAT TAG TTG ATT | 41 |
| S. aureus femB 3' Capture Probe | GAT CCG TAT TGG TTA TAT CAT CTT TTT TTT T/3AmMO/ | 42 |
| Internal Control | /5AmMC12/TTT TTT TTT TGG AAT AAT ACG CCG ACC AGC | 43 |
| Internal Control | AAG GAT CTA TTT CAG TAT GAT GCA GTT TTT TTT T/3AmMO/ | 44 |

Note:
5AmMC12 indicates 5' amino modifier C12 and 3AmMO indicates 3' amino modifier.

Detection of the *S. aureus* femA and femB amplicons was performed using the "scrambled" magnetic particle pairs described in Example 2. Detection of the amplicons for the remaining species was performed using magnetic particle pairs, with each member of the pair bearing either the 5' or 3' capture probe.

Other workflows besides that described above may be used. In one workflow, 50 µL of reaction mix including all PCR components are mixed with 50 µL of blood lysate, PCR is performed, and the sample is centrifuged prior to hybridization of magnetic particles. In a second workflow, 50 µL of blood lysate is denatured for 5 min at 95° C. and cooled to room temperature. 20 µL of DNA polymerase and dNTPs are added, the sample is centrifuged, and 30 µL of a PCR master mix including all components but the enzyme (e.g., MgClz, Tricine buffer, and glycerol) are added, PCR is performed to amplify the target nucleic acid, and then hybridization to the magnetic particles is performed without prior centrifugation. In a third workflow, 50 µL of blood lysate is added to 30 µL of a PCR reaction mix including all components but the DNA polymerase. This sample is denatured for 5 min at 95° C. and cooled to room temperature. The sample is then centrifuged, and 20 µL of DNA polymerase and dNTPs are added, PCR is performed, and hybridization to the magnetic particles is performed without prior centrifugation. In a fourth workflow, 50 µL of blood lysate is denatured for 5 min at 95° C. and cooled to room temperature. 50 µL of a PCR reaction mix including all PCR components including the DNA polymerase is added, the sample is centrifuged, DNA is performed, and hybridization to the magnetic particles is performed without prior centrifugation.

Example 4: 7-Plex Bacterial Panel Assay Inclusivity and Exclusivity

Inclusivity

The assay described in Example 3 in the 7-plex configuration and also in a 6-plex configuration (lacking the femA forward and reverse primers) was tested in presence of spiked DNA isolated from five *A. baumannii, E. faecium, E. faecalis, K. pneumoniae,* and *P. aeruginosa* strains each and six *S. aureus* strains, respectively, to determine its analytical sensitivity. The strains are summarized in Table 7. Note that the *S. aureus* strains were tested using a 6-plex configuration, i.e. with femB-specific primers present in the PCR reaction. All strains were procured from the American Type Culture Collection (ATCC, VA) as lyophilized cell pellets and genomic DNA was extracted using the GenElute™ kit (Sigma-Aldrich, St. Louis, Mo.). The concentration of the genomic DNA was determined using a NANODROP® 1000 apparatus and the copy number of the target region was estimated using copy calculator. Inclusivity testing was performed by spiking genomic DNA in negative whole blood lysate at 5 genome equivalents (cp) and 10 cp per reaction (n=4). PCR was performed on a MJ Reasearch Tetrad PTC-225 thermal cycler and $T_2$ detection performed using species-specific magnetic nanoparticle mixes having the configuration described in Example 3.

TABLE 7

List of strains tested for inclusivity

| A. baumannii | K. pneumoniae | E. faecium | E. faecalis | P. aeruginosa | S. aureus |
|---|---|---|---|---|---|
| ATCC 9955 | ATCC 6908 | ATCC 700221 | ATCC 4082 | ATCC 9027 | TCH916 |
| ATCC 19606 | ATCC 8045 | ATCC 6569 | ATCC 49149 | ATCC 10197 | Mu3 |
| ATCC 19003 | ATCC 8047 | ATCC 51559 | ATCC 828 | ATCC 14149 | TCH959 |
| ATCC 17904 | ATCC 8052 | ATCC 49224 | ATCC 11823 | ATCC 14203 | FRP |
| ATCC 17961 | ATCC 13885 | ATCC 349 | ATCC 29505 | ATCC 14210 | ATCC 33591 |
| — | — | — | — | — | ATCC 700699 |

The 7-plex (6-plex in case of *S. aureus*) panel assay is specific for all tested target species strains in the panel at or near LoD levels (FIGS. 5A-5F). The lack of T2MR signal in case of 5 genome equivalents of *S. aureus* strain FRP DNA is considered to be due to a lower than expected determined DNA concentration.

Exclusivity

An analytical specificity or exclusivity study was performed to assess potential cross-reactivity of organisms phylogenetically related to some of the species in the panel (specifically, *A. baumannii* and *S. aureus*). The testing was performed only on those species for which possible cross-reactivity was suggested based on in silico analysis (for example, homology searches of primers and probes against Genbank nr and wgs databases). The test included 3 related strains each from *Acinetobacter* spp. and *S. warneri*. Certain near-neighbors of *K. pneumoniae*, such as the *Enterobacter* spp., *Escherichia coli* (4 strains), and *Aeromonas hydrophilia* (2 strains) were also tested. As described in the Inclusivity section above, strains were procured from the American Type Culture Collection (ATCC, VA) as lyophilized samples and gDNA was isolated. Tested exclusivity strains are listed in Table 8. Genomic DNA was procured from ATCC except for *A. hydrophilia* strain ATCC 35654 (DNA was isolated from the cell pellet as described above).

TABLE 8

List of strains tested for exclusivity

| Acinetobacter spp. | S. warneri | E. coli | A. hydrophilia |
|---|---|---|---|
| ATCC 17905 | ATCC 25614 | ATCC 8739D-5 | ATCC 35654 |
| genomospecies 3 (ATCC 17922) | ATCC 27836 | ATCC 10798D-5 | CDC-359-60 (ATCC 7966D-5) |
| A. calcoaceticus ATCC 23055 | ATCC 27837 | MG1655 (ATCC 700926D-5) | |
| | | CFT073 (ATCC 700928D-5) | |

Figure 6A:
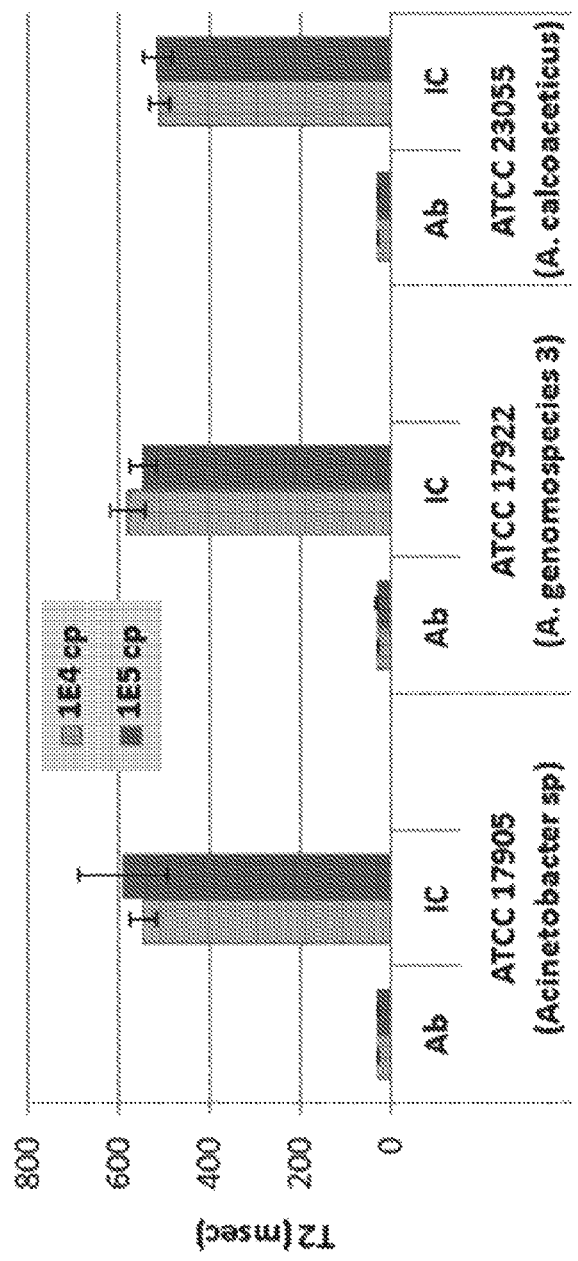
FIGS. 6A-6C are graphs showing average $T_2$ detection signals from exclusivity testing of species that were selected due to in silico data.
Figure 6B:
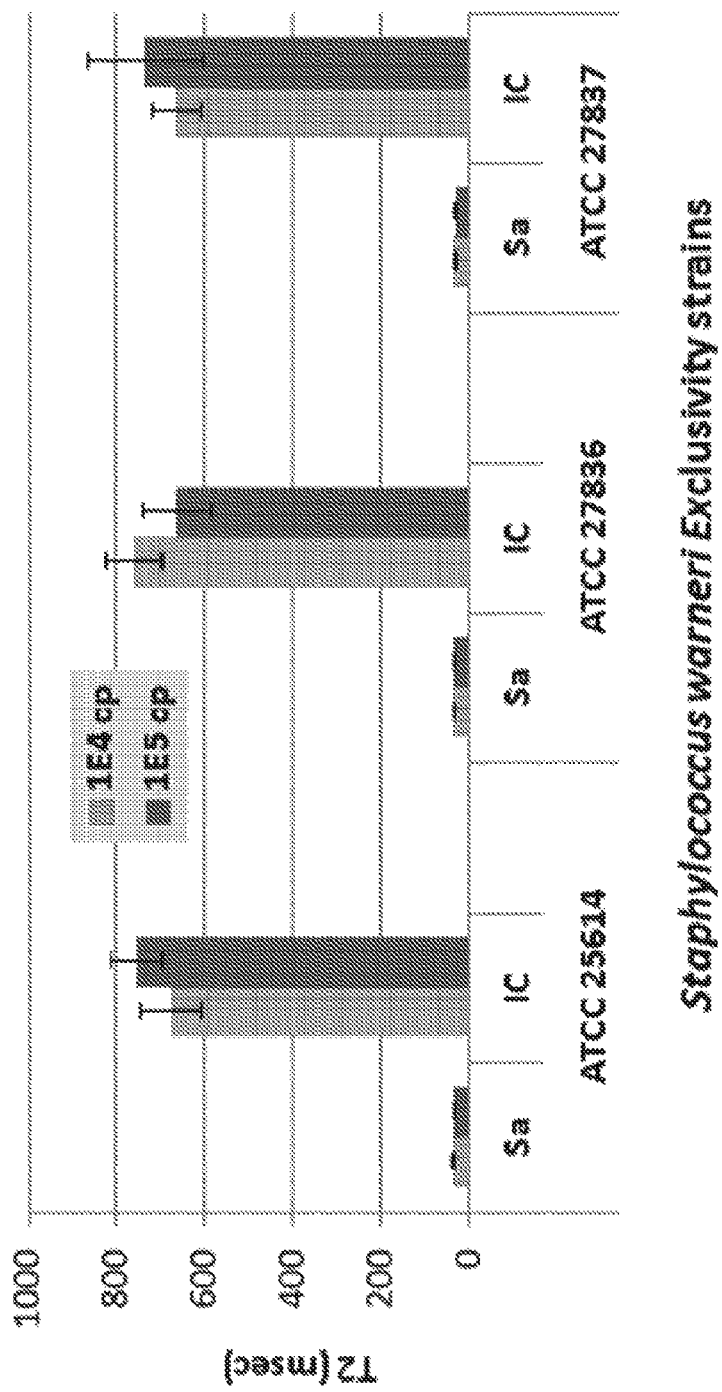
Figure 6C:
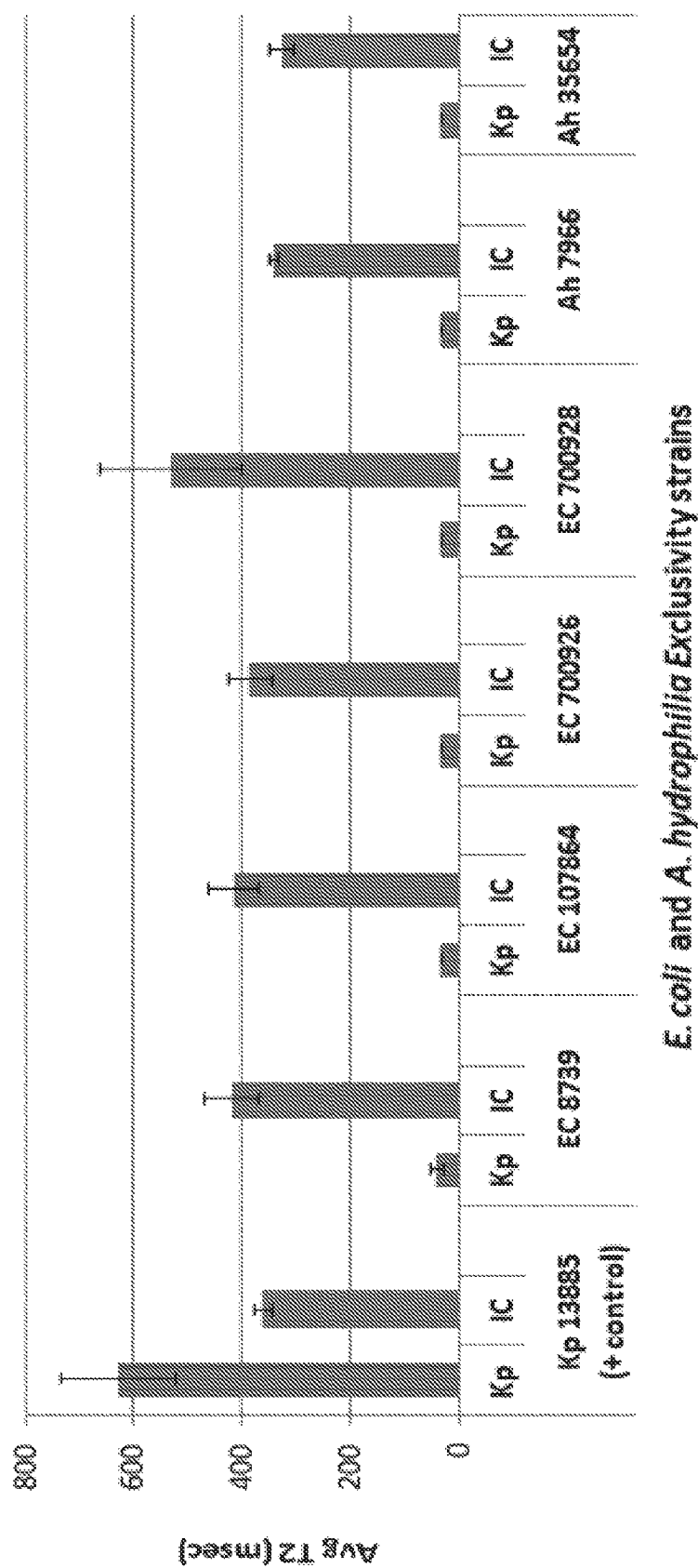

Exclusivity testing was performed by spiking genomic DNA in negative whole blood lysate at a high copy number ($1 \times 10^4$ and $1 \times 10^5$ genome equivalents per reaction) for *Acinetobacter* and *Staphylococcus* spp. strains, and $1 \times 10^6$ copies/reaction for *E. coli* and *A. hydrohilia* strains (n=4). No T2MR signals were detectable from any of the exclusive strains tested even at vast excess of target spiked into the whole blood lysate (FIGS. 6A-C).

In summary, the multiplex bacterial panel assay described in Example 3 is able to detect, for each constituent of the panel, strains within an individual species, but does not detect closely-related near neighbor species.

Example 5: 7-Plex Bacterial Panel Assay Limit of Detection (LoD) in Healthy Blood The LoD of the 7-plex PCR/8-T2MR bacterial panel assay configuration described in Example 3 (including amplification of both the femA and femB amplicons) was determined by spiking cells into healthy and unhealthy (see Example 6) blood specimens. All spiking experiments started from cell bullets that had been prepared from bacterial species while growing in the exponential phase. Bullets were frozen and stored at −80° C. after adding 12% glycerol (final concentration v/v). Isolated DNAs from strains used for the LoD study were used for inclusivity studies (see Example 4). The strains were: *Acinetobacter baumannii* 2208 (ATCC 19606), *Enterococcus faecium* TEX16 (ATCC BAA-472), *Enterococcus faecalis* V583 (ATCC 70080), *Klebsiella pneumoniae* ART 2008133 (ATCC 6908), *Pseudomonas aeruginosa* PAO1-LAC (ATCC 47085) and *Staphylococcus aureus* TCH959 (ATCC BAA-1718).

Healthy blood was obtained from one donor and spiking was done in bulk. All LoD data were determined as double-spikes by combining a gram-negative and a gram-positive panel species and as follows: *A. baumannii* and *S. aureus*; *P. aeruginosa* and *E. faecium*; *K. pneumoniae* and *E. faecalis*. Blood spiked with two target LoDs, 3 CFU/mL or 5 CFU/mL, were prepared and tested by 2 operators independently. To prepare one cell spike, cells were diluted to a target concentration of 0.3 CFU/μL or 0.5 CFU/μL in phosphate buffered saline (PBS). Two species were spiked as outlined above to a final target of either 3 CFU/mL or 5 CFU/mL each into whole blood. 1.75 mL aliquots of each spike concentration were then distributed to lysis tubes (N=20 per spike level and operator) filled with 1 scoop of 0.65 mm white beads ($ZrO_2$+$HfO_2$ and $Y_2O_3$, Glen Mills, N.J.) and 0.1 ml of lysis solution. The manual assay was then performed in parallel by two independent operators: 2 operators each processing 20 samples per double spike and 2 different spike levels.

The 7-plex PCR amplification and T2MR detection were performed according to the method described in Example 3.

Exact spike concentrations were determined by plating in parallel 100 μl of each final cell dilution onto TSB agar plates. Colonies were counted after 24-36 hours incubation at 37° C. Only spikes that were at or below the targeted LoD of 3 and 5 CFU/mL were deemed valid. At least one of the spike concentrations targeting a final of 4 CFU or less per mL were hit for each species, as shown in FIG. 7.

Figure 8:
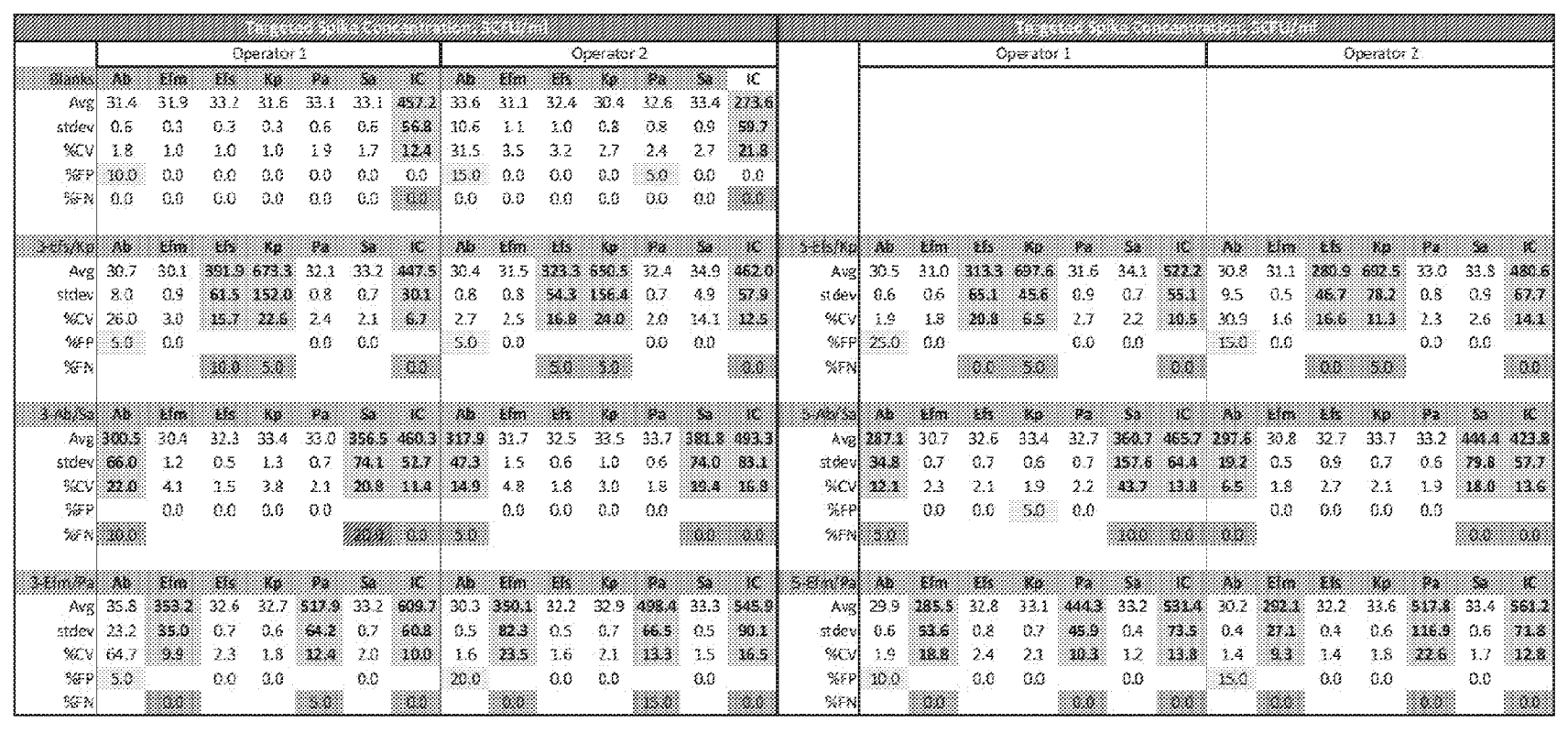

FIG. 8 summarizes all assays performed at 2 spike levels and by each of the 2 operators. A series of 20 blanks (no cells spiked) was also included. Average $T_2$ signals above a 75 ms threshold were counted as true positives. Since the internal control signal was detected in all of the assays performed, (100% IC detection in 140 total assays performed), all assays were counted as valid.

Except for one assay series (*S. aureus* target of 3 CFU/mL; Operator 1) all assays had at least 17 of 20 positive (95% confidence). In total, approximately 18% false positives (FP) were observed for *Acinetobacter baumannii*. This is likely due to contamination introduced by reagents rather than from manual assay executions (i.e., operator introduced commensals). In contrast to *Acinetobacter baumannii* FP rate of 18%, all other species combined were below 2% FP. A generally high signal-to-noise ratio was achieved, with at least 10-fold increase over baseline for all species, including IC.

Conclusion: the method described in Example 3 using manual manipulation has a sensitivity of 2-4 CFU/mL determined by double spiking cells into healthy blood (contrived blood specimens). Sensitivities are summarized in FIG. 9. This assay is also amenable to automation using a T2Dx® instrument (see FIG. 11).

Example 6: 7-Plex Bacterial Panel Assay Performance on Frozen Patient Discard Specimens In this Example, we assayed specimens that were BC-positive for one of the 6 bacterial species of the panel shown in FIG. 1B. Frozen discard specimens were collected at several collaborating sites and sent to T2 Biosystems, where they were stored at −80° C. until were used for evaluation in the 7-plex bacterial panel assay described in Example 3. Specimens were selected according to species ID as entered into the DISCARD database. A total of 74 DISCARD specimens were analyzed in this study. Among those, only 3 *A. baumannii* positive blood samples were present due to the low sepsis incidence rate of *A. baumannii*. Thus, an additional sample identified as "*Acinetobacter* sp." was included for a panel of 4. BC-positive specimens for all other species were present in the following numbers: 6 *Enterococcus faecium*, 9 *Enterococcus faecalis*, 12 *Klebsiella pneumoniae*, 11 *Pseudomonas aeruginosa*, and 13 *Staphylococcus aureus*. Several specimens had multiple species present as identified by BC. For this study only the first blood draws per patient were included. In addition, 21 specimens positive for exclusive species (i.e., not predicted to be detected by the 7-plex bacterial panel assay) were also included for analysis. FIG. 10 shows analyzed specimens together with their BC results as well as 7-plex bacterial panel assay results.

Of 53 specimens BC-positive for at least one bacterial panel assay species, 34 had concordant results in both assays (74% concordance). 4 BC-positive *A. baumannii* specimens were tested and one of these tested negative in the 7-plex bacterial panel assay (#15-039). Examination of the BC speciation data provided by the collection site showed an ambiguous designation of "*A. baumannii/haemolyticus*". If the species was indeed *A. haemolyticus*, this would explain the negative result, since this *Acinetobacter* species is exclusive to the 7-plex bacterial panel assay.

15 specimens tested T2MR-positive in the 7-plex bacterial panel assay for additional panel bacteria (shown in orange fields) that were not detected by BC. *A. baumannii* and *P. aeruginosa* positives were not included in this count because these could be false-positives introduced by reagents and handling (see Examples 5 and 6). It is very likely raw reagents are contaminated with *A. baumannii* and *P. aeruginosa*, two species that are common in the environment and that are known to contaminate reagents that are labeled as 'pure' and specimens prepared with water (see, e.g., Woyke et al. *PloS One*, 6(10): e26161 (2011); Grahn et al., *FEMS Microbiol. Lett.* 219(1): 87-91 (2003)).

Lastly, of the 22 selected specimens that were BC-negative for the members of the panel, 18 are also negative by T2MR in the 7-plex bacterial panel assay (81% concordance). Three tested positive for *K. pneumoniae* and one for *E. faecalis*.

In conclusion, the 7-plex bacterial panel assay described in Example 3 performed manually showed a high level of concordance with BC results. Further, the 7-plex bacterial panel assay also detected potential co-infections that were not detected by BC. This detection would allow for more accurate diagnosis and is significant even if the two environmental contaminants *A. baumannii* and *P. aeruginosa* are excluded from the analysis.

Example 7: Bacterial Panel Assay for Rapid and Sensitive Detection of *A. baumannii, E. faecium, K. pneumoniae, P. aeruginosa, E. coli*, and *S. aureus*

A rapid, accurate, and reproducible molecular diagnostic test was developed for the detection of the panel of microbial species shown in FIG. 1E directly within human whole blood with a limit of detection (LOD) of 1-3 CFU/mL. This diagnostic method is rapid, amenable to automation (e.g., in a fully-automated system such as a T2Dx® instrument), and offers clinicians the opportunity to detect multiple human pathogens within complex biological specimens for diagnosis and treatment of bacteremia, sepsis, and other diseases.

Table 9 shows primers that can be used for amplification of pathogen-specific amplicons for the panel shown in FIG. 1E. Alternative *A. baumannii* forward primers that can be used can include the oligonucleotide sequence of 5'-GGA AGG GAT CAG GTG GTT CAC TCT T-3' (SEQ ID NO: 110). Table 10 shows the nucleic acid sequences of the amplicon-specific portions of the probes used for detection of amplicons produced using the primer pairs shown in Table 9. The probes also include linker sequences that allow conjugation to magnetic particles at either the 5' or 3' end. Alternative 5' capture probes for *E. coli* that can be used include 5'-GAT GAT GAG TTG TTT GCC AGT G-3' (SEQ ID NO: 107). 5'-TGC CAG TGA TGA TGA GTT GT-3' (SEQ ID NO: 108), or 5'-GCC ACC TGA CAT TAG CCA TC-3' (SEQ ID NO: 109). Alternative *E. faecium* 5' capture probes that can be used can include the oligonucleotide sequence 5'-AAA ACT TAT GTG ACT TCA AAT CCA GTT TT-3' (SEQ ID NO: 111). Alternative *E. faecium* 3' capture probes that can be used can include the oligonucleotide sequence: 5'-TTT ACT CAA TAA AAG ATA ACA CCA CAG T-3' (SEQ ID NO: 112). Alternative *P. aeruginosa* 5' capture probes that can be used can include the oligonucleotide sequence 5'-TCT GAC GAT TGT GTG TTG TAA GG-3' (SEQ ID NO: 114). Alternative *P. aeruginosa* 3' capture probes that can be used can include the oligonucleotide sequence: 5'-GGA TAG ACG TAA GCC CAA GC-3' (SEQ ID NO: 115). The probes were conjugated to magnetic particles as described in Example 3 and in International Patent Application Publication No. WO 2012/054639. Some embodiments of the assay include the optional detection of an internal control (IC) to control for PCR inhibition. In this example, the orange (*Citrus sinensis*) IC template (which includes the nucleic acid sequence of SEQ ID NO: 94 cloned into plasmid pBR322) was used. The orange IC template was amplified with a forward primer having the sequence SEQ ID NO: 95 or SEQ ID NO: 96 and a reverse primer having the sequence of SEQ ID NO: 96 or SEQ ID NO: 97. The resulting amplicon was detected using a 5' capture probe that includes the oligonucleotide sequence 5'-GAG ACG TTT TGG ATA CAT GTG AAA GAA GGC-3' (SEQ ID NO: 99) and a 3' capture probe that includes the oligonucleotide sequence 5' CGA TGG TTC ACG GGA TTC TGC AAT TC-3' (SEQ ID NO: 100).

TABLE 9

Primers

| Primers | Sequence | SEQ ID NO: |
|---|---|---|
| *A. baumannii* Forward Primer | 5'-CGT TTT CCA AAT CTG TAA CAG ACT GGG-3' | 1 |
| *A. baumannii* Reverse Primer | 5'-AGG ACG TTG ATA GG TTG GAT GTG GA-3' | 2 |
| *Enterococcus* spp. Forward Primer | 5'-GGT AGC TAT GTA GGG AAG GGA TAA ACG CTG A-3' | 3 |
| *Enterococcus* spp. Reverse Primer | 5'-GCG CTA AGG AGC TTA ACT TCT GTG TTC G-3' | 4 |
| *K. pneumoniae* Forward Primer | 5'-GAC GGT TGT CCC GGT TTA AGC A-3' | 5 |
| *K. pneumoniae* Reverse Primer | 5'-GCT GGT ATC TTC GAC TGG TCT-3' | 6 |
| *P. aeruginosa* Forward Primer | 5'-AGG CTG GGT GTG TAA GCG TTG T-3' | 7 |
| *P. aeruginosa* Reverse Primer | 5'-CAA GCA ATT CGG TTG GAT ATC CGT T-3' | 8 |
| *S. aureus* femA Forward Primer | 5'-GGT AAT GAATTA CCT/i6diPr/TC TCT GCT GGTTTC TTC TT-3' | 9 |
| *S. aureus* femA Reverse Primer | 5'-ACC AGC ATC TTC/i6diPr/GC ATC TTC TGT AAA-3' | 10 |

TABLE 9-continued

Primers

| Primers | Sequence | SEQ ID NO: |
|---|---|---|
| S. aureus femB Forward Primer | 5'-GAA GTT ATG TTT/i6diPr/CT ATT CGA ATC GTG GTC CAGT-3' | 11 |
| S. aureus femB Reverse Primer | 5'-GTT GTA AAG CCA TGA TGC TCG TAA CCA-3' | 12 |
| E. coli Forward Primer | 5'-GCA TTA ATC GAC GGT ATG GTT GAC C-3' | 59 |
| E. coli Reverse Primer | 5'-CCT GCT GAA ACA GGT TTT CCC ACA TA-3' | 61 |

TABLE 10

Probes used in this Example

| Probes | Sequence | SEQ ID NO: |
|---|---|---|
| A. baumannii 5' Capture Probe | 5'-TGA GGC TTG ACT ATA CAA CAC C-3' | 15 |
| A. baumannii 3' Capture Probe | 5'-CTA AAA TGA ACA GAT AAA GTA AGA TTC AA-3' | 16 |
| E. faecium 5' Capture Probe | 5'-AAA ACT TAT ATG ACT TCA AAT CCA GTT TT-3' | 19 |
| E. faecium 3' Capture Probe | 5'-TTT ACT CAA TAA AAG ATA ACA CCA CAG-3' | 20 |
| E. coli 5' Capture Probe | 5'-AGT GAT GAT GAG TTG TTT GCC AGT G-3' | 63 |
| E. coli 3' Capture Probe | 5'-TGA ATT GTC GCC GCG TGA CCA G-3' | 64 |
| K. pneumoniae 5' Capture Probe | 5'-TAC CAA GGC GCT TGA GAG AAC TC-3' | 27 |
| K. pneumoniae 3' Capture Probe | 5'-CTG GTG TGT AGG TGA AGT C-3' | 28 |
| P. aeruginosa 5' Capture Probe | 5'-GTG TGT TGT AGG GTG AAG TCG AC-3' | 31 |
| P. aeruginosa 3' Capture Probe | 5'-CAC CTT GAA ATC ACA TAC CTG A-3' | 32 |
| S. aureus femA 5' Capture Probe | 5'-CCA TTT GAA GTT GTT TAT TAT GC-3' | 35 |
| S. aureus femA 3' Capture Probe | 5'-GGG AAA TGA TTA ATT ATG CAT TAA ATC-3' | 36 |
| S. aureus femB 5' Capture Probe | 5'-TT TTT CAG ATT TAG GAT TAG TTG ATT-3' | 39 |
| S. aureus femB 3' Capture Probe | 5'-GAT CCG TAT TGG TTA TAT CAT C-3' | 40 |

To assess the performance of the bacterial panel assay described in this assay, spiked whole blood samples for each pathogen were made by spiking each pathogen separately into whole blood at defined titers. For spiking experiments used for limit of detection studies, all specimens were prepared using cell cultures harvested in mid log phase for each of the target organisms. Concentrated suspensions were diluted to target concentrations and spiked into $K_2$EDTA-treated whole blood either from healthy or unhealthy blood samples. All CFU/mL concentrations were confirmed via parallel plating of the diluted inoculate. Inoculate dilutions were plated on TSA (trypticase soy agar) or YPD (yeast extract peptone dextrose agar), such that a final CFU count of 30-300 was expected. Final CFU counts were then divided by the total volume plated and multiplied by the total volume plated and multiplied by the spike volume to assign a final CFU/mL to the contrived specimen.

To perform the assays, 2 mL of spiked whole blood was added to a lysis tube, mixed with lysis detergent by pipetting, and incubated for about 5 minutes. The tubes were centrifuged for 5 min at 6000 g, and the supernatant was removed. 150 μL of Internal Control was added and mixed. The tubes were centrifuged for 5 min at 6000 g, and the supernatant was removed. 100 μL of Internal Control was added, and the samples were bead beat for 5 min at 3200 rpm using 1 mm tungsten carbide beads. The tubes were then centrifuged for 2 min at 6000 g. The lysate was mixed and 50 μL was added to 30 μL of a reaction mix containing PCR buffer, and PCR primers as described above (e.g., Table 7). This sample was denatured at 95° C. for 5 min followed by cooling to 25° C. The sample was centrifuged for 5 min at 8000 g, and 20 μL of Formulated Enzyme (including a hot start thermophilic DNA polymerase and dNTPs) was added. Thermocycling was conducted using the following cycle parameters: initial denaturation at 95° C., 46 cycles consisting of a 20 sec denaturation step at 95° C., a 30 sec annealing step at 58° C., a 30 sec extension step at 68° C., followed by a final extension of 3-10 min at 68° C. Each magnetic particle hybridization mix was vortexed prior to aspirating and dispensing. 15 μL of the magnetic particle hybridization mixes were added to each designated detection tube. 15 μL of diluted amplicon supernatants are added to the tubes containing the magnetic particle hybridization mixes, and the samples are hybridized for 30 min at 62° C. T2MR detection was performed as described in Example 3 and in International Patent Application Publication No. WO 2012/054639. Automated assay testing on the T2Dx® instrument followed the same assay workflow as the manual assay except all steps were fully automated and there is an automated addition of bleach decontamination of all liquids on the cartridge after assay processing was complete.

T2MR demonstrated high analytical sensitivity and high specificity for all bacterial targets. A limit of detection (LoD) as low as 1 CFU/mL (95% positive, n=20) was observed for the targeted bacteria species spiked into healthy blood. The LoD for all bacterial species tested was determined by the cell concentration (CFU/mL) that resulted in ≥95% detection rate, and the results are shown in Table 11.

TABLE 12

T2Dx® data for positive sample performance

| Species | Titer Level (CFU/ml) | #Positive/Total | Rate |
|---|---|---|---|
| A. baumannii | 1-2 | 27/37 | 73% |
|  | 2 | 25/25 | 100% |
| E. faecium | 3 | 19/20 | 95% |
| K. pneumoniae | 1 | 16/17 | 94.1% |
|  | 3 | 21/21 | 100.0% |
| P. aeruginosa | 1 | 20/20 | 100.0% |
| S. aureus | 1-2 | 74/96 | 77% |
|  | 3 | 20/20 | 100.0% |

A comparison between T2MR using the assay described in this Example and blood culture was performed. In this experiment, blood specimen discards that had been drawn in EDTA VACUTAINER® tubes on the same day as specimens drawn for blood culture were obtained from a clinical hematology laboratory. Blood sample retains were selected for T2MR if the patient's blood culture outcome was blood culture-positive for S. aureus. Specimens were run following the above-described procedure to measure for the presence of S. aureus using T2MR. The positive percent agreement (PPA) between T2MR and blood culture was calculated by dividing the number of T2MR-positive samples by the number of blood culture-positive samples. Upper and lower confidence intervals (UCL & LCL) were calculated based on the 95% confidence interval for the data set. Overall, T2MR detected 30 of the 33 samples as positive. From this, a PPA of 90% with an UCL of 98% for PPA and LCL for PPA was calculated. The 3 false negatives yielded valid IC signals demonstrating that the negative signal for the S. aureus channel was not caused by inhibition.

In conclusion, the bacterial panel assay described in this Example detects its target pathogens with high sensitivity at clinically relevant concentrations. Further, the panel assay provides results in 3-5 hours. This sensitivity and time to result has never been achieved for bacterial pathogens by a medical diagnostic directly from a patient's blood sample. The bacterial panel assay species cover greater than 55% of the species associated with true infection from positive blood culture and were specifically selected based on the

TABLE 11

Limit of Detection Results for Manual Multiplexed Bacterial Panel Assay

|  | A. baumannii | E. faecium | K. pneumoniae | P. aeruginosa | S. aureus | E. coli |
|---|---|---|---|---|---|---|
| CFU/mL | 2 | 2 | 3 | 2 | 1 | 3 |
| Hit Rate | 20/20 | 20/20 | 20/20 | 20/20 | 19/20 | 19/20 |
| Percent Detection | 100% | 100% | 100% | 100% | 95% | 95% |
| Average T2MR Signal | 255 | 293 | 599 | 484 | 293 | 531 |
| Standard Deviation T2MR | 55 | 51 | 76 | 104 | 72 | 201 |

In preliminary experiments, optimization on the T2Dx® instrument involved testing each target pathogen at and below the limit of detection measured on the manual assay. Aggregate data from this testing performed to date is shown in Table 12. As shown, the LoD was equivalent or better than that observed for the manual assay.

combined association of high rates of prevalence, mortality, and inappropriate empiric therapy. In combination with standard empiric therapy practices, the bacterial panel assay described in this Example and the T2Candida® (T2 Biosystems, Lexington, Mass.) panel's coverage would result in 95% of symptomatic patients receiving appropriate therapy within hours of clinical symptoms.

SEQUENCE LISTING

Table 13 shows a listing of sequences described in this application. "/i6diPr/" indicates 2,6-Diaminopurine, "/5AmMC12/" indicates 5' amino modifier C12, and "/3AmMO/" indicates 3' amino modifier.

TABLE 13

Sequence Listing

| Sequence | SEQ ID NO: |
|---|---|
| 5'-CGT TTT CCA AAT CTG TAA CAG ACT GGG-3' | 1 |
| 5'-AGG ACG TTG ATA GG TTG GAT GTG GA-3' | 2 |
| 5'-GGT AGC TAT GTA GGG AAG GGA TAA ACG CTG A-3' | 3 |
| 5'-GCG CTA AGG AGC TTA ACT TCT GTG TTC G-3' | 4 |
| 5'-GAC GGT TGT CCC GGT TTA AGC A-3' | 5 |
| 5'-GCT GGT ATC TTC GAC TGG TCT-3' | 6 |
| 5'-AGG CTG GGT GTG TAA GCG TTG T-3' | 7 |
| 5'-CAA GCA ATT CGG TTG GAT ATC CGT T-3' | 8 |
| 5'-GGT AAT GAATTA CCT/i6diPr/TC TCT GCT GGTTTC TTC TT-3' | 9 |
| 5'-ACC AGC ATC TTC/i6diPr/GC ATC TTC TGT AAA-3' | 10 |
| 5'-GAA GTT ATG TTT/i6diPr/CT ATT CGA ATC GTG GTC CAGT-3' | 11 |
| 5'-GTT GTA AAG CCA TGA TGC TCG TAA CCA-3' | 12 |
| 5'-GGC ATG CCT GTT TGA GCG TC-3' | 13 |
| 5'-GCT TAT TGA TAT GCT TAA GTT CAG CGG GT-3' | 14 |
| 5'-TGA GGC TTG ACT ATA CAA CAC C-3' | 15 |
| 5'-CTA AAA TGA ACA GAT AAA GTA AGA TTC AA-3' | 16 |
| /5AmMC12/TTT TTT TTT TGA GGC TTG ACT ATA CAA CAC C | 17 |
| CTA AAA TGA ACA GAT AAA GTA AGA TTC AAT TTT TTT TT/3AmMO/ | 18 |
| 5'-AAA ACT TAT ATG ACT TCA AAT CCA GTT TT-3' | 19 |
| 5'-TTT ACT CAA TAA AAG ATA ACA CCA CAG-3' | 20 |
| /5AmMC12/ttt ttt ttt AAA ACT TAT ATG ACT TCA AAT CCA GTT TT | 21 |
| TTT ACT CAA TAA AAG ATA ACA CCA CAG Ttt ttt ttt t/3AmMO/ | 22 |
| 5'-TGG ATA AGT AAA AGC AAC TTG GTT-3' | 23 |
| 5'-AAT GAA GAT TCA ACT CAA TAA GAA ACA ACA-3' | 24 |
| /5AmMC12/ttt ttt ttt TGG ATA AGT AAA AGC AAC TTG GTT | 25 |
| AAT GAA GAT TCA ACT CAA TAA GAA ACA ACA ttt ttt ttt/3AmMO/ | 26 |
| 5'-TAC CAA GGC GCT TGA GAG AAC TC-3' | 27 |
| 5'-CTG GTG TGT AGG TGA AGT C-3' | 28 |
| /5AmMC12/TTT TTT TTT TAC CAA GGC GCT TGA GAG AAC TC | 29 |
| CTG GTG TGT AGG TGA AGT CTT TTT TTT T/3AmMO/ | 30 |
| 5'-GTG TGT TGT AGG GTG AAG TCG AC-3' | 31 |
| 5'-CAC CTT GAA ATC ACA TAC CTG A-3' | 32 |
| /5AmMC12/ttt ttt ttt GTG TGT TGT AGG GTG AAG TCG AC | 33 |
| CAC CTT GAA ATC ACA TAC CTG Att ttt ttt t/3AmMO/ | 34 |

TABLE 13-continued

Sequence Listing

| Sequence | SEQ ID NO: |
|---|---|
| 5'-CCA TTT GAA GTT GTT TAT TAT GC-3' | 35 |
| 5'-GGG AAA TGA TTA ATT ATG CAT TAA ATC-3' | 36 |
| /5AmMC12/TTT TTT TTT CCA TTT GAA GTT GTT TAT TAT GC | 37 |
| GGG AAA TGA TTA ATT ATG CAT TAA ATC TTT TTT TTT/3AmMO/ | 38 |
| 5'-TT TTT CAG ATT TAG GAT TAG TTG ATT-3' | 39 |
| 5'-GAT CCG TAT TGG TTA TAT CAT C-3' | 40 |
| /5AmMC12/TT TTT TTT TTT TTT CAG ATT TAG GAT TAG TTG ATT | 41 |
| GAT CCG TAT TGG TTA TAT CAT CTT TTT TTT T/3AmMO/ | 42 |
| /5AmMC12/TTT TTT TTT TGG AAT AAT ACG CCG ACC AGC | 43 |
| AAG GAT CTA TTT CAG TAT GAT GCA GTT TTT TTT T/3AmMO/ | 44 |
| TGCCGAAGCGTTTTCCAAATCTGTAACAGACTGGGCTGATTGAATCTTACTTTATCT<br>GTTCATTTTAGCTAGAGGTATAACTAAATCAAGTTGTCTTGCATATTTAAGAATCGAT<br>TGATGCTTTATATACAACTGCTTGGGTGTTGTATAGTCAAGCCTCACGAGCAATTAG<br>TATTGGTCAGCTTCACATATCACTATGC | 45 |
| GCATGGGAACAGGTGTATCCTTCTCGCTATCGCCACCACACTGGGTGTTGTTTCTT<br>ATTGAGTTGAATCTTCATTCACTCAAAACTGGATTGAAGTTTGAATCAAAATAACCAA<br>GTTGCTTTTACTTATCCATTCTTTGGTTAAGTCCTCGACCGATTAGTATTGGTCCGC<br>TCCAACTATCACTAGCCTTCCACTTCCAA | 46 |
| GCATGGTTACAGGTGTATCCTTCTCGCTATCGCCACCACACTGTGGTGTTATCTTTT<br>ATTGAGTAAATTTTGTTCACTCAAAACTGGATTTGAAGTCATATAAGTTTTTTTCCGA<br>GTTCTTTTCTTTTAACCTATTGGTTAAGTCCTCGATCGATTAGTATCAGTCCGCTCC<br>ATACATCACTGTACTTCCACTCCTGACC | 47 |
| CAGCTCCATCCGCAGGGACTTCACCTACACACCAGCGTGCCTTCTCCCGAAGTTA<br>CGGCACCATTTTGCCTAGTTCCTTCACCCGAGTTCTCTCAAGCGCCTTGGTATTCT<br>CTACCTGACCACCTGTGTCGGTTTGGGGTACGATTTGATGTTACCTGATGCTTAGA<br>GGCTTTTCCTGGAAGCAGGGCATTTGTTACTTC | 48 |
| CGCTTGGGCTTACGTCTATCCGGATTCAGGTATGTGATTTCAAGGTGTTTTGCGGT<br>TCATGCGAACTTTCGGTTCGTCGACTTCACCTTACAACACACAATCGTCAGATTGTT<br>TGGGTGTTATATGGTCAAGCCTCACGGGCAATTAGTACTGGTTAGCTCAACGCCTC | 49 |
| TTTACCACTAACACCATAGAAATTATAACGGTCAATGCCATGATTTAATGCATAATTA<br>ATCATTTCCCATTGCACTGCATAACTTCCGGCAAAATGACGGAATGCATTTGATGTA<br>CCACCAGCATAATAAACAACTTCAAATGGGTTGATA | 50 |
| TGTGATTTAAACAAGTTTACTAAGGCATCATTTTTCTCGCGACCTTCAAATGGCACG<br>ATATCTTTATCATATAGATGATATAACCAATACGGATCTAATTTAACATATAAACATT<br>GATGTTGCTGTAAATATTTATCTAACTCTTTTAAATAATAATCAACTAATCCTAAATCT<br>GAAAAATCCATT | 51 |
| BLANK | 52 |
| 5'-ACC T/i6diPr/T CTC TGC TGG TTT CTT CTT-3' | 53 |
| 5'-CAG CAT CTT C/i6diPr/A GCA TCT TCT GTA AA-3' | 54 |
| 5'-GTT T/i6diPr/C TAT TCG AAT CGT GGT CCA GT-3' | 55 |
| ATGAAGTTTACAAATTTAACAGCTAAAGAGTTTGGTGCCTTTACAGATAGCATGCCA<br>TACAGTCATTTCACGCAAACTGTTGGCCACTATGAGTTAAAGCTTGCTGAAGGTTAT<br>GAAACACATTTAGTGGGAATAAAAAACAATAATAACGAGGTCATTGCAGCTTGCTTA<br>CTTACTGCTGTACCTGTTATGAAAGTGTTCAAGTATTTTTATTCAAATCGCGGTCCA<br>GTGATCGATTATGAAAATCAAGAACTCGTACACTTTTTCTTTAATGAATTATCAAAAT<br>ATGTTAAAAAACATCGTTGTCTATACCTACATATCGATCCATATTTACCATATCAATA<br>CTTGAATCATGATGGCGAGATTACAGGTAATGCTGGTAATGATTGGTTCTTTGATAA<br>AATGAGTAACTTAGGATTTGAACATACTGGATTCCATAAAGGATTTGATCCTGTGCT<br>ACAAATTCGTTATCACTCAGTGTTAGATTTAAAAGATAAAACAGCAGATGACATCAT<br>TAAAAATATGGATGGACTTAGAAAAAGAAACACGAAAAAAGTTAAAAAGAATGGTGT<br>TAAAGTAAGATATTTATCTGAAGAAGAACTGCCAATTTTTAGATCATTTATGGAAGAT<br>ACGTCAGAATCAAAAGCTTTTGCTGATCGTGATGACAAATTTTACTACAATCGCTTA<br>AAATATTACAAAGACCGTGTGTTAGTACCTTTAGCGTATATCAACTTTGATGAATATA<br>TTAAAGAACTAAACGAAGAGCGTGATATTTTAAATAAAGATTTAAATAAAGCGTTAAA<br>GGATATTGAAAAACGTCCTGAAAATAAAAAAAGCACACAACAAGCGAGATAACTTAC | 56 |

TABLE 13-continued

Sequence Listing

| Sequence | SEQ ID NO: |
|---|---|
| AACAACAACTTGATGCTAATGAGCAAAAGATTGAAGAAGGTAAACGTCTACAAGAA GAACATGGTAATGAATTACCTATCTCTGCTGGTTTCTTCTTTATCAACCCATTTGAA GTTGTTTATTATGCTGGTGGTACATCAAATGCATTCCGTCATTTTGCCGGAAGTTAT GCAGTGCAATGGGAAATGATTAATTATGCATTAAATCATGGCATTGACCGTTATAAT TTCTATGGTGTTAGTGGTAAATTTACAGAAGATGCTGAAGATGCTGGTGTAGTTAAA TTCAAAAAAGGTTACAATGCTGAAATTATTGAATATGTTGGTGACTTTATTAAACCAA TTAATAAACCTGTTTACGCAGCATATACCGCACTTAAAAAAGTTAAAGACAGAATTTT TTAGGAAGGGAATTATCAAAACATGAAATTTACAGAGTTAACTGTTACCGAATTTGA CAACTTTGTACAAAATCCATCATTGGAAAGTCATTATTTCCAAGTAAAAGAAAATATA GTTACCCGTGAGAATGATGGCTTTGAAGTAGTTTTATTAGGTATTAAAGACGACAAT AACAAAGTAATTGCAGCAAGCCTTTTCTCTAAAATTCCTACTATGGGAAGTTATGTT TACTATTCGAATCGTGGTCCAGTAATGGATTTTTCAGATTTAGGATTAGTTGATTATT ATTTAAAAGAGTTAGATAAATATTTACAGCAACATCAATGTTTATATGTTAAATTAGA TCCGTATTGGTTATATCATCTATATGATAAAGATATCGTGCCATTTGAAGGTCGCGA GAAAAATGATGCCTTAGTAAACTTGTTTAAATCACATGGTTACGAGCATCATGGCTT TACAACTGAGTATGATACATCGAGCCAAGTACGATGGATGGGCGTATTAAACCTTG AAGGTAAAACACCCGAAACATTGAAAAAGACATTTGATAGTCAACGTAAACGTAATA TTAATAAAGCGATAAACTATGGTGTTAAAGTCAGATTCCTTGAACGTGATGAGTTCA ATCTTTTCTTAGATTTATATCGTGAAACTGAAGAGCGTGCTGGATTTGTGTCAAAAA CAGATGATTATTTTTATAACTTTATTGACACATATGGAGATAAAGTATTAGTACCATT AGCATATATTGACCTTGATGAATATGTGTTAAAGTTGCAACAGGAATTGAATGACAA AGAAAATCGTCGTGATCAAATGATGGCGAAAGAAAACAAATCAGATAAACAAATGA AGAAAATTGCAGAATTAGATAAGCAAATTGATCATGATCAGCATGAATTATTGAATG CAAGTGAATTGAGCAAAACGGACGGCCCAATTCTAAACCTTGCTTCTGGCGTTTAT TTTGCAAATGCATATGAAGTGAATTATTTCTCTGGTGGTTCATCAGAAAAATATAATC AATTTATGGGACCATACATGATGCATTGGTTTATGATTAACTATTGCTTCGATAATG GCTATGATCGTTATAATTTCTATGGTTTATCAGGTGATTTTACGGAAAACAGTGAAG ATTATGGCGTATACCGCTTTAAACGTGGATTTAATGTACAAATCGAAGAATTAATAG GGGATTTCTATAAACCAATTCATAAAGTGAAATATTGGTTGTTCACAACATTGGATA AATTACGTAAAAAATTAAAGAAATAG | |
| 5'-GGA AGG GAT CAG GTG GTT CAC TCT T-3' | 57 |
| 5'-CTA TGT AGG GAA GGG ATA AAC GCT GA-3' | 58 |
| 5'-GCA TTA ATC GAC GGT ATG GTT GAC C-3' | 59 |
| 5'-CGA CGG TAT GGT TGA CCA TGC-3' | 60 |
| 5'-CCT GCT GAA ACA GGT TTT CCC ACA TA-3' | 61 |
| 5'-GAC GCC TGC TGA AAC AGG TTT TCC-3' | 62 |
| 5'-AGT GAT GAT GAG TTG TTT GCC AGT G-3' | 63 |
| 5'-TGA ATT GTC GCC GCG TGA CCA G-3' | 64 |
| 5'-GGT GCA TAC GAC CGT TAG CCA GAG TC-3' | 65 |
| 5'-CTG AGT TCG GGA AGG GAT CAG G-3' | 66 |
| 5'-CCA AAT CTG TAA CAG ACT GGG CTG A-3' | 67 |
| 5'-AAA CCA AAT CTG TAA CAG ACT GGG CTG A-3' | 68 |
| 5'-ATG GGT AAT CCC ACA CTA CCA TCA G-3' | 69 |
| 5'-ACT CTT GCT ATG GTC GCC AGC ACA ACT-3' | 70 |
| 5'-CGT GAG GCT TGA CTA TAC AAC ACC C-3' | 71 |
| 5'-CGT GAG GCT TGA CTA TAC AAC ACC C-3' | 72 |
| 5' CTT GAC TAT ACA ACA CCC AAG CAG TT-3' | 73 |
| 5'-GGC TTG ACT ATA CAA CAC CCA AGC AGT T-3' | 74 |
| 5'-GTG AAG CCC ACC TCA AGA TGA GAT-3' | 75 |
| 5'-TGT TCT GCC AAG GGC ATT GCT G-3' | 76 |
| 5'-CTA TGT AGG GAA GGG ATA AAC GCT GA-3' | 77 |
| 5'-ACA ATC GGC GCT AGA AGC TTA ACT-3' | 78 |
| 5'-ACA GGT GTA TCC TTC TCG CTA TCG C-3' | 79 |

TABLE 13-continued

Sequence Listing

| Sequence | SEQ ID NO: |
|---|---|
| 5'-GCG CTA AGG AGC TTA ACT TCT GTG TTC G-3' | 80 |
| 5'-TCG GCG CTA AGG AGC TTA ACT TCT GTG TTC G-3' | 81 |
| 5'-GAG GCA CTA CGG TGC TGA AGT A-3' | 82 |
| 5'-CTC ACT GGG AAC TTG ATT CCC CTG-3' | 83 |
| 5'-GGT GGT TCC AAC GCT CTA TGA TCG T-3' | 84 |
| 5'-ACT GCT GTA CCT GTT ATG AAA GTG T-3' | 85 |
| 5' GCT TGC TTA CTT ACT GCT GTA CCT G-3' | 86 |
| 5'-GCC ATA CAG TCA TTT CAC GCA AAC-3' | 87 |
| 5'-CCT GTG TTA CAA ATT CGT TAT CAC T-3' | 88 |
| 5' ACC T/i6diPr/T CTC TGC TGG TTT CTT CTT-3' | 89 |
| 5'-GCA TTA CCT GTA ATC TCG CCA TCA T-3' | 90 |
| 5'-AGC TTT TGA TTC TGA CGT ATC TTC C-3' | 91 |
| 5' GAT CAG CGA AAG CTT TTG ATT CTG ACG T-3' | 92 |
| 5'-CAG CAT CTT C/i6diPr/G CAT CTT CTG TAA A-3' | 93 |
| GGAAATCTAACGAGAGAGCATGCTCCTGCGGCCCCGGAGACGGTGCGCCGCGGG GTGCGGCGCCTTCTTTCACATGTATCCAAAACGTCTCTCGGCAACGGATATCTCGG CTCTCGCATCGATGAAGAACGTAGCGAAATGCGATACTTGGTGTGAATTGCAGAAT CCCGTGAACCATCGAGTCTTTGAACGCAAGTTGCGCCCCAAGCCATTAGGCCGAG GGCACGTCTGCCTGGGTGTCACGCATCG | 94 |
| 5'-GGA AAT CTA ACG AGA GAG CAT GCT-3' | 95 |
| 5'-GGA AAT CTA ACG AGA GAG CAT GC-3' | 96 |
| 5'-CGA TGC GTG ACA CCC AGG C-3' | 97 |
| 5'-GAT GCG TGA CAC CCA GGC-3' | 98 |
| 5'-GAG ACG TTT TGG ATA CAT GTG AAA GAA GGC-3' | 99 |
| 5' CGA TGG TTC ACG GGA TTC TGC AAT TC-3' | 100 |
| GAT GCA GCA ACA ACA GAT TCC TTG CTT CTC ATA CAA TAA CAT GAC AAA CCC CAT TAA TAA AAA CGC GGT CCA CTT ATC ATA CAG AAT ATC AGA TAG TGG CAA TTA ATT GTG ACA AAA ATT CGA AAG TTG TGT ACA GTT CTT CAT TGT TCG AAA AAT TGT TAT GAC AAG ATA CAC CAG GAC ATA ACG GCT AC | 101 |
| 5'-GCA GCA ACA ACA GAT TCC-3' | 102 |
| 5' GTA GCC GTT ATG TCC TGG TG-3' | 103 |
| 5'-TCG AAC AAT GAA GAA CTG TAC ACA ACT TTC G-3' | 104 |
| 5' GGT TTG TCA TGT TAT TGT ATG AGA AGC AAG-3' | 105 |
| 5'-GGC ATG CCT GTT TGA GCG TCC TGC ATC ATA CTG AAA TAG ATC CTT CGA CAA CCT CGG TAC ACT GGG AAC AAG GCC TCA AAC ATT GAT GCT CGA CTA CAC GTA GGG CAATGC GTC TTG CTA GAA GCG AAA TCT GTG GCT TGC TAG TGC AAG CTG GTC GGC GTA TTA TTC CAA CCC GCT GAA CTT AAG CAT ATC AAT AAG CA-3' | 106 |
| 5'-GAT GAT GAG TTG TTT GCC AGT G-3' | 107 |
| 5'-TGC CAG TGA TGA TGA GTT GT-3' | 108 |
| 5'-GCC ACC TGA CAT TAG CCA TC-3' | 109 |
| 5'-GGA AGG GAT CAG GTG GTT CAC TCT T-3' | 110 |
| 5'-AAA ACT TAT GTG ACT TCA AAT CCA GTT TT-3' | 111 |

TABLE 13-continued

Sequence Listing

| Sequence | SEQ ID NO: |
|---|---|
| 5'-TTT ACT CAA TAA AAG ATA ACA CCA CAG T-3' | 112 |
| /5AmMC12/ttt ttt ttt AAA ACT TAT GTG ACT TCA AAT CCA GTT TT | 113 |
| 5'-TCT GAC GAT TGT GTG TTG TAA GG-3' | 114 |
| 5'-GGA TAG ACG TAA GCC CAA GC-3' | 115 |
| /5AmMC12/ttt ttt ttt TCT GAC GAT TGT GTG TTG TAA GG | 116 |
| GGA TAG ACG TAA GCC CAA GCtt ttt ttt t/3AmMO/ | 117 |
| GCA TGG TTA CAG GTG TAT CCT TCT CGC TAT CGC CAC CAC ACT GTG GTG TTA TCT TTT ATT GAG TAA ATT TTG TTC ACT CAA AAC TGG ATT TGA AGT CAT ATA AGT TTT TTT CCG AGT TCT TTT CTT TTA ACC TAT TGG TTA AGT CCT CGA TCG ATT AGT ATC AGT CCG CTC CAT ACA TCA CTG TAC TTC CAC TCC TGA | 118 |

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method for detecting the presence of an *Enterococcus faecium* (*E. faecium*) cell, a *Klebsiella pneumoniae* (*K. pneumoniae*) cell, a *Pseudomonas aeruginosa* (*P. aeruginosa*) cell, an *Escherichia coli* (*E. coli*) cell, and/or a *Staphylococcus aureus* (*S. aureus*) cell in a liquid sample, the method comprising:

(a) lysing the cells in a liquid sample to form a lysate;

(b) in a multiplexed assay capable of detecting the following species: *Enterococcus faecium, Klebsiella pneumoniae, Pseudomonas aeruginosa, Escherichia coli*, and *S. aureus*:

(i) amplifying an *E. faecium* target nucleic acid in the lysate in the presence of a forward primer comprising the oligonucleotide sequence: 5'-GGT AGC TAT GTA GGG AAG GGA TAA ACG CTG A-3' (SEQ ID NO: 3) and a reverse primer comprising the oligonucleotide sequence: 5'-GCG CTA AGG AGC TTA ACT TCT GTG TTC G-3' (SEQ ID NO: 4) to form an amplified lysate comprising an *E. faecium* amplicon, (ii) amplifying a *K. pneumoniae* target nucleic acid in the lysate in the presence of a forward primer comprising the oligonucleotide sequence: 5'-GAC GGT TGT CCC GGT TTA AGC A-3' (SEQ ID NO: 5) and a reverse primer comprising the oligonucleotide sequence: 5'-GCT GGT ATC TTC GAC TGG TCT-3' (SEQ ID NO: 6) to form an amplified lysate comprising a *K. pneumoniae* amplicon, (iii) amplifying a *P. aeruginosa* target nucleic acid in the lysate in the presence of a forward primer comprising the oligonucleotide sequence 5'-AGG CTG GGT GTG TAA GCG TTG T-3' (SEQ ID NO: 7) and a reverse primer comprising the oligonucleotide sequence 5'-CAA GCA ATT CGG TTG GAT ATC CGT T-3' (SEQ ID NO: 8) to form an amplified lysate comprising a *P. aeruginosa* amplicon, (iv) amplifying an *E. coli* target nucleic acid in the lysate in the presence of a forward primer comprising the oligonucleotide sequence: 5'-GCA TTA ATC GAC GGT ATG GTT GAC C-3' (SEQ ID NO: 59) and a reverse primer comprising the oligonucleotide sequence: 5'-CCT GCT GAA ACA GGT TTT CCC ACA TA-3' (SEQ ID NO: 61) to form an amplified lysate comprising an *E. coli* amplicon, and/or (v) amplifying an *S. aureus* target nucleic acid in the lysate in the presence of a first primer pair or a second primer pair to form an amplified lysate comprising an *S. aureus* amplicon, wherein the first primer pair comprises a forward primer comprising the oligonucleotide sequence: 5'-GGT AAT GAA TTA CCT/i6diPr/TC TCT GCT GGTTTC TTC TT-3' (SEQ ID NO: 9) and a reverse primer comprising the oligonucleotide sequence: 5'-ACC AGC ATC TTC/i6diPr/GC ATC TTC TGT AAA-3' (SEQ ID NO: 10), and the second primer pair comprises a forward primer comprising the oligonucleotide sequence: 5'-GAA GTT ATG TTT/i6diPr/CT ATT CGA ATC GTG GTC CAGT-3' (SEQ ID NO: 11) and a reverse primer comprising the oligonucleotide sequence: 5'-GTT GTA AAG CCA TGA TGC TCG TAA CCA-3' (SEQ ID NO: 12);
(c) following step (b), for each species, adding magnetic particles to a separate portion of the amplified lysate to form a mixture, wherein the magnetic particles comprise binding moieties on their surface, the binding moieties operative to alter aggregation of the magnetic particles in the presence of the *E. faecium* amplicon, the *K. pneumoniae* amplicon, the *P. aeruginosa* amplicon, the *E. coli* amplicon, or the *S. aureus* amplicon;
(d) providing the mixtures for each species in a separate detection tube within a device, the device comprising a support defining wells for holding the detection tubes comprising the mixtures, and having an RF coil configured to detect a signal produced by exposing each mixture to a bias magnetic field created using one or more magnets and an RF pulse sequence;
(e) exposing the mixtures to a bias magnetic field and an RF pulse sequence;
(f) following step (e), measuring the signals from the detection tubes; and
(g) on the basis of the result of step (f), determining whether an *E. faecium* species, a *K. pneumoniae* cell, a *P. aeruginosa* cell, an *E. coli* cell, and/or a *S. aureus* cell was present in the liquid sample.

2. The method of claim 1, wherein the magnetic particles comprise a first population of magnetic particles conjugated to a first probe, and a second population of magnetic particles conjugated to a second probe, the first probe operative to bind to a first segment of the *E. faecium* amplicon and the second probe operative to bind to a second segment of the *E. faecium* amplicon, wherein the magnetic particles form aggregates in the presence of the *E. faecium* amplicon.

3. The method of claim 2, wherein the first probe comprises the oligonucleotide sequence: 5'-AAA ACT TAT GTG ACT TCA AAT CCA GTT TT-3' (SEQ ID NO: 111), and the second probe comprises the oligonucleotide sequence: 5'-TTT ACT CAA TAA AAG ATA ACA CCA CAG T-3' (SEQ ID NO: 112).

4. A method for detecting the presence of an *Escherichia coli* (*E. coli*) cell in a liquid sample, the method comprising:
(a) lysing the cells in a liquid sample to form a lysate;
(b) amplifying an *E. coli* target nucleic acid in the lysate in the presence of a forward primer comprising the oligonucleotide sequence: 5'-GCA TTA ATC GAC GGT ATG GTT GAC C-3' (SEQ ID NO: 59) and a reverse primer comprising the oligonucleotide sequence: 5'-CCT GCT GAA ACA GGT TTT CCC ACA TA-3' (SEQ ID NO: 61) to form an amplified lysate comprising an *E. coli* amplicon;
(c) following step (b), adding magnetic particles to the amplified lysate to form a mixture, wherein the magnetic particles comprise binding moieties on their surface, the binding moieties operative to alter aggregation of the magnetic particles in the presence of the *E. coli* amplicon;
(d) providing the mixture in a detection tube within a device, the device comprising a support defining a well for holding the detection tube comprising the mixture, and having an RF coil configured to detect a signal produced by exposing the mixture to a bias magnetic field created using one or more magnets and an RF pulse sequence;
(e) exposing the mixture to a bias magnetic field and an RF pulse sequence;
(f) following step (e), measuring the signal from the detection tube; and
(g) on the basis of the result of step (f), determining whether an *E. coli* cell was present in the liquid sample.

5. The method of claim 4, wherein the magnetic particles comprise a first population of magnetic particles conjugated to a first probe, and a second population of magnetic particles conjugated to a second probe, the first probe operative to bind to a first segment of the *E. coli* amplicon and the second probe operative to bind to a second segment of the *E. coli* amplicon, wherein the magnetic particles form aggregates in the presence of the *E. coli* amplicon.

6. The method of claim 5, wherein the first probe comprises the oligonucleotide sequence:
5'-AGT GAT GAT GAG TTG TTT GCC AGT G-3' (SEQ ID NO: 63), and the second probe comprises the oligonucleotide sequence: 5'-TGA ATT GTC GCC GCG TGA CCA G-3' (SEQ ID NO: 64).

7. The method of claim 1, wherein:
(i) the steps (a) through (g) of the method are completed within 3 hours;
(ii) the method is capable of detecting a concentration of 10 colony-forming units (CFU)/mL of *E. faecium, K. pneumoniae, P. aeruginosa,* or *S. aureus* in the liquid sample;
(iii) the liquid sample is selected from whole blood, urine, liquid biopsy, synovial fluid, skin biopsy, cerebrospinal fluid, sputum, gastric lavage, bronchoalveolar lavage, or homogenized tissue;
(iv) step (b) comprises adding to the liquid sample from $1 \times 10^6$ to $1 \times 10^{13}$ magnetic particles per milliliter of the liquid sample;
(v) the magnetic particles have a mean diameter of from 700 nm to 950 nm;
(vi) the magnetic particles have a $T_2$ relaxivity per particle of from $1 \times 10^9$ to $1 \times 10^{12}$ mM$^{-1}$ s$^{-1}$;
(vii) the magnetic particles are substantially monodisperse; or
(viii) amplifying is performed by asymmetric polymerase chain reaction (PCR).

8. The method of claim 7, wherein the liquid sample is whole blood, and step (a) comprises lysing the red blood cells in a whole blood sample from a subject, centrifuging the sample to form a supernatant and a pellet, discarding some or all of the supernatant, optionally washing the pellet, and lysing the cells in the pellet to form a lysate.

9. A composition, comprising:
(a) a portion of an extract from a whole blood sample suspected of containing a bacterial pathogen prepared by (i) lysing the red blood cells, (ii) centrifuging the sample to form a supernatant and a pellet, (iii) discarding some or all of the supernatant and optionally washing the pellet, and (iv) lysing any residual cells to form the extract;
(b) a plurality of forward primers, wherein the plurality of forward primers comprises oligonucleotide sequences that are at least 80% identical to SEQ ID NOs: 3, 5, 7, 9, 11, and 59;

(c) a plurality of reverse primers, wherein the plurality of reverse primers comprises oligonucleotide sequences that are at least 80% identical to SEQ ID NOs: 4, 6, 8, 10, 12, and 61;
(d) a thermally stable polymerase; and
(e) deoxynucleotide triphosphates, buffer, and magnesium.

10. A method of diagnosing a bloodstream infection or sepsis in a subject, the method comprising:
detecting, in a liquid sample obtained from the patient, the presence of an *E. faecium* cell, a *K. pneumoniae* cell, a *P. aeruginosa* cell, an *E. coli* cell, or a *S. aureus* cell according to the method of claim 1;
wherein the presence of an *E. faecium* cell, a *K. pneumoniae* cell, a *P. aeruginosa* cell, an *E. coli* cell, or a *S. aureus* cell in the liquid sample identifies the subject as one who may have a bloodstream infection or sepsis.

11. A method of treating a bloodstream infection or sepsis in a subject, the method comprising:
detecting, in a liquid sample obtained from the patient, the presence of an *E. faecium* cell, a *K. pneumoniae* cell, a *P. aeruginosa* cell, an *E. coli* cell, or a *S. aureus* cell according to the method of claim 1, wherein the presence of an *E. faecium* cell, a *K. pneumoniae* cell, a *P. aeruginosa* cell, an *E. coli* cell, or a *S. aureus* cell in the liquid sample identifies the subject as one who may have a bloodstream infection or sepsis; and
administering a bloodstream infection or sepsis therapy to the subject identified as one who may have a bloodstream infection or sepsis.

* * * * *

SEQUENCE LISTING

```
<160> NUMBER OF SEQ ID NOS: 118

<210> SEQ ID NO 1
<211> LENGTH: 27
<212> TYPE: DNA
<213> ORGANISM: Artificial Sequence
<220> FEATURE:
<223> OTHER INFORMATION: Synthetic Construct

<400> SEQUENCE: 1
cgttttccaa atctgtaaca gactggg                                         27

<210> SEQ ID NO 2
<211> LENGTH: 25
<212> TYPE: DNA
<213> ORGANISM: Artificial Sequence
<220> FEATURE:
<223> OTHER INFORMATION: Synthetic Construct

<400> SEQUENCE: 2
aggacgttga taggttggat gtgga                                           25

<210> SEQ ID NO 3
<211> LENGTH: 31
<212> TYPE: DNA
<213> ORGANISM: Artificial Sequence
<220> FEATURE:
<223> OTHER INFORMATION: Synthetic Construct

<400> SEQUENCE: 3
ggtagctatg tagggaaggg ataaacgctg a                                    31

<210> SEQ ID NO 4
<211> LENGTH: 28
<212> TYPE: DNA
<213> ORGANISM: Artificial Sequence
<220> FEATURE:
```

<223> OTHER INFORMATION: Synthetic Construct

<400> SEQUENCE: 4
gcgctaagga gcttaacttc tgtgttcg                                28

<210> SEQ ID NO 5
<211> LENGTH: 22
<212> TYPE: DNA
<213> ORGANISM: Artificial Sequence
<220> FEATURE:
<223> OTHER INFORMATION: Synthetic Construct

<400> SEQUENCE: 5
gacggttgtc ccggtttaag ca                                     22

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
gctggtatct tcgactggtc t                                      21

<210> SEQ ID NO 7
<211> LENGTH: 22
<212> TYPE: DNA
<213> ORGANISM: Artificial Sequence
<220> FEATURE:
<223> OTHER INFORMATION: Synthetic Construct

<400> SEQUENCE: 7
aggctgggtg tgtaagcgtt gt                                     22

<210> SEQ ID NO 8
<211> LENGTH: 25
<212> TYPE: DNA
<213> ORGANISM: Artificial Sequence
<220> FEATURE:
<223> OTHER INFORMATION: Synthetic Construct

<400> SEQUENCE: 8
caagcaattc ggttggatat ccgtt                                  25

<210> SEQ ID NO 9
<211> LENGTH: 35
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: n is 2,6-Diaminopurine

<400> SEQUENCE: 9
ggtaatgaat tacctntctc tgctggtttc ttctt                       35

<210> SEQ ID NO 10
<211> LENGTH: 27
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: n is 2,6-Diaminopurine

<400> SEQUENCE: 10
accagcatct tcngcatctt ctgtaaa                                              27

<210> SEQ ID NO 11
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: n is 2,6-Diaminopurine

<400> SEQUENCE: 11
gaagttatgt ttnctattcg aatcgtggtc cagt                                      34

<210> SEQ ID NO 12
<211> LENGTH: 27
<212> TYPE: DNA
<213> ORGANISM: Artificial Sequence
<220> FEATURE:
<223> OTHER INFORMATION: Synthetic Construct

<400> SEQUENCE: 12
gttgtaaagc catgatgctc gtaacca                                              27

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
ggcatgcctg tttgagcgtc                                                      20

<210> SEQ ID NO 14
<211> LENGTH: 29
<212> TYPE: DNA
<213> ORGANISM: Artificial Sequence
<220> FEATURE:
<223> OTHER INFORMATION: Synthetic Construct

<400> SEQUENCE: 14
gcttattgat atgcttaagt tcagcgggt                                            29

<210> SEQ ID NO 15
<211> LENGTH: 22
<212> TYPE: DNA
<213> ORGANISM: Artificial Sequence
<220> FEATURE:
<223> OTHER INFORMATION: Synthetic Construct

<400> SEQUENCE: 15
tgaggcttga ctatacaaca cc                                                   22

<210> SEQ ID NO 16
<211> LENGTH: 29
<212> TYPE: DNA
<213> ORGANISM: Artificial Sequence
<220> FEATURE:
<223> OTHER INFORMATION: Synthetic Construct

```
<400> SEQUENCE: 16
ctaaaatgaa cagataaagt aagattcaa                                  29

<210> SEQ ID NO 17
<211> LENGTH: 31
<212> TYPE: DNA
<213> ORGANISM: Artificial Sequence
<220> FEATURE:
<223> OTHER INFORMATION: Synthetic Construct

<400> SEQUENCE: 17
tttttttttt gaggcttgac tatacaacac c                               31

<210> SEQ ID NO 18
<211> LENGTH: 38
<212> TYPE: DNA
<213> ORGANISM: Artificial Sequence
<220> FEATURE:
<223> OTHER INFORMATION: Synthetic Construct

<400> SEQUENCE: 18
ctaaaatgaa cagataaagt aagattcaat tttttttt                        38

<210> SEQ ID NO 19
<211> LENGTH: 29
<212> TYPE: DNA
<213> ORGANISM: Artificial Sequence
<220> FEATURE:
<223> OTHER INFORMATION: Synthetic Construct

<400> SEQUENCE: 19
aaaacttata tgacttcaaa tccagtttt                                  29

<210> SEQ ID NO 20
<211> LENGTH: 27
<212> TYPE: DNA
<213> ORGANISM: Artificial Sequence
<220> FEATURE:
<223> OTHER INFORMATION: Synthetic Construct

<400> SEQUENCE: 20
tttactcaat aaaagataac accacag                                    27

<210> SEQ ID NO 21
<211> LENGTH: 38
<212> TYPE: DNA
<213> ORGANISM: Artificial Sequence
<220> FEATURE:
<223> OTHER INFORMATION: Synthetic Construct

<400> SEQUENCE: 21 tttttttta aaacttatat gacttcaaat ccagtttt                         38

<210> SEQ ID NO 22
<211> LENGTH: 37
<212> TYPE: DNA
<213> ORGANISM: Artificial Sequence
<220> FEATURE:
<223> OTHER INFORMATION: Synthetic Construct

<400> SEQUENCE: 22
tttactcaat aaaagataac accacagttt tttttt                          37

<210> SEQ ID NO 23
<211> LENGTH: 24
```

```
<212> TYPE: DNA
<213> ORGANISM: Artificial Sequence
<220> FEATURE:
<223> OTHER INFORMATION: Synthetic Construct

<400> SEQUENCE: 23
tggataagta aaagcaactt ggtt                                           24

<210> SEQ ID NO 24
<211> LENGTH: 30
<212> TYPE: DNA
<213> ORGANISM: Artificial Sequence
<220> FEATURE:
<223> OTHER INFORMATION: Synthetic Construct

<400> SEQUENCE: 24
aatgaagatt caactcaata agaaacaaca                                     30

<210> SEQ ID NO 25
<211> LENGTH: 33
<212> TYPE: DNA
<213> ORGANISM: Artificial Sequence
<220> FEATURE:
<223> OTHER INFORMATION: Synthetic Construct

<400> SEQUENCE: 25
tttttttttt ggataagtaa aagcaacttg gtt                                 33

<210> SEQ ID NO 26
<211> LENGTH: 39
<212> TYPE: DNA
<213> ORGANISM: Artificial Sequence
<220> FEATURE:
<223> OTHER INFORMATION: Synthetic Construct

<400> SEQUENCE: 26
aatgaagatt caactcaata agaaacaaca tttttttttt                          39

<210> SEQ ID NO 27
<211> LENGTH: 23
<212> TYPE: DNA
<213> ORGANISM: Artificial Sequence
<220> FEATURE:
<223> OTHER INFORMATION: Synthetic Construct

<400> SEQUENCE: 27
taccaaggcg cttgagagaa ctc                                            23

<210> SEQ ID NO 28
<211> LENGTH: 19
<212> TYPE: DNA
<213> ORGANISM: Artificial Sequence
<220> FEATURE:
<223> OTHER INFORMATION: Synthetic Construct

<400> SEQUENCE: 28
ctggtgtgta ggtgaagtc                                                 19

<210> SEQ ID NO 29
<211> LENGTH: 32
<212> TYPE: DNA
<213> ORGANISM: Artificial Sequence
<220> FEATURE:
<223> OTHER INFORMATION: Synthetic Construct

<400> SEQUENCE: 29
```
tttttttttt accaaggcgc ttgagagaac tc                                    32

<210> SEQ ID NO 30
<211> LENGTH: 28
<212> TYPE: DNA
<213> ORGANISM: Artificial Sequence
<220> FEATURE:
<223> OTHER INFORMATION: Synthetic Construct

<400> SEQUENCE: 30
ctggtgtgta ggtgaagtct tttttttt                                         28

<210> SEQ ID NO 31
<211> LENGTH: 23
<212> TYPE: DNA
<213> ORGANISM: Artificial Sequence
<220> FEATURE:
<223> OTHER INFORMATION: Synthetic Construct

<400> SEQUENCE: 31
gtgtgttgta gggtgaagtc gac                                              23

<210> SEQ ID NO 32
<211> LENGTH: 22
<212> TYPE: DNA
<213> ORGANISM: Artificial Sequence
<220> FEATURE:
<223> OTHER INFORMATION: Synthetic Construct

<400> SEQUENCE: 32
caccttgaaa tcatatacct ga                                               22

<210> SEQ ID NO 33
<211> LENGTH: 32
<212> TYPE: DNA
<213> ORGANISM: Artificial Sequence
<220> FEATURE:
<223> OTHER INFORMATION: Synthetic Construct

<400> SEQUENCE: 33
tttttttttg tgtgttgtag ggtgaagtcg ac                                    32

<210> SEQ ID NO 34
<211> LENGTH: 31
<212> TYPE: DNA
<213> ORGANISM: Artificial Sequence
<220> FEATURE:
<223> OTHER INFORMATION: Synthetic Construct

<400> SEQUENCE: 34
caccttgaaa tcatatacct gattttttt t                                      31

<210> SEQ ID NO 35
<211> LENGTH: 23
<212> TYPE: DNA
<213> ORGANISM: Artificial Sequence
<220> FEATURE:
<223> OTHER INFORMATION: Synthetic Construct

<400> SEQUENCE: 35
ccatttgaag ttgtttatta tgc                                              23

<210> SEQ ID NO 36
<211> LENGTH: 27
<212> TYPE: DNA
<213> ORGANISM: Artificial Sequence
<220> FEATURE:
<223> OTHER INFORMATION: Synthetic Construct

<400> SEQUENCE: 36
gggaaatgat taattatgca ttaaatc                                27

<210> SEQ ID NO 37
<211> LENGTH: 32
<212> TYPE: DNA
<213> ORGANISM: Artificial Sequence
<220> FEATURE:
<223> OTHER INFORMATION: Synthetic Construct

<400> SEQUENCE: 37 ttttttttc catttgaagt tgtttattat gc                           32

<210> SEQ ID NO 38
<211> LENGTH: 36
<212> TYPE: DNA
<213> ORGANISM: Artificial Sequence
<220> FEATURE:
<223> OTHER INFORMATION: Synthetic Construct

<400> SEQUENCE: 38
gggaaatgat taattatgca ttaaatcttt tttttt                      36

<210> SEQ ID NO 39
<211> LENGTH: 26
<212> TYPE: DNA
<213> ORGANISM: Artificial Sequence
<220> FEATURE:
<223> OTHER INFORMATION: Synthetic Construct

<400> SEQUENCE: 39
tttttcagat ttaggattag ttgatt                                 26

<210> SEQ ID NO 40
<211> LENGTH: 22
<212> TYPE: DNA
<213> ORGANISM: Artificial Sequence
<220> FEATURE:
<223> OTHER INFORMATION: Synthetic Construct

<400> SEQUENCE: 40
gatccgtatt ggttatatca tc                                     22

<210> SEQ ID NO 41
<211> LENGTH: 35
<212> TYPE: DNA
<213> ORGANISM: Artificial Sequence
<220> FEATURE:
<223> OTHER INFORMATION: Synthetic Construct

<400> SEQUENCE: 41
tttttttttt ttttcagatt taggattagt tgatt                       35

<210> SEQ ID NO 42
<211> LENGTH: 31
<212> TYPE: DNA
<213> ORGANISM: Artificial Sequence
<220> FEATURE:
<223> OTHER INFORMATION: Synthetic Construct

<400> SEQUENCE: 42
gatccgtatt ggttatatca tctttttttt t                           31

<210> SEQ ID NO 43
<211> LENGTH: 30
<212> TYPE: DNA
<213> ORGANISM: Artificial Sequence
<220> FEATURE:
<223> OTHER INFORMATION: Synthetic Construct

<400> SEQUENCE: 43
tttttttttt ggaataatac gccgaccagc                                30

<210> SEQ ID NO 44
<211> LENGTH: 34
<212> TYPE: DNA
<213> ORGANISM: Artificial Sequence
<220> FEATURE:
<223> OTHER INFORMATION: Synthetic Construct

<400> SEQUENCE: 44
aaggatctat ttcagtatga tgcagttttt tttt                           34

<210> SEQ ID NO 45
<211> LENGTH: 200
<212> TYPE: DNA
<213> ORGANISM: Artificial Sequence
<220> FEATURE:
<223> OTHER INFORMATION: Synthetic Construct

<400> SEQUENCE: 45
tgccgaagcg ttttccaaat ctgtaacaga ctgggctgat tgaatcttac tttatctgtt     60
cattttagct agaggtataa ctaaatcaag ttgtcttgca tatttaagaa tcgattgatg    120
ctttatatac aactgcttgg gtgttgtata gtcaagcctc acgagcaatt agtattggtc    180
agcttcacat atcactatgc                                               200

<210> SEQ ID NO 46
<211> LENGTH: 200
<212> TYPE: DNA
<213> ORGANISM: Artificial Sequence
<220> FEATURE:
<223> OTHER INFORMATION: Synthetic Construct

<400> SEQUENCE: 46
gcatgggaac aggtgtatcc ttctcgctat cgccaccaca ctgggtgttg tttcttattg     60
agttgaatct tcattcactc aaaactggat tgaagtttga atcaaaataa ccaagttgct    120
tttacttatc cattctttgg ttaagtcctc gaccgattag tattggtccg ctccaactat    180
cactagcctt ccacttccaa                                               200

<210> SEQ ID NO 47
<211> LENGTH: 200
<212> TYPE: DNA
<213> ORGANISM: Artificial Sequence
<220> FEATURE:
<223> OTHER INFORMATION: Synthetic Construct

<400> SEQUENCE: 47
gcatggttac aggtgtatcc ttctcgctat cgccaccaca ctgtggtgtt atcttttatt     60
gagtaaattt tgttcactca aaactggatt tgaagtcata taagtttttt tccgagttct    120
tttcttttaa cctattggtt aagtcctcga tcgattagta tcagtccgct ccatacatca    180
ctgtacttcc actcctgacc                                               200

<210> SEQ ID NO 48
<211> LENGTH: 200
<212> TYPE: DNA
<213> ORGANISM: Artificial Sequence
<220> FEATURE:
<223> OTHER INFORMATION: Synthetic Construct

<400> SEQUENCE: 48

```
cagctccatc cgcagggact tcacctacac accagcgtgc cttctcccga agttacggca      60
ccattttgcc tagttccttc acccgagttc tctcaagcgc cttggtattc tctacctgac     120
cacctgtgtc ggtttggggt acgatttgat gttacctgat gcttagaggc ttttcctgga     180
agcagggcat ttgttacttc                                                 200
```

<210> SEQ ID NO 49
<211> LENGTH: 169
<212> TYPE: DNA
<213> ORGANISM: Artificial Sequence
<220> FEATURE:
<223> OTHER INFORMATION: Synthetic Construct

<400> SEQUENCE: 49

```
cgcttgggct tacgtctatc cggattcagg tatgtgattt caaggtgttt tgcggttcat      60
gcgaactttc ggttcgtcga cttcacctta caacacacaa tcgtcagatt gtttgggtgt     120
tatatggtca agcctcacgg gcaattagta ctggttagct caacgcctc                 169
```

<210> SEQ ID NO 50
<211> LENGTH: 151
<212> TYPE: DNA
<213> ORGANISM: Artificial Sequence
<220> FEATURE:
<223> OTHER INFORMATION: Synthetic Construct

<400> SEQUENCE: 50

```
tttaccacta acaccataga aattataacg gtcaatgcca tgatttaatg cataattaat      60
catttcccat tgcactgcat aacttccggc aaaatgacgg aatgcatttg atgtaccacc     120
agcataataa acaacttcaa atgggttgat a                                   151
```

<210> SEQ ID NO 51
<211> LENGTH: 186
<212> TYPE: DNA
<213> ORGANISM: Artificial Sequence
<220> FEATURE:
<223> OTHER INFORMATION: Synthetic Construct

<400> SEQUENCE: 51

```
tgtgatttaa acaagtttac taaggcatca tttttctcgc gaccttcaaa tggcacgata      60
tctttatcat atagatgata taaccaatac ggatctaatt taacatataa acattgatgt     120
tgctgtaaat atttatctaa ctcttttaaa taataatcaa ctaatcctaa atctgaaaaa     180
tccatt                                                                186
```

<210> SEQ ID NO 52

<400> SEQUENCE: 52

000

<210> SEQ ID NO 53
<211> LENGTH: 24
<212> TYPE: DNA
<213> ORGANISM: Artificial Sequence

```
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: n is 2,6-Diaminopurine

<400> SEQUENCE: 53
acctntctct gctggtttct tctt                                            24

<210> SEQ ID NO 54
<211> LENGTH: 26
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: n is 2,6-Diaminopurine

<400> SEQUENCE: 54
cagcatcttc nagcatcttc tgtaaa                                          26

<210> SEQ ID NO 55
<211> LENGTH: 26
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: n is 2,6-Diaminopurine

<400> SEQUENCE: 55
gtttnctatt cgaatcgtgg tccagt                                          26

<210> SEQ ID NO 56
<211> LENGTH: 2541
<212> TYPE: DNA
<213> ORGANISM: Staphylococcus aureus

<400> SEQUENCE: 56
atgaagttta caaatttaac agctaaagag tttggtgcct ttacagatag catgccatac     60
agtcatttca cgcaaactgt tggccactat gagttaaagc ttgctgaagg ttatgaaaca    120
catttagtgg gaataaaaaa caataataac gaggtcattg cagcttgctt acttactgct    180
gtacctgtta tgaaagtgtt caagtatttt tattcaaatc gcggtccagt gatcgattat    240
gaaaatcaag aactcgtaca cttttttcttt aatgaattat caaaatatgt taaaaaacat    300
cgttgtctat acctacatat cgatccatat ttaccatatc aatacttgaa tcatgatggc    360
gagattacag gtaatgctgg taatgattgg ttctttgata aaatgagtaa cttaggattt    420
gaacatactg gattccataa aggatttgat cctgtgctac aaattcgtta tcactcagtg    480
ttagatttaa aagataaaac agcagatgac atcattaaaa atatggatgg acttagaaaa    540
agaaacacga aaaagtaa aaagaatggt gttaaagtaa gatatttatc tgaagaagaa     600
ctgccaattt ttagatcatt tatggaagat acgtcagaat caaaagcttt tgctgatcgt    660
gatgacaaat tttactacaa tcgcttaaaa tattacaaag accgtgtgtt agtacctta    720 gcgtatatca actttgatga atatattaaa gaactaaacg aagagcgtga tattttaaat    780
aaagatttaa ataaagcgtt aaaggatatt gaaaaacgtc ctgaaaataa aaaagcacac    840
```

```
aacaagcgag ataacttaca acaacaactt gatgctaatg agcaaaagat tgaagaaggt    900
aaacgtctac aagaagaaca tggtaatgaa ttacctatct ctgctggttt cttctttatc    960
aacccatttg aagttgttta ttatgctggt ggtacatcaa atgcattccg tcattttgcc   1020
ggaagttatg cagtgcaatg ggaaatgatt aattatgcat aaatcatgg cattgaccgt   1080
tataatttct atggtgttag tggtaaattt acagaagatg ctgaagatgc tggtgtagtt   1140
aaattcaaaa aaggttacaa tgctgaaatt attgaatatg ttggtgactt tattaaacca   1200
attaataaac ctgtttacgc agcatatacc gcacttaaaa aagttaaaga cagaattttt   1260
taggaaggga attatcaaaa catgaaattt acagagttaa ctgttaccga atttgacaac   1320
tttgtacaaa atccatcatt ggaaagtcat tatttccaag taaaagaaaa tatagttacc   1380
cgtgagaatg atggctttga agtagtttta ttaggtatta aagacgacaa taacaaagta   1440
attgcagcaa gccttttctc taaaattcct actatgggaa gttatgttta ctattcgaat   1500
cgtggtccag taatggattt ttcagattta ggattagttg attattattt aaaagagtta   1560
gataaatatt tacagcaaca tcaatgttta tatgttaaat tagatccgta ttggttatat   1620
catctatatg ataaagatat cgtgccattt gaaggtcgcg agaaaaatga tgccttagta   1680
aacttgttta aatcacatgg ttacgagcat catggcttta caactgagta tgatacatcg   1740
agccaagtac gatggatggg cgtattaaac cttgaaggta aaacacccga acattgaaa    1800
aagacatttg atagtcaacg taaacgtaat attaataaag cgataaacta tggtgttaaa   1860
gtcagattcc ttgaacgtga tgagttcaat cttttcttag atttatatcg tgaaactgaa   1920
gagcgtgctg gatttgtgtc aaaaacagat gattattttt ataactttat tgacacatat   1980
ggagataaag tattagtacc attagcatat attgaccttg atgaatatgt gttaaagttg   2040
caacaggaat tgaatgacaa agaaaatcgt cgtgatcaaa tgatggcgaa agaaaacaaa   2100
tcagataaac aaatgaagaa aattgcagaa ttagataagc aaattgatca tgatcagcat   2160
gaattattga atgcaagtga attgagcaaa acggacggcc caattctaaa ccttgcttct   2220
ggcgtttatt ttgcaaatgc atatgaagtg aattatttct ctggtggttc atcagaaaaa   2280
tataatcaat ttatgggacc atacatgatg cattggttta tgattaacta ttgcttcgat   2340
aatggctatg atcgttataa tttctatggt ttatcaggtg attttacgga aaacagtgaa   2400
gattatggcg tataccgctt taaacgtgga tttaatgtac aaatcgaaga attaataggg   2460
gatttctata aaccaattca taagtgaaaa tattggttgt tcacaacatt ggataaatta   2520
cgtaaaaaat taaagaaata g                                             2541
```

<210> SEQ ID NO 57
<211> LENGTH: 25
<212> TYPE: DNA
<213> ORGANISM: Artificial Sequence
<220> FEATURE:
<223> OTHER INFORMATION: Synthetic Construct

<400> SEQUENCE: 57
ggaagggatc aggtggttca ctctt                                           25

<210> SEQ ID NO 58
<211> LENGTH: 26
<212> TYPE: DNA
<213> ORGANISM: Artificial Sequence
<220> FEATURE:
<223> OTHER INFORMATION: Synthetic Construct

<400> SEQUENCE: 58
ctatgtaggg aagggataaa cgctga    26

<210> SEQ ID NO 59
<211> LENGTH: 25
<212> TYPE: DNA
<213> ORGANISM: Artificial Sequence
<220> FEATURE:
<223> OTHER INFORMATION: Synthetic Construct

<400> SEQUENCE: 59
gcattaatcg acggtatggt tgacc    25

<210> SEQ ID NO 60
<211> LENGTH: 21
<212> TYPE: DNA
<213> ORGANISM: Artificial Sequence
<220> FEATURE:
<223> OTHER INFORMATION: Synthetic Construct

<400> SEQUENCE: 60
cgacggtatg gttgaccatg c    21

<210> SEQ ID NO 61
<211> LENGTH: 26
<212> TYPE: DNA
<213> ORGANISM: Artificial Sequence
<220> FEATURE:
<223> OTHER INFORMATION: Synthetic Construct

<400> SEQUENCE: 61
cctgctgaaa caggttttcc cacata    26

<210> SEQ ID NO 62
<211> LENGTH: 24
<212> TYPE: DNA
<213> ORGANISM: Artificial Sequence
<220> FEATURE:
<223> OTHER INFORMATION: Synthetic Construct

<400> SEQUENCE: 62
gacgcctgct gaaacaggtt ttcc    24

<210> SEQ ID NO 63
<211> LENGTH: 25
<212> TYPE: DNA
<213> ORGANISM: Artificial Sequence
<220> FEATURE:
<223> OTHER INFORMATION: Synthetic Construct

<400> SEQUENCE: 63
agtgatgatg agttgtttgc cagtg    25

<210> SEQ ID NO 64
<211> LENGTH: 22
<212> TYPE: DNA
<213> ORGANISM: Artificial Sequence
<220> FEATURE:
<223> OTHER INFORMATION: Synthetic Construct

<400> SEQUENCE: 64
tgaattgtcg ccgcgtgacc ag    22

<210> SEQ ID NO 65
<211> LENGTH: 26
<212> TYPE: DNA

```
<213> ORGANISM: Artificial Sequence
<220> FEATURE:
<223> OTHER INFORMATION: Synthetic Construct

<400> SEQUENCE: 65
ggtgcatacg accgttagcc agagtc                                          26

<210> SEQ ID NO 66
<211> LENGTH: 22
<212> TYPE: DNA
<213> ORGANISM: Artificial Sequence
<220> FEATURE:
<223> OTHER INFORMATION: Synthetic Construct

<400> SEQUENCE: 66
ctgagttcgg gaagggatca gg                                              22

<210> SEQ ID NO 67
<211> LENGTH: 25
<212> TYPE: DNA
<213> ORGANISM: Artificial Sequence
<220> FEATURE:
<223> OTHER INFORMATION: Synthetic Construct

<400> SEQUENCE: 67
ccaaatctgt aacagactgg gctga                                           25

<210> SEQ ID NO 68
<211> LENGTH: 28
<212> TYPE: DNA
<213> ORGANISM: Artificial Sequence
<220> FEATURE:
<223> OTHER INFORMATION: Synthetic Construct

<400> SEQUENCE: 68
aaaccaaatc tgtaacagac tgggctga                                        28

<210> SEQ ID NO 69
<211> LENGTH: 25
<212> TYPE: DNA
<213> ORGANISM: Artificial Sequence
<220> FEATURE:
<223> OTHER INFORMATION: Synthetic Construct

<400> SEQUENCE: 69
atgggtaatc ccacactacc atcag                                           25

<210> SEQ ID NO 70
<211> LENGTH: 27
<212> TYPE: DNA
<213> ORGANISM: Artificial Sequence
<220> FEATURE:
<223> OTHER INFORMATION: Synthetic Construct

<400> SEQUENCE: 70
actcttgcta tggtcgccag cacaact                                         27

<210> SEQ ID NO 71
<211> LENGTH: 25
<212> TYPE: DNA
<213> ORGANISM: Artificial Sequence
<220> FEATURE:
<223> OTHER INFORMATION: Synthetic Construct

<400> SEQUENCE: 71
cgtgaggctt gactatacaa caccc                                           25
```

<210> SEQ ID NO 72
<211> LENGTH: 25
<212> TYPE: DNA
<213> ORGANISM: Artificial Sequence
<220> FEATURE:
<223> OTHER INFORMATION: Synthetic Construct

<400> SEQUENCE: 72
cgtgaggctt gactatacaa caccc                                        25

<210> SEQ ID NO 73
<211> LENGTH: 26
<212> TYPE: DNA
<213> ORGANISM: Artificial Sequence
<220> FEATURE:
<223> OTHER INFORMATION: Synthetic Construct

<400> SEQUENCE: 73
cttgactata caacacccaa gcagtt                                       26

<210> SEQ ID NO 74
<211> LENGTH: 28
<212> TYPE: DNA
<213> ORGANISM: Artificial Sequence
<220> FEATURE:
<223> OTHER INFORMATION: Synthetic Construct

<400> SEQUENCE: 74
ggcttgacta tacaacaccc aagcagtt                                     28

<210> SEQ ID NO 75
<211> LENGTH: 24
<212> TYPE: DNA
<213> ORGANISM: Artificial Sequence
<220> FEATURE:
<223> OTHER INFORMATION: Synthetic Construct

<400> SEQUENCE: 75
gtgaagccca cctcaagatg agat                                         24

<210> SEQ ID NO 76
<211> LENGTH: 22
<212> TYPE: DNA
<213> ORGANISM: Artificial Sequence
<220> FEATURE:
<223> OTHER INFORMATION: Synthetic Construct

<400> SEQUENCE: 76
tgttctgcca agggcattgc tg                                           22

<210> SEQ ID NO 77
<211> LENGTH: 26
<212> TYPE: DNA
<213> ORGANISM: Artificial Sequence
<220> FEATURE:
<223> OTHER INFORMATION: Synthetic Construct

<400> SEQUENCE: 77
ctatgtaggg aagggataaa cgctga                                       26

<210> SEQ ID NO 78
<211> LENGTH: 24
<212> TYPE: DNA
<213> ORGANISM: Artificial Sequence
<220> FEATURE:

<223> OTHER INFORMATION: Synthetic Construct

<400> SEQUENCE: 78
acaatcggcg ctagaagctt aact                                          24

<210> SEQ ID NO 79
<211> LENGTH: 25
<212> TYPE: DNA
<213> ORGANISM: Artificial Sequence
<220> FEATURE:
<223> OTHER INFORMATION: Synthetic Construct

<400> SEQUENCE: 79
acaggtgtat ccttctcgct atcgc                                         25

<210> SEQ ID NO 80
<211> LENGTH: 28
<212> TYPE: DNA
<213> ORGANISM: Artificial Sequence
<220> FEATURE:
<223> OTHER INFORMATION: Synthetic Construct

<400> SEQUENCE: 80
gcgctaagga gcttaacttc tgtgttcg                                      28

<210> SEQ ID NO 81
<211> LENGTH: 31
<212> TYPE: DNA
<213> ORGANISM: Artificial Sequence
<220> FEATURE:
<223> OTHER INFORMATION: Synthetic Construct

<400> SEQUENCE: 81
tcggcgctaa ggagcttaac ttctgtgttc g                                  31

<210> SEQ ID NO 82
<211> LENGTH: 22
<212> TYPE: DNA
<213> ORGANISM: Artificial Sequence
<220> FEATURE:
<223> OTHER INFORMATION: Synthetic Construct

<400> SEQUENCE: 82
gaggcactac ggtgctgaag ta                                            22

<210> SEQ ID NO 83
<211> LENGTH: 24
<212> TYPE: DNA
<213> ORGANISM: Artificial Sequence
<220> FEATURE:
<223> OTHER INFORMATION: Synthetic Construct

<400> SEQUENCE: 83
ctcactggga acttgattcc cctg                                          24

<210> SEQ ID NO 84
<211> LENGTH: 25
<212> TYPE: DNA
<213> ORGANISM: Artificial Sequence
<220> FEATURE:
<223> OTHER INFORMATION: Synthetic Construct

<400> SEQUENCE: 84
ggtggttcca acgctctatg atcgt                                         25

```
<210> SEQ ID NO 85
<211> LENGTH: 25
<212> TYPE: DNA
<213> ORGANISM: Artificial Sequence
<220> FEATURE:
<223> OTHER INFORMATION: Synthetic Construct

<400> SEQUENCE: 85
actgctgtac ctgttatgaa agtgt                                               25

<210> SEQ ID NO 86
<211> LENGTH: 25
<212> TYPE: DNA
<213> ORGANISM: Artificial Sequence
<220> FEATURE:
<223> OTHER INFORMATION: Synthetic Construct

<400> SEQUENCE: 86
gcttgcttac ttactgctgt acctg                                               25

<210> SEQ ID NO 87
<211> LENGTH: 24
<212> TYPE: DNA
<213> ORGANISM: Artificial Sequence
<220> FEATURE:
<223> OTHER INFORMATION: Synthetic Construct

<400> SEQUENCE: 87
gccatacagt catttcacgc aaac                                                24

<210> SEQ ID NO 88
<211> LENGTH: 25
<212> TYPE: DNA
<213> ORGANISM: Artificial Sequence
<220> FEATURE:
<223> OTHER INFORMATION: Synthetic Construct

<400> SEQUENCE: 88
cctgtgttac aaattcgtta tcact                                               25

<210> SEQ ID NO 89
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: n is 2,6-Diaminopurine

<400> SEQUENCE: 89
acctntctct gctggtttct tctt                                                24

<210> SEQ ID NO 90
<211> LENGTH: 25
<212> TYPE: DNA
<213> ORGANISM: Artificial Sequence
<220> FEATURE:
<223> OTHER INFORMATION: Synthetic Construct

<400> SEQUENCE: 90
gcattacctg taatctcgcc atcat                                               25

<210> SEQ ID NO 91
<211> LENGTH: 25
<212> TYPE: DNA
```

```
<213> ORGANISM: Artificial Sequence
<220> FEATURE:
<223> OTHER INFORMATION: Synthetic Construct

<400> SEQUENCE: 91
agcttttgat tctgacgtat cttcc                                          25

<210> SEQ ID NO 92
<211> LENGTH: 28
<212> TYPE: DNA
<213> ORGANISM: Artificial Sequence
<220> FEATURE:
<223> OTHER INFORMATION: Synthetic Construct

<400> SEQUENCE: 92
gatcagcgaa agcttttgat tctgacgt                                       28

<210> SEQ ID NO 93
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: n is 2,6-Diaminopurine

<400> SEQUENCE: 93
cagcatcttc ngcatcttct gtaaa                                          25

<210> SEQ ID NO 94
<211> LENGTH: 249
<212> TYPE: DNA
<213> ORGANISM: Artificial Sequence
<220> FEATURE:
<223> OTHER INFORMATION: Synthetic Construct

<400> SEQUENCE: 94
ggaaatctaa cgagagagca tgctcctgcg gccccggaga cggtgcgccg cggggtgcgg     60
cgccttcttt cacatgtatc caaaacgtct ctcggcaacg gatatctcgg ctctcgcatc    120
gatgaagaac gtagcgaaat gcgatacttg gtgtgaattg cagaatcccg tgaaccatcg    180
agtctttgaa cgcaagttgc gccccaagcc attaggccga gggcacgtct gcctgggtgt    240
cacgcatcg                                                           249

<210> SEQ ID NO 95
<211> LENGTH: 24
<212> TYPE: DNA
<213> ORGANISM: Artificial Sequence
<220> FEATURE:
<223> OTHER INFORMATION: Synthetic Construct

<400> SEQUENCE: 95
ggaaatctaa cgagagagca tgct                                           24

<210> SEQ ID NO 96
<211> LENGTH: 23
<212> TYPE: DNA
<213> ORGANISM: Artificial Sequence
<220> FEATURE:
<223> OTHER INFORMATION: Synthetic Construct

<400> SEQUENCE: 96
ggaaatctaa cgagagagca tgc                                            23
```

<210> SEQ ID NO 97
<211> LENGTH: 19
<212> TYPE: DNA
<213> ORGANISM: Artificial Sequence
<220> FEATURE:
<223> OTHER INFORMATION: Synthetic Construct

<400> SEQUENCE: 97
cgatgcgtga cacccaggc                                                    19

<210> SEQ ID NO 98
<211> LENGTH: 18
<212> TYPE: DNA
<213> ORGANISM: Artificial Sequence
<220> FEATURE:
<223> OTHER INFORMATION: Synthetic Construct

<400> SEQUENCE: 98
gatgcgtgac acccaggc                                                     18

<210> SEQ ID NO 99
<211> LENGTH: 30
<212> TYPE: DNA
<213> ORGANISM: Artificial Sequence
<220> FEATURE:
<223> OTHER INFORMATION: Synthetic Construct

<400> SEQUENCE: 99
gagacgtttt ggatacatgt gaaagaaggc                                        30

<210> SEQ ID NO 100
<211> LENGTH: 26
<212> TYPE: DNA
<213> ORGANISM: Artificial Sequence
<220> FEATURE:
<223> OTHER INFORMATION: Synthetic Construct

<400> SEQUENCE: 100
cgatggttca cgggattctg caattc                                            26

<210> SEQ ID NO 101
<211> LENGTH: 191
<212> TYPE: DNA
<213> ORGANISM: Artificial Sequence
<220> FEATURE:
<223> OTHER INFORMATION: Synthetic Construct

<400> SEQUENCE: 101
gatgcagcaa caacagattc cttgcttctc atacaataac atgacaaacc ccattaataa       60
aaacgcggtc cacttatcat acagaatatc agatagtggc aattaattgt gacaaaaatt      120
cgaaagttgt gtacagttct tcattgttcg aaaaattgtt atgacaagat acaccaggac      180
ataacggcta c                                                           191

<210> SEQ ID NO 102
<211> LENGTH: 18
<212> TYPE: DNA
<213> ORGANISM: Artificial Sequence
<220> FEATURE:
<223> OTHER INFORMATION: Synthetic Construct

<400> SEQUENCE: 102
gcagcaacaa cagattcc                                                     18

<210> SEQ ID NO 103
<211> LENGTH: 20
<212> TYPE: DNA
<213> ORGANISM: Artificial Sequence
<220> FEATURE:
<223> OTHER INFORMATION: Synthetic Construct

<400> SEQUENCE: 103
gtagccgtta tgtcctggtg					20

<210> SEQ ID NO 104
<211> LENGTH: 31
<212> TYPE: DNA
<213> ORGANISM: Artificial Sequence
<220> FEATURE:
<223> OTHER INFORMATION: Synthetic Construct

<400> SEQUENCE: 104
tcgaacaatg aagaactgta cacaactttc g				31

<210> SEQ ID NO 105
<211> LENGTH: 30
<212> TYPE: DNA
<213> ORGANISM: Artificial Sequence
<220> FEATURE:
<223> OTHER INFORMATION: Synthetic Construct

<400> SEQUENCE: 105
ggtttgtcat gttattgtat gagaagcaag				30

<210> SEQ ID NO 106
<211> LENGTH: 200
<212> TYPE: DNA
<213> ORGANISM: Artificial Sequence
<220> FEATURE:
<223> OTHER INFORMATION: Synthetic Construct

<400> SEQUENCE: 106
ggcatgcctg tttgagcgtc ctgcatcata ctgaaataga tccttcgaca acctcggtac	60 actgggaaca aggcctcaaa cattgatgct cgactacacg tagggcaatg cgtcttgcta	120 gaagcgaaat ctgtggcttg ctagtgcaag ctggtcggcg tattattcca acccgctgaa	180 cttaagcata tcaataagca					200

<210> SEQ ID NO 107
<211> LENGTH: 22
<212> TYPE: DNA
<213> ORGANISM: Artificial Sequence
<220> FEATURE:
<223> OTHER INFORMATION: Synthetic Construct

<400> SEQUENCE: 107
gatgatgagt tgtttgccag tg					22

<210> SEQ ID NO 108
<211> LENGTH: 20
<212> TYPE: DNA
<213> ORGANISM: Artificial Sequence
<220> FEATURE:
<223> OTHER INFORMATION: Synthetic Construct

<400> SEQUENCE: 108
tgccagtgat gatgagttgt					20

```
<210> SEQ ID NO 109
<211> LENGTH: 20
<212> TYPE: DNA
<213> ORGANISM: Artificial Sequence
<220> FEATURE:
<223> OTHER INFORMATION: Synthetic Construct

<400> SEQUENCE: 109
gccacctgac attagccatc                                              20

<210> SEQ ID NO 110
<211> LENGTH: 25
<212> TYPE: DNA
<213> ORGANISM: Artificial Sequence
<220> FEATURE:
<223> OTHER INFORMATION: Synthetic Construct

<400> SEQUENCE: 110
ggaagggatc aggtggttca ctctt                                        25

<210> SEQ ID NO 111
<211> LENGTH: 29
<212> TYPE: DNA
<213> ORGANISM: Artificial Sequence
<220> FEATURE:
<223> OTHER INFORMATION: Synthetic Construct

<400> SEQUENCE: 111
aaaacttatg tgacttcaaa tccagtttt                                    29

<210> SEQ ID NO 112
<211> LENGTH: 28
<212> TYPE: DNA
<213> ORGANISM: Artificial Sequence
<220> FEATURE:
<223> OTHER INFORMATION: Synthetic Construct

<400> SEQUENCE: 112
tttactcaat aaaagataac accacagt                                     28

<210> SEQ ID NO 113
<211> LENGTH: 38
<212> TYPE: DNA
<213> ORGANISM: Artificial Sequence
<220> FEATURE:
<223> OTHER INFORMATION: Synthetic Construct

<400> SEQUENCE: 113 tttttttta aaactaatgt gacttcaaat ccagtttt                           38

<210> SEQ ID NO 114
<211> LENGTH: 23
<212> TYPE: DNA
<213> ORGANISM: Artificial Sequence
<220> FEATURE:
<223> OTHER INFORMATION: Synthetic Construct

<400> SEQUENCE: 114
tctgacgatt gtgtgttgta agg                                          23

<210> SEQ ID NO 115
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 115
ggatagacgt aagcccaagc                                                    20

<210> SEQ ID NO 116
<211> LENGTH: 32
<212> TYPE: DNA
<213> ORGANISM: Artificial Sequence
<220> FEATURE:
<223> OTHER INFORMATION: Synthetic Construct

<400> SEQUENCE: 116 ttttttttt ctgacgattg tgtgttgtaa gg                                       32

<210> SEQ ID NO 117
<211> LENGTH: 29
<212> TYPE: DNA
<213> ORGANISM: Artificial Sequence
<220> FEATURE:
<223> OTHER INFORMATION: Synthetic Construct

<400> SEQUENCE: 117
ggatagacgt aagcccaagc ttttttttt                                          29

<210> SEQ ID NO 118
<211> LENGTH: 198
<212> TYPE: DNA
<213> ORGANISM: Artificial Sequence
<220> FEATURE:
<223> OTHER INFORMATION: Synthetic Construct

<400> SEQUENCE: 118
gcatggttac aggtgtatcc ttctcgctat cgccaccaca ctgtggtgtt atcttttatt        60
gagtaaattt tgttcactca aaactggatt tgaagtcata taagtttttt tccgagttct       120
tttcttttaa cctattggtt aagtcctcga tcgattagta tcagtccgct ccatacatca      180
ctgtacttcc actcctga                                                    198
```